(12) United States Patent
Venkatraman et al.

(10) Patent No.: US 6,914,122 B2
(45) Date of Patent: Jul. 5, 2005

(54) MACROCYCLIC NS-3 SERINE PROTEASE INHIBITORS OF HEPATITIS C VIRUS COMPRISING ALKYL AND ARYL ALANINE P2 MOIETIES

(75) Inventors: Srikanth Venkatraman, Woodbridge, NJ (US); Kevin X. Chen, Iselin, NJ (US); Ashok Arasappan, Bridgewater, NJ (US); F. George Njoroge, Warren, NJ (US); Viyyoor Moopil Girijavallabhan, Parsippany, NJ (US); Ashit K. Ganguly, Upper Montclair, NJ (US); Tin-Yau Chan, Edison, NJ (US); Brian Alexander Mc Kittrick, Bloomfield, NJ (US); Nanhua Hugh Yao, Irvine, CA (US); Andrew Joseph Prongay, Stewartsville, NJ (US); Vincent Stewart Madison, Mountain Lakes, NJ (US)

(73) Assignee: Schering Corporation, Kenilworth, NJ (US)

( * ) Notice: Subject to any disclaimer, the term of this patent is extended or adjusted under 35 U.S.C. 154(b) by 373 days.

(21) Appl. No.: 09/836,636

(22) Filed: Apr. 17, 2001

(65) Prior Publication Data

US 2002/0016294 A1 Feb. 7, 2002

Related U.S. Application Data

(60) Provisional application No. 60/198,204, filed on Apr. 19, 2000.

(51) Int. Cl.[7] ............................................... C07K 7/50
(52) U.S. Cl. ......................................... 530/317; 514/11
(58) Field of Search ............................. 514/11; 530/317

(56) References Cited

U.S. PATENT DOCUMENTS

| | | | | |
|---|---|---|---|---|
| 4,260,601 A | * | 4/1981 | Reichelt et al. | ............... 514/18 |
| 4,499,081 A | * | 2/1985 | Laerum | ....................... 514/17 |
| 4,956,344 A | * | 9/1990 | Fossli et al. | .................... 514/18 |
| 5,712,145 A | | 1/1998 | Houghton et al. | ........... 435/219 |
| 5,874,529 A | * | 2/1999 | Gilon et al. | ................. 530/317 |
| 6,265,375 B1 | * | 7/2001 | Gilon et al. | ..................... 514/9 |
| 6,407,066 B1 | * | 6/2002 | Dressen et al. | ............... 514/19 |
| 6,569,993 B1 | * | 5/2003 | Sledeski et al. | ............ 530/333 |

FOREIGN PATENT DOCUMENTS

| | | |
|---|---|---|
| EP | 381 216 | 8/1990 |
| JP | 53-77083 | * 7/1978 |
| JP | 7-228594 | * 8/1995 |
| WO | WO 89/04669 | 6/1989 |
| WO | WO 00/09558 | 2/1998 |
| WO | WO 98/07734 | 2/1998 |
| WO | WO 98/17679 | 4/1998 |
| WO | WO 98/22496 | 5/1998 |
| WO | WO 99/64442 | 6/1999 |
| WO | WO 00/09543 | 5/2000 |

OTHER PUBLICATIONS

Marchetti, Synlett (Spec.), 1000_1002, 1999.*
Koiso Journal of Antibiotics 47, 765, 1994.*
Dutta, J. Med. Chem. 33, 2552 1990.*
Pizzi, (1994) *Proc. Natl. Acad. Sci(USA)* 91:888–892.
Failla (1996) *folding & Design* 1:35–42.
Kollykhalov (1994) *J. Virol.* 68:7525–7533.
Komoda (1994) *J. Virol.* 68:7351–7357.
Landro (1997) *Biochem* 36:9340–9348.
Ingallinella (1998) *Biochem* 37:8906–8914.
Llinas–Brunet (1998) *Bioorg. Med. Chem. Lett*, 8:1713–1718.
Martin (1998) *Biochem* 37:11459–11468.
Dimasi (1997) *J. Virol.* 71:7461–7469.
Martin (1997) *Protein Eng.* 10:607–614.
Elzouki (1997) *J. Hepat.* 27:42–48.
*Bio World Today* 9(217): 4 (Nov. 10, 1998).
Berenguer (1998) *Proc. Assoc. Am. Physicians* 110(2): 98–112.
Hoofnagle (1997) *New England Journal Med.* 336:347.
Zhang *Analytical Biochemistry* 270:268–275 (1999).
Sali (1998) *Biochemistry* 3392–3401.
Barlos (1991) *Int. J. Pept. Protein Res* 513–520.
Holmberg (1979) *Acta Chem. Scand.*, B33:410–412.
Agrawal(1999) *Hepatology Supplement to vol 30* "Development and Characterization of Hepatitis C Virus Serine Protease Cell–based Trans–Cleavage Assay".
Hughes (1992) *Org. Reactions* 42:335.
Heck (1989) *Org. Reactions* 27:345–390.

* cited by examiner

*Primary Examiner*—Christopher S. F. Low
*Assistant Examiner*—David Lukton
(74) *Attorney, Agent, or Firm*—Palaiyur S. Kalyanaraman

(57) ABSTRACT

The present invention discloses novel macrocyclic compounds which have HCV protease inhibitory activity as well as methods for preparing such compounds. In another embodiment, the invention discloses pharmaceutical compositions comprising such macrocycles as well as methods of using them to treat disorders associated with the HCV protease.

36 Claims, No Drawings

SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: substrate peptide
<220> FEATURE:
<221> NAME/KEY: MOD_RES
<222> LOCATION: 1
<223> OTHER INFORMATION: ACETYLATION
<220> FEATURE:
<221> NAME/KEY: MISC_FEATURE
<222> LOCATION: 7
<223> OTHER INFORMATION: Alanine or Proline
<220> FEATURE:
<221> NAME/KEY: MISC_FEATURE
<222> LOCATION: 8
<223> OTHER INFORMATION: Norvaline
<220> FEATURE:
<221> NAME/KEY: MISC_FEATURE
<222> LOCATION: 8
<223> OTHER INFORMATION: Carboyx terminal group esterified with one of
    3-nitrophenol, 4-nitrophenol, 7-hydroxy-4-methyl-coumarin and
    4-phenylazophenol

<400> SEQUENCE: 1

```
Asp Thr Glu Asp Val Val Xaa Xaa
1               5
```

<210> SEQ ID NO 2
<211> LENGTH: 6
<212> TYPE: PRT
<213> ORGANISM: Artificial Sequence
<220> FEATURE:
<223> OTHER INFORMATION: competitive inhibitor peptide
<220> FEATURE:
<221> NAME/KEY: MISC_FEATURE
<222> LOCATION: 2
<223> OTHER INFORMATION: gamma-carboxyglutamic acid (D-Gla)
<220> FEATURE:
<221> NAME/KEY: MISC_FEATURE
<222> LOCATION: 5
<223> OTHER INFORMATION: cyclohexyl alanine
<220> FEATURE:
<221> NAME/KEY: MOD_RES
<222> LOCATION: 1
<223> OTHER INFORMATION: ACETYLATION

<400> SEQUENCE: 2

```
Asp Xaa Leu Ile Xaa Cys
1               5
```

<210> SEQ ID NO 3
<211> LENGTH: 8
<212> TYPE: PRT
<213> ORGANISM: Artificial Sequence
<220> FEATURE:
<223> OTHER INFORMATION: competitive inhibitor peptide
<220> FEATURE:
<221> NAME/KEY: MOD_RES
<222> LOCATION: 1
<223> OTHER INFORMATION: ACETYLATION
<220> FEATURE:
<221> NAME/KEY: MISC_FEATURE
<222> LOCATION: 8
<223> OTHER INFORMATION: norvaline

<400> SEQUENCE: 3

```
Asp Thr Glu Asp Val Val Ala Xaa
1               5
```

<210> SEQ ID NO 4
<211> LENGTH: 8
<212> TYPE: PRT
<213> ORGANISM: Artificial Sequence
<220> FEATURE:
<223> OTHER INFORMATION: competitive inhibitor peptide
<220> FEATURE:
<221> NAME/KEY: MOD_RES
<222> LOCATION: 1
<223> OTHER INFORMATION: ACETYLATION
<220> FEATURE:
<221> NAME/KEY: MISC_FEATURE
<222> LOCATION: 8
<223> OTHER INFORMATION: norvaline

<400> SEQUENCE: 4

```
Asp Thr Glu Asp Val Val Pro Xaa
1               5
```

<210> SEQ ID NO 5
<211> LENGTH: 25
<212> TYPE: PRT
<213> ORGANISM: Artificial Sequence
<220> FEATURE:
<223> OTHER INFORMATION: cleavage sequence

<400> SEQUENCE: 5

```
Ser Ser Gly Ala Asp Thr Glu Asp Val Val Cys Cys Ser Met Ser Tyr
1           5                   10                  15

Thr Trp Thr Gly Ala Leu Val Thr Pro
            20              25
```

MACROCYCLIC NS-3 SERINE PROTEASE INHIBITORS OF HEPATITIS C VIRUS COMPRISING ALKYL AND ARYL ALANINE P2 MOIETIES

The disclosure herein is related to that in pending patent application, Ser. No. 09/825,399 filed Apr. 3, 2001, which claims priority to provisional application. Ser. No. 60/194,607, filed Apr. 5, 2000. This application claims priority from provisional application. Ser. No. 60/198,204, filed Apr. 19, 2000.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel macrocyclic compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888–892, Failla et al. (1996) *Folding & Design* 1:35–42. The NS3/NS4a cleavage site is also more tolerant of mutagenesis than the other sites. See, e.g., Kollykhalov et al. (1994) *J. Virol.* 68:7525–7533. It has also been found that acidic residues in the region upstream of the cleavage site are required for efficient cleavage. See, e.g. Komoda et al. (1994) *J. Virol.* 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340–9348, Ingallinella et al. (1998) *Biochem.* 37:8906–8914, Llinas-Brunet et al. (1998) *Bioorg. Med. Chem. Lett.* 8:1713–1718), inhibitors based on the 70-amino acid polypeptide eglin c (Martin et al. (1998) *Biochem.* 37:11459–11468, inhibitors affinity selected from human pancreatic secretory trypsin inhibitor (hPSTI-C3) and mini-body repertoires (MBip) (Dimasi et al. (1997) *J. Virol.* 71:7461–7469), cV$_H$E2 (a "camelized" variable domain antibody fragment) (Martin et al.(1997) *Protein Eng.* 10:607–614), and α1-antichymotrypsin (ACT)(Elzouki et al.) (1997) *J. Hepat.* 27:42–28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, *Synlett, S1*, 1000–1002 (1999) describing the synthesis of bicylic analogs of an inhibitor of HCV NS3 protease. A compound disclosed therein has the formula:

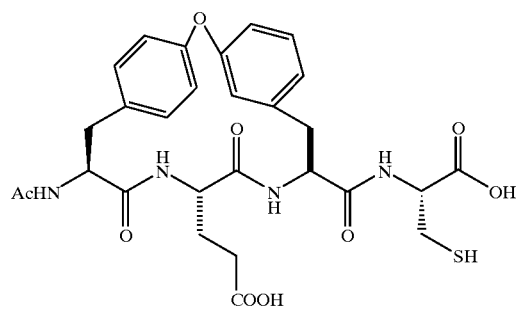

Reference is also made to WO 00/09558 (Assignee: Boehringer Ingelheim Limited; Published Feb. 24, 2000) which discloses peptide derivatives of the formula:

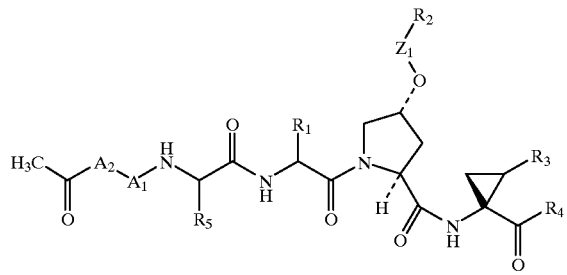

where the various elements are defined therein. An illustrative compound of that series is:

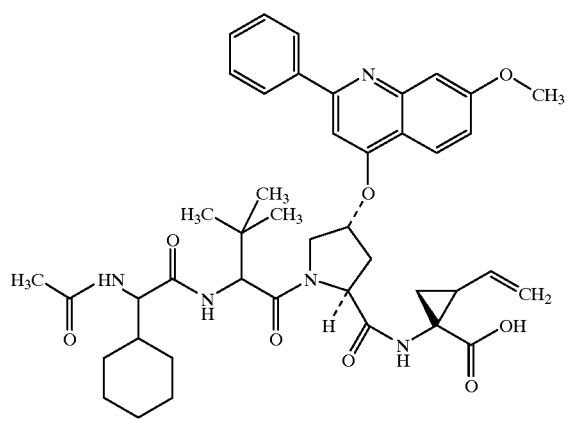

Reference is also made to WO 00/09543 (Assignee: Boehringer Ingelheim Limited; Published Feb. 24, 2000) which discloses peptide derivatives of the formula:

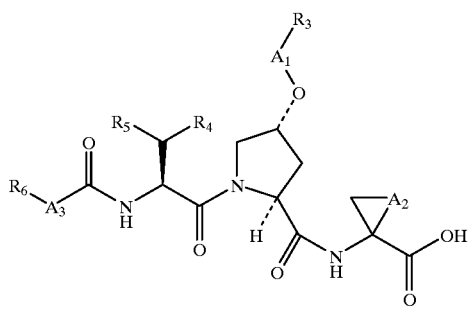

where the various elements are defined therein. An illustrative compound of that series is:

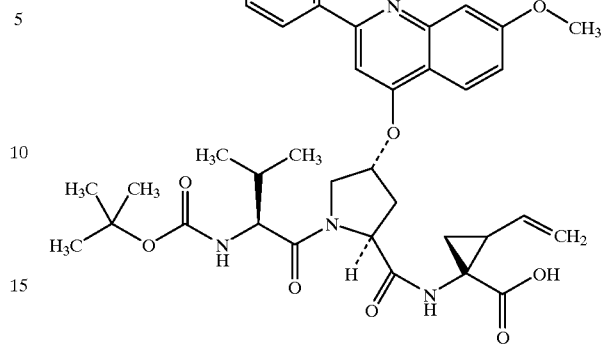

Current therapies for hepatitis C include interferon-α (INF$_\alpha$) and combination therapy with ribavirin and interferon. See, e.g., Beremguer et al. (1998) *Proc. Assoc. Am. Physicians* 110(2):98–112. These therapies suffer from a low sustained response rate and frequent side effects. See, e.g., Hoofnagle et al. (1997) *N. Engl. J. Med.* 336:347. Currently, no vaccine is available for HCV infection.

Pending patent application, Ser. No. 09/825,399 filed Apr. 3, 2001 which claims priority to provisional application Ser. No. 60/194,607, filed Apr. 5, 2000, discloses certain macrocyclic compounds as inhibitors of the HCV protease as well as pharmaceutical compositions containing said compounds.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of macrocyclic inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The presently disclosed compounds generally contain about four or more amino acid residues and less than about twelve amino acid residues.

In its principal embodiment, the present invention provides a macrocyclic compound of Formula 1:

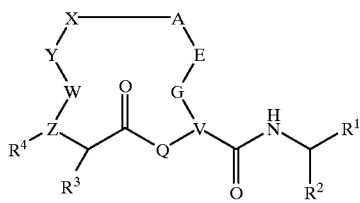

Formula I wherein:
E, X and Y may be independently present or absent, and if present are independently selected from the moieties: alkyl, aryl, alkyl-aryl, heteroalkyl, heteroaryl, aryl-heteroaryl, alkyl-heteroaryl, cycloalkyl, alkyl ether, alkyl-aryl ether, aryl ether, alkyl amino, aryl amino, alkyl-aryl amino, alkyl sulfide, alkyl-aryl sulfide, aryl sulfide, alkyl sulfone, alkyl-aryl sulfone, aryl sulfone, alkyl-alkyl sulfoxide, alkyl-aryl sulfoxide, alkyl amide, alkyl-aryl amide, aryl amide, alkyl sulfonamide, alkyl-aryl sulfonamide, aryl sulfonamide, alkyl urea, alkyl-aryl urea, aryl urea, alkyl carbamate, alkyl-aryl carbamate, aryl carbamate, alkyl-hydrazide, alkyl-aryl hydrazide, alkyl hydroxamide, alkyl-aryl hydroxamide, alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof, with the proviso that E, X and Y may optionally be additionally substituted with moieties selected from the group consisting of aromatic, alkyl, alkyl-aryl, heteroalkyl, aryl-heteroaryl, alkyl-heteroaryl, cycloalkyl, alkyl ether, alkyl-aryl ether, alkyl sulfide, alkyl-aryl sulfide, alkyl sulfone, alkyl-aryl sulfone, alkyl amide, alkyl-aryl amide, alkyl sulfonamide, alkyl amines, alkyl-aryl amines, alkyl-aryl sulfonamide, alkyl urea, alkyl-aryl urea, alkyl carbamate, alkyl-aryl carbamate, halogen, hydroxyl amino, alkyl carbazate, aryl carbazate;

$R^1$=$COR^5$ or $B(OR)_2$, wherein $R^5$=H, OH, $OR^8$, $NR^9R^{10}$, $CF_3$, $C_2F_5$, $C_3F_7$, $CF_2R^6$, $R^6$, $COR^7$ wherein $R^7$=H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COO$ $R^{1'}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO$ $R^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COO$ $R^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COO$ $R^{11}$, $CH(R^{1'})CONHCH(R^{2'})CONHCH(R^{3'})CONHCH(R^{4'})CONHCH(R^{5'})$ $CONR^{12}R^{13}$, wherein $R^{1'}$, $R^{2'}$, $R^{3'}$, $R^{4'}$, $R^{5'}$, $R^{11}$, $R^{12}$, $R^{13}$, and R' are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;
W may be present or absent, and if W is present, W is selected from C=O, C=S, $SO_2$ or C=NR;
Q is (NR)P, O, S, $CH_2$, CHR, CRR' or a double bond towards V;

A is O, $CH_2$, $(CHR)_p$, $(CHR—CHR')_p$, $(CRR')_p$, NR, S, $SO_2$, C=O or a bond;
G is $(CH_2)_p$, $(CHR)_p$, $(CRR')_p$, NR, O, S, $SO_2$, $S(O)_2NH$, C=O, or a double bond towards E or V;
V is CH, CR or N;
p is a number from 0 to 6; and
R, R', $R^2$, $R^3$ and $R^4$ are independently selected from the group consisting of H; C1–C10 alkyl; C2–C10 alkenyl; C3–C8 cycloalkyl; C3–C8 heterocycloalkyl, aryl, alkoxy, aryloxy, alkylthio, arylthio, amino, amido, ester, carboxylic acid, carbamate, urea, ketone, aldehyde, cyano, nitro; heteroaryl; alkyl-aryl; alkyl-heteroaryl; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate and thiourea.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted;

heterocyclic—represents, in addition to the heteroaryl groups defined below, saturated and unsaturated cyclic organic groups having at least one O, S and/or N atom interrupting a carbocyclic ring structure that consists of one or more rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2-or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; Such heteroaryl groups may also be optionally substituted.

Also included in the invention are tautomers, rotamers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula i, as well as methods for treating diseases such as, for example, HCV and related disorders. The methods for treating comprise administering to a patient suffering from said disease or diseases a therapeutically effective amount of a compound of Formula I, or pharmaceutical compositions comprising a compound of Formula I.

Also disclosed is the use of a compound of Formula I for the manufacture of a medicament for treating HCV and related disorders.

DETAILED DESCRIPTION OF PREFERRED EMBODIMENTS

In one embodiment, the present invention discloses compounds of Formula I as inhibitors of HCV protease, especially the HCV NS3/NS4a serine protease:

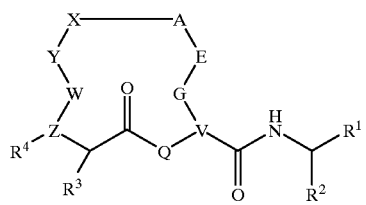

where the various moieties are defined above. Some of the preferred embodiments include, but are not limited to, the following definitions of the various functionalities in the above-noted general formula I; other desired definitions for the same and additional functionalities may be found in the structures and claims of this application which are also within the contemplation of the present invention. Among the preferred embodiments, $R^2$ in formula I may be selected from the following moieties:

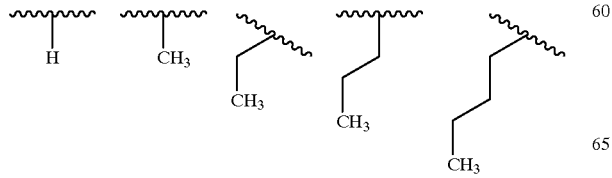

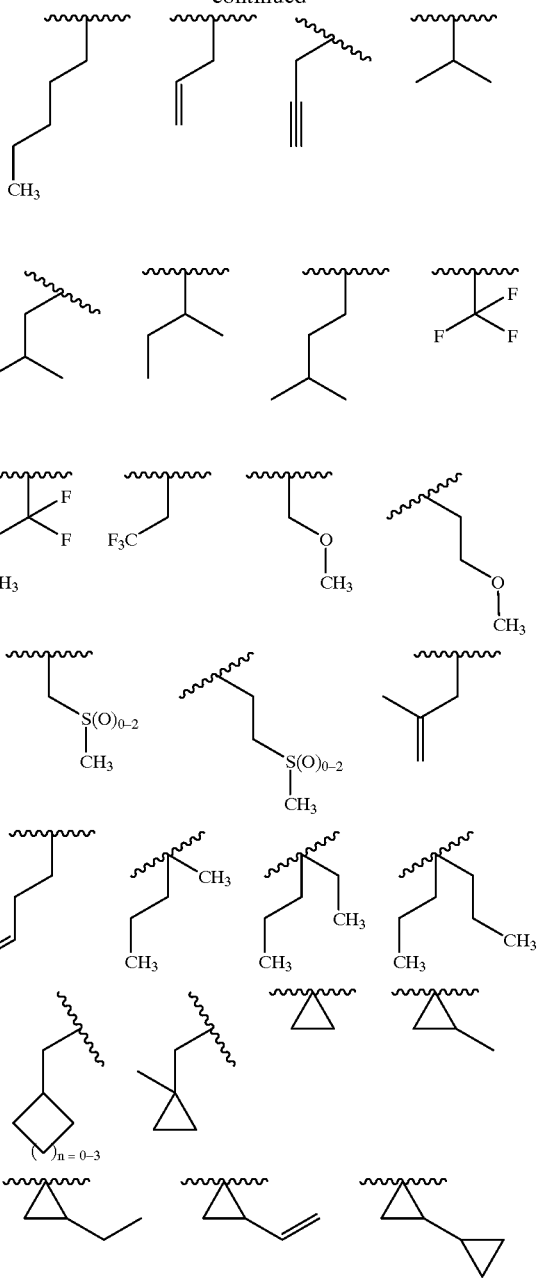

E may be a substituted or unsubstituted alkyl, substituted or unsubstituted aryl, substituted or unsubstituted heteroalkyl, substituted or unsubstituted heteroaryl or substituted or unsubstituted cycloalkyl, with preferred representations for E being:

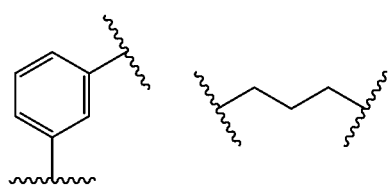

-continued
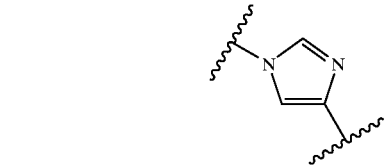
Preferred embodiments for $R^3$ include the moieties:
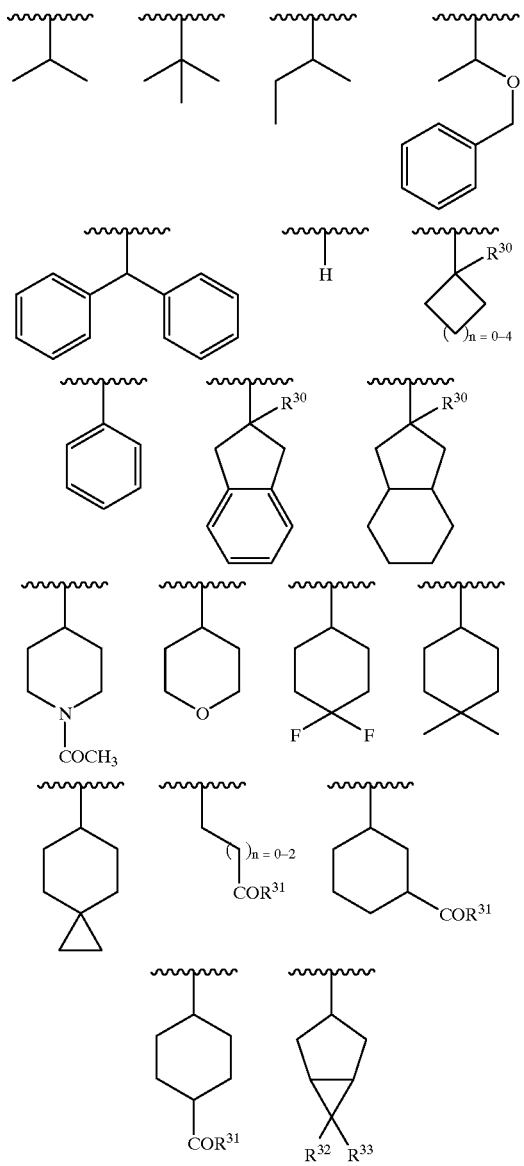
wherein
$R^{30}$=H, $CH_3$ or other alkyl groups;
$R^{31}$=OH, O-alkyl, $NH_2$, N-alkyl; and
$R^{32}$ and $R^{33}$ may be the same or different and are selected independently from H, F, Cl, Br and $CH_3$.
Preferred embodiments for the moiety X-Y are the following structures:
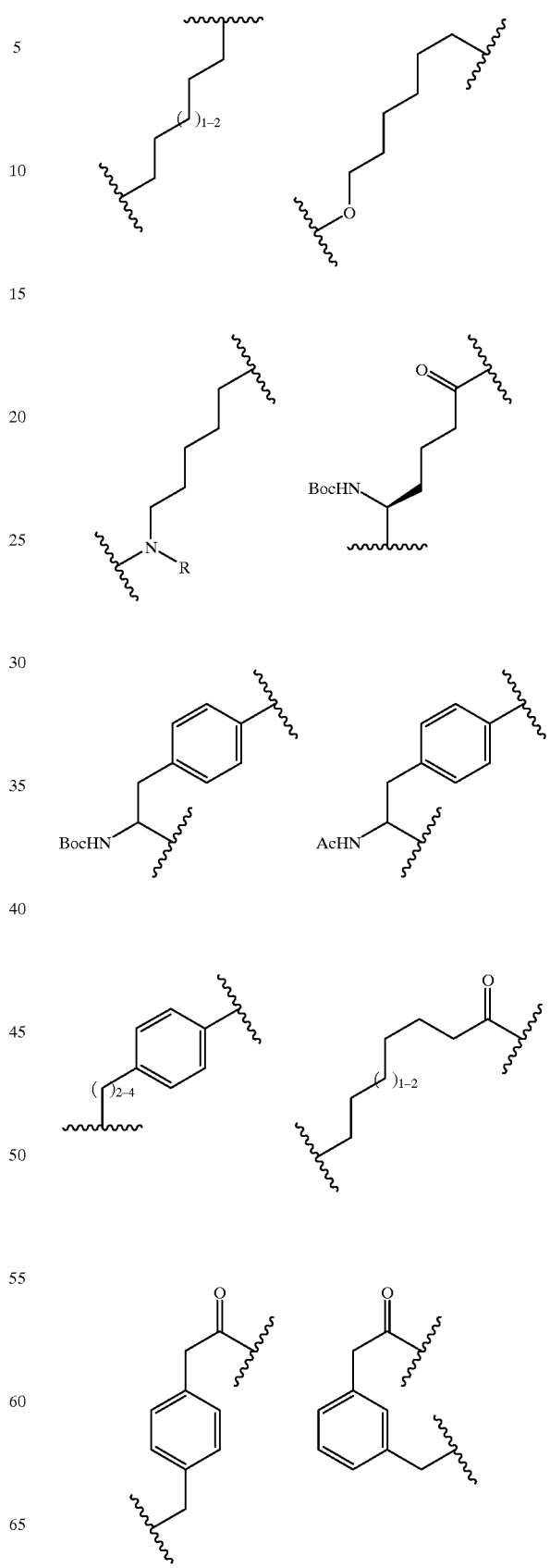

11

-continued

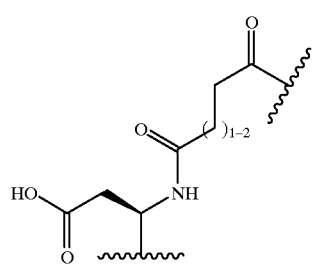

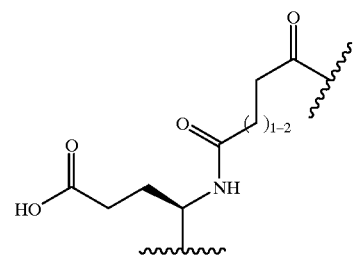

12

-continued

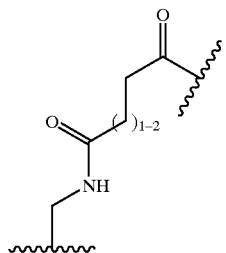

Several additional and further refinements of the above-noted various definitions for the compounds represented by Formula I are noted in the claims section of this application. They are also represented by the various compounds listed in the specification and claims. Such refinements, definitions and limitations are to be considered as representing the entire invention of this application.

Representative compounds of the invention which exhibit excellent HCV protease inhibitory activity are listed below:

1

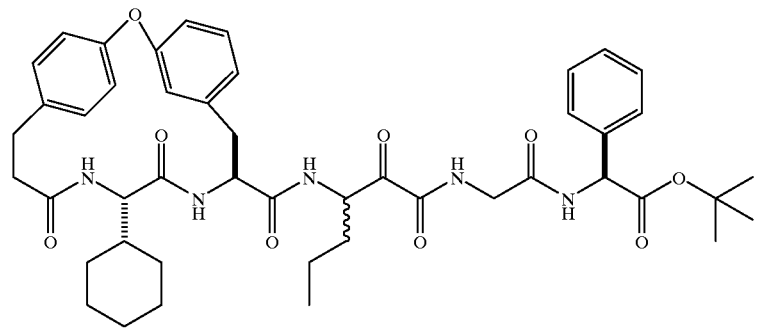

2

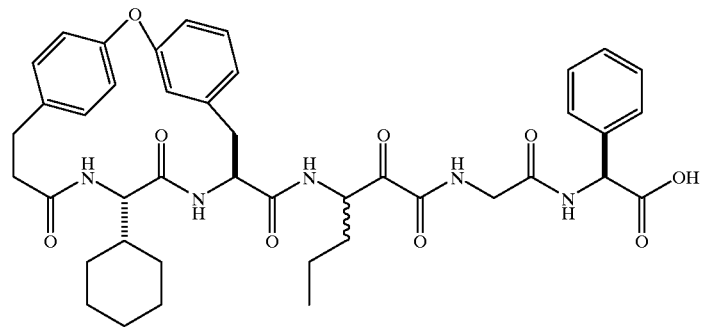

3

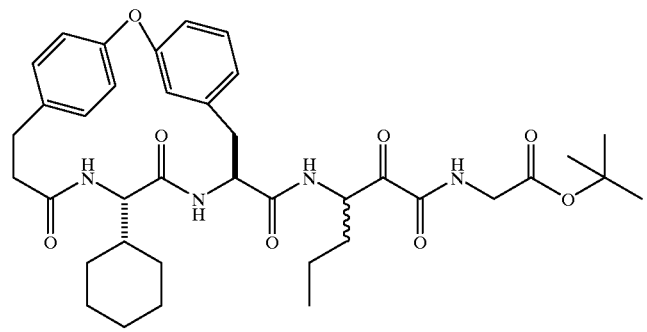

-continued
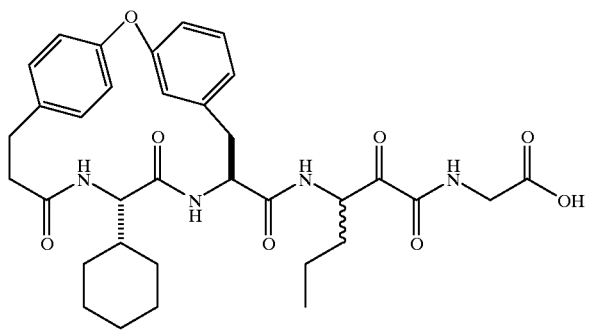
4
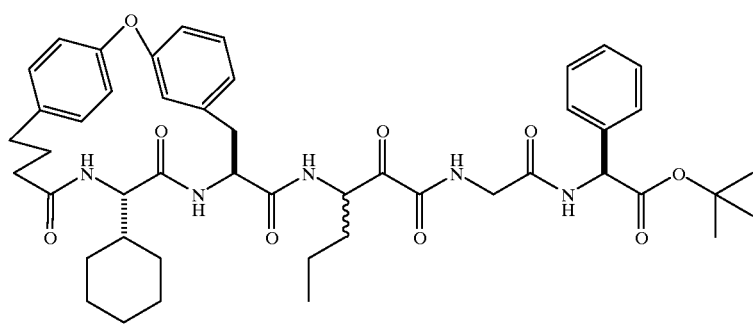
5
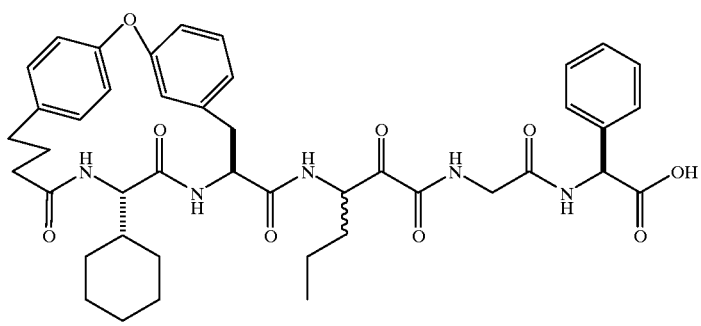
6
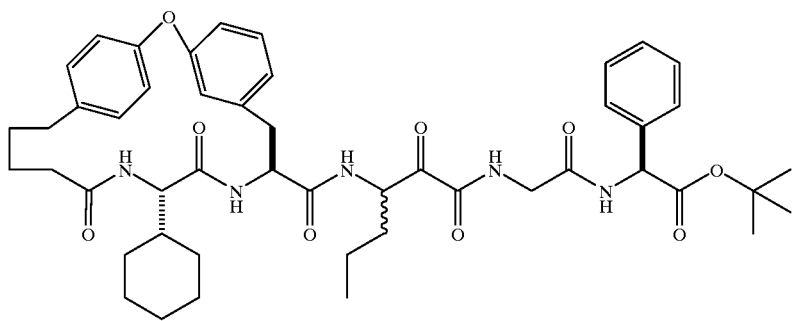
7

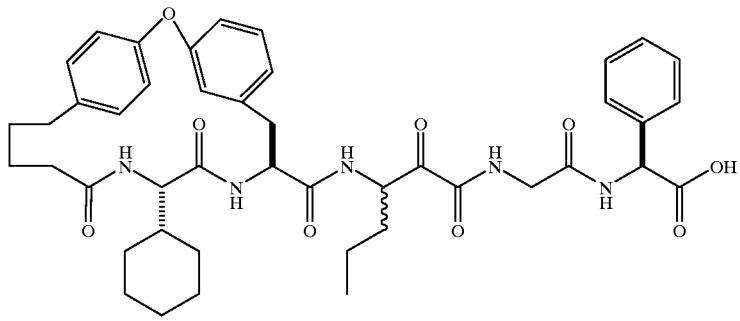
8
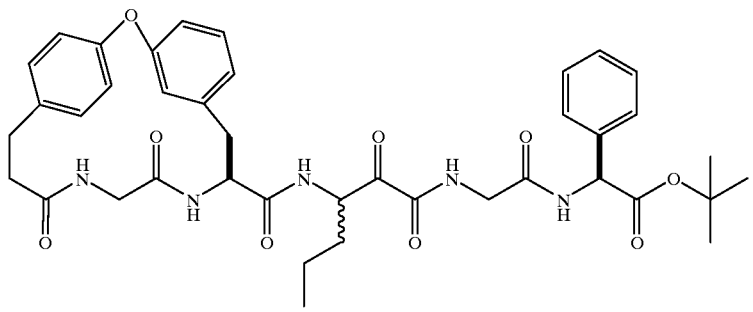
9
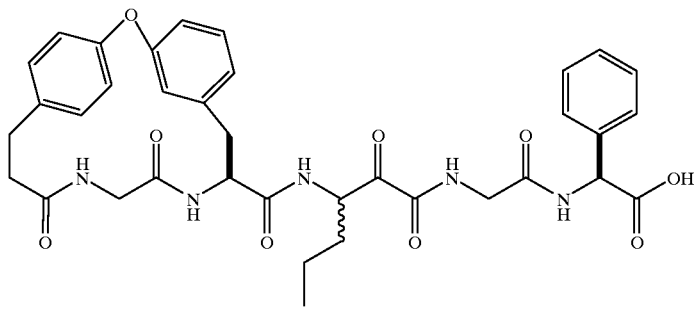
10
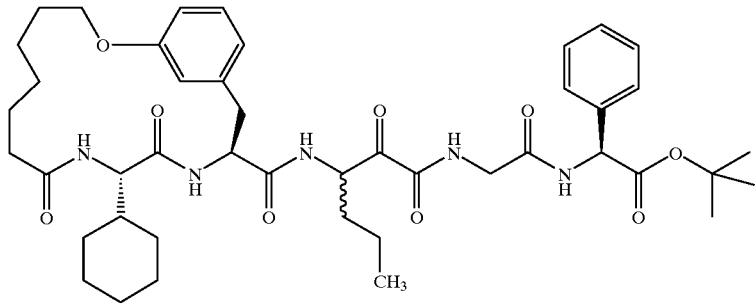
11
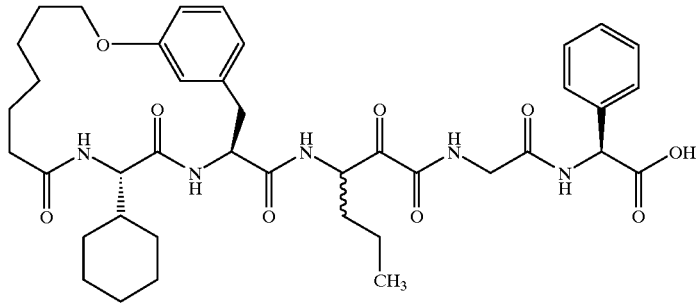
12

13
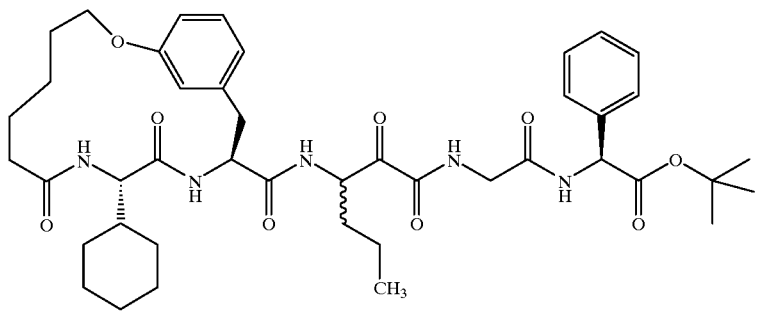
14
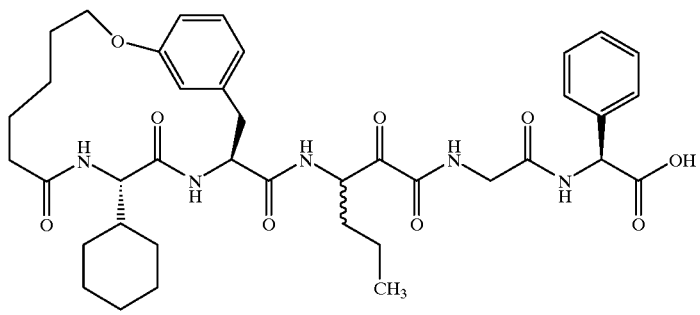
15
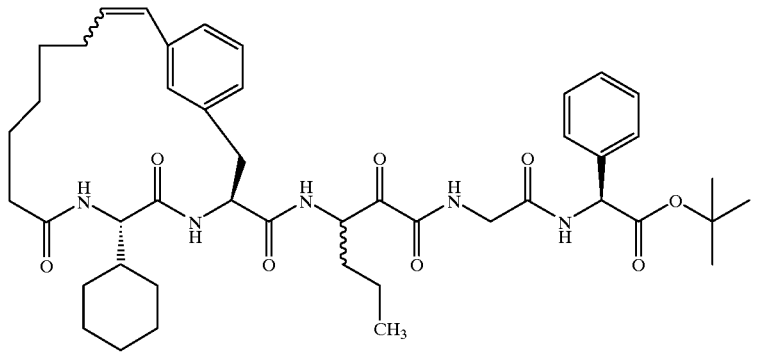
16
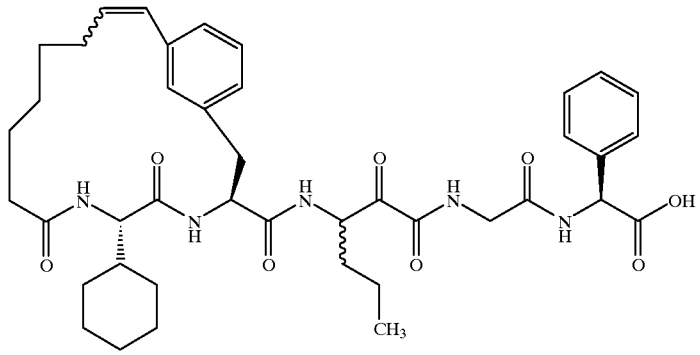

17
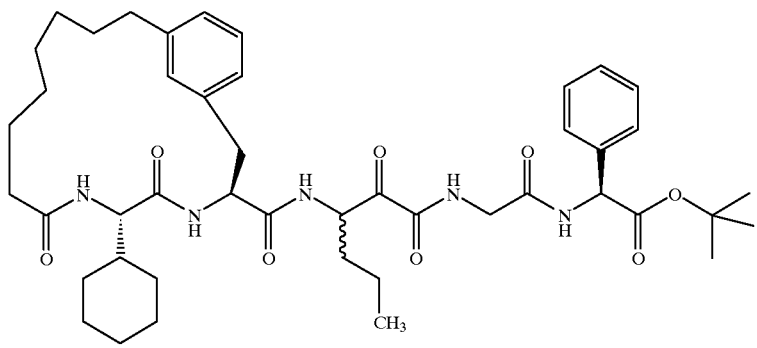
18
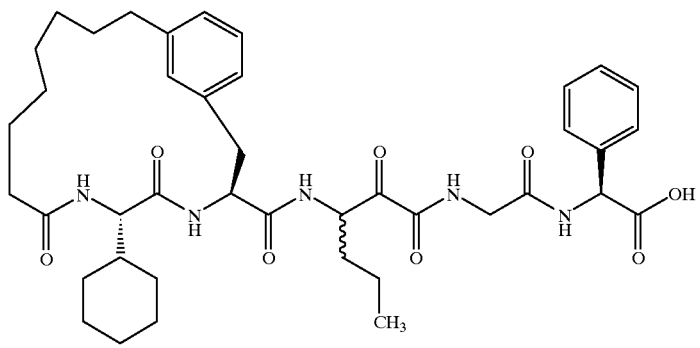
19
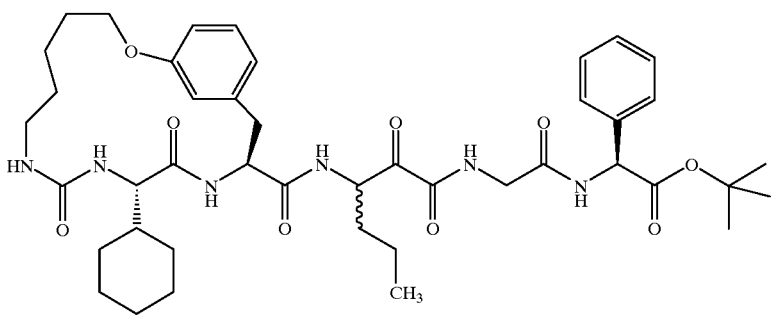
20
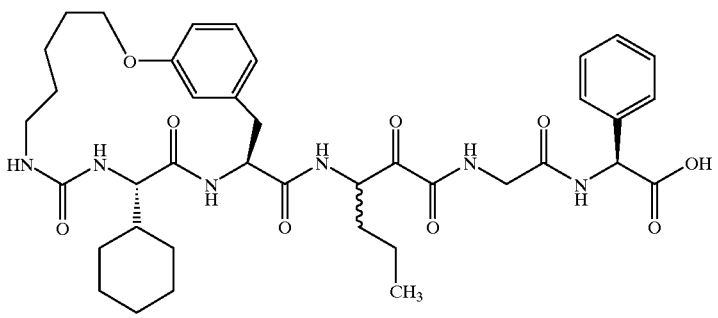

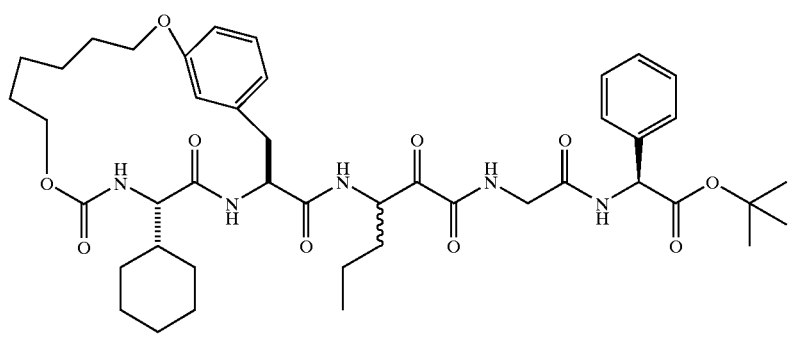
21
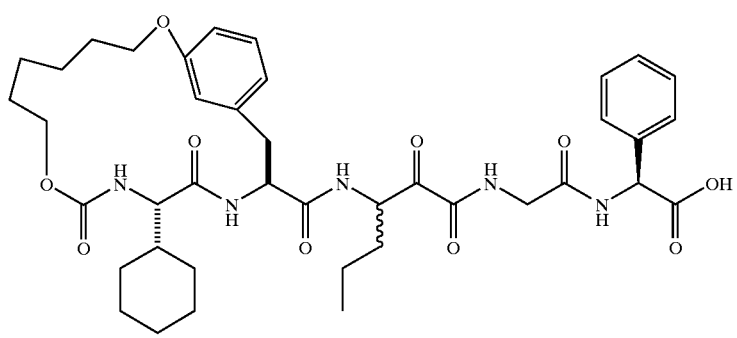
22
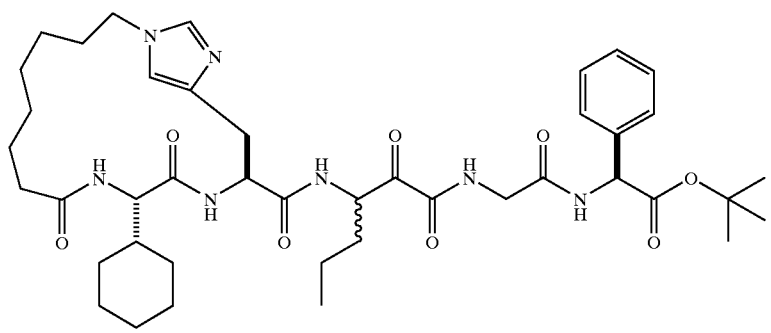
23
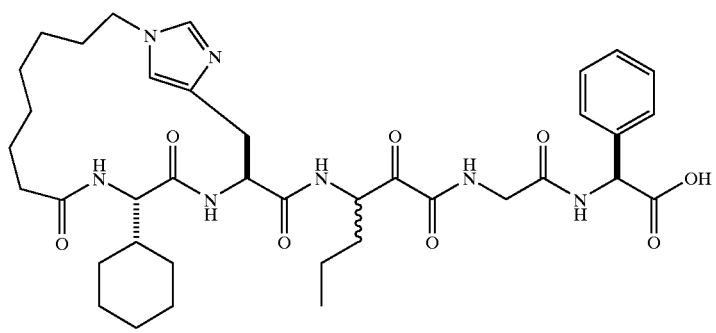
24

-continued
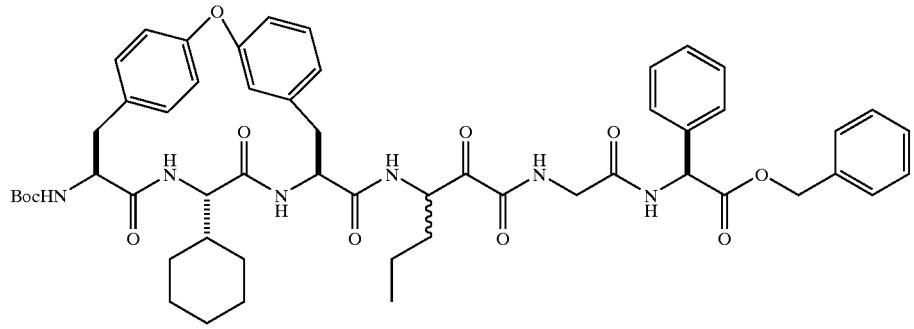
25
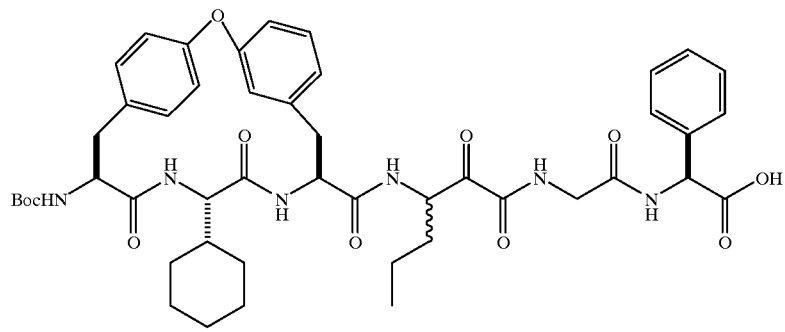
26
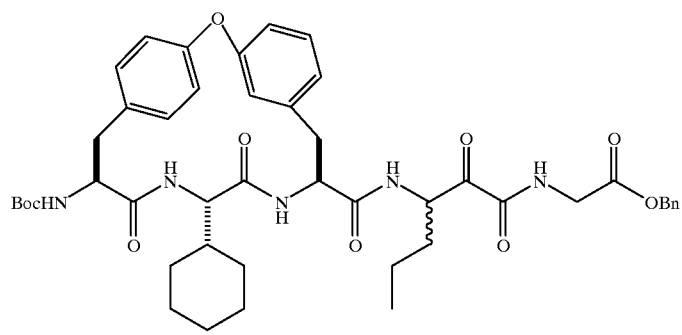
27
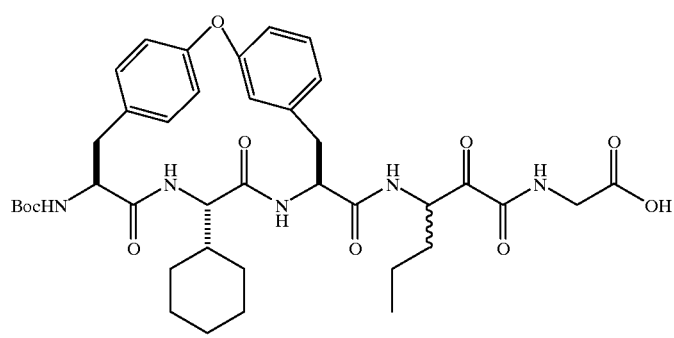
28

29
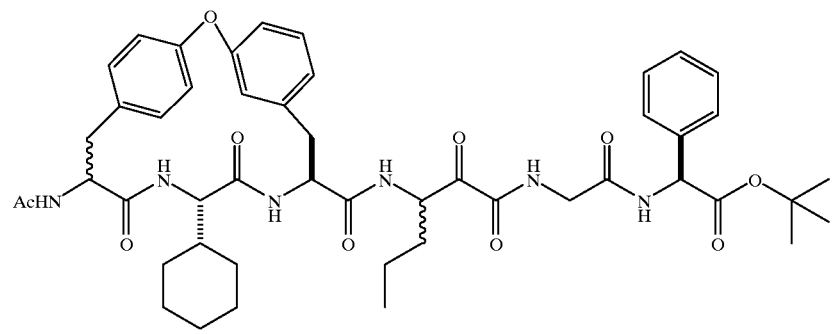
30
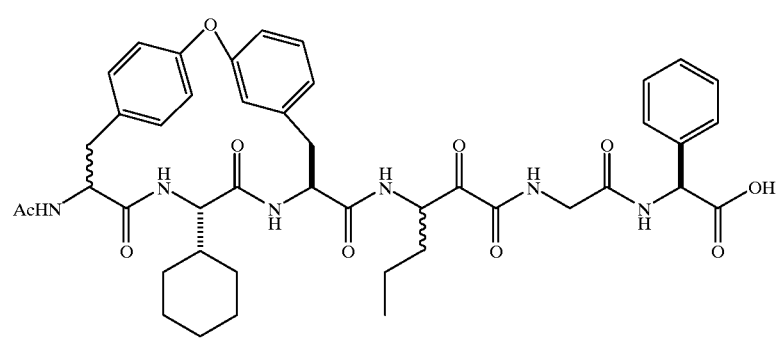
31
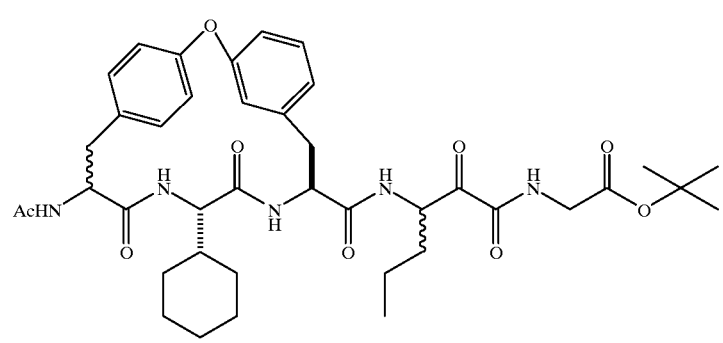
32
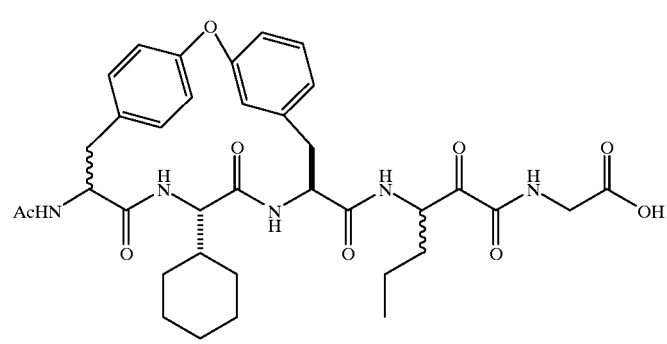

-continued
33
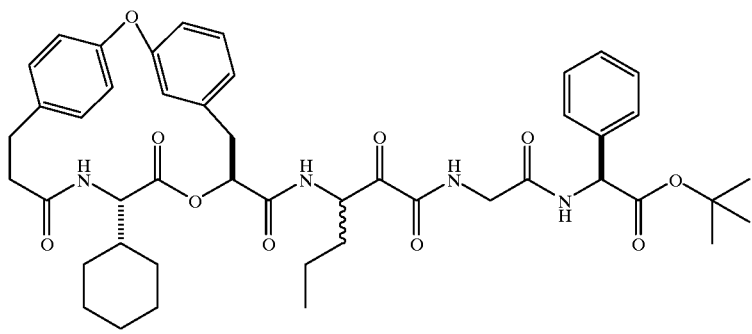
34
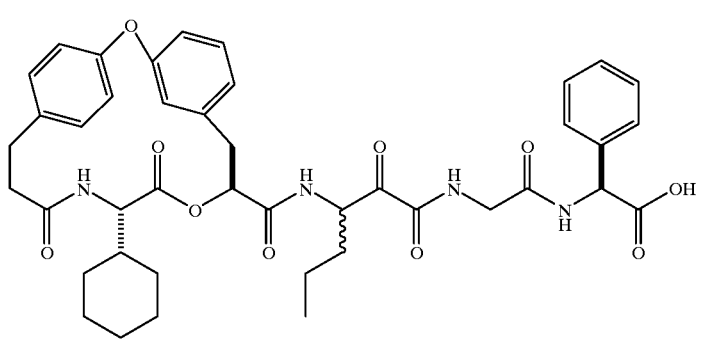
35
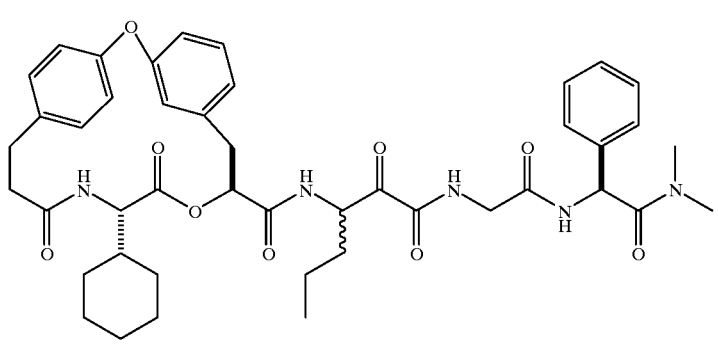
36
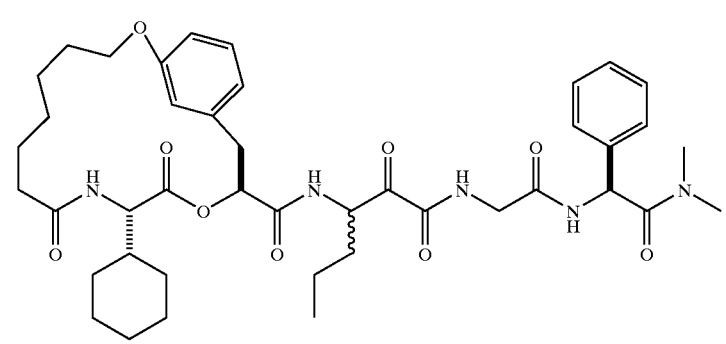

37
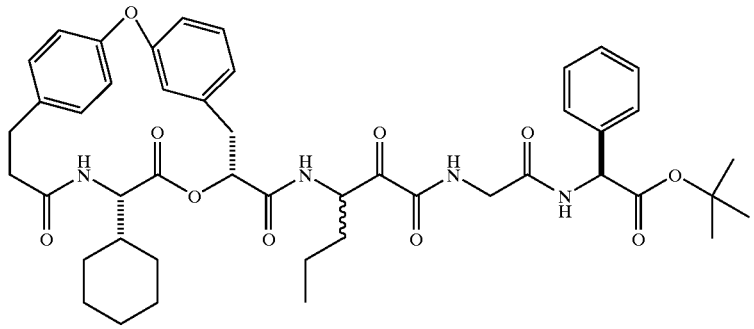
38
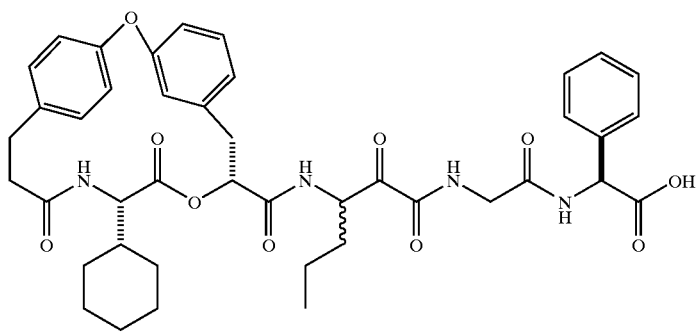
39
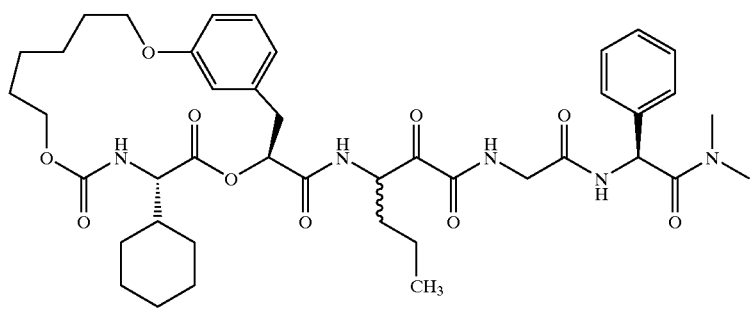
40
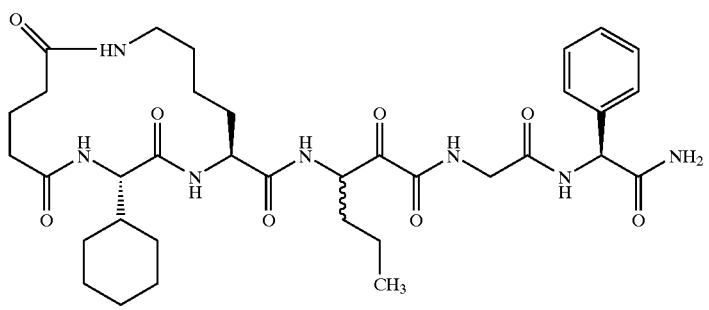
41
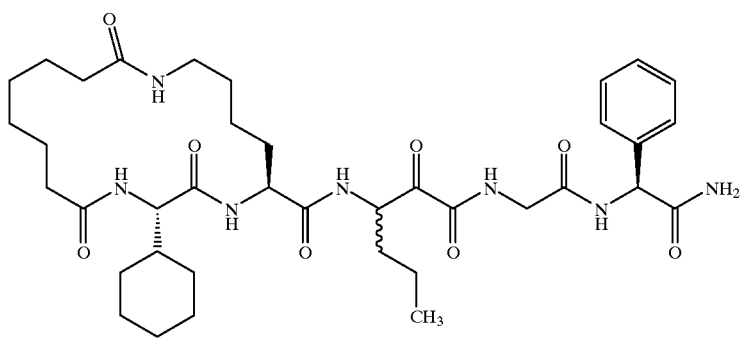

42
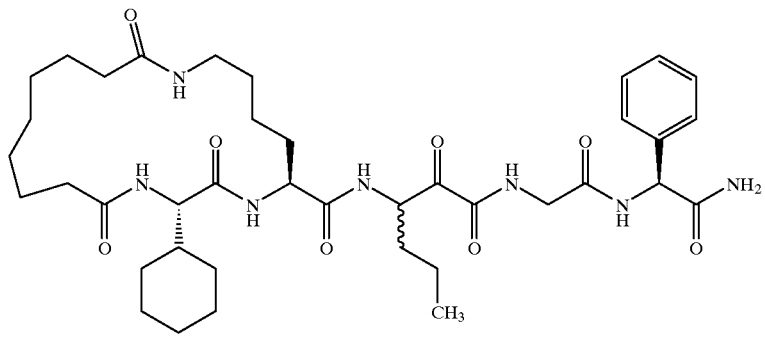
43
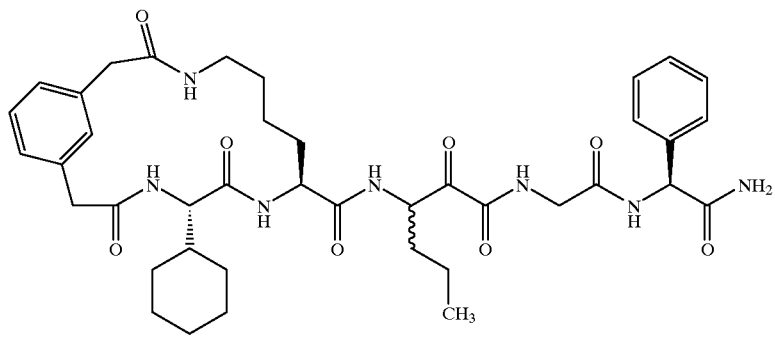
44
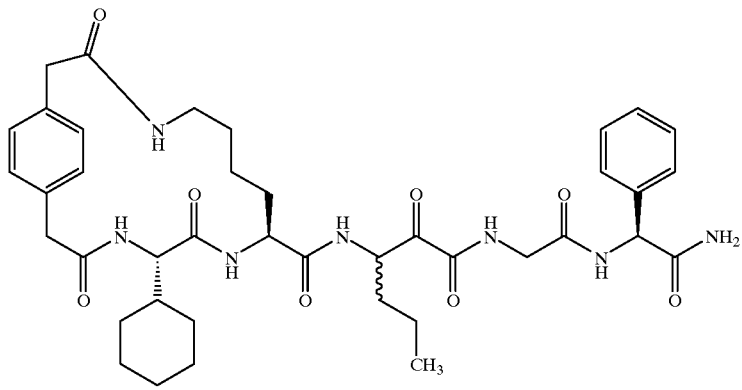
45
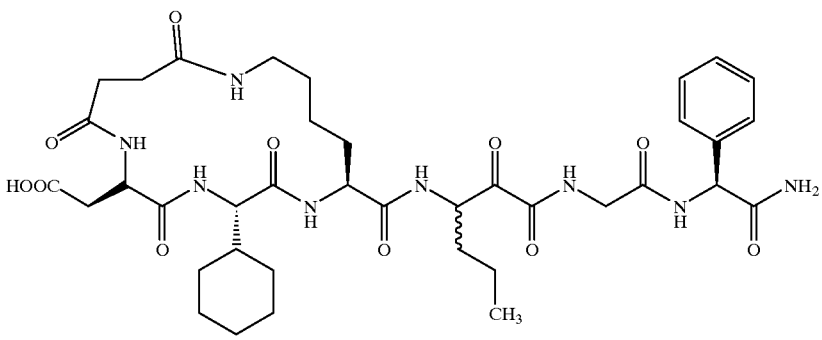

46
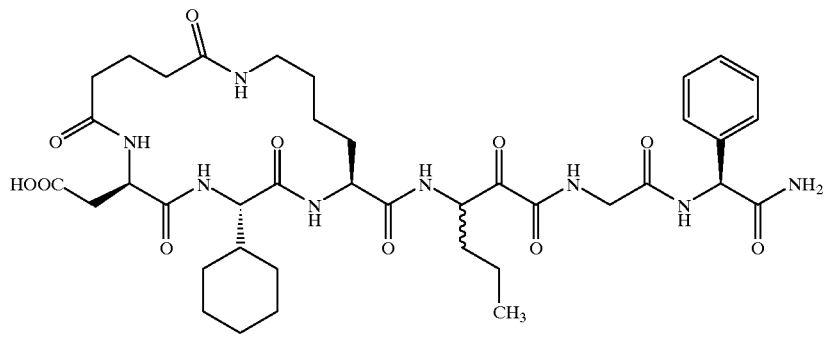
47
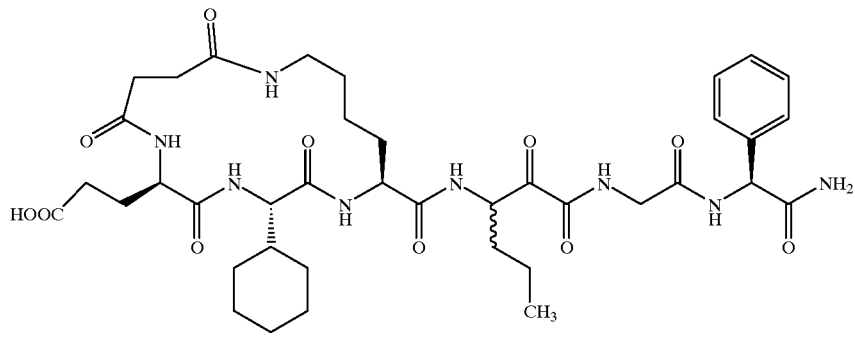
48
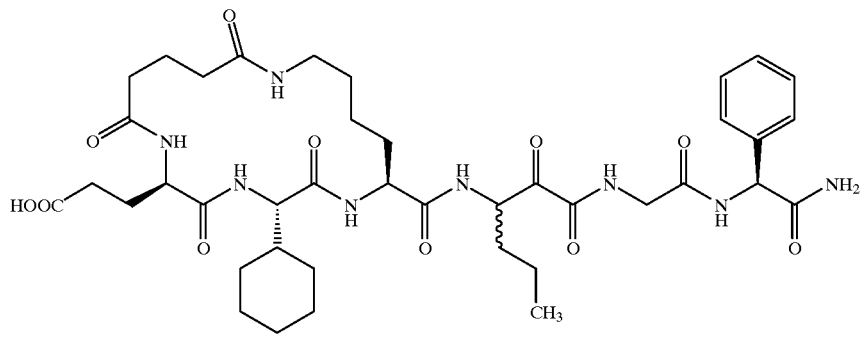
49
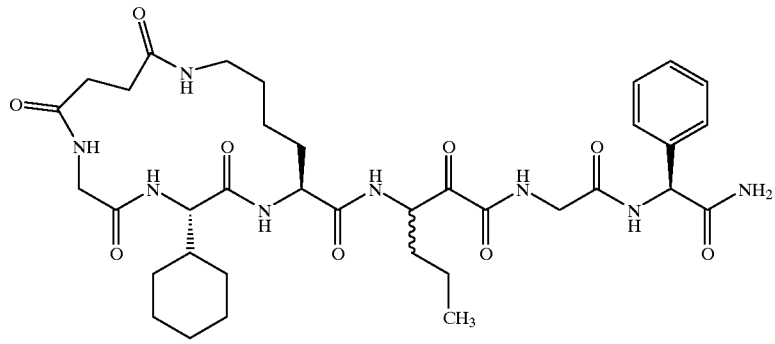

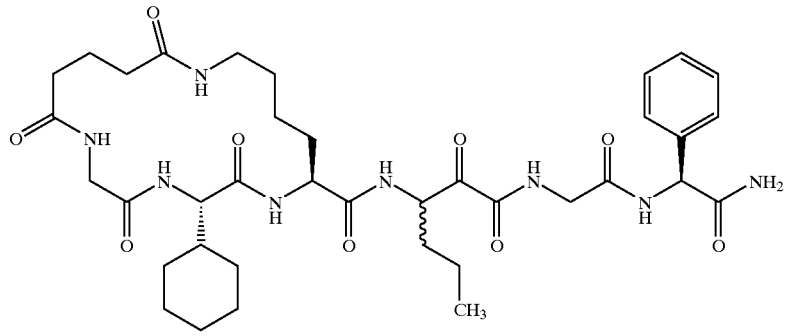
50
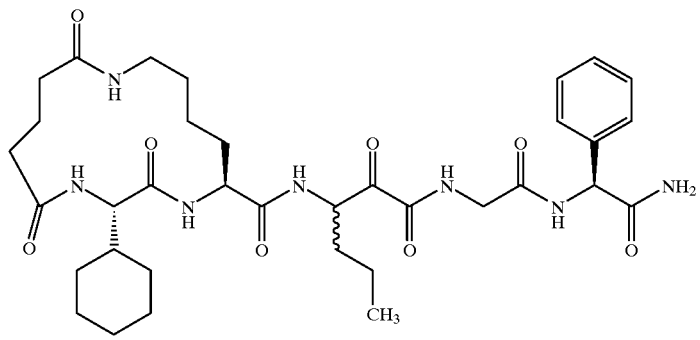
51
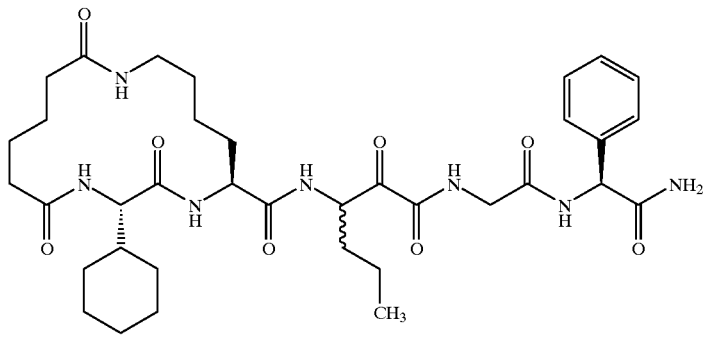
52
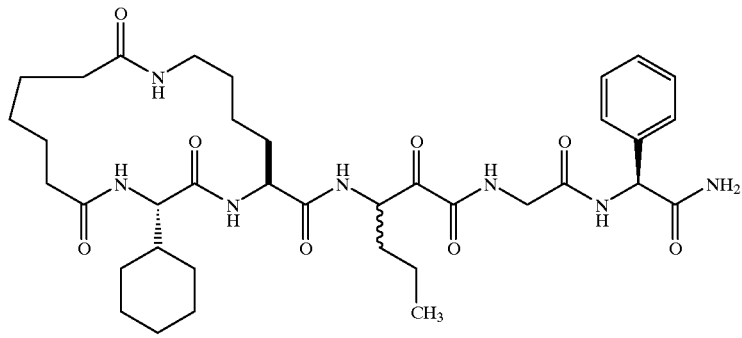
53

54

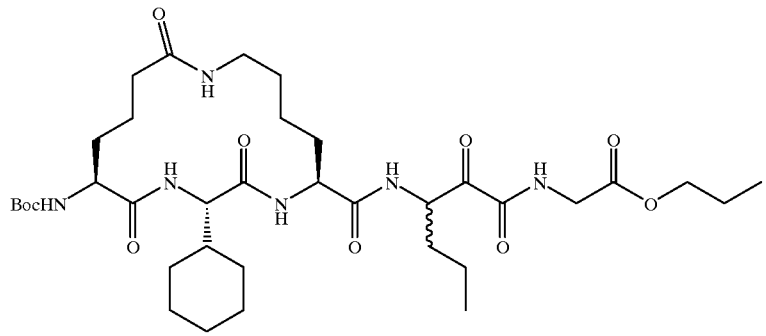

The activity of some of the compounds are presented in Table 1 as ranges of $K_i$ values in nanomolar (nM). The Example numbers in Table 1 refer to the numbers for the various structures in the EXAMPLES section found in the later parts of this application.

TABLE 1

HCV protease continuous assay results

| Example number | $K_i^*$ nM |
|---|---|
| 1 | B |
| 2 | A |
| 3 | B |
| 4 | B |
| 5 | B |
| 6 | A |
| 7 | B |
| 8 | A |
| 9 | B |
| 10 | B |
| 11 | B |
| 12 | A |
| 13 | B |
| 14 | B |
| 15 | B |
| 16 | A |
| 17 | B |
| 18 | A |
| 19 | B |
| 20 | A |
| 21 | B |
| 22 | A |
| 23 | B |
| 24 | B |
| 25 | B |
| 26 | B |
| 27 | B |
| 28 | B |
| 29 | B |
| 30 | A |
| 31 | B |
| 32 | B |
| 33 | B |
| 34 | B |
| 35 | B |
| 36 | B |
| 37 | B |
| 38 | B |
| 39 | A |
| 40 | B |
| 41 | A |
| 42 | B |
| 43 | A |
| 44 | A |
| 45 | B |
| 46 | B |
| 47 | B |
| 48 | B |
| 49 | B |
| 50 | B |
| 51 | B |
| 52 | A |
| 53 | A |
| 54 | B |

HCV continuous assay $K_i^*$ range:
Category A=0.001–1.0 µM, Category B=1.1–100 µM Some methods of synthesizing the various types of the inventive compounds are described later in this section, and also schematically described, followed by the illustrative Examples.

Depending upon the structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, NH$_4$OH, tetraalkylammonium hydroxide, and the like.

In another embodiment, this invention provides pharmaceutical compositions comprising the above-described inventive macrocycles as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive macrocycle compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C the like. The method comprises administering a therapeutically effective amount of the inventive pharmaceutical composition to a patient having such a disease or diseases and in need of such a treatment.

As stated earlier, the invention includes tautomers, enantiomers and other stereoisomers of the compounds also. Thus, as one skilled in the art knows, some of the inventive compounds may exist in isomeric forms. Such variations are contemplated to be within the scope of the invention.

Another embodiment of the invention discloses a method of making the macrocyclic compounds disclosed herein. The compounds may be prepared by several techniques known in the art. Representative illustrative procedures are outlined in the following reaction schemes. It is to be understood that while the following illustrative schemes describe the preparation of macrocycles predominantly derived from meta-tyrosine or lysine at the P2 position. Suitable substitution of any of both the natural and unnatural amino acids will result in the formation of the desired macrocycles based on such substitution.

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et$_2$O: Diethyl ether
Bn: Benzyl
Boc: tert-Butyloxycarbonyl
Cbz: Benzyloxycarbonyl
Cp: Cylcopentyldienyl
Ts: p-toluenesulfonyl
Me: Methyl
HATU: O-(7-Azabenzotriazol-1-yl)-N,N.N',N'-tetramethyluronium hexafluorophosphate
Chg: Cyclohexylglycine
Tyr: Tyrosine
G: Glycerol
TG: Thioglycerol
alloc: allyloxycarbonyl
FMOC: 9-Fluorenyl methyloxycarbonyl
Dde: N-1-(4,4-dimethyl-2,6-dioxocyclohex-1-ylidene)ethyl
tBu: tert-butyl
equiv: equivalent
rel. int.: relative intensity
aq: aqueous
rt: room temperature
satd: saturated
Hex: hexane(s)
NBA: Nitrobenzoic acid
PyBrOP: Tris(pyrrolidino)bromophosphonium hexafluorophosphate
DMSO: Dimethyl sulfoxide
TFA: Trifluoroacetic acid
HOBt: Hydroxybezotriazole
Hünigs base: Diisoprpylethyl amine
BOP: Benzotrizaol-1-yloxytris(dimethylamino) phosphonium hexafluorophosphate
LDA: Lithium diisopropyl amide
Ph3P: Triphenyl phosphine
LAH: Lithium Aluminum Hydride
DMAP: 4-Dimethyl aminopyridine
DCC: Dicyclohexylcarbodiimide MCPBA: meta-Chloroperbenzoic acid
BINAP: 2,2'-Bis(diphenylphosphino)-1,1'-binaphtol
MeCN: acetonitrile
Pr: Propyl
Ac: Acetyl
Ph: Phenyl General Schemes for Synthesis of Inventive Compounds: In the following Schemes, n is a number from 1 to 6.

Scheme 1

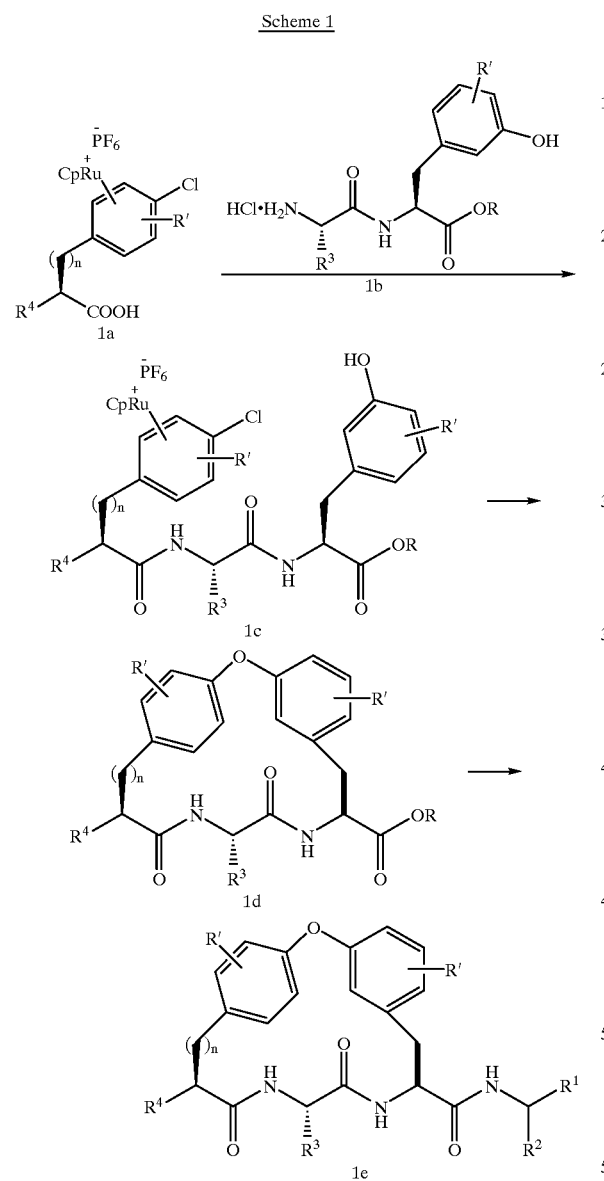

Scheme 2

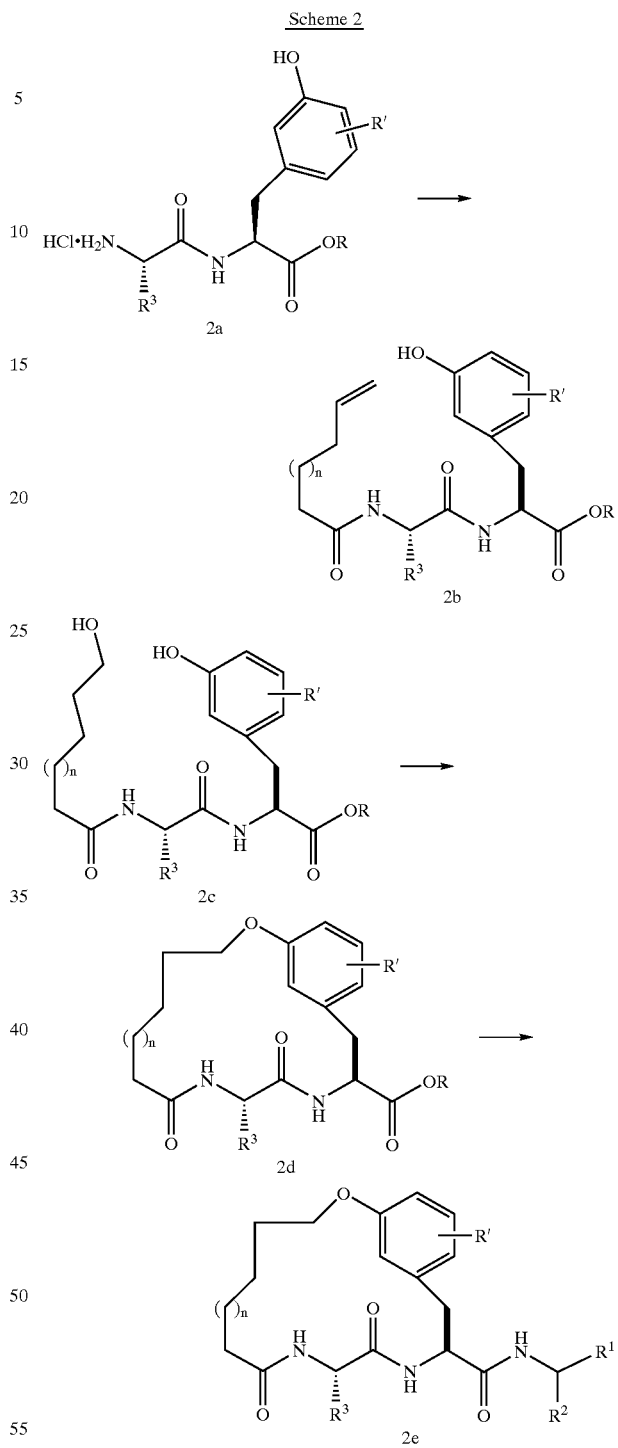

The synthesis of compounds of type 1e wherein $R^1$, $R^2$, $R^3$, R' are defined above, $R^4$ being amide, carbamate, or hydrogen, R being alkyl, aryl or arylalkyl, began with the coupling of 1a with the dipeptide 1b using NMM, HOBt, and EDCl to obtain the intermediate 1c. The intermediate 1c was treated with $Cs_2CO_3$ in DMF followed by photolysis to obtain compound 1d. The macrocyclic ester 1d was hydrolyzed and coupled with a suitable amine intermediate to generate compounds of type 1e.

The preparation of the compound of formula 2e, wherein $R^1$, $R^2$, $R^3$ and n are defined above, R' is alkyl, heteroalkyl (OR", SR''', NR"R''' wherein R" and R''' are alkyl groups), halo substituent at ortho, meta, or para-position to oxygen atom, R is alkyl, aryl, or alkylaryl groups, and n is from zero to five, is outlined in Scheme 2. The meta-tyrosine-dipeptide 2a is coupled to an alkenyl carboxylic acid in the presence of HOOBt, EDCl.HCl and NMM. Hydroboration of the resulting product affords compound 2c. The macrocyclization is achieved under Mitsunobu conditions by using triphenylphosphine and ADDP. (The Mitsunobu reaction is reviewed by D. L. Hughes, *Org. Reactions,* 42 (1992) 335, John Wiley & Sons, New York, L. Paquette, ed.). After the ester is hydrolyzed to an acid with lithium hydroxide, it is coupled to an amine intermediate to afford 2e.

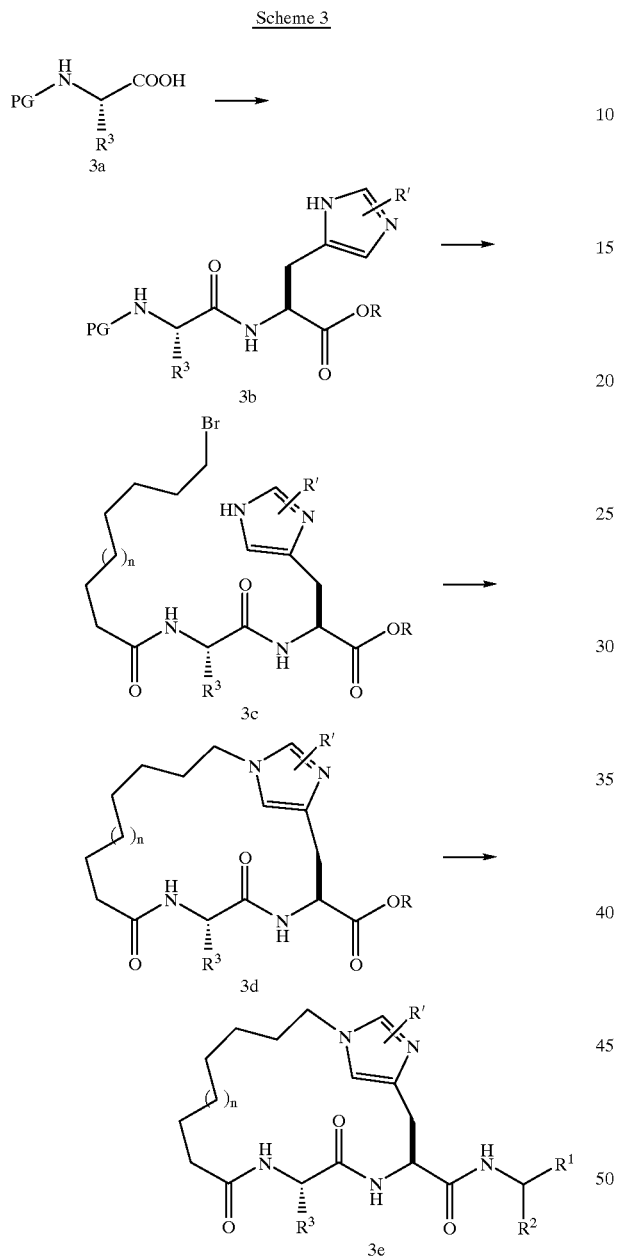

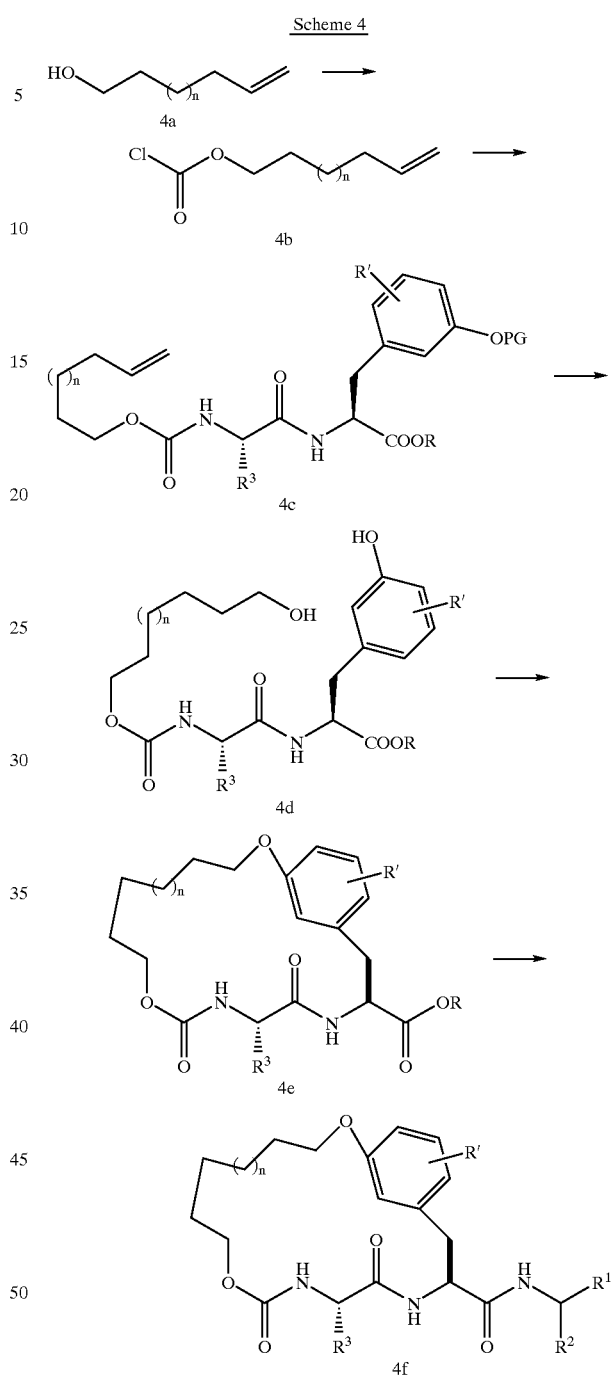

The preparation of compounds of formula 3e wherein R', $R^1$, $R^2$, $R^3$, R and n are defined in Scheme 1 and PG is Cbz, Boc, or alloc is outlined in Scheme 3. The compound 3a was coupled with substituted histidine derivative using DCC. This compound 3b was deprotected and further treated with ω-bromo acids to obtain compound of the type 3c. Cyclization of 3c was accomplished with NaI and $Na_2CO_3$ in boiling methylvinyl ketone to afford 3d. The compound 3d was converted to compounds of type 3e by hydrolysis of the ester followed by coupling with the appropriate amine intermediate.

The preparation of the compounds of type 4f where R', $R^1$, $R^2$, $R^3$, R, n and PG are defined in Scheme 1 was initiated from compound of the type 4a. The alcohol of 4a was converted to 4b by treatment with phosgene. 4b was converted to 4c by coupling with alloc protected 1b and $Et_3N$. The alloc group of 4c was deprotected using $Pd(PPh_3)_4$ to obtain 4d which underwent cyclization under the Mitsunobu conditions to yield 4e. The ester of 4e was hydrolyzed and further coupled with an amine using EDCl, HOOBt to obtain compounds of the type 4f.

Scheme 5

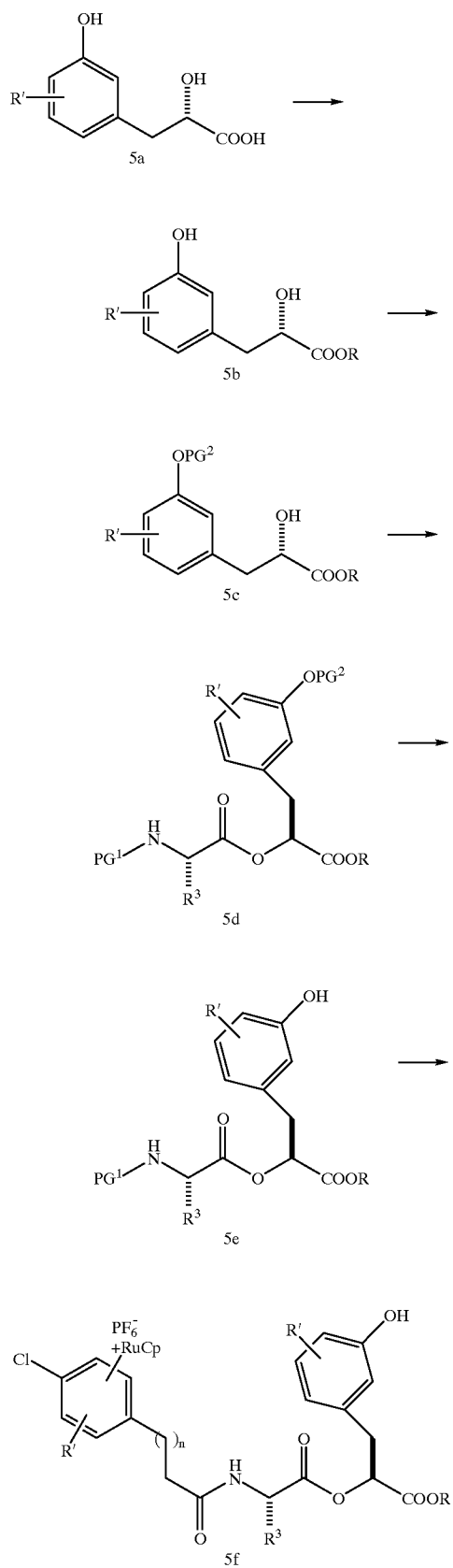

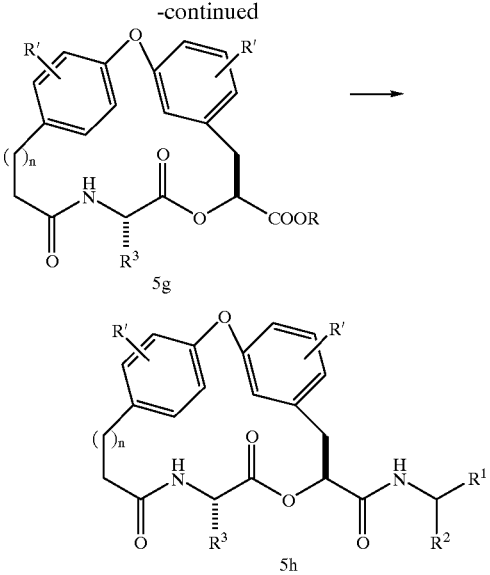

The preparation of compounds of type 5h wherein $R^1$, $R^2$, $R^3$, R', PG and n are defined in Schemes 1–3 and $PG^1$ being Cbz or Boc and $PG^2$ being alloc, began with the known compound 5a. The acid 5a was converted to the ester by refluxing it with ROH and TsOH. The phenolic oxygen of 5b was converted to the alloc group by the treatment with alloc-chloride and triethyl amine to yield 5c. The secondary alcohol of 5c was converted to compounds of type 5d by coupling with protected cyclohexyl glycine using DCC and HOBt. The alloc group of compound 5d was deprotected using $Pd(Ph_3P)_4$, and dimedone. 5e was deprotected and treated with EDCl, HOOBt and appropriately activated ruthenium complex to obtain compounds of the formula of 5f. The compounds of the type 5f were converted to cyclic compounds of the formula 5g by the use of $Cs_2CO_3$, and subsequent photolytic removal of ruthenium. The ester group of 5g was hydrolyzed and coupled to an amine intermediate to obtain compounds of the type 5h.

Scheme 6

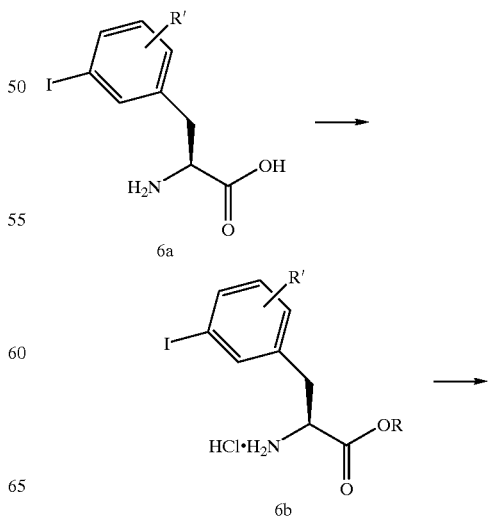

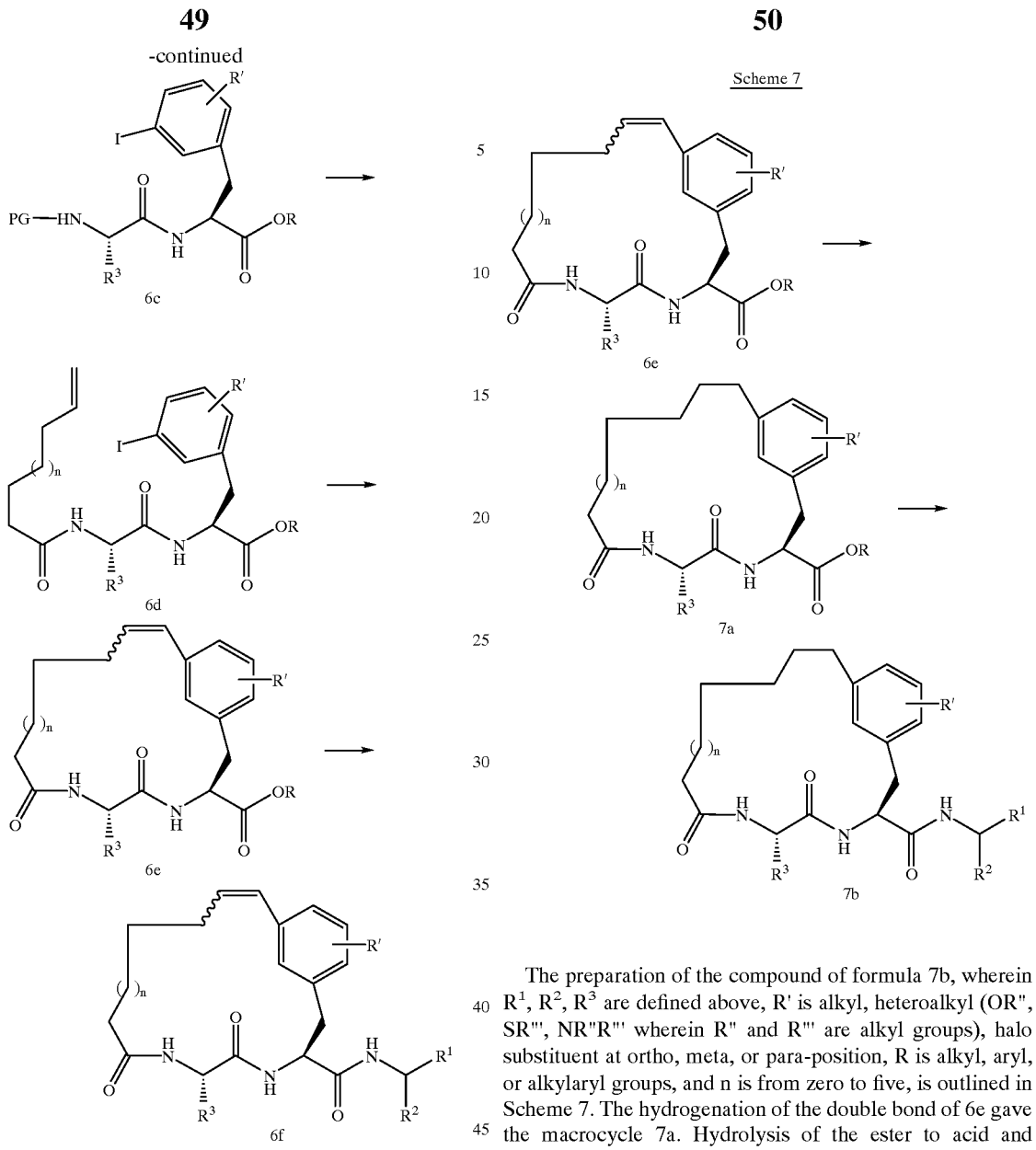

The preparation of the compound of formula 6f, wherein $R^1$, $R^2$, $R^3$ are defined above, R' is alkyl, heteroalkyl (OR", SR''', NR"R''' wherein R" and R''' are alkyl groups), halo substituent at ortho, meta, or para-position, R is alkyl, aryl, or alkylaryl groups, PG is Cbz or Boc, and n is from zero to five, is outlined in Scheme 6. The meta-Iodophenylglycine 6a is converted to its ester under usual esterification conditions (ROH, HCl). The product is then coupled to an N-protected amino acid in the presence of HOOBt, EDCl.HCl and NMM. After deprotection, the resulting amine is coupled again to a terminal alkenyl carboxylic acid to give product 6d. The intramolecular Heck reaction with a palladium catalyst provides the desired macrocyclic compound 6e. (The Heck reaction has been reviewed in detail by R. F. Heck, *Org. React.*, 27 (1989) 345–390.). After the ester is hydrolyzed to an acid with lithium hydroxide, it is coupled to an amine intermediate to afford 6f.

The preparation of the compound of formula 7b, wherein $R^1$, $R^2$, $R^3$ are defined above, R' is alkyl, heteroalkyl (OR", SR''', NR"R''' wherein R" and R''' are alkyl groups), halo substituent at ortho, meta, or para-position, R is alkyl, aryl, or alkylaryl groups, and n is from zero to five, is outlined in Scheme 7. The hydrogenation of the double bond of 6e gave the macrocycle 7a. Hydrolysis of the ester to acid and subsequent coupling with an amine intermediate afforded 7b.

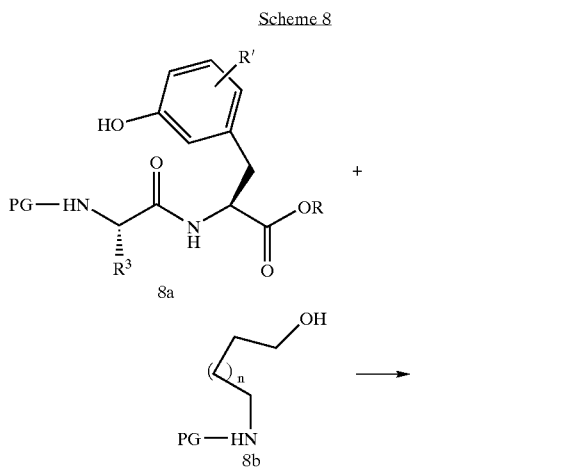

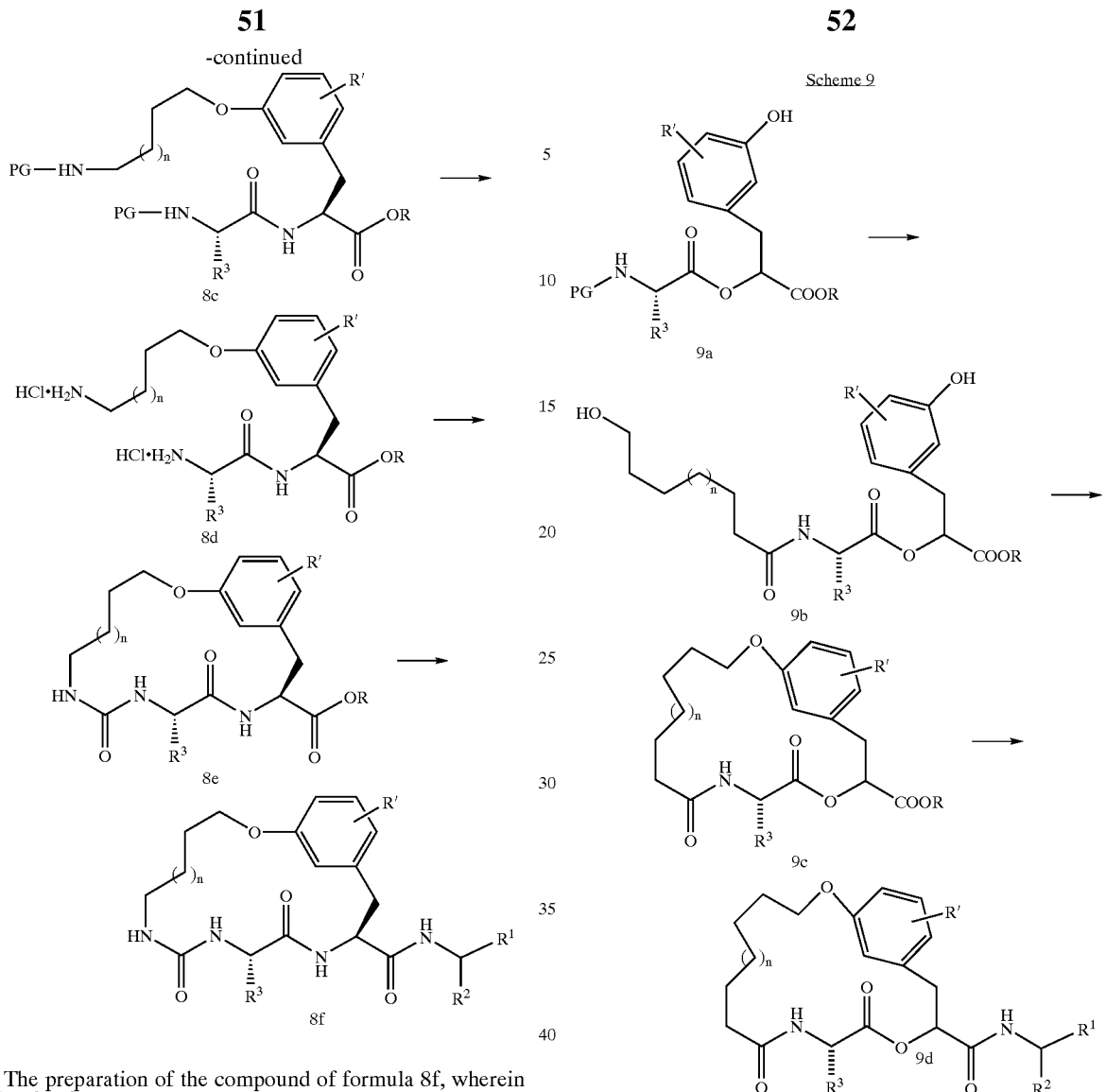

The preparation of the compound of formula 8f, wherein R$^1$, R$^2$, R$^3$ are defined above, R' is alkyl, heteroalkyl (OR'', SR''', NR''R''' wherein R'' and R''' are alkyl groups), halo substituent at ortho, meta, or para-position to oxygen atom, R is alkyl, aryl, or alkylaryl groups, PG is Boc, and n is from zero to five, is outlined in Scheme 8. The meta-tyrosine-dipeptide 8a is coupled to a terminal N-protected amino alcohol 8b under Mitsunobu conditions (triphenylphosphine and ADDP). The protecting groups are removed to give diamine hydrochloride 8d. The macrocyclization is achieved by forming the urea linkage using phosgene or carbonyl diimidazole. The resulting ester is then hydrolyzed to an acid with lithium hydroxide and is subsequently coupled to an amine intermediate to afford the desired product 8f.

The synthesis of compounds of the type 9d wherein the substituents R$^1$, R$^2$, R$^3$, R', R and PG are defined in Scheme 1, was initiated by the deprotection of 9a with HCl in dioxane and coupling with (o-hydroxy acid using EDCl, HOOBt to yield compounds of the type 9b. The compounds of the type 9b were further cyclized using Ph$_3$P, ADDP to generate compounds of the type 9c. The cyclic compound 9c was deprotected and coupled with an appropriate amine intermediate to generate compound of type 9d.

Scheme 10

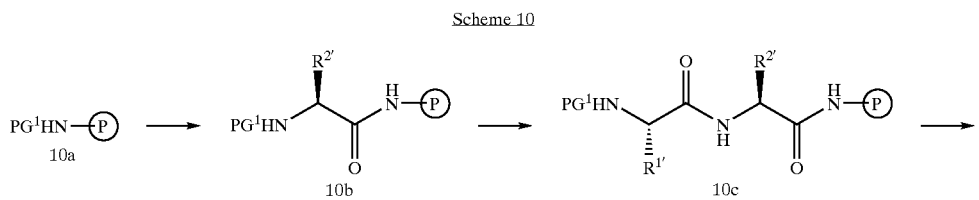

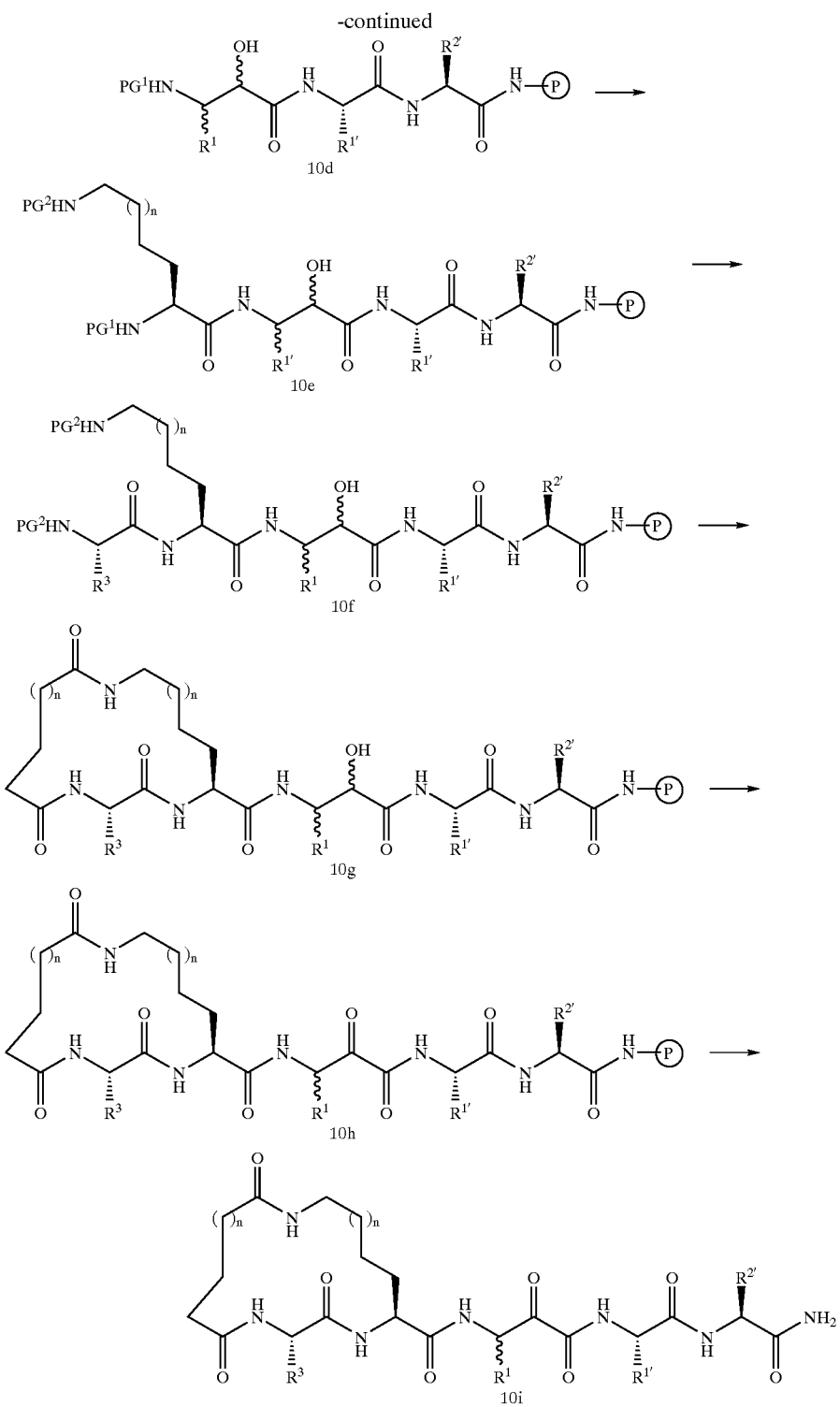

The synthesis of the compounds of the type 10i wherein $R^{2'}$, $R^{1'}$, $R^1$, $R^3$ are defined in Scheme 1. $PG^1$ and $PG^2$ are defined as protecting groups namely Fmoc and Dde. P is defined as a polymer support wherein the compound is immobilized, and n is a number from 1–6. The methodology used for the synthesis of molecules of type 10i is a standard solid phase peptide synthesis with Fmoc protecting group. Fmoc protected Sasarin resin 10a is first deprotected by the treatment of piperidine followed by coupling with the Fmoc protected amino acid using HATU to obtain compound of type 10b. The protecting group of 10b was removed and coupled with amino acid to using HATU to obtain 10c. The polymer supported 10c was deprotected by treatment with piperidine and coupled with hydroxy acid to obtain hydroxy amide of type 10d. The protecting group of 10d was cleaved and coupled with protected lysine derivative using HATU to obtain compounds of type 10e. The protecting group of 10e was once again deprotected and coupled with Fmoc protected amino acid to obtain compound of the type 10f. The protecting groups PG¹ and PG² were removed and cyclzed using a diacid and HATU to obtain the macrocycle 10g. The compound of 10g was oxidized using Dess-Martin reagent and finally cleaved from the resin using TFA to obtain compound 10i.

Scheme 11

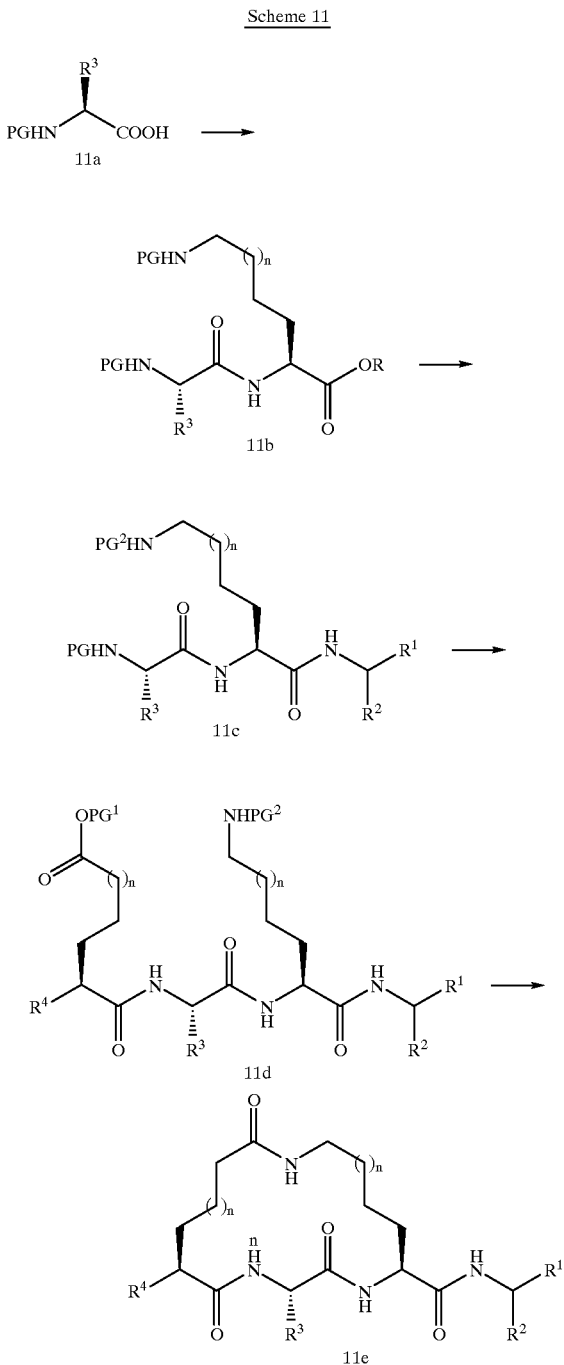

The synthesis of the compounds of type 11e wherein $R^1$, $R^2$, $R^3$, $R^4$ and n are defined in Scheme 1 and $PG^2$ is Cbz, $PG^1$ is Bn and PG is Boc, was initiated from protected acid 11a. 11a was converted to compounds of type 11b by coupling with lysine derivative using EDCl, HOOBt methodology. The ester group of 1b was hydrolyzed using LiOH.H₂O followed by the coupling with an appropriate amine intermediate to obtain the compound 11c. This was further treated with HCl in dioxane and coupled with lysine intermediate using EDCl, HOOBt to form compounds of the type 11d. The compounds 11d were deprotected and cyclized using EDCl, HOOBt to form compounds of type 11e.

Preparation of Intermediates:

Intermediate A:

Step 1:

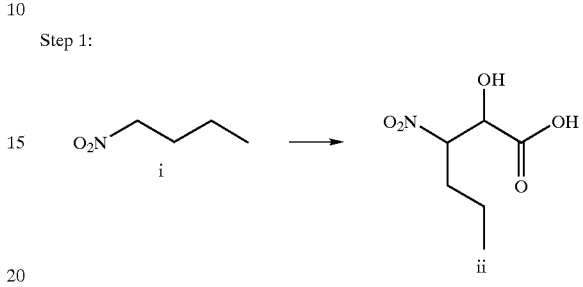

To a stirred solution of 1-nitrobutane (16.5 g, 0.16 mol) and glyoxylic acid in H₂O (28.1 g, 0.305 mol) and MeOH (122 mL) at 0° C.–5° C., was added dropwise triethyl amine (93 mL, 0.667 mol) over 2 hrs. The solution was warmed to room temperature, stirred overnight and concentrated to dryness to give an oil. The oil was then dissolved in H₂O and acidified to pH=1 with 10% HCl, followed by extraction with EtOAc. The combined organic solution was washed with brine, dried over Na₂SO₄, filtered and concentrated to dryness to give the product ii (28.1 g, 99% yield).

Step 2:

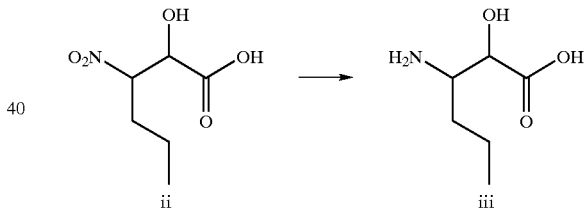

To a stirred solution of starting material ii (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to give iii as an off white solid (131 g, 0.891 mol, 66%).

Step 3:

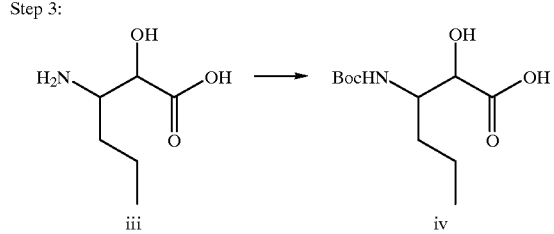

To a stirred solution of the amino acid iii (2.0 g, 013.6 mmol) in dioxane (10 mL) and H₂O (5 mL) at 0° C., was added 1N NaOH solution (4.3 mL, 14.0 mmol). The resulting solution was stirred for 10 minutes, followed by addition of di-t-butyldicarbonate (0.110 g, 14.0 mmol) and stirred at 0° C. for 15 minutes. The solution was then warmed to room temperature, stirred for 45 minutes and kept in refrigerator overnight and concentrated to dryness to give a crude material. To the solution of this crude material in EtOAc (100 mL) and ice, was added KHSO₄ (3.36 g) and H₂O (32 mL) and stirred for 4–6 minutes. The organic layer was then separated and the aqueous layer was extracted twice with EtOAc and the combined organic layer was washed with water, brine, dried over Na₂SO₄, filtered and concentrated to dryness to give the product iv as a clear gum (3.0 g, 89% yield).

Step 4:

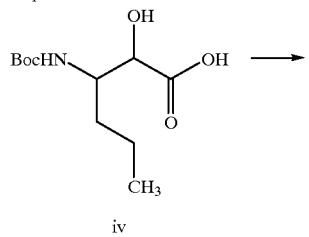

iv

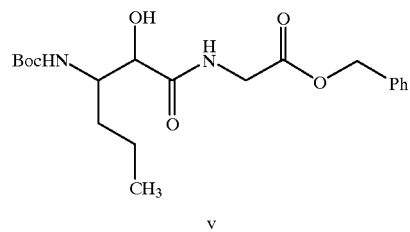

v

To a stirred solution of iv (3.00 g, 12.0 mmol) in DMF (15 mL) and CH₂Cl₂ (15 mL) at −20° C. was added HOOBt (1.97 g, 12.0 mmol), N-methyl morpholine (4.0 mL, 36.0 mmol) and EDCl (2.79 g, 14.5 mmol) and stirred for 10 minutes, followed by addition of HCl.H₂N-Gly-OBn (2.56 g, 13.0 mmol). The resulting solution was stirred at −20° C. for 2 hrs, then kept in refrigerator overnight and concentrated to dryness, followed by dilution with EtOAc (150 mL). The EtOAc solution was then washed twice with saturated NaHCO₃, H₂O, 5% H₃PO₄, brine, dried over Na₂SO₄, filtered and concentrated to dryness to give the product v (4.5 g, 94%). LRMS m/z MH⁺=395.1.

Step 5:

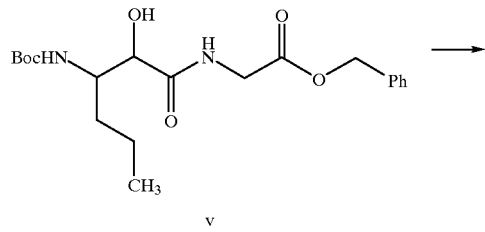

v

-continued

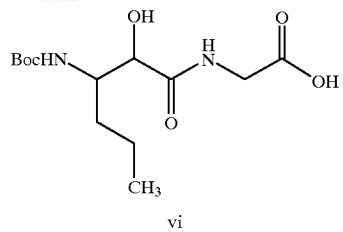

vi

The solution of starting material v (7.00 g, 17.8 mmol) in absolute ethanol (300 mL) was stirred at room temperature under a hydrogen atmosphere in the presence of Pd-C (300 mg, 10%). The reaction progress was monitored by tlc. After 2 h, the mixture was filtered through a celite pad and the resulting solution was concentrated in vacuo to give the product vi (5.40 g, quantitative). LRMS m/z MH⁺=305.1.

Step 6:

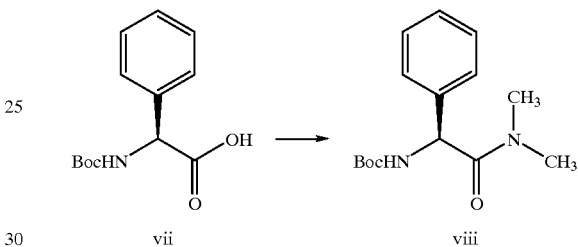

vii    viii

To a solution of dimethylamine hydrochloride (1.61 g, 19.7 mmol), N-Boc-phenylglycine (4.50 g, 17.9 mmol), HOOBt (3.07 g, 18.8 mmol) and EDCl (4.12 g, 21.5 mmol) in anhydrous DMF (200 mL) and CH₂Cl₂ (150 mL) at −20° C. was added NMM (5.90 mL, 53.7 mmol). After being stirred at this temperature for 30 min, the reaction mixture was kept in a freezer overnight (18 h). It was then allowed to warm to rt, and EtOAc (450 mL), brine (100 mL) and 5% H₃PO₄ (100 mL) were added. After layers were separated, the organic solution was washed with 5% H₃PO₄ (100 mL), saturated aqueous sodium bicarbonate solution (2×150 mL), water (150 mL), and brine (150 mL), dried (MgSO₄), filtered and concentrated in vacuo to afford crude product viii (4.86 g) as a white solid, which was used without further purification.

Step 7:

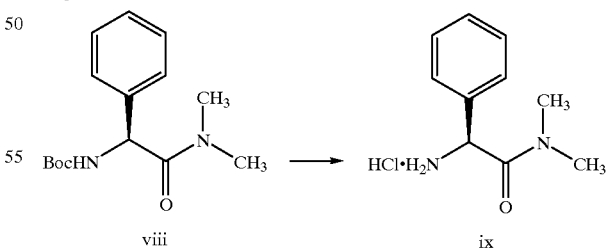

viii    ix

The N-Boc-phenylglycine dimethylamide viii (4.70 g, crude) was dissolved in 4 N HCl (60 mL, 240 mmol) and the resulting solution was stirred at room temperature. The progress of the reaction was monitored by TLC. After 4 h, the solution was concentrated in vacuo to yield ix as a white solid which was used in the next reaction without further purification. LRMS m/z MH⁺=179.0.

Step 8:

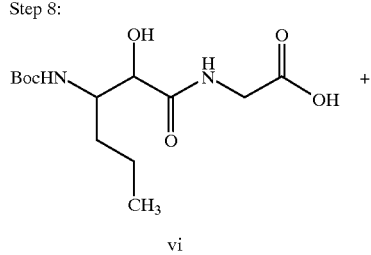

vi

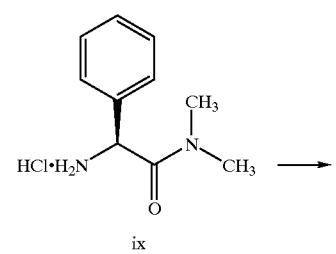

ix

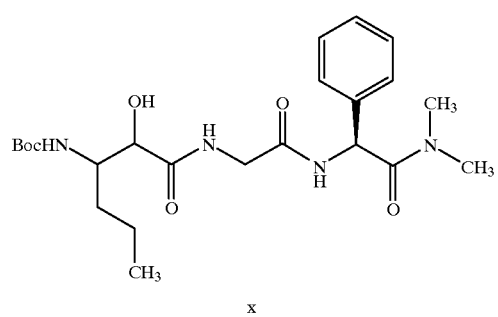

x

The desired compound x was prepared according to the coupling procedures described in Step 4. LRMS m/z MH$^+$= 465.1.

Step 9:

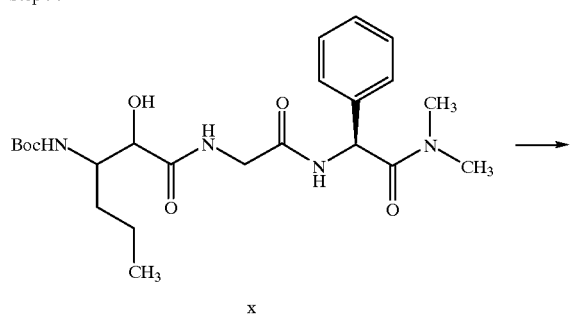

x

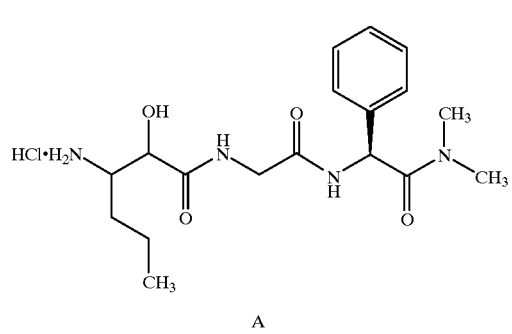

A

The desired intermediate A was prepared from tripeptide x according to the procedures described in Step 7. LRMS m/z MH$^+$=365.1.

Intermediate B:

Step 1:

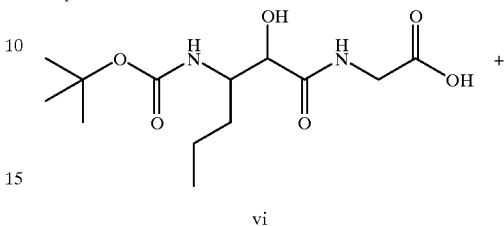

vi

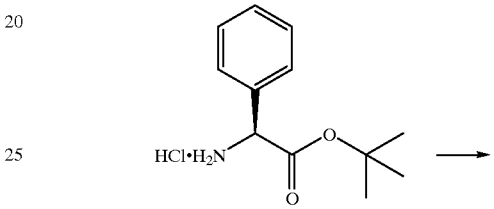

xi

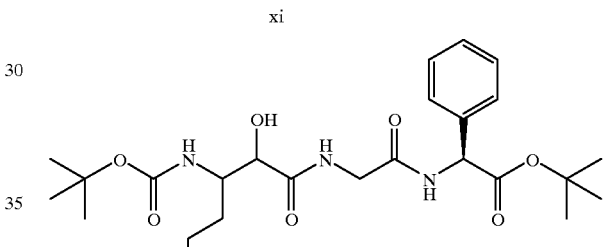

xii

The desired product xii was obtained by the procedure described for Intermediate A, Step 8 using commercially available xi as the coupling partner. The crude material was sufficiently pure for further studies. A portion of the product was purified by flash chromatography using 97/3 dichloromethane/MeOH. HRMS (FAB) Calcd for $C_{25}H_{40}N_3O_7$: 494.2866 (M+H)$^+$. Found: 494.2863.

Step 2:

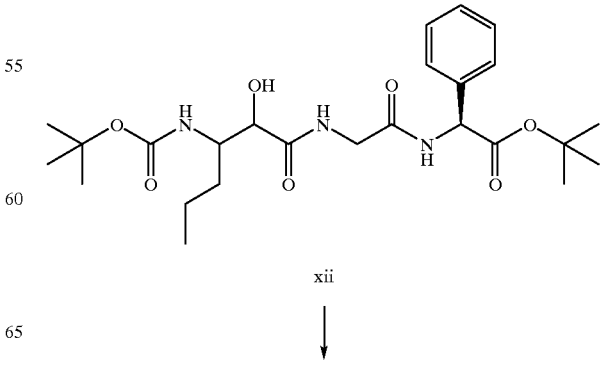

xii

↓

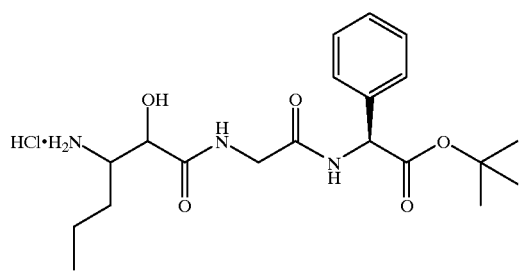

B

The desired product B was obtained by the procedure described for Intermediate A, Stop 7. The crude material was used without further purification.

Intermediate C:

Step 1:

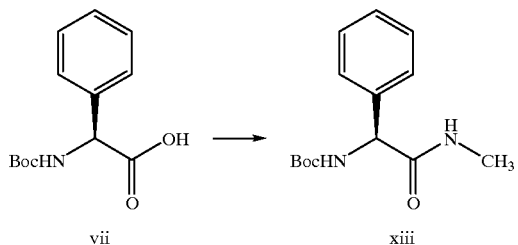

The desired compound xiii was prepared according to the coupling procedures described in Step 6 for intermediate A.

Step 2:

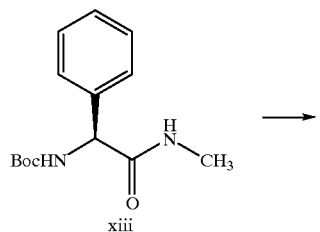

The desired compound xiv was prepared according to the procedures described in Step 7 for intermediate A.

Step 3:

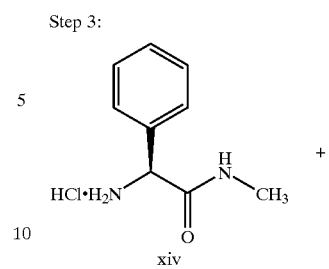

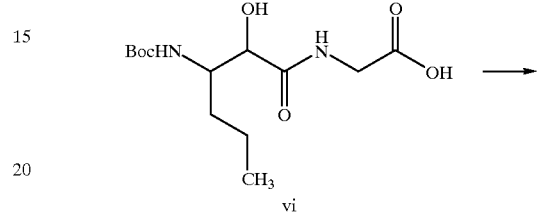

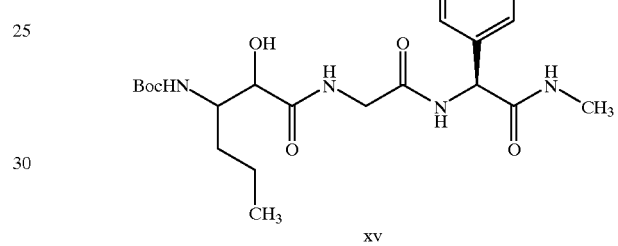

The desired compound xv was prepared according to the coupling procedures described in Step 6 for intermediate A. LRMS m/z MH$^+$=451.1.

Step 4:

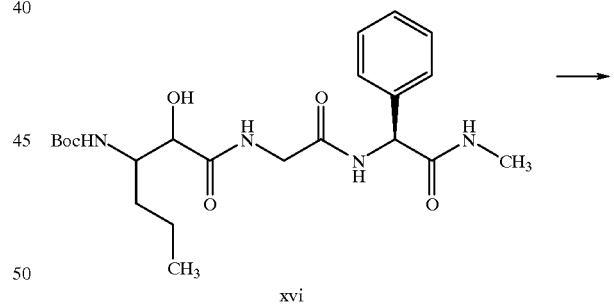

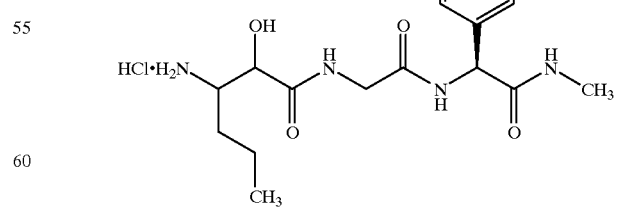

C

The desired intermediate C was prepared according to the procedures described in Step 7 for intermediate A. LRMS m/z MH$^+$=351.1. It was used without further purification.

Intermediate D:

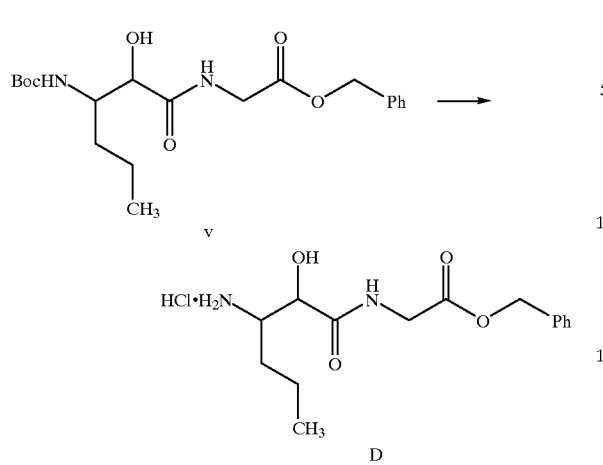

The desired intermediate D was prepared from compound v according to the procedures described in Step 7 for intermediate A. It was used without further purification.

Intermediate E:

Step 1:

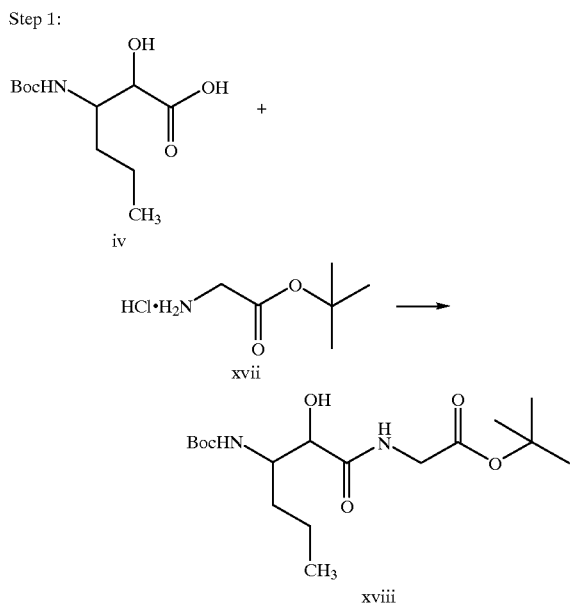

The desired product xviii was obtained by the procedure described for Intermediate A, Step 8 using commercially available xvii as the coupling partner. The crude material was sufficiently pure for further studies.

Step 2

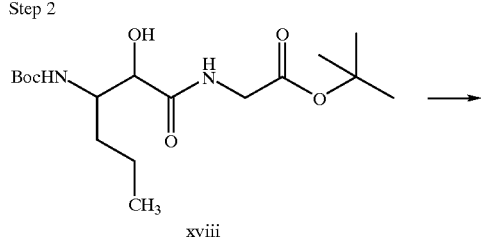

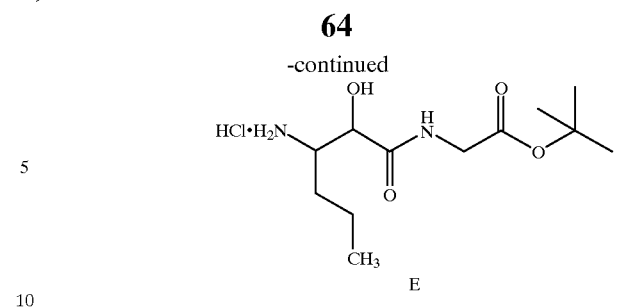

The desired product E was obtained by the procedure described for Intermediate A, Step 7. The crude material was used without further purification.

Intermediate F:

Step 1

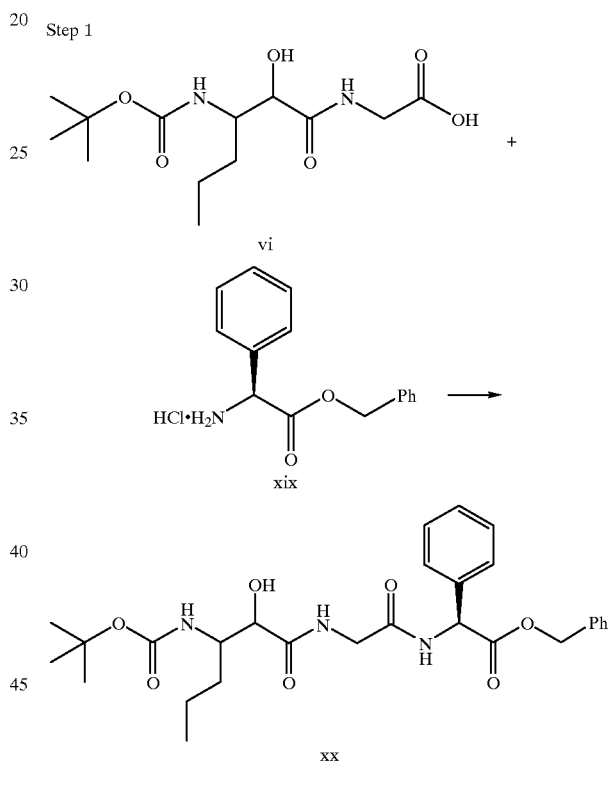

The desired product xx was obtained by the procedure described for Intermediate A, Step 4 using commercially available xix as the coupling partner. The crude material was sufficiently pure for further studies.

Step 2

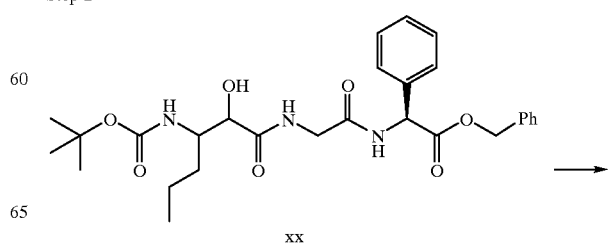

-continued

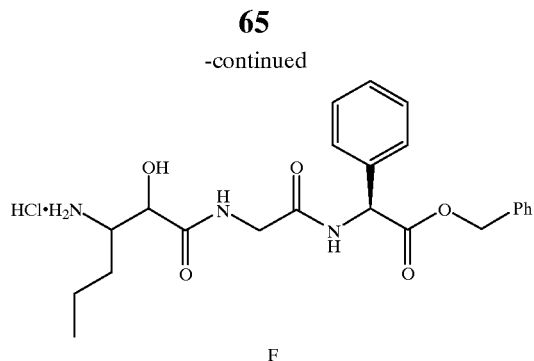

F

The desired product F was obtained by the procedure described for Intermediate D.

Intermediate G:

Step 1

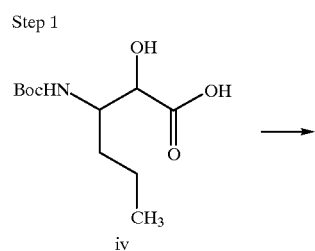

iv

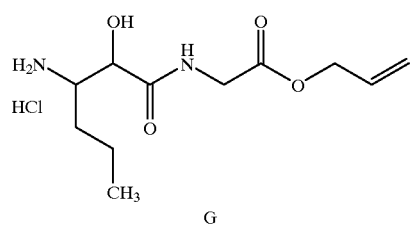

G

The desired product G was obtained by the procedure described for Intermediate A, Step 4 using allylglycine as the coupling partner. The crude material was sufficiently pure. The crude product was treated with 4N HCl/Dioxane and stirred at rt. for 50 min. The reaction mixture was concentrated to dryness to yield intermediate G which was used without further purification.

EXAMPLES

Example 1

Preparation of Compound of Formula 1:

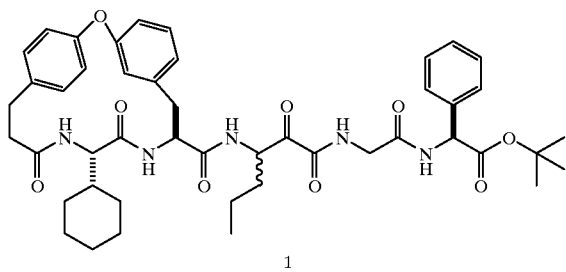

1

Step A:

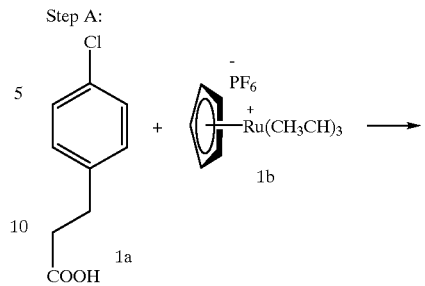

A solution of 4-chloropropionic acid (2.0 g, 10.8 mmol) of 1a in dichloroethane (200 mL) was treated with CpRu(CH$_3$CN)$_3$ PF$_6$ (4.7 g, 10.8 mmol, 1.0 equiv) and heated at reflux for 2 h. The reaction mixture was cooled to rt when colorless crystals of the product 1c precipitated out. The crystals were filtered and washed with 1:1 mixture of Et$_2$O/CH$_2$Cl$_2$ and dried in vacuo. The colorless crystals (3.3 g) were analytically pure. $^1$H NMR (CD$_3$C(O)CD$_3$, 400 MHz, ppm, δ, J) 6.77 (d, 2H, J=7.0 Hz), 6.53 (d, 2H, J=7 Hz), 5.64 (s, 5H), 2.87 (t, 2H, J=7.0 Hz), 2.74 (t, 2H, J=7.0 Hz); MS: (Electron spray, m/z relative intensity): 350.9 (C$_{14}$H$_{14}$ClRu$^+$, M$^+$, 100); CHN calcd for C$_{14}$H$_{14}$ClF$_6$O$_2$PRu C=33.92% H=2.85% Cl=7.15% P=6.25% found: C=34.04% H=3.04% Cl=7.09% P=5.71%.

Step B:

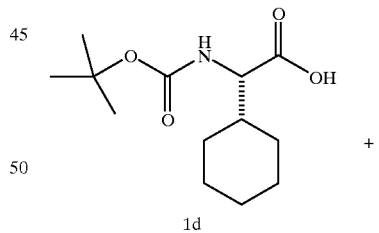

1d

+

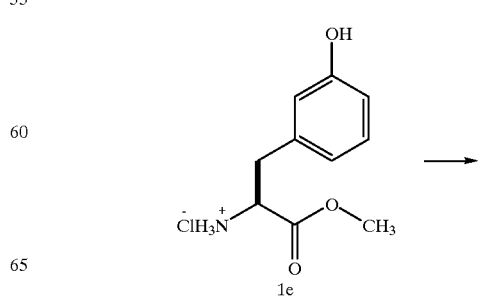

1e

-continued

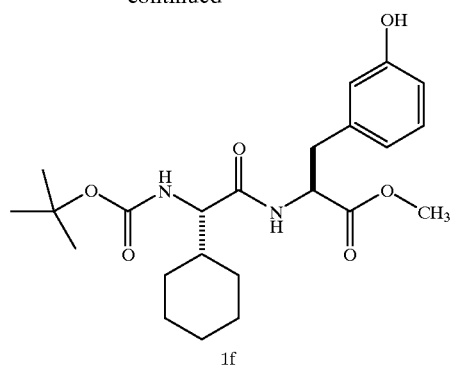

1f

A solution of Boc-cyclohexylgylcine monohydrate 1d (6.17 g, 24.00 mmol) in dry $CH_2Cl_2$ (50.0 mL) was treated with 4-methylmorpholine (2.64 g, 26.0 mmol, 1.1 equiv.) and cooled to −10° C. To this mixture was added isobutyl chloroformate (3.62 g, 3.5 mL, 1.1 equiv.) and the white suspension was stirred until the bath temperature was −5° C. meta-Tyrosine methyl ester hydrochloride salt (6.5 g, 26.5 mmol, 1.1 equiv.) was dissolved in DMF (30 mL) in a separate beaker and treated with 4-methyl morpholine (2.64 g, 26.0 mmol, 1.1 equiv.) and stirred at rt. for 15 min. This mixture was added to the reaction which was accompanied by evolution of $CO_2$. The reaction mixture was stirred at rt for 1 h and diluted with 1 M aq. HCl (100 mL). The aqueous layer was extracted with ethyl acetate (3×200 mL) and the combined organic layer was extracted with 1 M HCl (1×100 mL), aq NaOH (1×100 mL), brine (1×100 mL), dried ($Na_2SO_4$), concentrated in vacuo and purified by chromatography ($SiO_2$, EtOAc/Hexanes 3/7) to yield 5.3 g (53%) of coupled compound 1f as a colorless foam.

Step C:

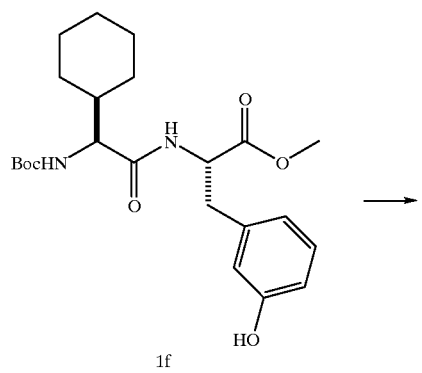

1f

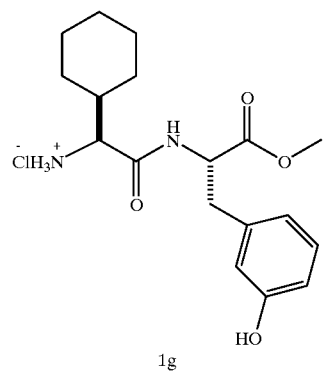

1g

A solution of 1f (10 g, 23.04 mmol) was dissolved in HCl (4M solution in dioxane, 100 mL) and stirred at rt for 2–4 h. The reaction mixture was concentrated in vacuo and the solid was resuspended in ether. It was filtered and the solid was washed with ether which was dried to give a colorless solid 1g (8.2 g, 96%) $^1$H NMR ($d_4$-$CD_3OD$, 400 MHz, δ, ppm) 7.09 (t, 1H, J=8.0 Hz), 6.71–6.36 (m, 3H), 4.69 (dd, 1H, J=6.0 Hz, 3.2 Hz), 3.69 (s, 3H), 3.66 (d, 1H, J=5.2 Hz), 3.15–3.10 (dd, 1H, J=5.6 Hz, 4.0 Hz), 1.87–1.69 (m, 6H), 1.32–1.10 (m, 5H).

Step D:

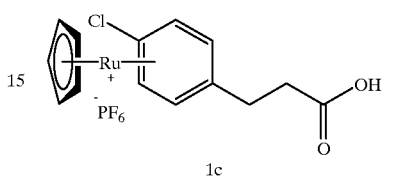

1c

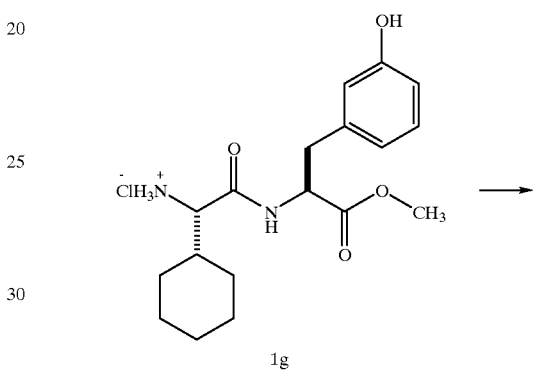

1g

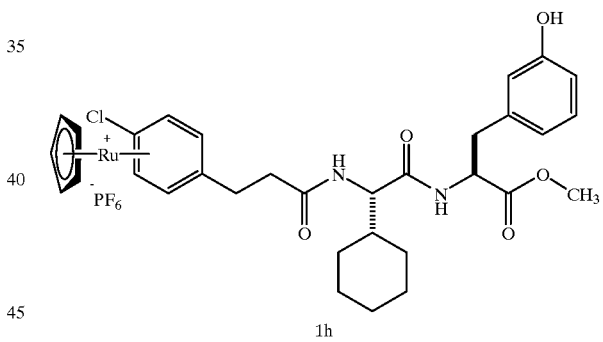

1h

A solution of cyclopentadiene-$\eta^6$-4-chlorophenylpropionic acid-ruthenium hexanesafluorophosphate 1c (2.0 g, 4.0 mmol) in DMF (20 mL) was treated with HOBt (810 mg, 6.0 mmol, 1.5 equiv) and Hünigs base (2.6 g, 16.0 mmol, 4.0 equiv.) The reaction mixture was cooled to 0° C. and treated with EDCl.HCl (888 mg, 5.0 mmol, 1.25 equiv.) The reaction mixture was stirred at 0° C. for 30 min and amine salt 1g (1.48 g, 4.0 mmol) was added to the mixture and stirred at rt for 12 h. The reaction mixture was concentrated in vacuo and the residue was diluted with $H_2O$ (200 mL) and extracted into $CH_2Cl_2$ (3×100 mL). The combined organic layers were extracted with aq. HCl (1×100 mL), $NaHCO_3$ (1×100 mL), brine (1×100 mL) and dried ($Na_2SO_4$), filtered concentrated in vacuo and the brown solid 1h was used for cyclization without any further purification.

Step E:

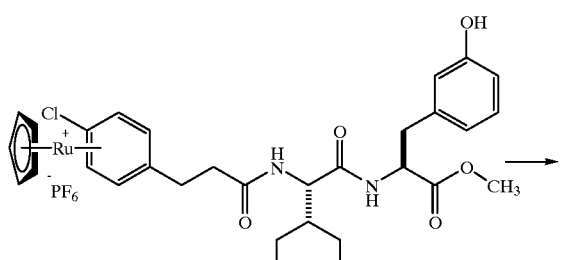

1h

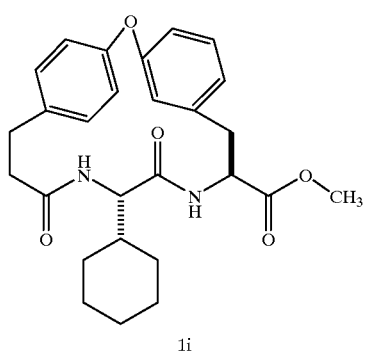

1i

A solution of cyclopentadiene-η6-ruthenium-4-chlorophenylpropionic acid-cyclohexyglycine-meta-tyrosine-OCH₃ 1h (1.47 g crude) in dry DMF (150 mL) was treated with Cs₂CO₃ (2.40 g, 7.37 mmol, 5.0 equiv) and degassed by bubbling dry N₂ into the reaction mixture. The reaction mixture was stirred at rt for 16 h and the excess DMF was distilled off. The residue was dissolved in H₂O (200 mL) and extracted with CH₂Cl₂ (3×100 mL). The combined organic layer was extracted with brine (100 mL), dried (Na₂SO₄), filtered concentrated in vacuo and the residue was used for photolytic decomplexation of ruthenium without further purification.

The crude ruthenium complex was dissolved in acetonitrile (35 mL), degassed and photolysed in a Raynot (λ=350 nM) for 48 h. The reaction mixture was concentrated in vacuo and the residue was purified by chromatography (SiO₂, EtOAc/Hexanes 7:3) to yield 360 mg (52%) of a colorless solid 1i.

Step F:

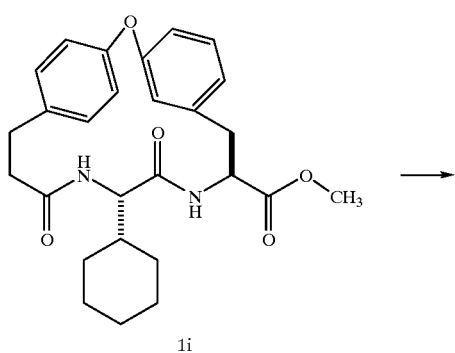

1i

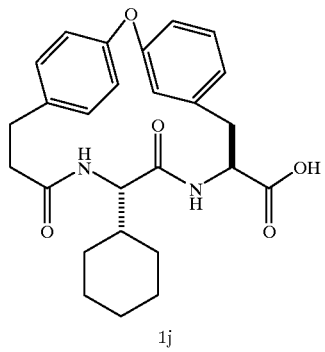

1j

A solution of biphenyl ether 1i (300 mg, 0.65 mmol) in CH₃OH (10 mL), CH₂Cl₂ (20 mL) and H₂O (5 mL) was treated with LiOH.H₂O (90 mg, 2.2 mmol, 3.4 equiv.) and stirred at rt for 2 h. The reaction mixture was acidified with aq. HCl (6 M) and extracted into CH₂Cl₂ (3×30 mL). The combined organic layers were dried (Na₂SO₄), filtered, and concentrated in vacuo to yield colorless acid 1j (200 mg, 66%).

Step G:

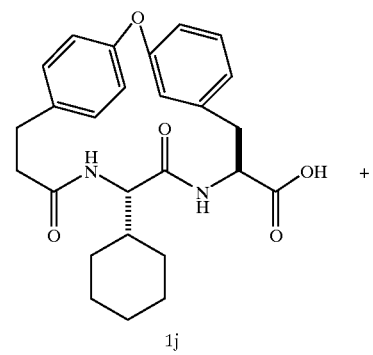

1j

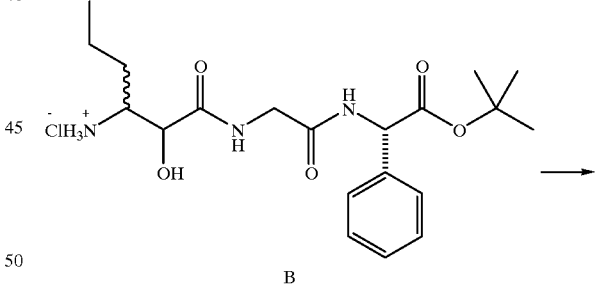

B

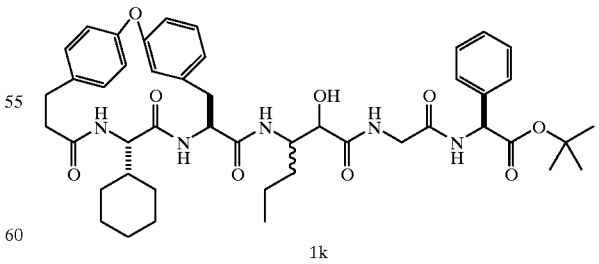

1k

A solution of acid 1j (100 mg, 0.22 mmol) in dry DMF (2.5 mL) was treated with HOOBt (45 mg, 0.33 mmol) and Hünigs base (141 mg, 1.1 mmol, 5.0 equiv.) The reaction mixture was cooled to 0° C. and treated with EDCl (63 mg, 0.33 mmol, 1.5 equiv) and stirred for 20 min. The reaction mixture was treated with amine B (118 mg, 0.27 mmol, 1.22 equiv.) and stirred at rt for 12 h. The reaction mixture was concentrated in vacuo and diluted with $H_2O$ (30 mL). The aqueous layer was extracted with $CH_2Cl_2$ (3×50 mL) and EtOAc (3×50 mL). The combined organic layers were extracted with aq. HCl (2M), aq. NaOH (2M), dried ($Na_2SO_4$) filtered concentrated in vacuo to obtain a colorless solid 1k (79 mg) which was used for oxidation. MS: (Electron spray, m/z rel int): 826 [(M+1)$^+$, 100], 494 (20), 94 (30).

Step H:

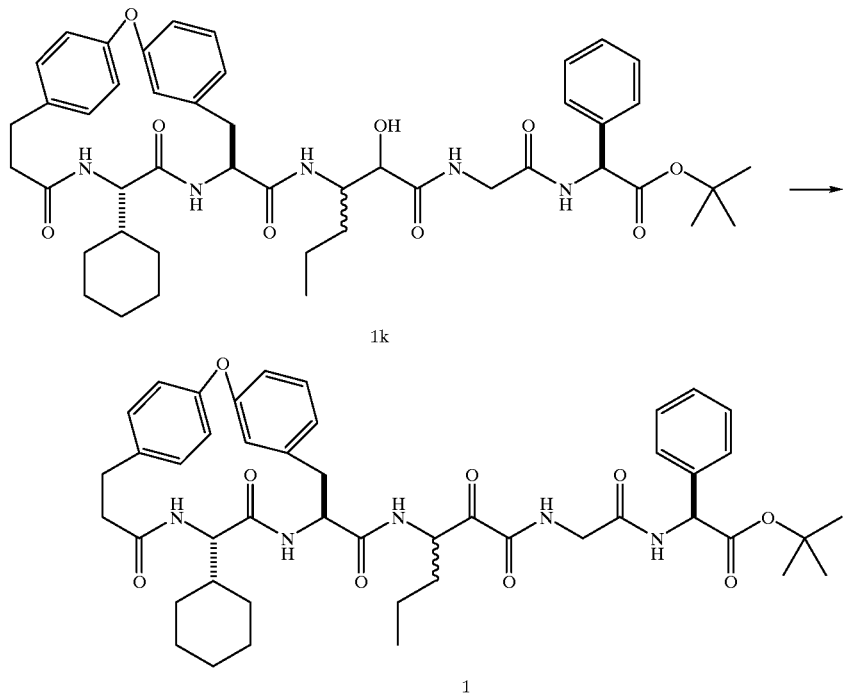

A solution of hydroxy amide 1k (130 mg, 0.16 mmol) in DMF (2.0 mL) was treated with Dess-Martin reagent (130 mg, 0.32 mmol, 2.0 equiv.). The reaction mixture was stirred at rt for 2 h and the mixture was concentrated in vacuo. The residue was purified by chromatography ($SiO_2$, $CH_3OH$/$CH_2Cl_2$: 1:49) to yield oxidized product 1 (55 mg, 42%) as a colorless solid. MS: (Electron spray, m/z rel int): 858 [(M+$CH_3OH$+1)$^+$, 100], 824 [(M+1)$^+$, 63).

Example 2
Preparation of Compound of Formula 2:

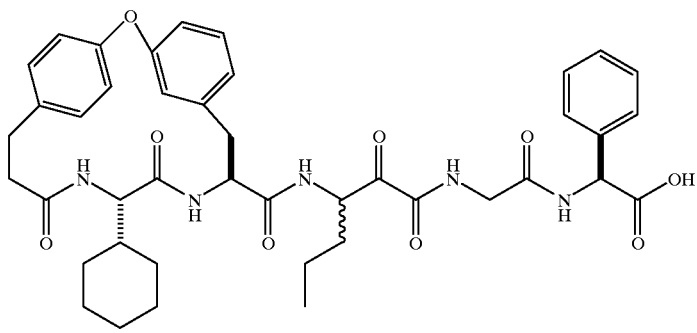

Step A:

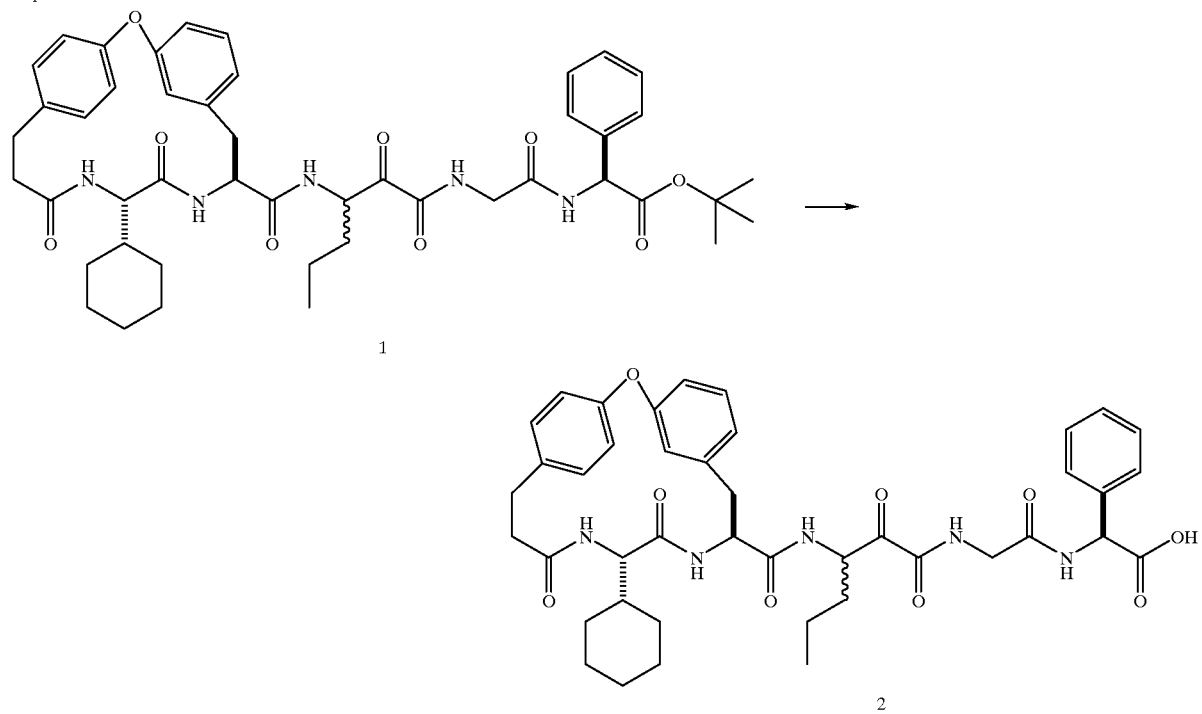

A solution of tert-butyl ester 1 (50.0 mg, 60.0 μmol) was treated with TFA/CH$_2$Cl$_2$ (1:1, 4 mL) and stirred at rt for 2 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes (4.0 mL) and concentrated to yield a white solid 2 (49 mg, 100%). MS: (Electron spray, m/z rel int): 768 [(M+1)$^+$, 100).

Example 3
Preparation of Compound of Formula 3:

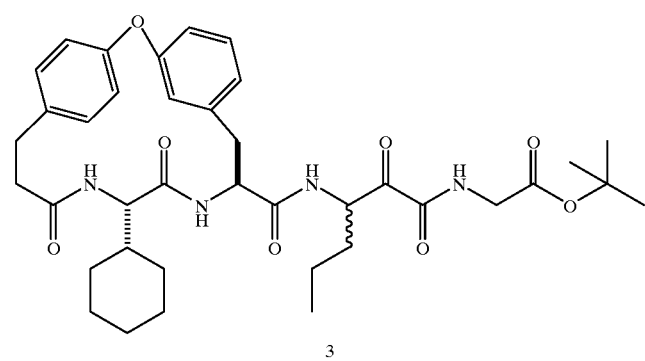

Step A:

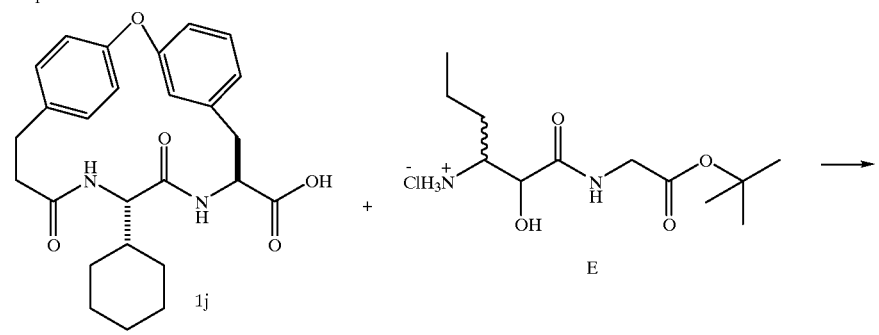

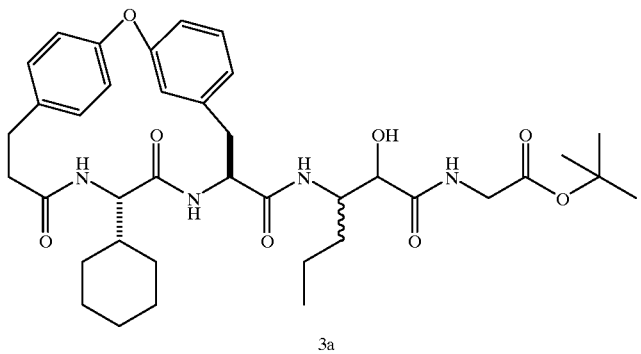

3a

A solution of acid 1j (100 mg, 0.22 mmol) in dry DMF (2.5 mL) was treated with HOOBt (45 mg, 0.33 mmol) and Hünigs base (141 mg, 1.1 mmol, 5.0 equiv.) The reaction mixture was cooled to 0° C. and treated with EDCl (63 mg, 0.33 mmol, 1.5 equiv) and stirred for 20 min. The reaction mixture was treated with amine E (79 mg, 0.27 mmol, 1.22 equiv.) and stirred at rt for 12 h. The reaction mixture was concentrated in vacuo and diluted with H$_2$O (30 mL). The aqueous layer was extracted with CH$_2$Cl$_2$ (3×50 mL). The combined organic layers were extracted with aq. HCl (1M, 30 mL) aq. NaOH (1M, 30 mL), dried (Na$_2$SO$_4$) filtered concentrated in vacuo to obtain a colorless solid 3a (58 mg) which was used for oxidation. MS: (Electron spray, m/z rel int): 693 [(M+1)$^+$, 100], 637 (41), 494 (55), 394 (51), 338 (13).

Step B:

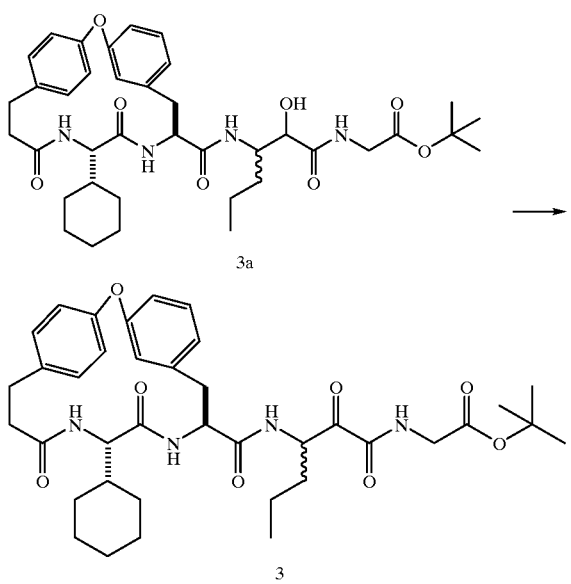

A solution of alcohol 3a (95 mg, 0.14 mmol) in CH$_2$Cl$_2$ (2.0 mL) was treated with Dess-Martin reagent (116 mg, 0.28 mmol, 2.0 equiv.) The reaction mixture was stirred at rt for 2 h and the mixture was concentrated in vacuo. The residue was purified by chromatography (SiO$_2$, CH$_3$OH/CH$_2$Cl$_2$ 1:32) to yield oxidized product 3 (47 mg, 42%) as a colorless solid. MS: (Electron spray, m/z rel int): 691 (M+1)$^{30}$.

Example 4
Preparation of Compound of Formula 4:

Step A:

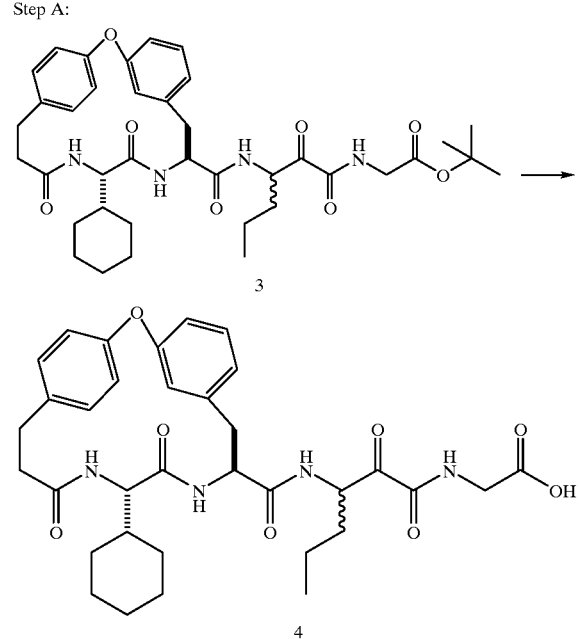

A solution of tert-butyl ester 3 (47.0 mg, 68.0 μmol) was treated with HCl (4M Dioxane, 5 mL) and stirred at rt for 25 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes (5.0 mL) and concentrated to yield a white solid 4 (43 mg, 100%). MS: (Electron spray, m/z rel int): 635 [(M+1)$^+$, 100)], 465 (62), 336 (62).

Example 5

Preparation of Compound of Formula 5:

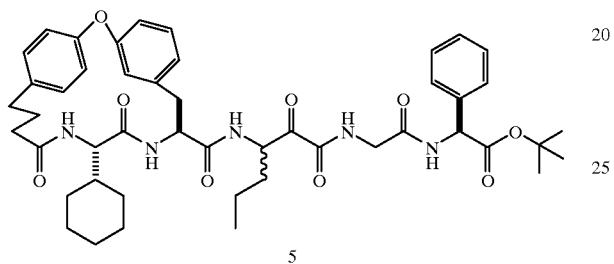

5

Step A:

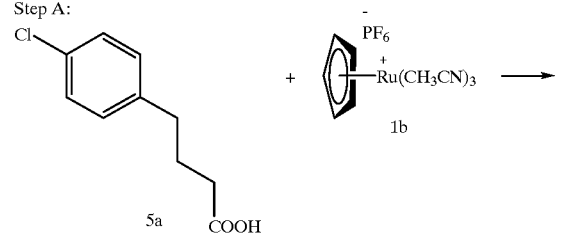

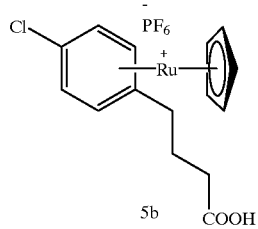

A solution of 4-chlorobutyric acid 5a (3.0 g, 15.10 mmol) in dichloroethane (200 mL) was treated with CpRu(CH$_3$CN)$_3$ PF$_6$ 1b (6.6 g, 15.10 mmol, 1.0 equiv) and heated at reflux for 2.5 h. The reaction mixture was cooled to 0° C. and filtered. The filtrate was concentrated in vacuo and dissolved in CH$_3$CN (10 mL) and treated with a large excess of Et$_2$O. The gum separating out was separated by decanting the ether and the residue was dissolved in CH$_2$Cl$_2$/CH$_3$OH (1:1, 100 mL) and concentrated in vacuo to obtain 5b as a brown gum which solidifies (3.5 g, 46%).

Step B:

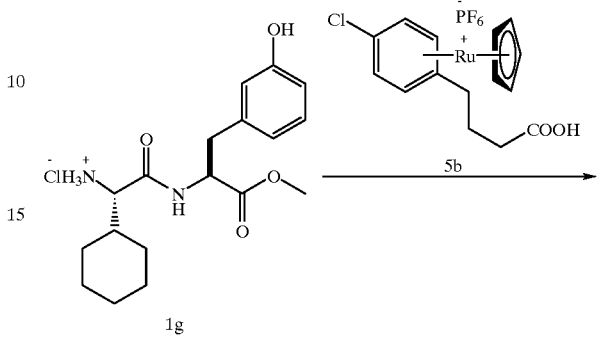

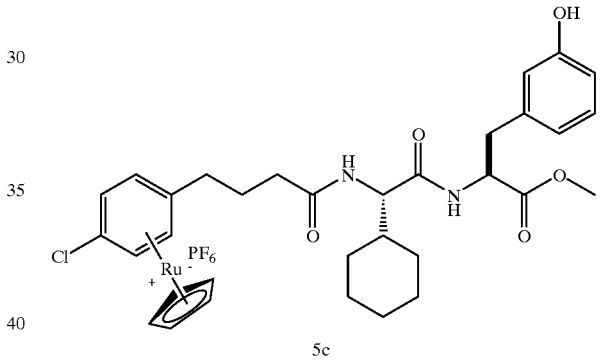

A solution of carboxylic acid 5b (3.12 g, 5.95 mmol) in dry DMF (20 mL) was treated with Hünigs base (3.07 g, 24.0 mmol, 4.0 equiv, 4.4 mL) and HOBt (1.2 g, 8.93 mmol, 1.5 equiv). The reaction mixture was cooled to 0° C. and the treated with EDCl (1.35 g, 7.43 mmol, 1.25 equiv) and stirred for 1 h. To this reaction mixture was added amine hydrochloride 1g (2.65 g, 7.14 mmol, 1.2 equiv), and the reaction mixture was stirred at rt for 12 h. DMF was distilled out and the residue was diluted with water and the aqueous layer was extracted with CH$_2$Cl$_2$. The combined organic layers were extracted with aq NaHCO$_3$, aq. HCl, brine, dried (Na$_2$SO$_4$), filtered, concentrated in vacuo and the crude product 5c (4.3 g) was used for cyclization without further purification. $^1$H NMR (d$_4$–CD$_3$OD, 400 MHz, δ, ppm) 7.35 (t, 1H), 6.72–6.60 (m, 5H), 6.33–6.20 (dd, 2H), 5.51 (s, 5H), 4.19 (d, 1H), 3.68 (s, 3H), 3.19–2.83 (m, 2H), 2.51–2.40 (m, 2H), 2.40–2.25 (m, 2H), 1.99–1.59 (m, 8H), 1.35–0.98 (m, 5H); MS (FAB, NBA-G/TG-DMSO, m/z relative intensity) 695.3 ([M-PF$_6$]$^+$, 100), 232 (20), 171(30); HRMS calcd for C$_{34}$H$_{42}$N$_2$O$_5$ClRu$^+$ (M-PF$_6$)$^+$ 695.1832; found 695.1845.

Step C:

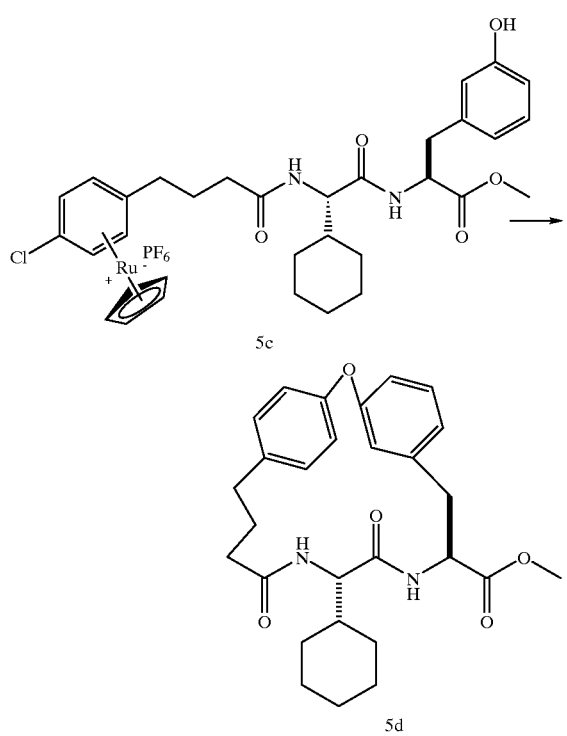

A solution of chloro-compound 5c (3.0 g 3.6 mmol) in dry DMF (300 mL) was degassed with dry N₂ and Cs₂CO₃ (5.2 g, 16 mmol, 4.0 equiv) and stirred at rt. for 16 h. The solvent DMF was distilled off and the residue was diluted with water and extracted with CH₂Cl₂ (3×100 mL). The combined organic layers were dried (Na₂SO₄), filtered, concentrated in vacuo and dried under vacuum overnight. It was used for photolytic removal of Ru without further purification. MS FAB (NBA-G/TG-DMSO 695 ([M-PF₆]⁺, 100].

The cyclized compound from the previous step was dissolved in CH₃CN (35 mL) and photolysed in a Raynot (λ=350 nm) for 48 h. The reaction mixture was concentrated in vacuo and the residue was purified by chromatography (SiO₂, EtOAc/Hexanes 1:1) to yield a tan colored solid 5d (600 mg, 34%). ¹H NMR (CDCl₃, 400 MHz, δ, ppm) 7.58 (d, 1H, J=7.6 Hz), 7.14 (t, 1H, J=8.0 Hz), 6.94 (d, 2H, J=8.4 Hz), 6.87 (dd, 1H, J=2.4, 5.6 Hz), 6.73 (d, 1H, J=7.2 Hz), 6.59 (s, 1H), 6.57 (s, 2H), 6.39 (d, 1H, J=8.0 Hz), 4.51 (dt, 1H, J=2.8, 8.0 Hz), 3.80–3.62 (m, 1H), 3.62 (s, 3H), 3.05–3.00 (dd, 1H, J=2.8, 11.6 Hz), 2.85 (dd, 1H, J=8.4, 6.0 Hz), 2.76–2.72 (m, 1H), 2.36–2.19 (m, 3H), 2.02 (dd, 1H, J=6.4, 9.2 Hz), 1.8–1.73 (m, 1H), 1.61–1.34(m, 7H), ,1.41–0.71 (m, 7H). MS (FAB, NBA-G/TG-DMSO, m/z relative intensity), 493 [(M+1)⁺, 100], 465 (20), 232 (30), 171 (40); HRMS calcd. for C₂₉H₃₇N₂O₅ (M+1)⁺: 493.2702; found 493.2699.

Step D:

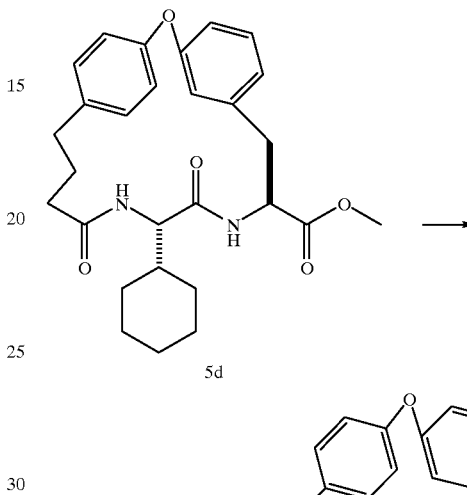

A solution of ether 5d (200 mg, 0.42 mmol) in CH₃OH (5 mL), CH₂Cl₂ (10 mL) and H₂O (0.5 mL) was treated with LiOH.H₂O (18 mg, 0.44 mmol, 1.1 equiv.) and stirred at rt for 12 h. The reaction mixture was acidified with aqueous HCl (12 N, 1 mL) and concentrated in vacuo to yield acid 5e which was used directly for the coupling without further purification.

Step E:

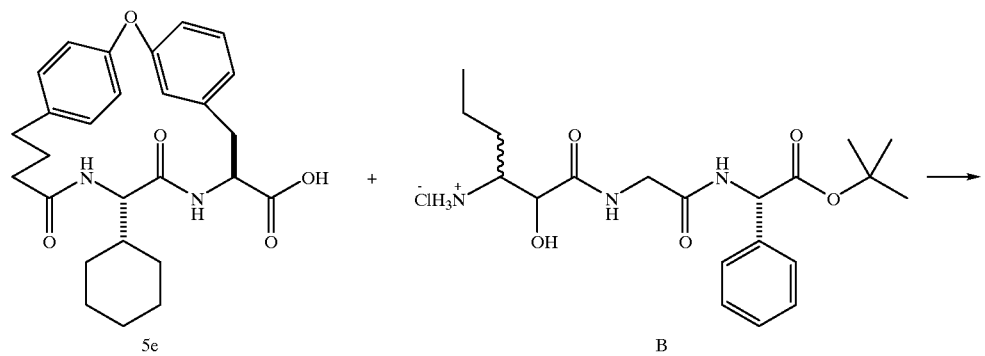

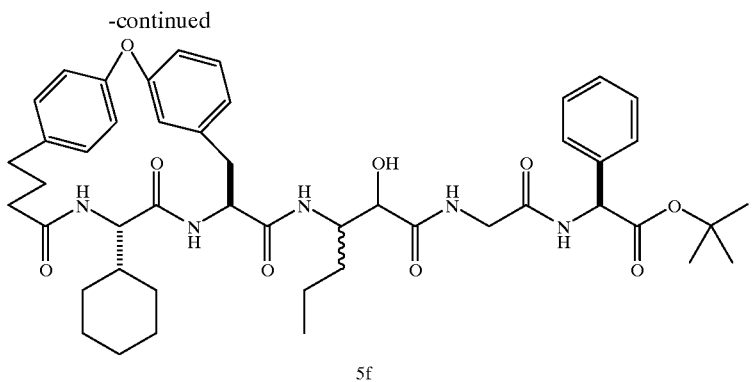

5f

A solution of acid 5e in dry DMF (5.0 mL) was treated with HOOBt (103 mg, 0.63 mmol, 1.5 equiv.), Hünigs base (216 mg, 1.68 mmol, 4.0 equiv.) and amine B (270 mg, 0.63 mmol, 1.47 equiv.) The reaction mixture was cooled to 0° C. and treated with EDCl (101 mg, 0.52 mmol, 1.25 equiv) and stirred at rt for 12 h. The reaction mixture was concentrated in vacuo and diluted with $H_2O$ (30 mL). The aqueous layer was extracted with $CH_2Cl_2$ (3×50 mL) and EtOAc (3×50 mL). The combined organic layers were extracted with aq. HCl (2M) aq. NaOH (2M), dried ($Na_2SO_4$) filtered concentrated in vacuo to obtain a colorless solid 5f (177 mg) which was used for oxidation. MS: (Electron spray, m/z rel int): 840 [$(M+1)^+$, 100], 394 (100).

Step F:

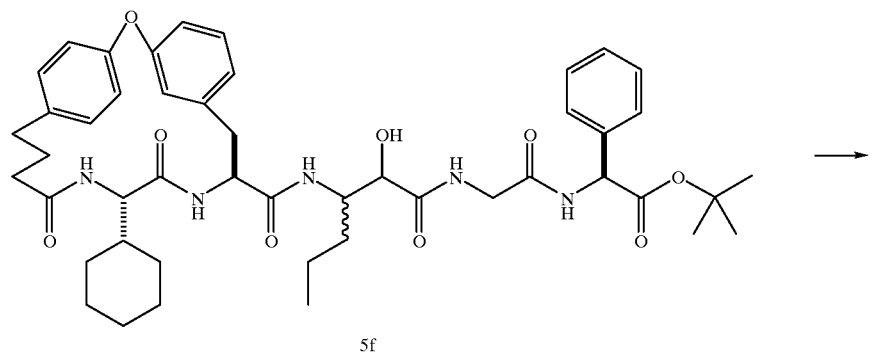

5f

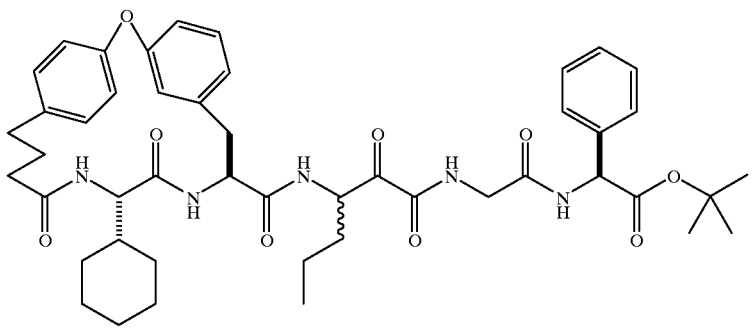

5

A solution of alcohol 5f (177 mg, 0.21 mmol) in $CH_2Cl_2$ (10.0 mL) was treated with Dess-Martin reagent (178 mg, 0.42 mmol, 2.0 equiv.) The reaction mixture was stirred at rt for 3 h and the mixture was concentrated in vacuo. The residue was purified by chromatography ($SiO_2$, $CH_3OH$/ $CH_2Cl_2$ 1:49) to yield oxidized product 5 (23 mg, 13%) as a colorless solid. MS: (Electron spray, m/z rel int): 870 [$(M+CH_3OH+1)^+$, 50], 838 [$(M+1)^+$, 100].

Example 6

Preparation of Compound of Formula 6:

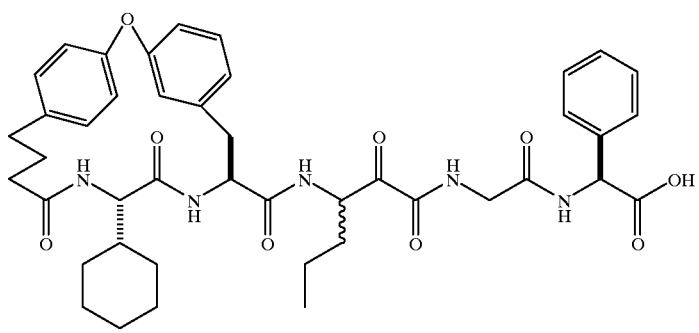

6

Step A:

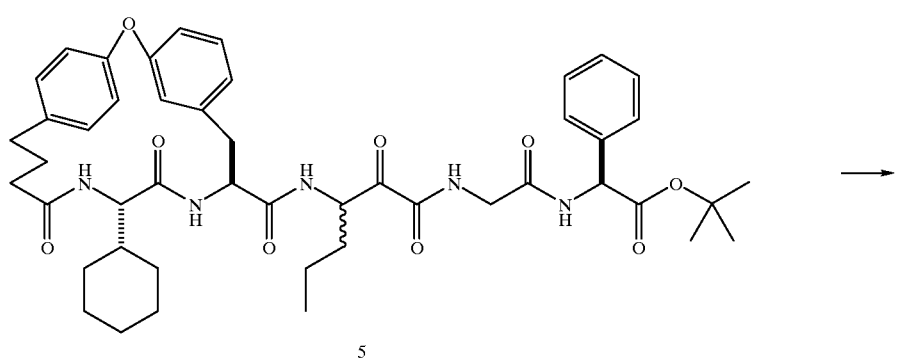

5

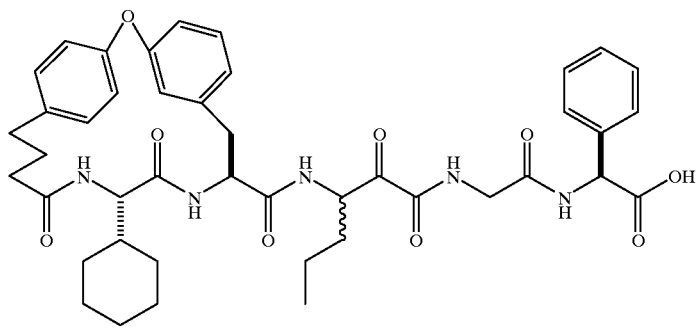

6

A solution of tert-butyl ester 5 (50.0 mg, 60.0 μmol) was treated with TFA/CH$_2$Cl$_2$ (1:1, 4 mL) and stirred at rt for 7 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes (4.0 mL) and concentrated to yield a white solid 6 (14 mg, 100%). MS: (Electron spray, m/z rel int): 782 [(M+1)$^+$, 100).

Example 7
Preparation of Compound of Formula 7:

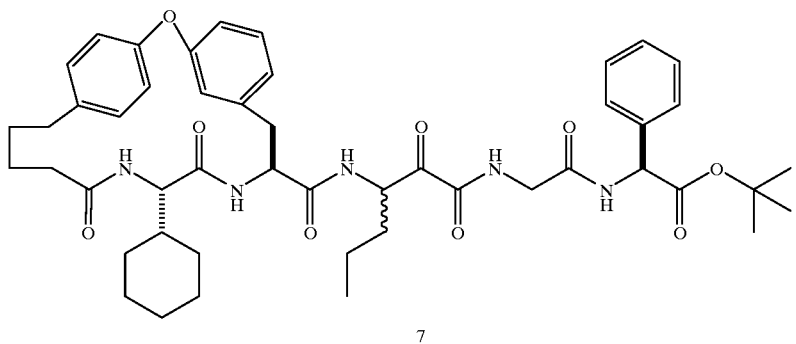

Step A:

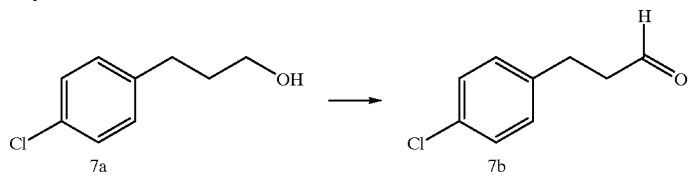

A solution of alcohol 7a (9.2 g, 54.1 mmol) in dry CH$_2$Cl$_2$ (200 mL) was treated with DMSO (35 mL) and Et$_3$N (16.4 g, 16.3 mmol, 23.4 mL). The reaction mixture was cooled to 0° C. and treated with Py.SO$_3$ (12.9 g, 81.2 mmol, 1.50 equiv.) dissolved in DMSO (30 mL). The reaction mixture was stirred at 0° C. for 0.5 h and rt for 6 h. The reaction mixture was concentrated in vacuo and diluted with Et$_2$O (100 mL) and H$_2$O (200 mL). The layers were separated and the aqueous layer was extracted with Et$_2$O (3×100 mL). The combined organic layers were extracted with HCl (2M, 3×100 mL), brine (1×100 mL) concentrated in vacuo and purified by chromatography (SiO$_2$, EtOAc/Hexanes 1:7) to yield aldehyde 7b which solidified to a waxy solid on standing (7.1 g, 77%). CHN calcd for C$_9$H$_9$ClO: C=64.1 1% H=5.38%; found: C=64.08% H=5.30%.

Step B:

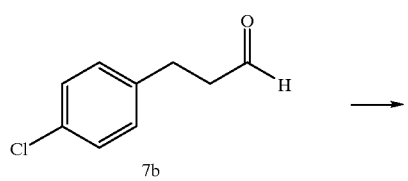

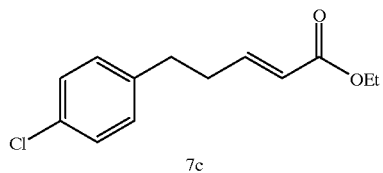

A solution of thiethylphosponoacetate (6.72 g, 30 mmol, 1.2 equiv) in dry THF (100 mL) was treated with NaH (60% dispersion, 1.5 g, 35 mmol, 1.4 equiv) at 0° C. The reaction mixture was stirred at 25° C. for 1 h until the H$_2$ evolution ceased. A solution of aldehyde 7b (4.2 g, 25.0 mmol) in dry THF (5.0 mL) was added and the reaction mixture was stirred for 36 h. The reaction mixture was diluted with H$_2$O (100 mL) and extracted with Et$_2$O (3×70 mL). The combined organic layer was dried (MgSO$_4$), filtered, concentrated in vacuo and chromatographed to yield α,β-unsaturated ester 7c (4.2 g, 71%) which was used for reduction.

Step C:

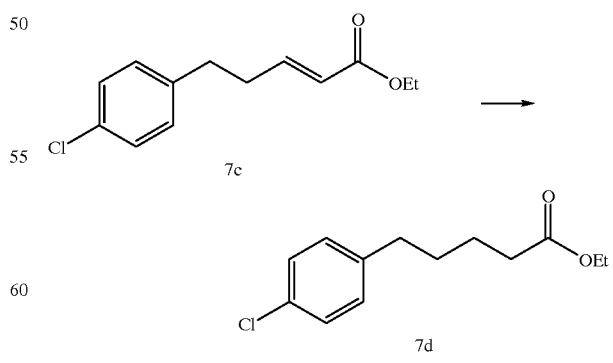

A solution of α,β-unsaturated ester 7c (4.2 g, 8.0 mmol) in EtOAc (50 mL) was treated with Pd/C (10% w/w, 500 mg) and hydrogenated at 50 psi for 12 h. The reaction Step D:

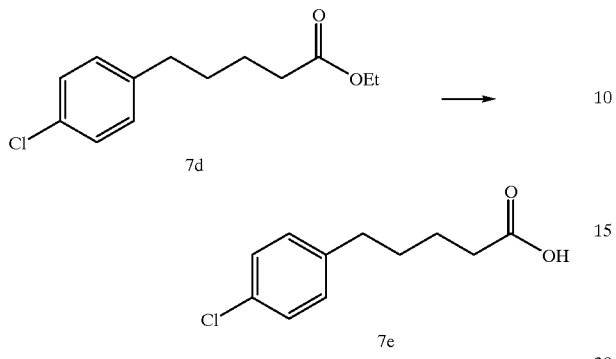

Step E:

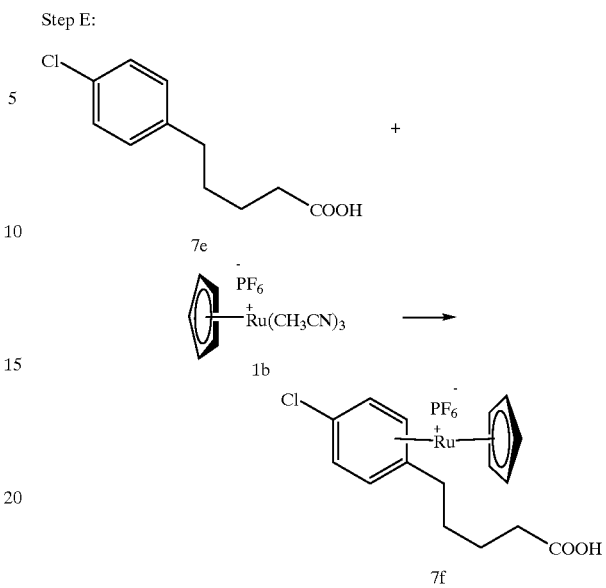

A solution of the ester 7d (3.9 g, 16.2 mmol) in CH₃OH/THF/H₂O(1:1:0.1, 110 mL) was treated with LiOH.H₂O (1.2 g, 30 mmol, 2.0 equiv) and stirred at rt for 5 h. The reaction mixture was concentrated in vacuo and the residue was diluted with H₂O (100 mL) and extracted into Et₂O (3×50 mL). The aqueous layer was acidified to pH~1 (13 M HCl) and the turbid aqueous layer was extracted with Et₂O (3×100 mL). The combined organic layers were dried (MgSO₄) filtered concentrated in vacuo to yield a colorless solid 7e (3.1 g, 96%). CHN calcd for $C_{11}H_{13}ClO_2$ C=62.12% H=6.16%; found: C=62.27% H=6.23%.

A solution of 4-chlorophenyl pentanoic acid 7e (3.0 g, 14.15 mmol) in dichloroethane (150 mL) was treated with CpRu(CH₃CN)₃ PF₆ 1b (6.75 g, 15.10 mmol, 1.0 equiv) and heated at reflux for 2.5 h. The reaction mixture was cooled to 0° C. and filtered. The filtrate was concentrated in vacuo and dissolved in CH₃CN (20 mL) and treated with a large excess of Et₂O. The gum separating out was separated by decanting the ether and the residue was dissolved in CH₂Cl₂/CH₃OH (1:1, 100 mL) and concentrated in vacuo to obtain 7f a brown gum which solidifies (4.36 g, 58%). MS: (Electron spray, m/z rel int): 379 [(M-PF₆)⁺, 100].

Step F:

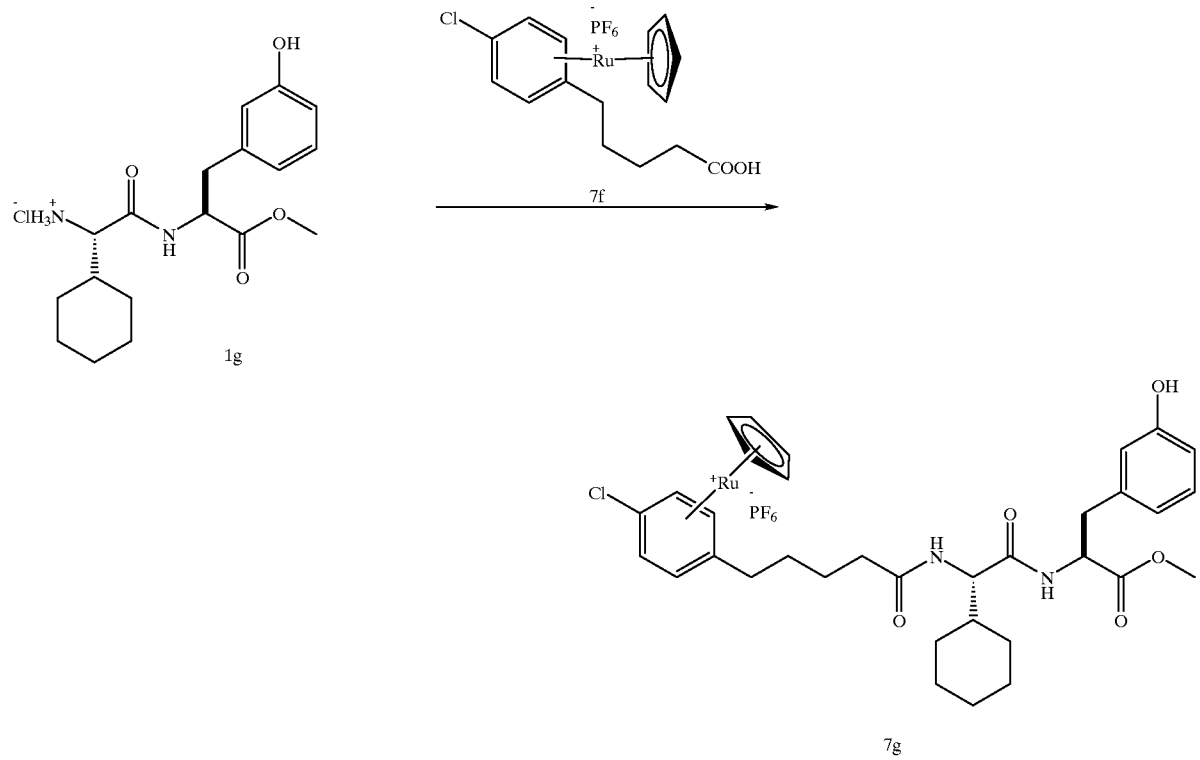

A solution of carboxylic acid 7f (3.12 g, 5.95 mmol) in dry DMF (20 mL) was treated with Hünigs base (3.07 g, 24.0 mmol, 4.0 equiv, 4.4 mL) and HOBt (1.2 g, 8.93 mmol, 1.5 equiv). The reaction mixture was cooled to 0° C. and the treated with EDCl (1.35 g, 7.43 mmol, 1.25 equiv) and stirred for 1 h. To this reaction mixture was added amine hydrochloride 1g (2.65 g, 7.14 mmol, 1.2 equiv) was added and the reaction mixture was stirred at rt for 12 h. The DMF was distilled out and the residue was diluted with water and the aqueous layer was extracted with $CH_2Cl_2$. The combined organic layers were extracted with aq $NaHCO_3$, aq. HCl, brine, dried ($Na_2SO_4$) filtered concentrated in vacuo and the crude product 7g (4.3 g) was used for further cyclization without purification. $^1$H NMR ($d_4$-$CD_3OD$, 400 MHz, δ, ppm) 7.35 (t, 1H), 6.72–6.60 (m, 5H), 6.33–6.20 (dd, 2H), 5.51 (s, 5H), 4.19 (d, 1H), 3.68 (s, 3H), 3.19–2.83 (m, 2H), 2.51–2.40 (m, 2H), 2.40–2.25 (m, 2H), 1.99–1.59 (m, 8H), 1.35–0.98 (m, 5H); MS (FAB, NBA-G/TG-DMSO, m/z relative intensity) 695.3 ([M-$PF_6$]$^+$, 100), 232 (20), 171 (30); HRMS calcd for $C_{34}H_{42}N_2O_5ClRu^+$ (M-$PF_6$) 695.1832; found 695.1845.

Step G:

The cyclized compound from the previous step was dissolved in $CH_3CN$ (35 mL) and photolysed in a Raynot (λ=350 nm) for 48 h. The reaction mixture was concentrated in vacuo and the residue was purified by chromatography ($SiO_2$, EtOAc/Hexanes 1:1) to yield a tan colored solid 7h (600 mg, 34%). $^1$H NMR ($CDCl_3$, 400 MHz, δ, ppm) 7.58 (d, 1H, J=7.6 Hz), 7.14 (t, 1H, J=8.0 Hz), 6.94 (d, 2H, J=8.4 Hz), 6.87 (dd, 1H, J=2.4, 5.6 Hz), 6.73 (d, 1H, J=7.2 Hz), 6.59 (s, 1H), 6.57 (s, 2H), 6.39 (d, 1H, J=8.0 Hz), 4.51 (dt, 1H, J=2.8, 8.0 Hz), 3.80–3.62 (m, 1H), 3.62 (s, 3H), 3.05–3.00 (dd, 1H, J=2.8, 11.6 Hz), 2.85 (dd, 1H, J=8.4, 6.0 Hz), 2.76–2.72 (m, 1H), 2.36–2.19 (m, 3H), 2.02 (dd, 1H, J=6.4, 9.2 Hz), 1.8–1.73 (m, 1H), 1.61–1.34(m, 7H), ,1.41–0.71 (m, 7H). MS (FAB, NBA-G/TG-DMSO, m/z relative intensity), 493 [(M+1)$^+$, 100], 465 (20), 232 (30), 171 (40); HRMS calcd. for $C_{29}H_{37}N_2O_5$ (M+1)$^+$: 493.2702; found; 493.2699.

Step H:

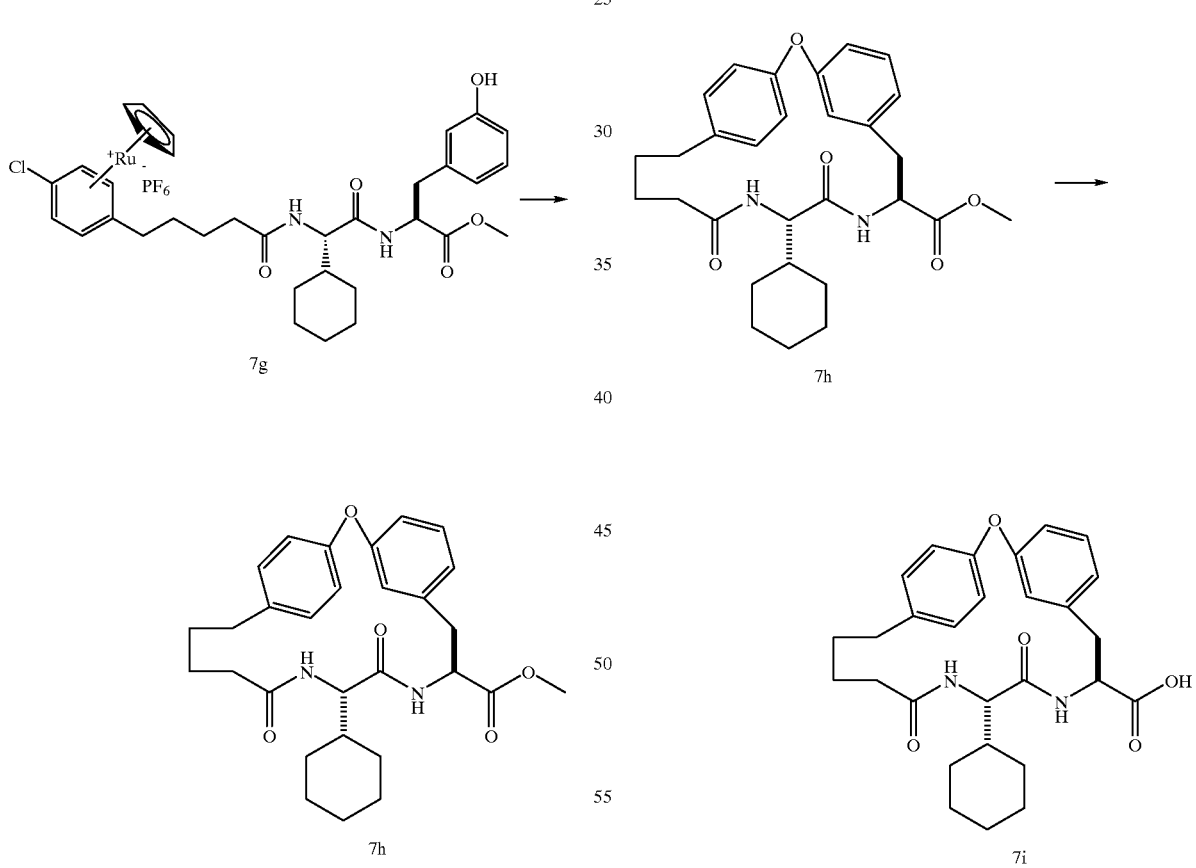

A solution of chloro-compound 7g (3.0 g 3.6 mmol) in dry DMF (300 mL) was degassed with dry $N_2$ and $Cs_2CO_3$ (5.2 g, 16 mmol, 4.0 equiv) and stirred at rt. for 16 h. The solvent DMF was distilled off and the residue was diluted with water and extracted with $CH_2Cl_2$ (3×100 mL). The combined organic layers were dried ($Na_2SO_4$) filtered, concentrated in vacuo and dried in vacuum overnight. It was used for photolytic removal of Ru without further purification. MS FAB (NBA-G/TG-DMSO 695 ([M-$PF_6$]$^+$, 100].

A solution of ether 7h (220 mg, 0.46 mmol) in $CH_3OH$ (3.0 mL), $CH_2Cl_2$ (10 mL) and $H_2O$(0.5 mL) was treated with LiOH.$H_2O$ (18 mg, 0.44 mmol, 1.1 equiv.) and stirred at rt for 12 h. The reaction mixture was acidified with aq.HCl (13 M, 1 mL) and concentrated in vacuo to yield acid 7i which was used directly for the coupling without further purification.

Step I:

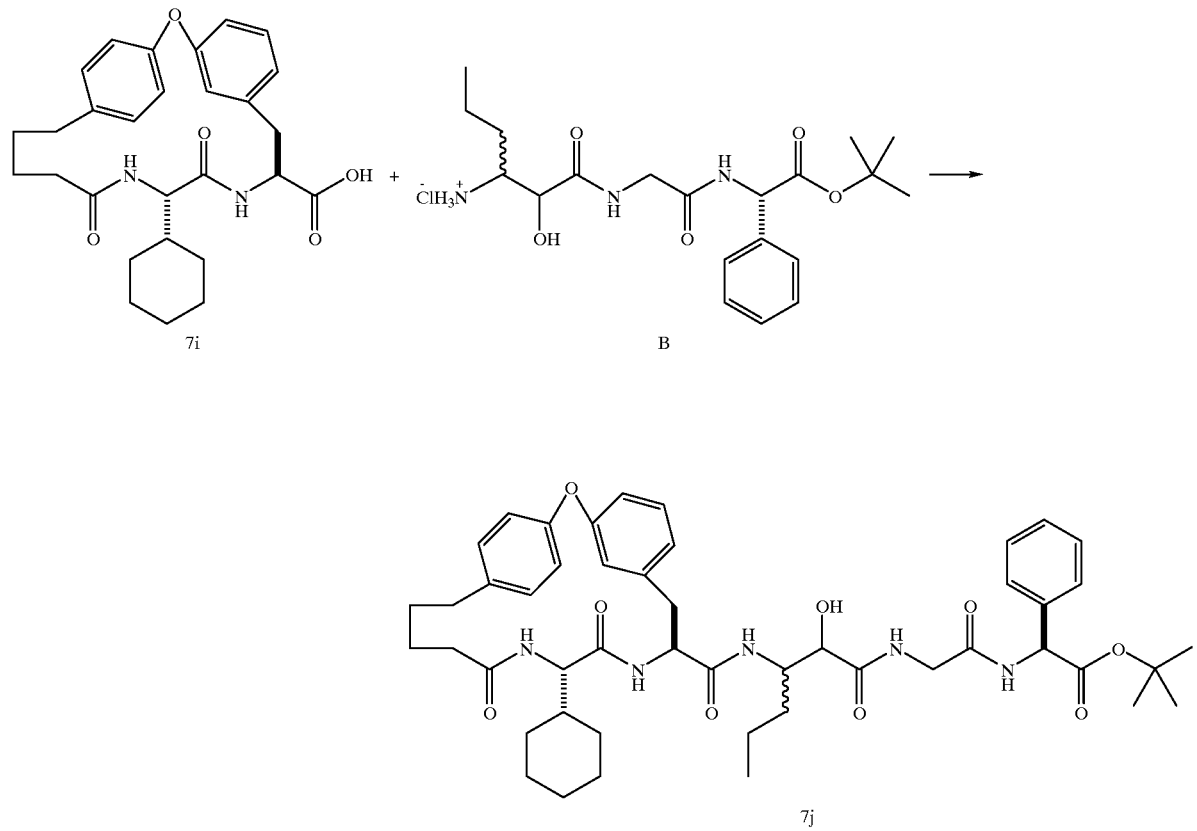

A solution of acid 7i in dry DMF (3.0 mL) was treated with HOOBt (94 mg, 0.75 mmol, 1.6 equiv.), Hünigs base (237 mg, 1.84 mmol, 4.0 equiv.) and amine B (246 mg, 0.58 mmol, 1.47 equiv.) The reaction mixture was cooled to 0° C. and treated with EDCl (110 mg, 0.58 mmol, 1.25 equiv) and stirred at 0° C. for 25 min for 12 h. The reaction mixture was concentrated in vacuo and diluted with $H_2O$ (30 mL). The combined aqueous layers were extracted with $CH_2Cl_2$ (3×30 mL). The organic layers were extracted with aq. HCl (1 M, 60 mL) aq. NaOH (60 mL), dried ($Na_2SO_4$) filtered concentrated in vacuo to obtain a colorless solid 7j (230 mg) which was used for oxidation. MS: (Electron spray, m/z rel int): 854 [$(M+1)^+$, 100], 479 (70), 327 (50), 271.1 (100).

Step J:

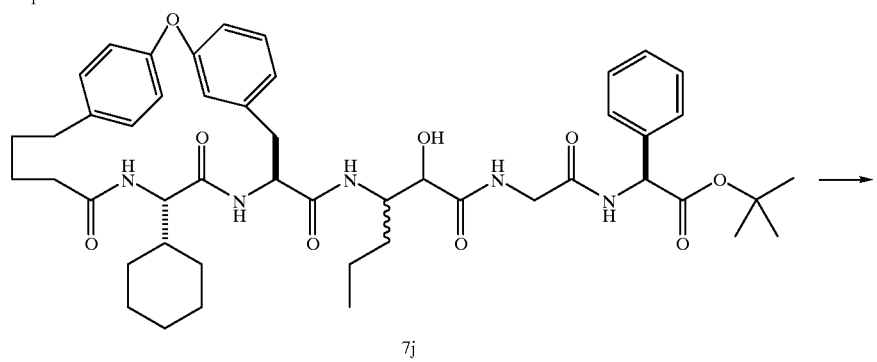

-continued

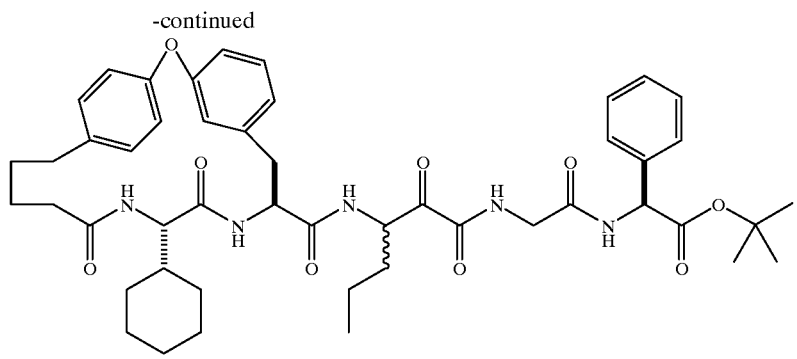

7

A solution of alcohol 7j (220 mg, 0.26 mmol) in CH$_2$Cl$_2$ (3.0 mL) was treated with Dess-Martin reagent (218 mg, 0.51 mmol, 2.0 equiv.) The reaction mixture was stirred at rt and the mixture was concentrated in vacuo. The residue was purified by chromatography (SiO$_2$, CH$_3$OH/CH$_2$Cl$_2$ 1:24) to yield oxidized product 7 (23 mg, 13%) as a colorless solid. MS: (FAB, m/z, rel. int.) 852 [(M+1)$^+$, 43), 796 (100), 768 (20), 461 (20), 433 (50), 405 (50), 336 (30), 294, (50).

Example 8

Preparation of Compound of Formula 8:

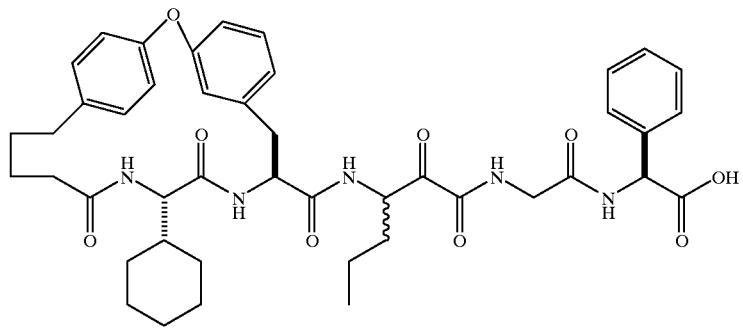

8

Step A:

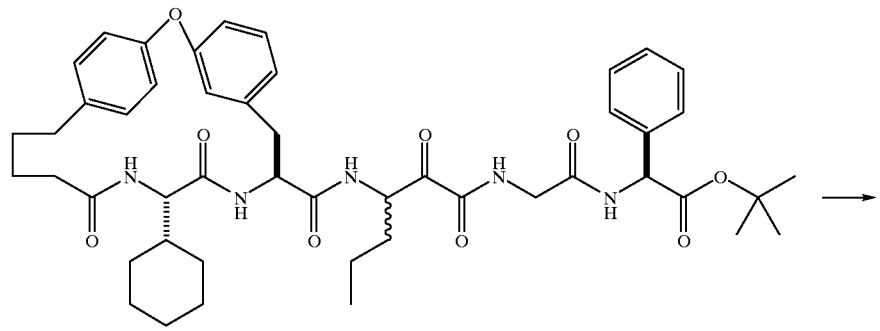

7

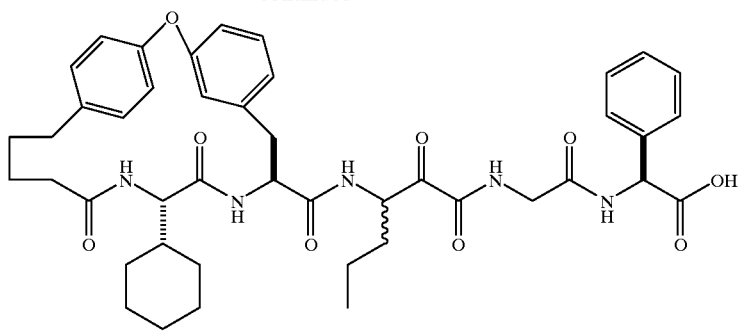

8

A solution of ten-butyl ester 7 (32.0 mg, 37.0 μmol) was treated with TFA/CH$_2$Cl$_2$ (1:1, 5.0 mL) and stirred at rt for 4 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes/CH$_3$OH (4.0 mL) and concentrated to yield a tan solid 8 (29.0 mg, 100%). MS: (Electron spray, m/z rel int): 796 [(M+1)$^+$, 100).

Example 9

Preparation of Compound of Formula 9:

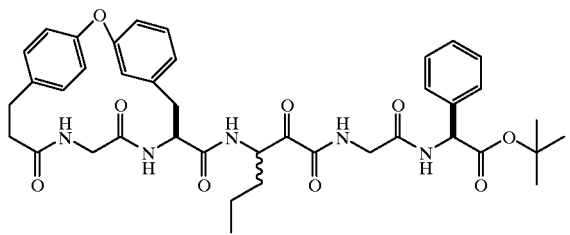

9

-continued

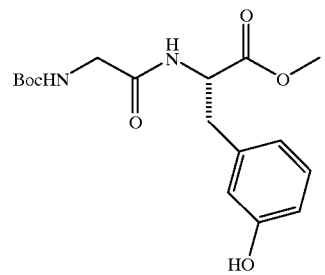

9b

A solution of Boc-Glycine 9a (1.75 g, 10.0 mmol) in dry DMF (50 mL) was treated with HOOBt (2.65 g, 15 mmol, 1.5 equiv) and EDCl (2.86 g, 15.0 mmol, 1.5 equiv). The reaction mixture was treated with Hünigs base (5.16 g, 40 mmol, 4.0 equiv. 7.3 mL). The reaction mixture was stirred for 1 h and meta-tyrosine-OCH$_3$.HCl 1e (2.5 g, 11.5 mmol, 1.1 equiv.) was added and stirred at 25° C. for 12 h. The reaction mixture was concentrated in vacuo and the residue was diluted with aq. NaHCO$_3$ and extracted into CH$_2$Cl$_2$. The combined organic layer were concentrated and the residue purified by chromatography (SiO$_2$, EtOAc/Hexanes 1:1) to yield a colorless solid 9b (3.4 g, 90%).

Step A:

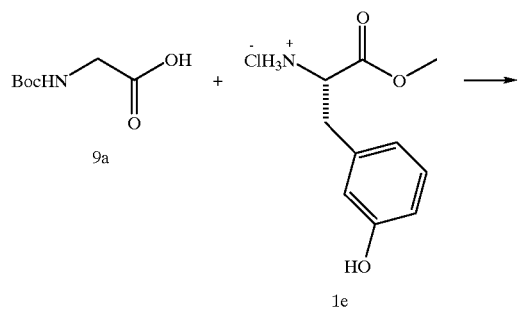

9a    1e

Step B:

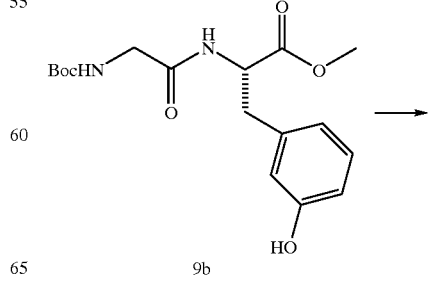

9b

-continued

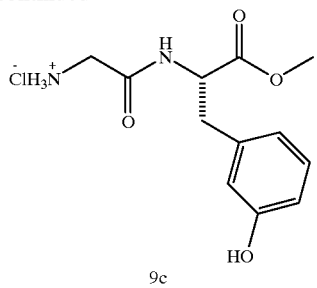

9c

A solution of 9b (4.6 g, 13.06 mmol) in HCl (4M solution in Dioxane, 50 mL) was stirred at rt. for 3 h. The reaction mixture was concentrated in vacuo and the residue was dried in high vacuum to yield 9c as a fine powder which was used for the next step. $^1$H NMR (CD$_3$OD, 400 MHz, δ, ppm) 8.67 (d, 1H, J=7.9 Hz), 7.10–7.07 (m, 1H), 6.68–6.64 (m, 2H), 4.75–4.70 (m, 1H), 3.75–3.61 (m, 2H), 3.66 (s, 3H), 3.10 (dd, 1H, J=5.2, 8.5 Hz), 2.90 (dd, 1H, J=8.8 Hz, 5.0 Hz).

Step C:

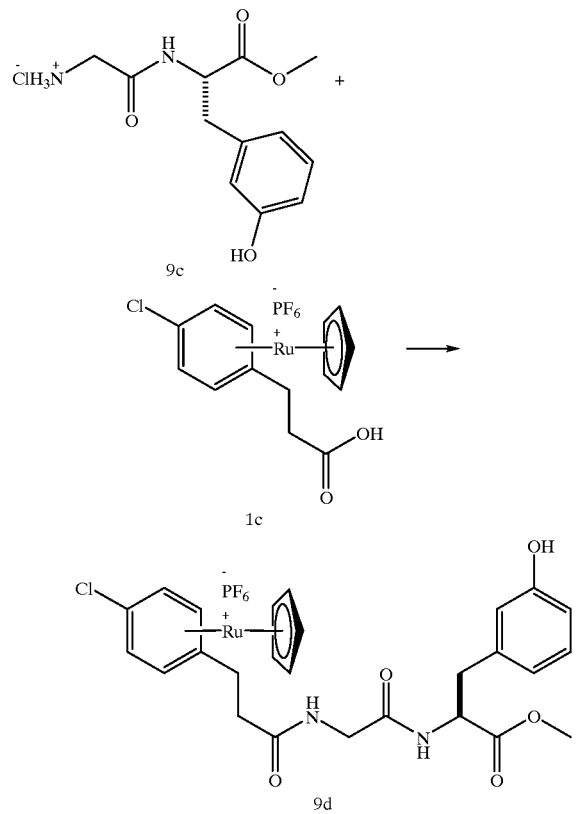

A solution of [CpRu(η$^6$–4-chlorophenylpropionic acid)] PF$_6$ 1c (3.0 g, 46.01 mmol) in dry DMF (60 mL) was treated with HOBt (1.3 g, 9.16 mmol, 1.5 equiv.) and Hünigs base (3.22 g, 4.60 mL, 25.0 mmol, 4.0 equiv.) The reaction mixture was cooled to 0° C. and treated with EDCl (1.75 g, 9.16 mmol, 1.5 equiv.) The reaction mixture was stirred at 0° C. for 30 min and the glycine ammonium salt 9c (1.75 g, 6.06 mmol, 1.0 equiv.) was added. The reaction mixture was stirred at rt for 12 and the DMF was distilled out in vacuo. The residue was diluted with aq. HCl (1M, 100 mL) and extracted into CH$_2$Cl$_2$ (3×100 mL). The combined organic layers were extracted with aq. NaHCO$_3$ (1×100 mL), brine (50 mL), dried (Na$_2$SO$_4$), filtered, concentrated in vacuo to yield a brown solid 9d (1.5 g, 34%) which was used for cyclization. MS: (Electron spray, m/z relative intensity): 585 [(M-PF$_6$)$^+$, 100], 459 (30), 373 (30), 198 (20).

Step D:

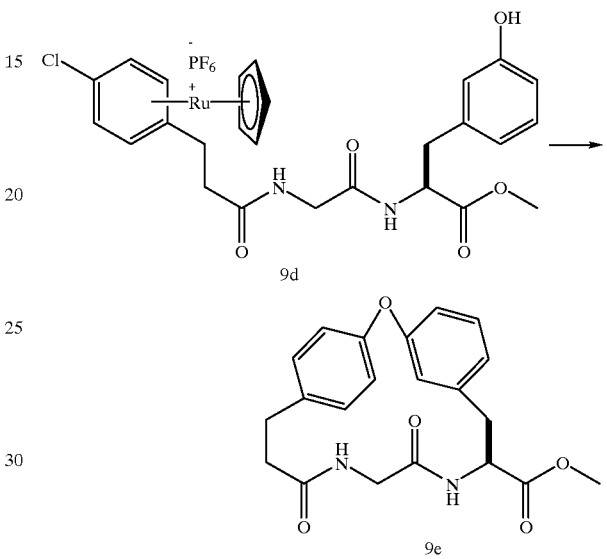

A solution of the ruthenium complex 9d (1.5 g 2.05 mmol) in dry DMF (100 mL) was degassed with dry N$_2$ at rt. and Cs$_2$CO$_3$ (5.0 g, 15 mmol, 7.5 equiv) was added and stirred at rt. for 12 h. The solvent DMF was distilled off and the residue was diluted with water (100 mL) and extracted with CH$_2$Cl$_2$ (3×100 mL). The combined organic layers were extracted with brine (100 mL), dried (Na$_2$SO$_4$), filtered, concentrated in vacuo and dried in vacuum overnight. It was used for photolytic removal of Ru without further purification.

The cyclized compound from the previous step was dissolved in CH$_3$CN (30 mL) and filtered into a quartz tube. The solution was degassed and photolyzed in a Raynot (λ=350 nm) for 48 h. The reaction mixture was concentrated in vacuo and the residue was purified by chromatography (SiO$_2$, EtOAc) to yield a tan colored solid 9e (230 mg, 30%). $^1$H NMR (CDCl$_3$, 400 MHz, δ, ppm) 7.23–7.18 (m, 2H), 7.09–7.01 (m, 3H), 6.76 (dd, 1H, J=2.4, 8.8 Hz), 6.66 (d, 1H, J=7.6 Hz), 6.47 (d, 1H, J=5.6 Hz), 6.17 (s, 1H), 5.64 (s, 1H), 4.69 (q, 1H, J=4.4 Hz), 3.77 (s, 3H), 3.68–3.51 (m, 2H), 3.35 (dd, 1H, J=4.0, 10.8 Hz), 3.05 (dd, 1H, J=5.2, 9.2 Hz), 2.96–2.92 (m, 2H), 2.61–2.56 (m, 1H), 2.30–2.29 (m, 1H); $^{13}$C NMR : (CDCl$_3$, 100 MHz, δ ppm) 172.3, 171.4, 168.1, 159.9, 155.4, 137.6, 136.4, 131.0, 130.0, 129.5, 123.3, 122.4, 121.0, 117.7, 117.1, 53.6, 53.0, 43.6, 39.9, 36.1, 32.3. MS: (Electron spray, m/z relative intensity): 383 [(M+1)$^+$, 100], 279 (20)

Step E:
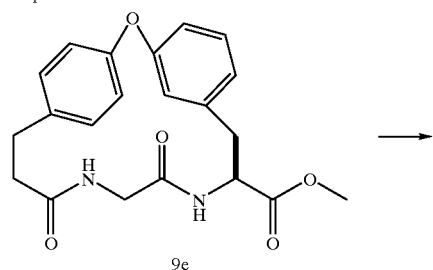
9e
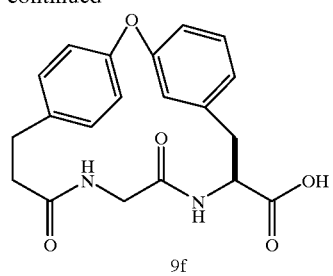
9f
A solution of cyclic compound 9e (150 mg, 0.4 mmol) in THF (4.0 mL), H₂O (4.0 mL) was stirred at rt with LiOH.H₂O (41.0 mg, 1.0 mmol, 2.5 equiv) for 3 h. The reaction mixture was acidified with conc. HCl (2.0 mL) and concentrated in vacuo. The solid 9f was dried in vacuo and used for further coupling without further purification.
Step F:
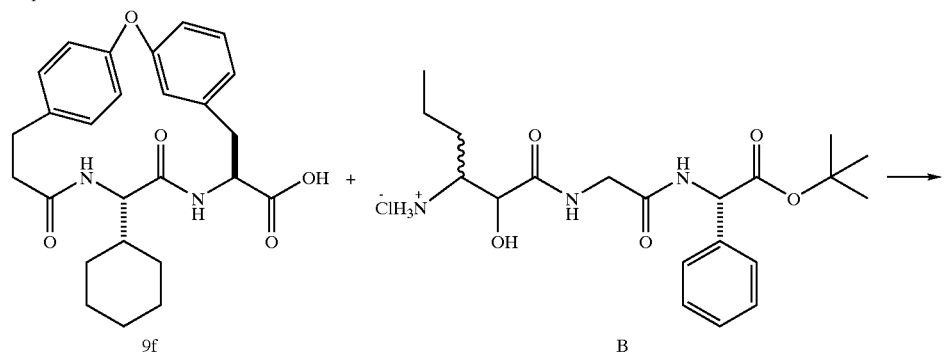
9f + B
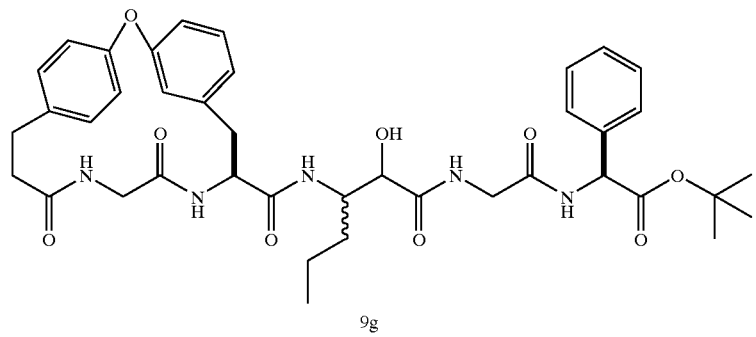
9g A solution of the hydrolyzed acid 9f in dry DMF (4.0 mL) and CH$_2$Cl$_2$ (4.0 mL) was treated with HOOBt (103 mg, 0.58 mmol, 1.5 equiv) and cooled to 0° C. and Hünigs base (206 mg, 1.60 mmol, 4.0 equiv, 295 μL) was added. To this mixture was added EDCl (112 mg, 0.58 mmol, 1.5 equiv) and the reaction mixture was stirred at 0° C. for 0.5 h and treated with the amine hydrochloride B (206 mg, 0.48 mmol, 1.2 equiv.). The reaction mixture was stored in freezer for 48 h and concentrated in vacuo to remove DMF and CH$_2$Cl$_2$. The residue was diluted with aq. HCl (2M) and extracted with CH$_2$Cl$_2$ (3×50 mL) The combined organic layer was extracted with aq. HCl (1M, 3×50 mL), aq. NaOH (2M) brine (100 mL), dried (Na$_2$SO$_4$) and concentrated in vacuo. The residue 9g (200 mg) was oxidized without further purification.

Step G:

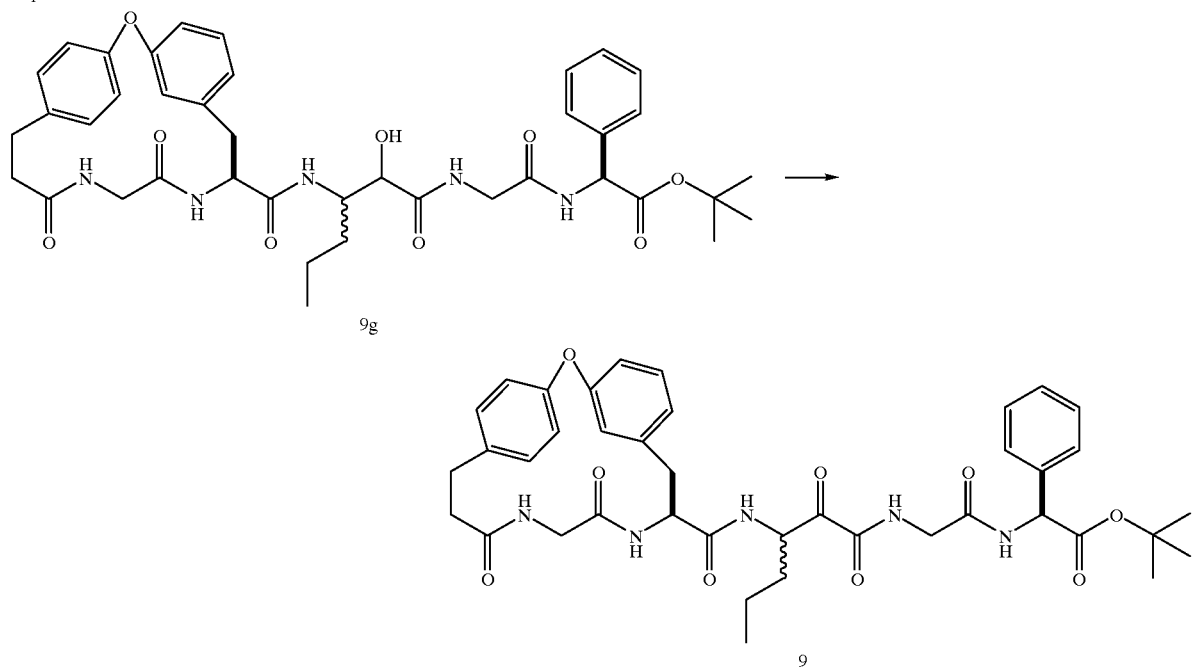

A solution of alcohol 9g (200 mg, 0.27 mmol) in CH$_2$Cl$_2$ (3.0 mL) was treated with Dess-Martin reagent (342 mg, 0.81 mmol, 3.0 equiv.). The reaction mixture was stirred at rt for 3 h and diluted with aq. NaHCO$_3$ and aq. Na$_2$S$_2$O$_3$. The reaction mixture was stirred at rt for 20 min and the reaction mixture was extracted with CH$_2$Cl$_2$ (3×30 mL). The combined organic layers were extracted with brine (50 mL), dried (Na$_2$SO$_4$), filtered concentrated in vacuo and the residue was purified by chromatography (SiO$_2$, CH$_3$OH (2M NH$_3$)/CH$_2$C$_2$ 1:19) to yield ketoamide 9 (100 mg, 50%) of a colorless solid. MS: (Electron spray, m/z relative intensity): 742 ([M+]$^+$, 100), 686 (80).

Example 10
Preparation of Compound of Formula 10:

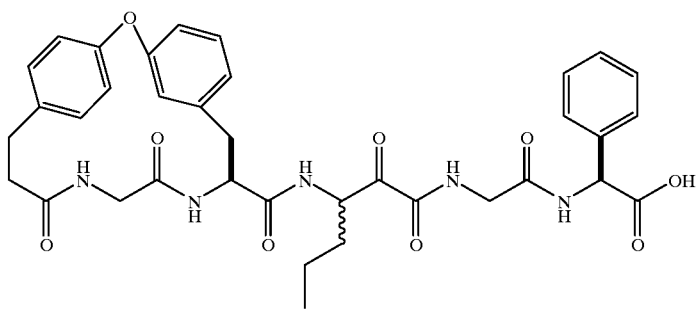

Step A:

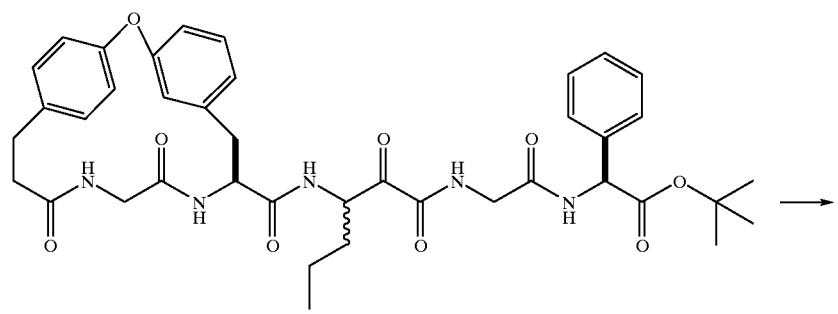

9

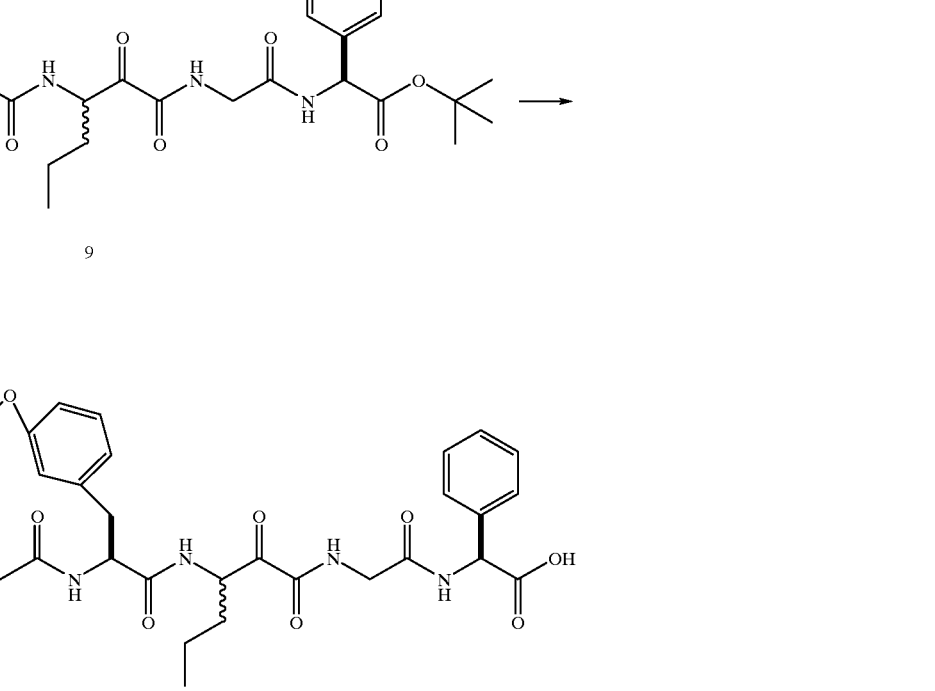

10

A solution of tert-butyl ester 9 (100 mg, 0.13 mmol) in dry $CH_2Cl_2$ (4.0 mL) was treated with TFA (4.0 mL) and stirred at rt. for 5 h. The reaction mixture was concentrated in vacuo and the residue was repeatedly dissolved in toluene/$CH_2Cl_2$ and concentrated in vacuo several times to yield a fine colorless solid 10. MS (FAB, NBA/DMSO, m/z relative intensity), 686 [(M+1)$^+$, 40], 460 (20), 307 (100), 289 (60); HRMS calcd. for $C_{36}H_{40}N_5O_9$ (M+1)$^+$: 686.2825; found: 686.2840.

Example 11

Preparation of Compound of Formula 11:

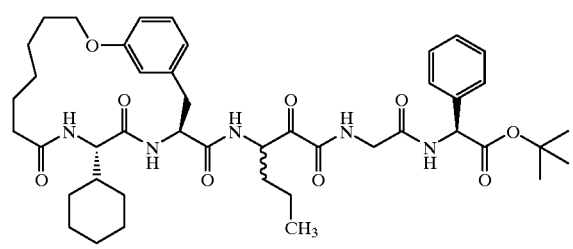

11

Step A:

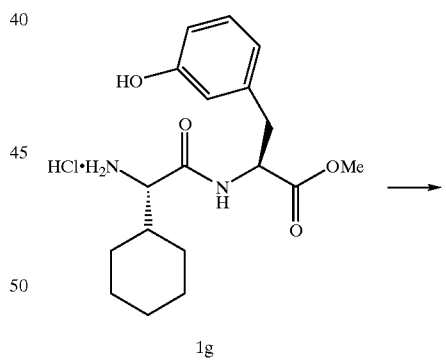

1g

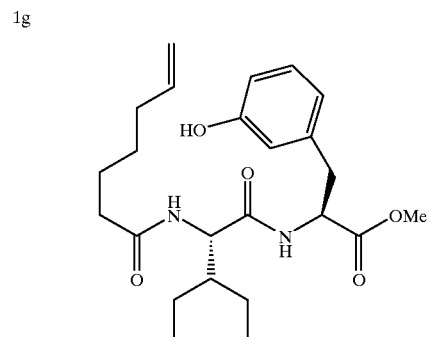

11a

To a solution of amine hydrochloride 1g (1.20 g, 3.23 mmol), 6-heptenoic acid (0.610 g, 4.68 mmol), HOOBt (0.765 g, 4.69 mmol) and EDCl (1.07 g, 5.58 mmol) in anhydrous DMF (50 mL) and CH$_2$Cl$_2$ (50 mL) at −20° C. was added NMM (1.55 mL, 14.1 mmol). After stirring at this temperature for 30 min, the reaction mixture was kept in a freezer for 18 h. It was then allowed to warm to rt. EtOAc 150 mL), brine (50 mL) and 5% H$_3$PO$_4$ (50 mL) were added. After separation, the organic solution was washed with 5% H$_3$PO$_4$ (80 mL), saturated aqueous sodium bicarbonate solution (2×80 mL), water (80 mL), and brine (80 mL), dried with magnesium sulfate, filtered and concentrated in vacuo. Flash chromatography (2 to 5% MeOH—CH$_2$Cl$_2$) afforded 11a (1.46 g, 3.28 mmol, quant.) as a white solid. $^1$H NMR (400 MHz, d$_6$-DMSO) δ 9.25 (s, 1H), 8.31 (d, J=7.2 Hz, 1H), 7.70 (d, J=9.2 Hz, 1H), 7.05–7.01 (m, 1H), 6.62–6.58 (m, 3H), 5.82–5.72 (m, 1H), 5.02–4.91 (m, 1H), 4.43–4.38 (m, 1H), 4.23–4.19 (m, 1H), 3.55 (s, 3H), 2.93–2.80 (m, 2H), 2.51–1.97 (m, 2H), 1.66–0.86 (m, 15H); $^{13}$C NMR (d$_6$-DMSO, 125 MHz), δ 171.9, 171.8, 171.1, 157.2, 138.6, 138.4, 129.1, 119.5, 115.8, 114.6, 113.5, 56.5, 53.5, 51.6, 36.5, 34.8, 32.8, 29.0, 28.0, 27.8, 25.8, 25.5, 24.8; HRMS, m/z 445.2683 (calcd for C$_{25}$H$_{36}$N$_2$O$_5$: 445.2702, error: 4 ppm).

Then ethanol (4 mL) and pH 7 buffer (8 mL) were added, followed by aqueous 30% H$_2$O$_2$ solution (7.5 mL). After stirred at 0° C. for 20 min, it was warmed to rt and stirred for 2 h. EtOAc (200 mL) and brine (100 mL) were added and layers were separated. Aqueous solution was extracted with EtOAc (2×150 mL). Combined organic solution was dried with magnesium sulfate, filtrated, concentrated in vacuo. Flash chromatography (2 to 5% MeOH—CH$_2$Cl$_2$) afforded 11b (1.05 g, 2.18 mmol, 68%) as a white solid. $^1$H NMR (400 MHz, d$_6$-DMSO) δ 9.25 (s, 1H), 8.30 (d, J=7.2 Hz, 1H), 7.68 (d, J=9.2 Hz, 1H), 7.05–7.01 (m, 1H), 6.62–6.58 (m, 3H), 4.43–4.18 (m, 3H), 3.55 (s, 3H), 3.37–3.33 (m, 2H), 2.93–2.80 (m, 2H), 2.20–2.03 (m, 2H), 1.66–0.87 (m, 19H); $^{13}$C NMR (d$_6$-DMSO, 125 MHz), d 172.1, 171.8, 171.2, 157.2, 138.4, 129.1, 119.5, 115.8, 113.5, 60.7, 56.5, 53.5, 51.7, 36.5, 35.1, 32.6, 32.4, 29.0, 28.5, 28.0, 25.8, 25.6, 25.4, 25.2; HRMS, m/z 463.2813 (calcd for C$_{25}$H$_{36}$N$_2$O$_5$: 463.2808, error: 1 ppm).

Step B:

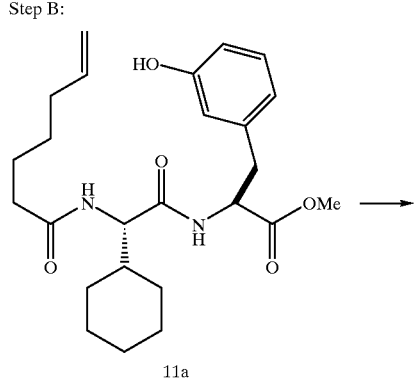

11a

Step C:

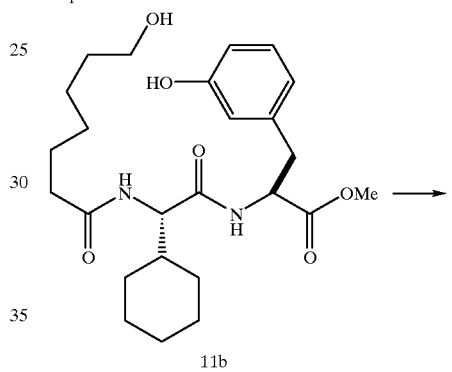

11b

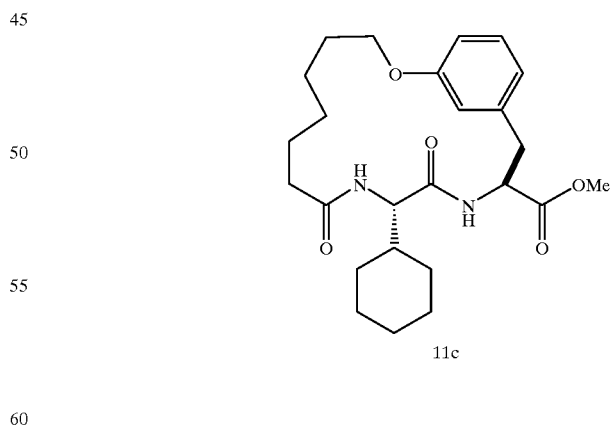

11c

To the solution of 11a (1.46 g, 3.28 mmol) in anhydrous THF (60 mL) under nitrogen at 0° C. was added borane-THF solution (12 mL, 1.0 M, 12 mmol) cautiously. The resulting solution was stirred at 0° C. under nitrogen for 1 h 40 min.

To a solution of phenol alcohol 11b (1.00 g, 2.16 mmol) and tri-n-butylphosphine (1.10 mL, 4.28 mmol) in anhydrous CH$_2$Cl$_2$ (100 mL) and THF (40 mL) at 0° C. was added ADDP (1.08 g, 4.28 mmol). After stirring at 0° C. for 1 h, the solution was warmed to rt and stirred for 3 h under nitrogen. TLC indicated complete consumption of the start ing material. After removal of solvent in vacuo, the residue was partially purified by flash chromatography (0 to 3% MeOH in $CH_2Cl_2$) to afford the macrocycle 11c (650 mg, 1.46 mmol, 68%). $^1$H NMR (400 MHz, $d_6$-DMSO) δ 8.58 (d, J=8.3 Hz, 1H), 7.76 (d, J=9.2 Hz, 1H), 7.18–7.14 (m, 1H), 6.76–6.65 (m, 3H), 4.77–4.71 (m, 1H), 4.32 (t, J=8.5 Hz, 1H), 3.97–3.93 (m, 1H), 3.82–3.78 (m, 1H), 3.67 (s, 3H), 3.18–3.14 (m, 1H), 2.98–2.92 (m, 2H), 2.32–2.25 (m, 1H), 2.02–2.01 (m, 1H), 1.99–0.87 (m, 19H); $^{13}$C NMR ($d_6$-DMSO, 125 MHz), δ 172.1, 171.6, 171.4, 160.1, 158.8, 139.0, 129.1, 121.1, 113.0, 111.9, 66.4, 56.1, 52.0, 50.1, 40.6, 34.9, 34.2, 28.7, 28.3, 26.8, 26.3, 25.9, 25.5, 25.2, 24.2; HRMS, m/z 445.2685 (calcd for $C_{25}H_{36}N_2O_5$: 445.2702, error: 4 ppm).

Step D:

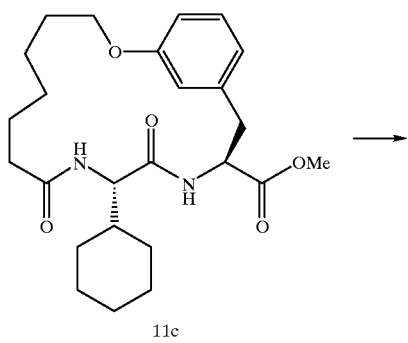

Aqueous lithium hydroxide solution (70 mg, 15 mL $H_2O$, 2.92 mmol) was added to a solution of methyl ester 11c (330 mg, 0.742 mmol) in THF (20 mL) and ethanol (10 mL) at rt. The mixture was stirred at rt for 3 h. The progress of the reaction was monitored by TLC. After the solution was concentrated in vacuo, EtOAc (100 mL), 6 N HCl solution (10 mL) and water (50 mL) were added and the layers were separated. The aqueous solution was extracted with EtOAc (2×80 mL). Organic solutions were combined, dried with magnesium sulfate, filtered and concentrated in vacuo to afford 11d (260 mg, 0.604 mmol, 81%) as a white solid. $^1$H NMR (400 MHz, $d_6$-DMSO) δ 8.43 (d, J=8.3 Hz, 1H), 7.73 (d, J=9.3 Hz, 1H), 7.17–7.13 (m, 1H), 6.77–6.66 (m, 3H), 4.67–4.62 (m, 1H), 4.32–4.28 (m, 1H), 3.98–3.93 (m, 1H), 3.81–3.75 (m, 1H), 3.17–3.13 (m, 1H), 2.97–2.90 (m, 1H), 2.32–2.26 (m, 1H), 2.01–1.97 (m, 1H), 1.67–0.85 (m, 19H); $^{13}$C NMR ($d_6$-DMSO, 125 MHz), δ 173.2, 171.6, 171.3, 158.8, 139.3, 129.0, 121.1, 113.1, 111.9, 66.4, 56.1, 50.8, 35.1, 34.3, 28.8, 28.3, 26.9, 26.3, 25.9, 25.6, 25.5, 25.2, 24.2; HRMS, m/z 431.2564 (calcd for $C_{25}H_{36}N_2O_5$: 431.2546, error: 4 ppm).

Step E:

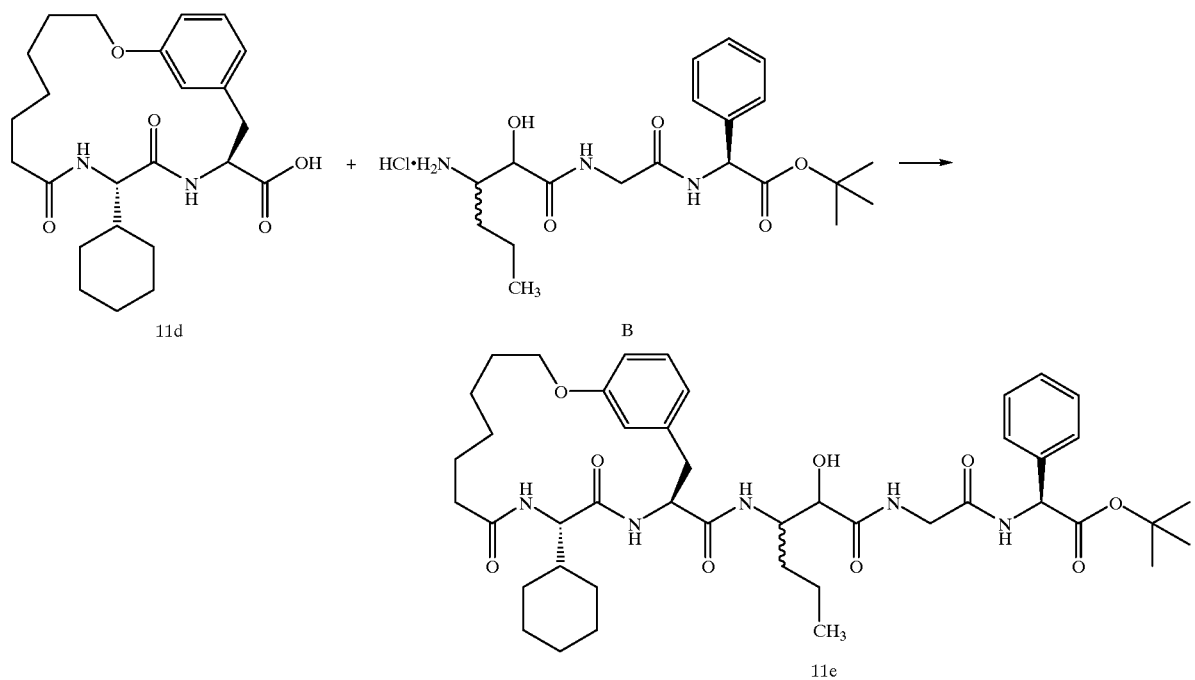

To a solution of acid 11d (0.140 g, 0.325 mmol), amine B (0.140 g, 0.325 mmol), HOOBt (56 mg, 0.343 mmol) and EDCl (75 mg, 0.391 mmol) in anhydrous DMF (40 mL) and $CH_2Cl_2$ (20 mL) at $-20°$ C. was added NMM (0.107 mL, 0.973 mmol). After stirred at this temperature for 30 min, the reaction mixture was kept in a freezer for 18 h. Then EtOAc, brine and 5% $H_3PO_4$ were added. The separated organic solution was washed, successively, with 5% $H_3PO_4$, saturated aqueous sodium bicarbonate solution, water, and brine, dried with magnesium sulfate, filtered and concentrated in vacuo. Flash chromatography (2 to 5% MeOH—$CH_2Cl_2$) afforded 11e as a mixture of diastereomers (0.170 g, 0.211 mmol, 65%) as a white solid, which is used in the next reaction without further purification.

Step F:

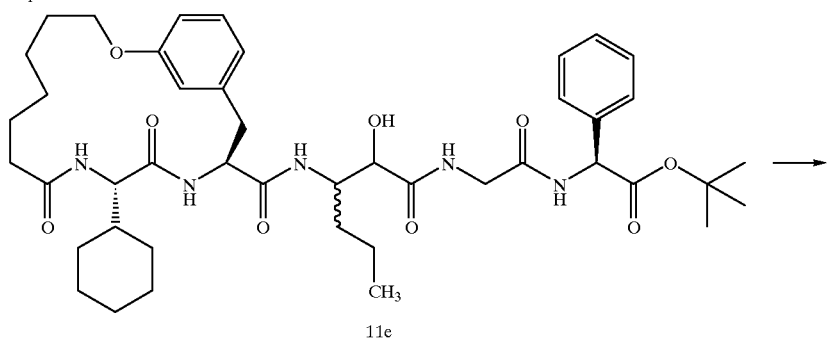

11e

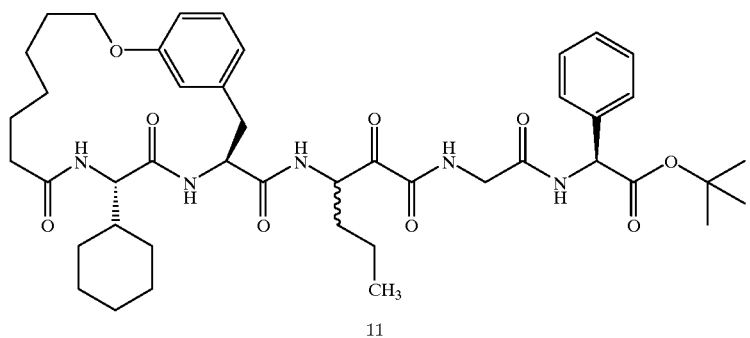

11

To the mixture of hydoxy amide 11e (0.29 g, 0.36 mmol) and Dess-Martin reagent (0.45 g, 1.06 mmol) at rt was added anhydrous $CH_2Cl_2$ (60 mL), DMF (3 mL) and DMSO (3 mL). The resulting solution was vigorously stirred at rt for 2.5 h. More Dess-Martin reagent (300 mg, 0.71 mmol) was added and the reaction mixture was stirred for another hour. Saturated aqueous sodium bicarbonate and sodium bisulfite solutions (40 mL each) were added and the mixture was vigorously stirred for 10 min before EtOAc (200 mL) and water (30 mL) were added and the layers were separated. The organic solution was washed with 5% $H_3PO_4$ solution (2×100 mL) and saturated $NaHCO_3$ solution (100 mL), dried with magnesium sulfate, filtered and concentrated in vacuo. Flash chromatography (1 to 5% MeOH—$CH_2Cl_2$) afforded 11 (100 mg, 0.124 mmol, 35%) as a white solid. $^1$H NMR (400 MHz, $d_6$-DMSO) δ 8.79–8.69 (m, 2H), 8.36–8.16 (m, 2H), 7.72–7.68 (m, 1H), 7.42–7.33 (m, 5H), 7.17–7.13 (m, 1H), 6.77–6.63 (m, 3H), 5.30–5.27 (m, 1H), 5.09–5.04 (m, 1H), 4.85–4.76 (m, 1H), 4.29–4.25 (m, 1H), 3.98–3.74 (m, 1H), 3.02–2.85 (m, 2H), 2.32–2.27 (m, 1H), 2.04–1.96 (m, 1H), 1.72–0.81 (m, 35H); $^{13}$C NMR (d$_6$-DMSO, 125 MHz), δ 196.5, 196.2, 171.65, 171.61, 171.5, 171.14, 171.07, 169.4, 167.6, 160.7, 158.84, 158.79, 139.5, 139.3, 136.6, 136.5, 128.92, 128.90, 128.7, 128.6, 128.1, 127.7, 127.4, 124.9, 121.34, 121.28, 113.1, 112.9, 112.0, 111.9, 81.3, 66.34, 66.30, 56.92, 56.87, 56.3, 56.2, 53.4, 53.3, 51.5, 50.9, 41.5, 41.4, 40.8, 40.7, 36.6, 36.1, 34.4, 34.3, 31.8, 31.6, 30.4, 29.1, 28.9, 28.4, 28.3, 27.5, 26.8, 26.21, 26.17, 25.9, 25.59, 25.55, 25.0, 24.2, 18.74, 18.66, 13.5, 13.4; HRMS, m/z 804.4542 (calcd for $C_{25}H_{36}N_2O_5$: 804.4548, error: 1 ppm).

Example 12

Preparation of Compound of Formula 12:

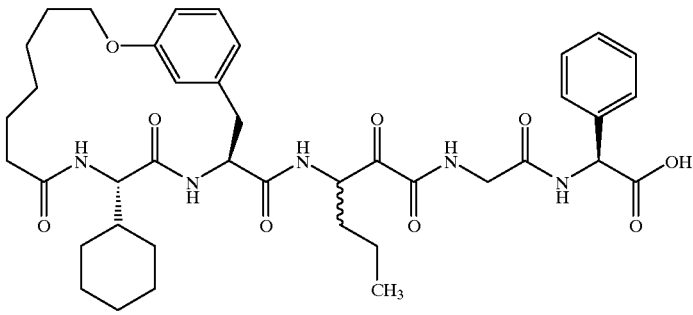

12

Step A:

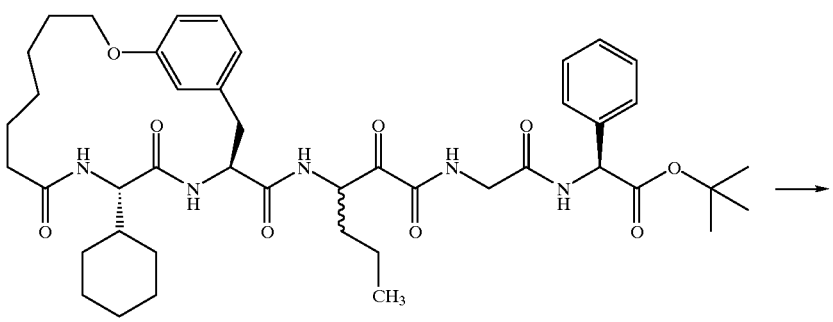

11

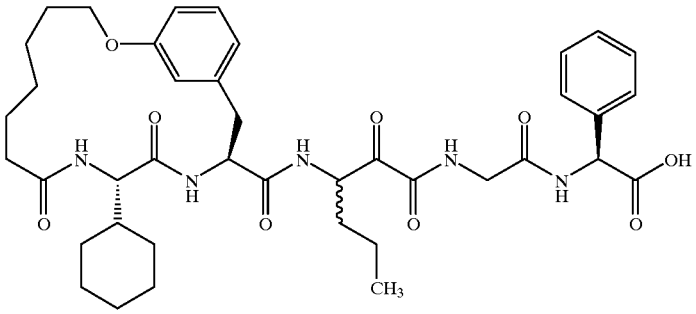

12

A solution of the t-Butyl ester 11 (56.8 mg, 0.0706 mmol) in trifluoroacetic acid (15 mL) and CH$_2$Cl$_2$ (15 mL) was stirred at rt for 4 h. After the volatiles were removed in vacuo, the residue was dissolved in 50% MeOH—CH$_2$Cl$_2$ (3 mL), and concentrated to dryness in vacuo to afford an off-white solid 12 (50 mg, 0.0669 mmol, 95%). $^1$H NMR (400 MHz, d$_6$-DMSO) δ 8.75–8.71 (m, 2H), 8.36–8.16 (m, 2H), 7.72–7.69 (m, 1H), 7.39–7.31 (m, 5H), 7.17–7.13 (m, 1H), 6.76–6.63 (m, 3H), 5.37–5.35 (m, 1H), 5.07–5.04 (m, 1H), 4.85–4.76 (m, 1H), 4.29–4.25 (m, 1H), 3.97–3.74 (m, 4H), 3.02–2.86 (m, 2H), 2.32–2.26 (m, 1H), 2.01–1.97 (m, 1H), 1.70–0.82 (m, 26H); $^{13}$C NMR (d$_6$-DMSO, 125 MHz), δ 196.5, 196.2, 171.63, 171.59, 171.52, 171.48, 171.1, 171.06, 167.4, 160.6, 158.82, 158.78, 153.4, 139.4, 137.1, 137.0128.91, 128.88, 128.7, 128.65, 128.61, 128.5, 128.43, 128.39, 128.33, 128.32, 128.14, 128.12, 128.0, 127.7, 128.7, 127.63, 127.59, 127.5, 127.4, 126.8, 121.3, 115.9, 113.1, 112.9, 112.8, 112.0, 111.9, 111.88, 66.33, 66.29, 56.3, 56.2, 56.17, 53.34, 53.31, 53.27, 51.1, 50.9, 41.5, 40.84, 40.77, 40.7, 40.6, 40.56, 40.53, 40.5, 38.7, 38.6, 38.56, 38.53, 36.6, 36.1, 34.4, 34.3, 31.8, 31.6, 29.4, 29.1, 29.0, e28.9, 28.4, 28.3, 28.2, 26.9, 26.8, 26.79, 26.20, 26.16, 25.88, 25.86, 25.79, 25.75, 25.71, 25.66, 25.57, 25.54, 25.4, 25.0, 24.2, 18.7, 18.6, 13.5, 13.4; HRMS, m/z 748.3947 (calcd for $C_{25}H_{36}N_2O_5$: 748.3922, error: 3 ppm).

Example 13
Preparation of Compound of Formula 13:

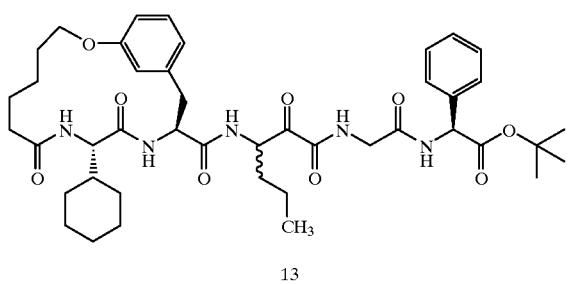

13

Step A:

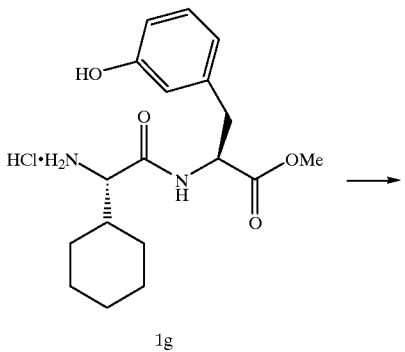

1g

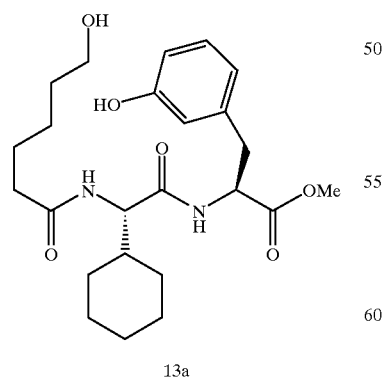

13a

The desired compound 13a was prepared according to the method of Example 11, Step A, except substituting 6-hydroxyhexanoic acid for 6-heptenoic acid (39%).

Step B:

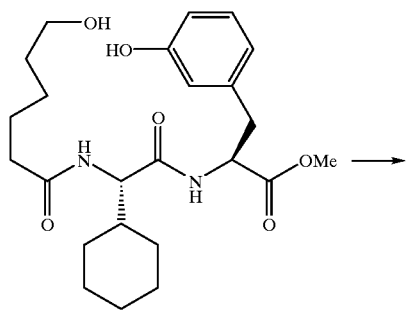

13a

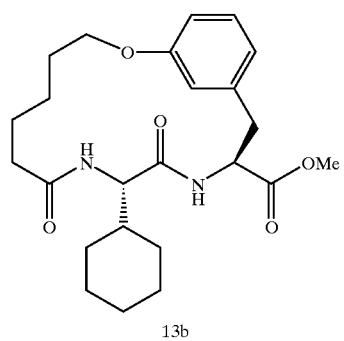

13b

The desired compound 13b was prepared from 13a according to the method of Example 11, Step C in 74% yield.

Step C:

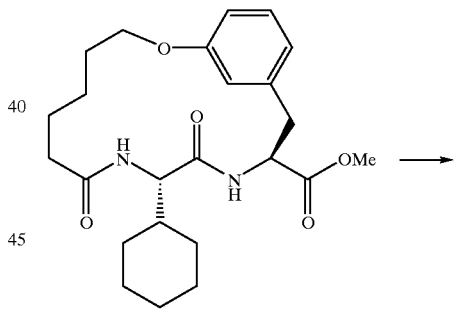

13b

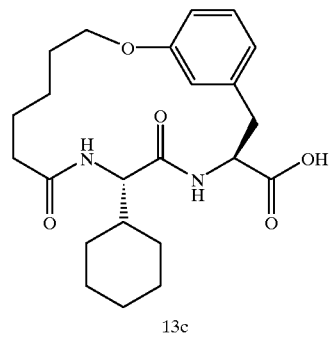

13c

The desired macrocyclic acid 13c was prepared from its corresponding methyl ester 13b according to the method of Example 11, Step D in 88% yield as a white solid.

Step D:
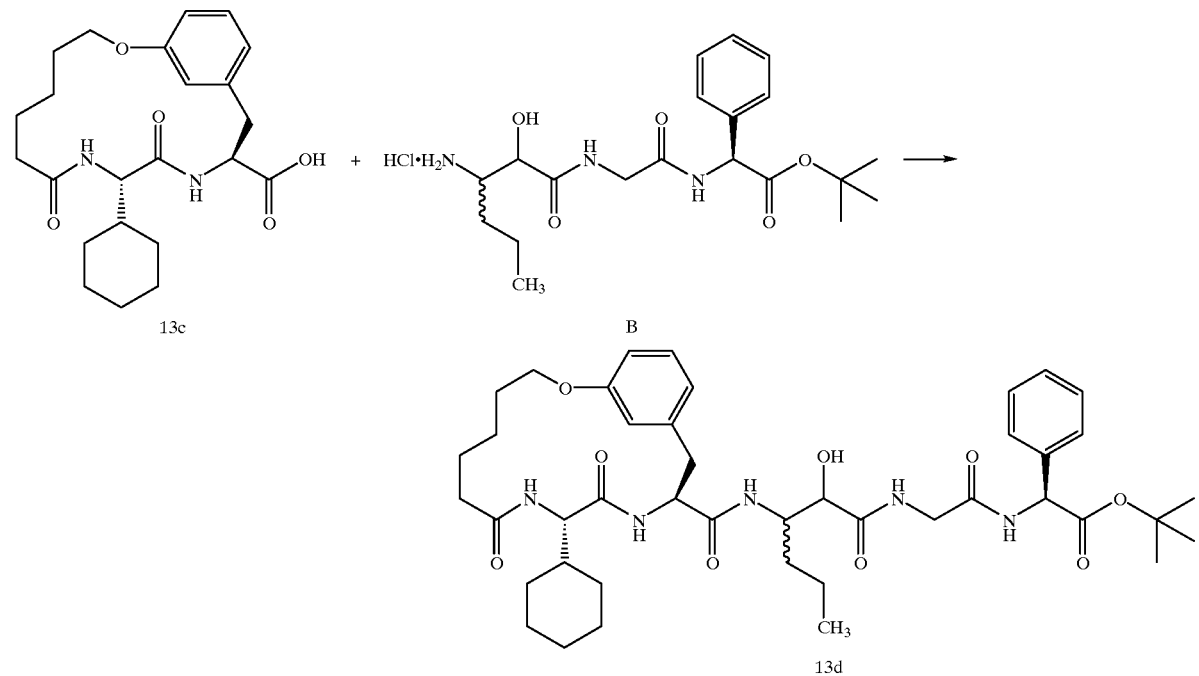
The desired compound 13d was prepared from 13c and B according to the method of Example 11, Step E in 48% yield.
Step E:
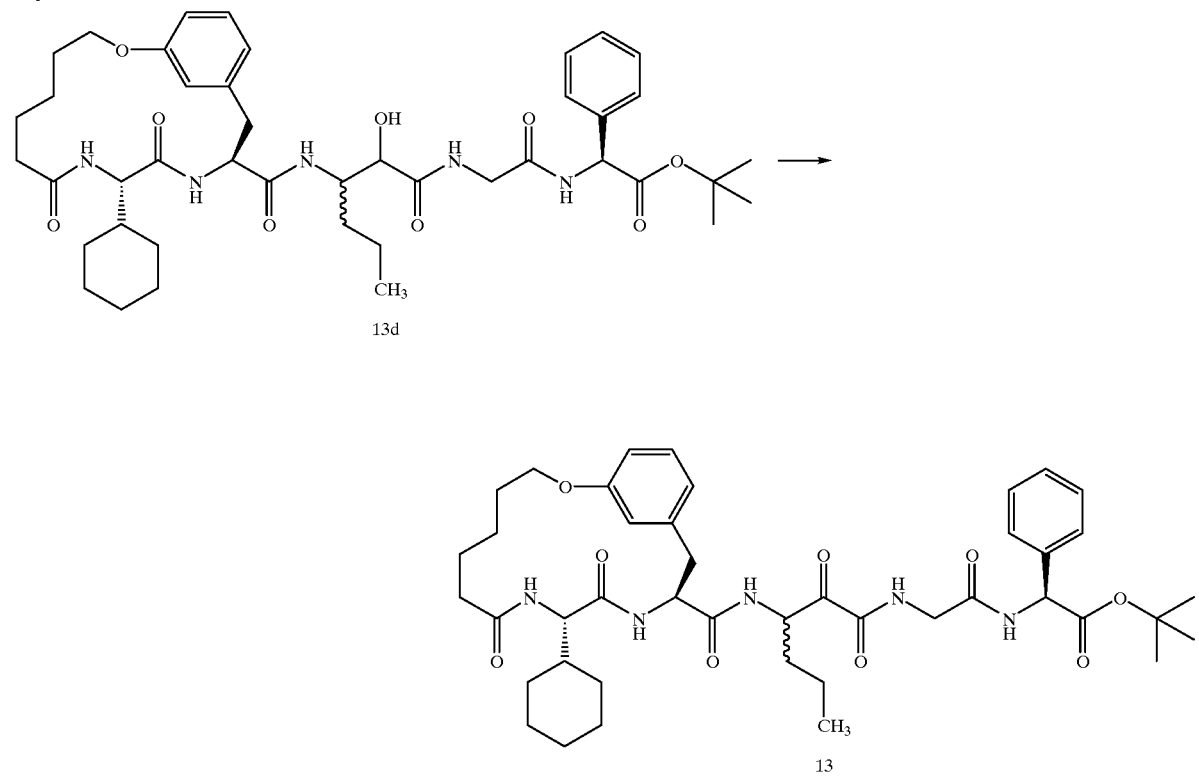

The desired compound 13 was prepared from 13d according to the method of Example 11, Step F in 70% yield.
Example 14
Preparation of Compound of Formula 14:
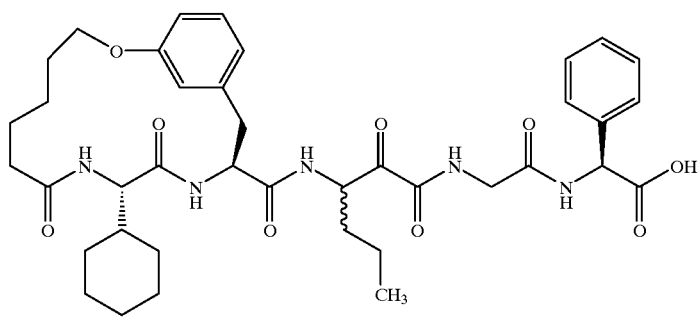
14
Step A:
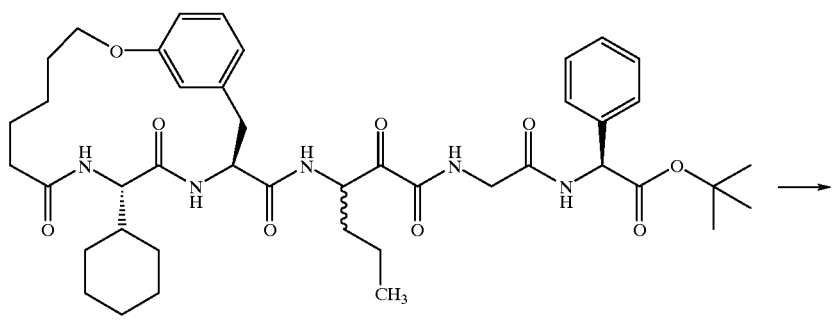
13
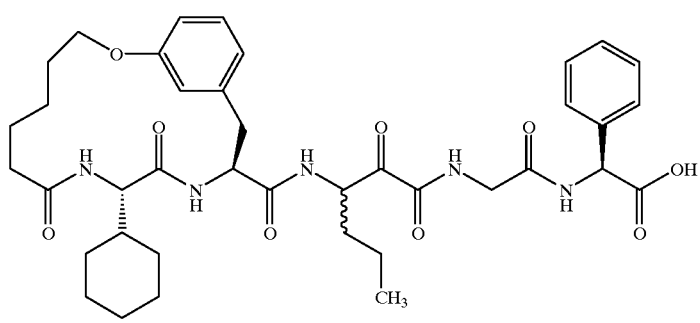
14

The desired compound 14 was prepared from 13 according to the method of Example 12, Step A in quantitative yield.

Example 15

Preparation of Compound of Formula 15:

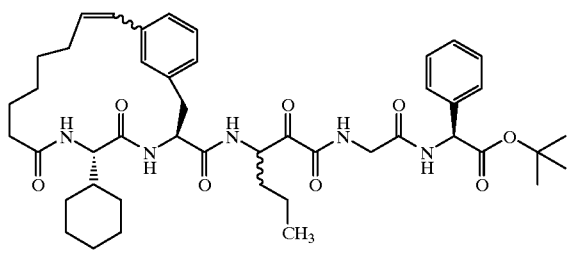

15

Step A:

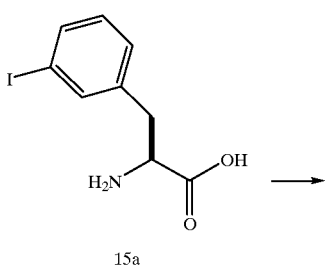

A solution of 3-iodo-phenylanaline 15a, (2.50 g, 8.59 mmol) and concentrated hydrochloric acid (2 mL, 24 mmol) in methanol was heated to reflux for 18 h. Removal of solvents in vacuo afforded a white solid 15b, which was used in Step B without further purification.

Step B:

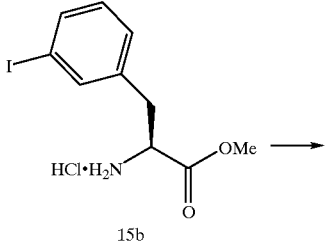

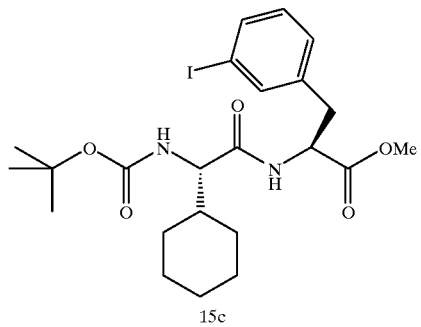

15c

The desired compound 15c was prepared in 84% yield from 15b according to the method of Example 11, Step A. It was used in the next reaction without further purification.

Step C:

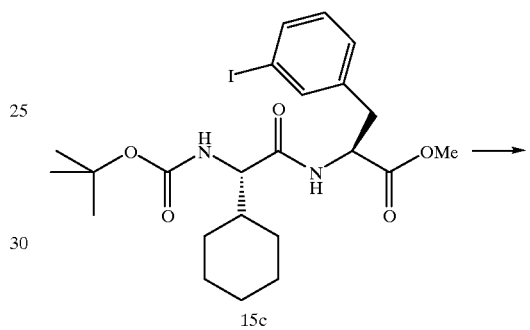

The desired compound 15d was prepared from 15c according to the method of Example 11, Step A (quantitative). It was used in the next reaction without further purification.

Step D:

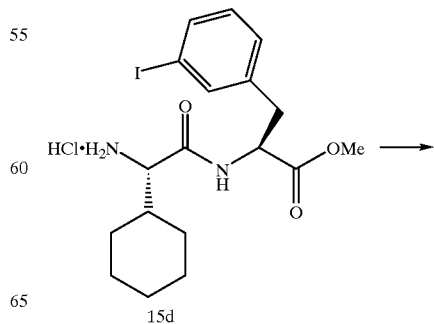

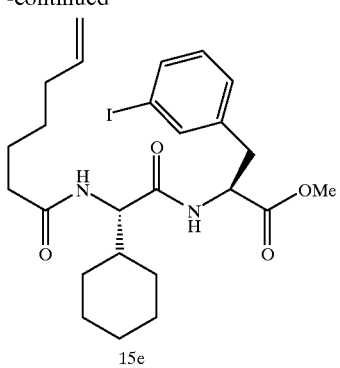

15e

The desired compound 15e was prepared in 68% yield from 15d according to the method of Example 11, Step A. It was used in the next reaction without further purification.

Step E:

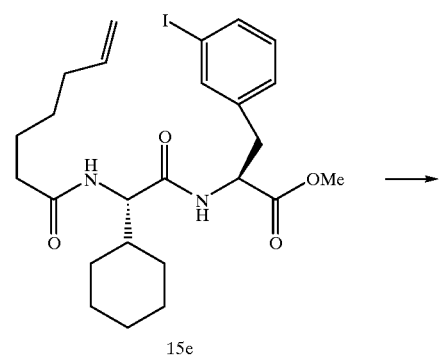

15e

→

15f

A solution of 15e (1.16 g, 2.04 mmol), triethylamine (2.90 mL, 20.6 mmol) in anhydrous acetonitrile (25 mL) and DMF (20 mL) in a thick walled tube was bubbled with Argon for 5 min. To this solution at rt was quickly added tetrakistriphenylphosphine palladium (0) (235 mg, 0.203 mmol). The tube was sealed with Teflon screw cap and heated to 85–90° C. in an oil bath. After stirring for 3 h, it was cooled to rt, opened cautiously and poured onto EtOAc (100 mL). The solution was washed with 5% $H_3PO_4$ (4×50 mL) and water (50 mL). Organic layer was dried with magnesium sulfate, filtrated, concentrated in vacuo. Flash chromatography (1 to 4% MeOH—$CH_2Cl_2$) afforded the macrocycle 15f (330 mg, 0.749 mmol, 37%).

Step F:

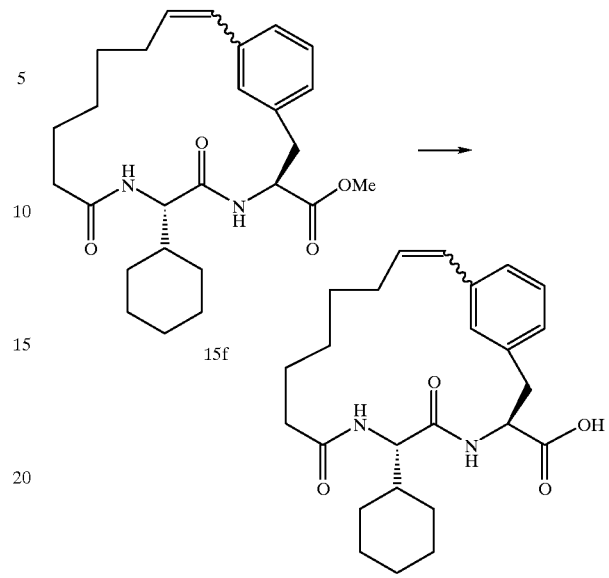

15f

15g

The desired compound 15g was prepared quantitatively from 15f according to the method of Example 11, Step D. It was used in the next reaction without further purification.

Step G:

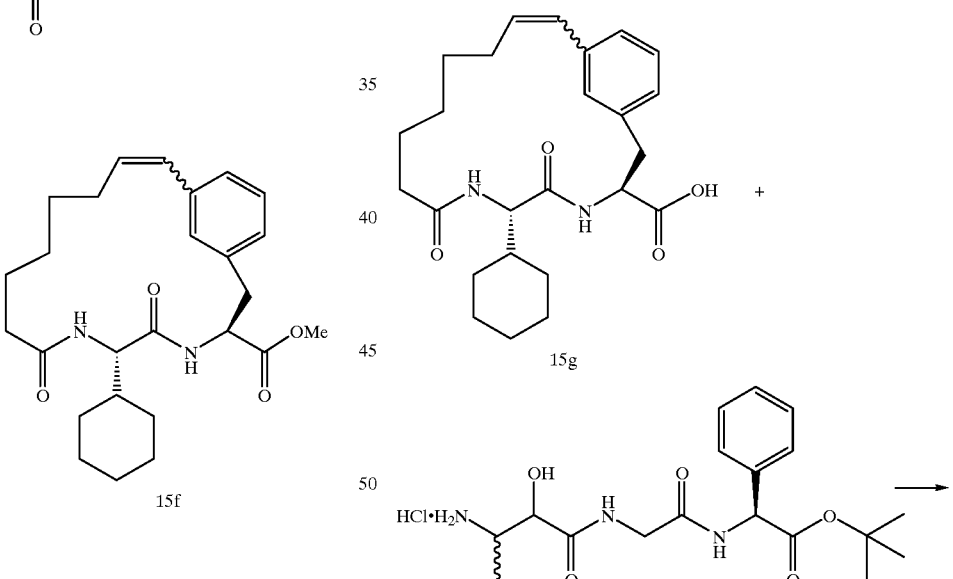

15g  +

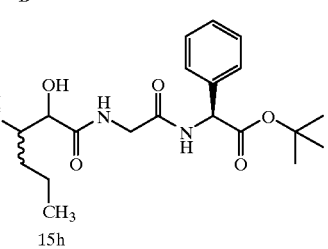

15h

The desired compound 15h was prepared in 77% yield from 15g according to the method of Example 11, Step F. It was used in the next reaction without further purification.
Step H:
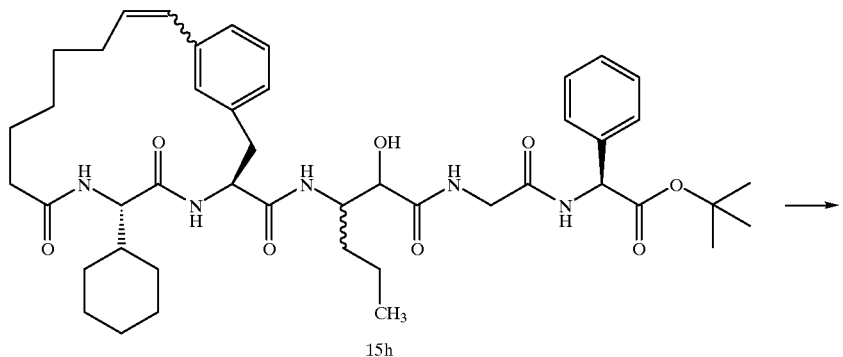
15h
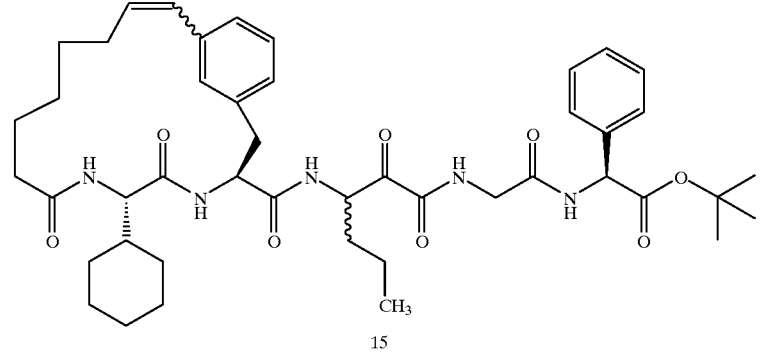
15
The desired compound 15 was prepared in 55% yield from 15 h according to the method of Example 1, Step H.
Example 16
Preparation of Compound of Formula 16:
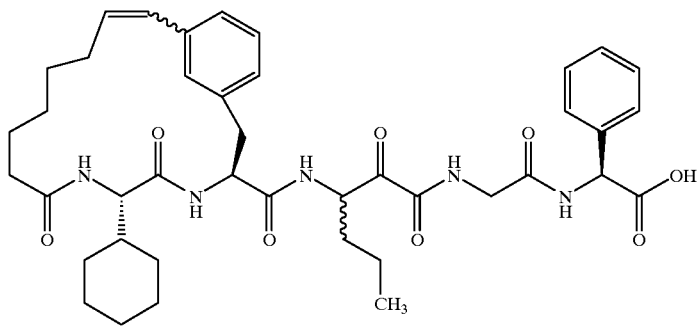
16

Step A:

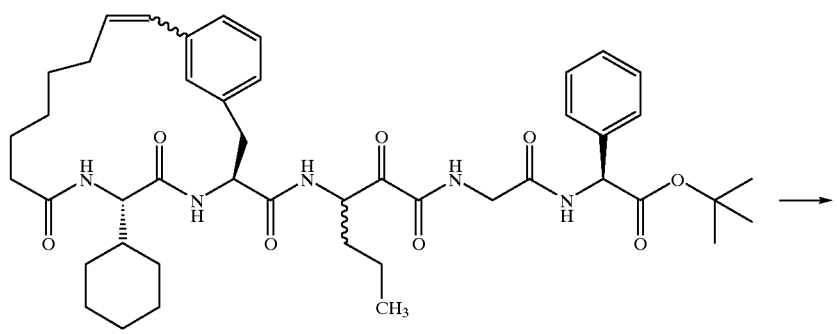

15

16

The desired compound 16 was prepared quantitatively from 15 according to the method of Example 12, Step A.

Example 17
Preparation of Compound of Formula 17:

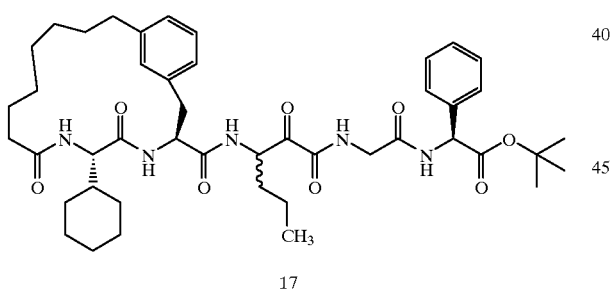

17

Step A:

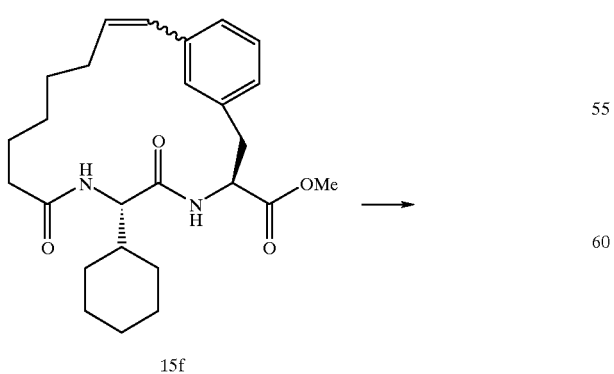

15f

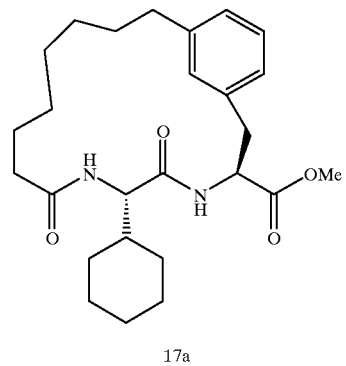

17a

To the solution of 15f (150 mg, 0.340 mmol) in EtOH (10 mL) and EtOAc (5 mL) was added 10% palladium on carbon (20 mg). The suspension was stirred under hydrogen for 8 h during which the reaction progress was monitored by TLC. After filtration through a celite pad, solvents were removed in vacuo to afford the product as a white solid 17a (150 mg, 0.339 mmol, quantitative). It was used in the next reaction without further purification.

Step B:
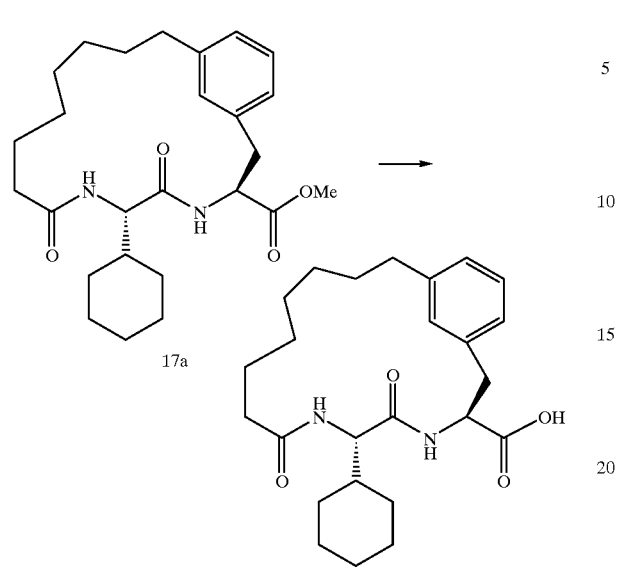
17a
17b
The desired compound 17b was prepared from 17a according to the method of Example 11, Step D. It was used in the next reaction without further purification.
Step C:
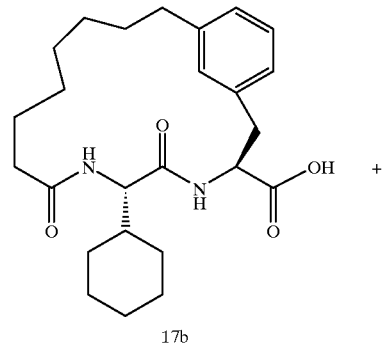
17b
+
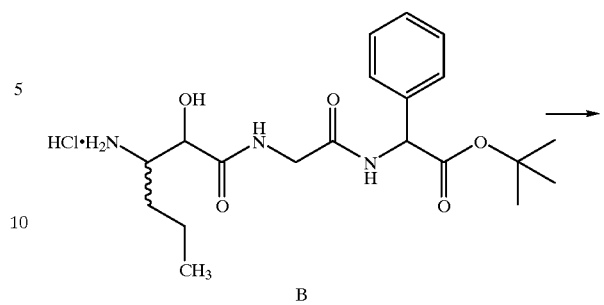
B
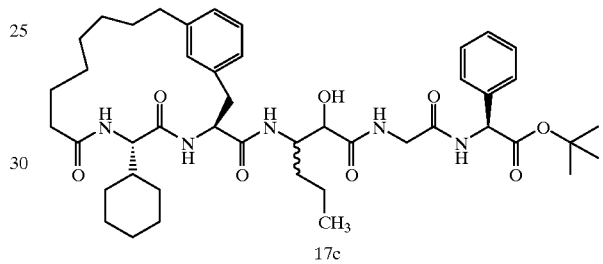
17c
The desired compound 17c was prepared in 73% yield (Steps B and C) from 17b according to the method of Example 11, Step E. It was used in the next reaction without further purification.
Step D:
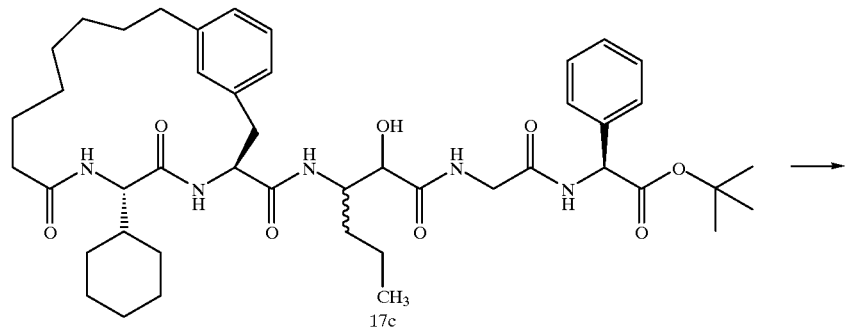
17c

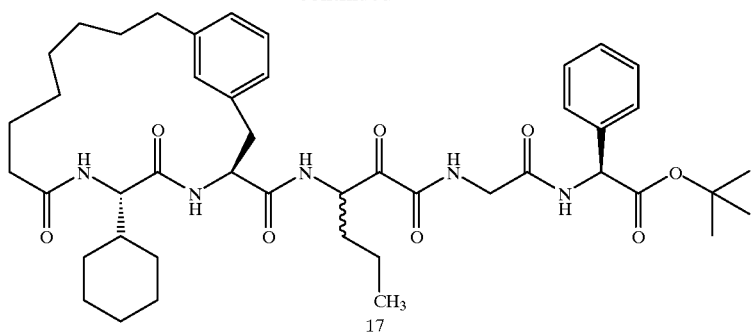
The desired compound 17 was prepared in 46% yield from 17c according to the method of Example 11, Step F.
Example 18
Preparation of Compound of Formula 18:
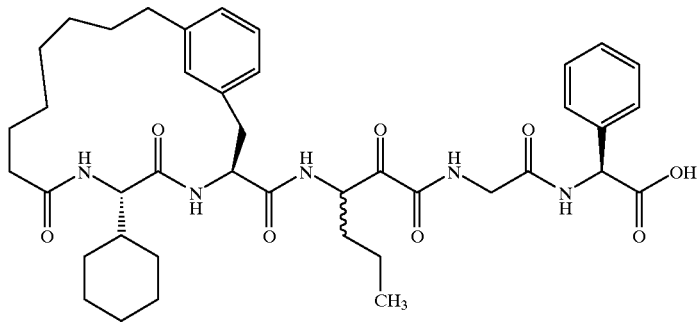
Step A:
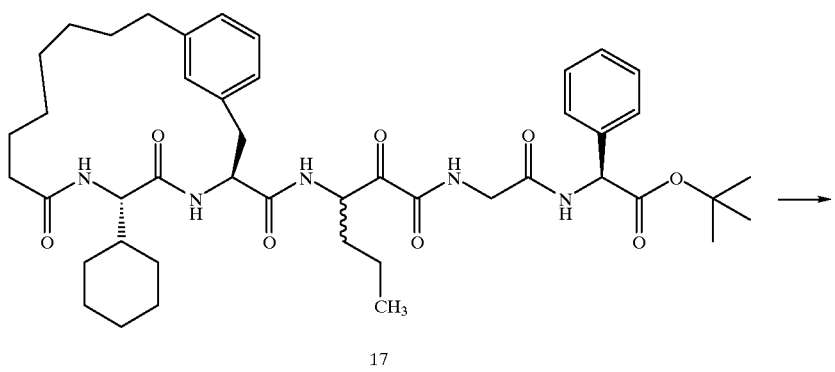
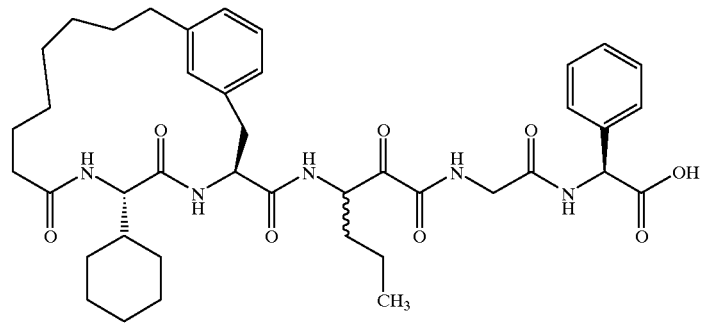

The desired compound 18 was prepared quantitatively from 17 according to the method of Example 12, Step A.

Example 19
Preparation of Compound of Formula 19:

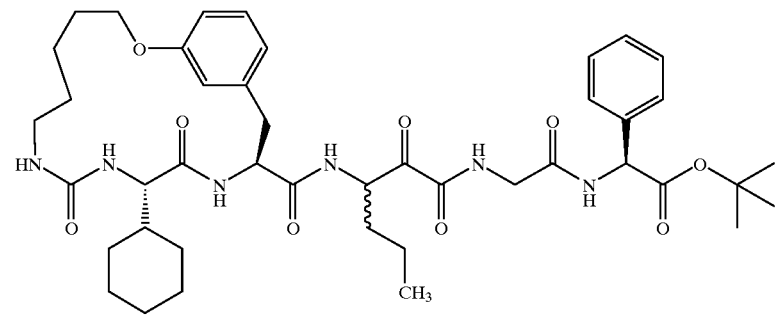

19

Step A:

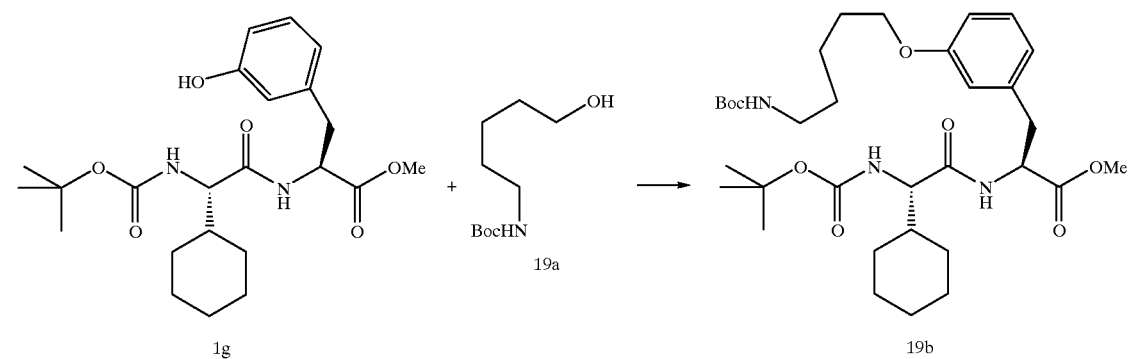

The desired compound 19b was prepared in 64% yield from 1g and 19a according to the method of Example 11, Step C.

Step B:

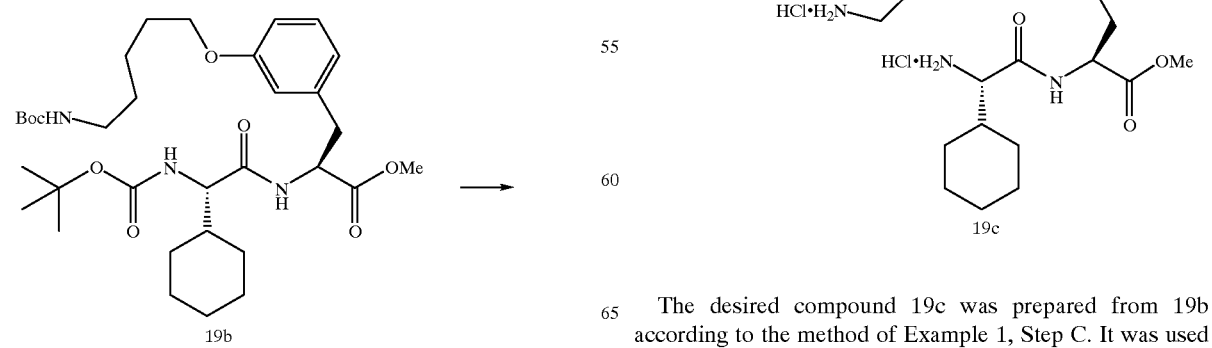

The desired compound 19c was prepared from 19b according to the method of Example 1, Step C. It was used in the next reaction without further purification.

Step C:

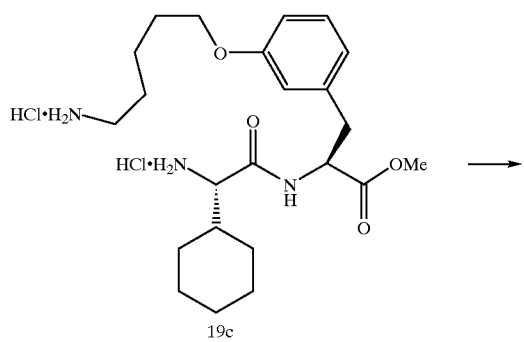

19c

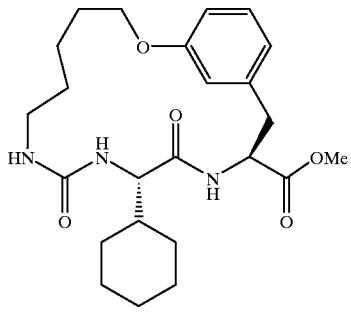

19d

To a suspension of di-amine salt 19c (75 mg, 1.52 mmol) and carbonyl diimidazole (260 mg, 1.60 mmol) in acetonitrile (400 mL) at rt was added triethylamine (0.26 mL, 1.85 mmol). The mixture was stirred for 3 days. Solvent was removed in vacuo. The residue dissolved in EtOAc/THF (100/50 mL) and the solution was washed with 5% $H_3PO_4$, dried with magnesium sulfate, filtered, concentrated in vacuo. Flash chromatography (2 to 10% MeOH—$CH_2Cl_2$) afforded 19d (290 mg, 0.651 mmol, 43%) as a white solid.

Step D:

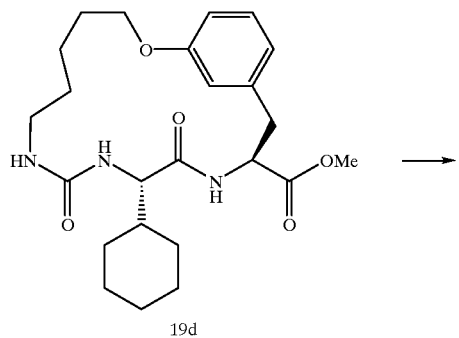

19d

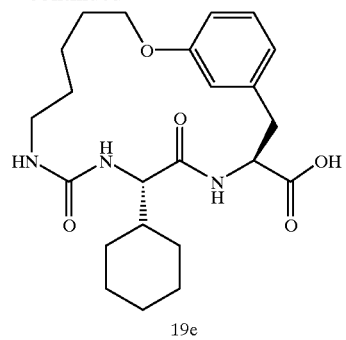

19e

The desired compound 19e was prepared in 97% yield from 19d according to the method of Example 11, Step D. It was used in the next reaction without further purification.

Step E:

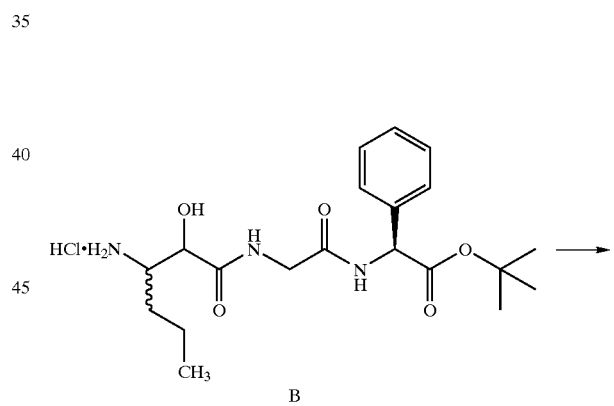

19e

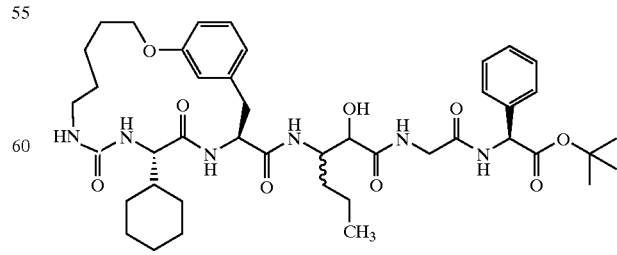

19f

The desired compound 19f was prepared in 66% yield from 19e and B according to the method of Example 11, Step E.
Step F:
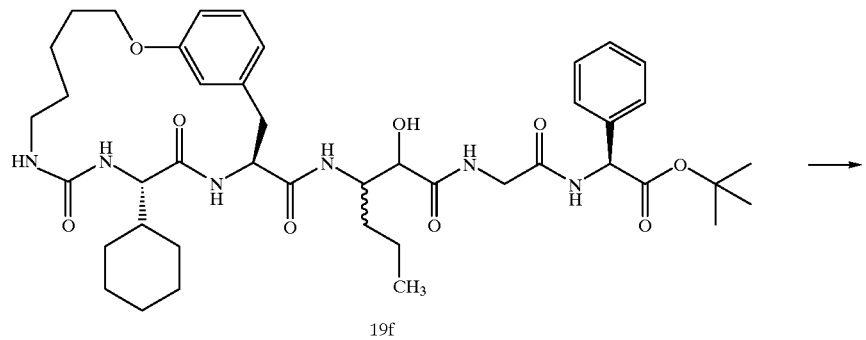
19f
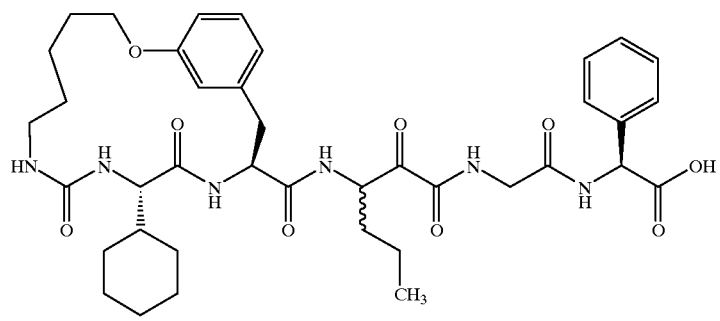
19
The desired compound 19 was prepared in 66% yield from 19f according to the method of Example 11, Step F. Two products were partially separated by flash chromatography (0 to 5% MeOH—CH$_2$Cl$_2$).
Example 20
Preparation of Compound of Formula 20:
20

Step A:
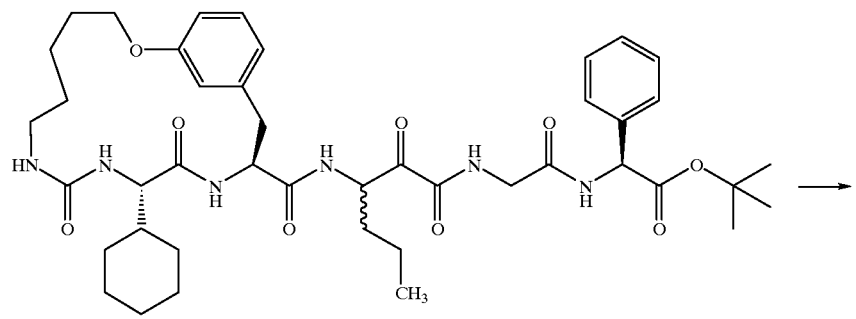
19
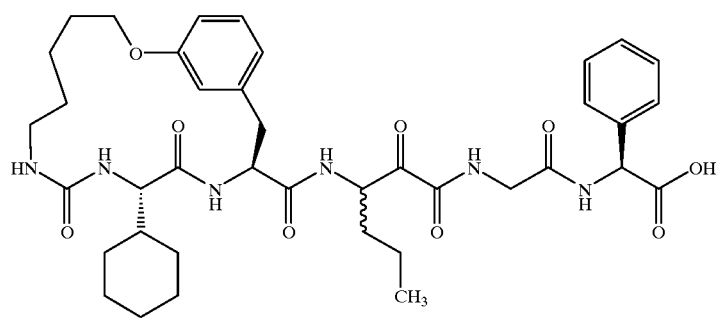
20
The desired compound 20 was prepared from 19 according to the method of Example 12, Step A.
Example 21
Preparation of Compound of Formula 21:
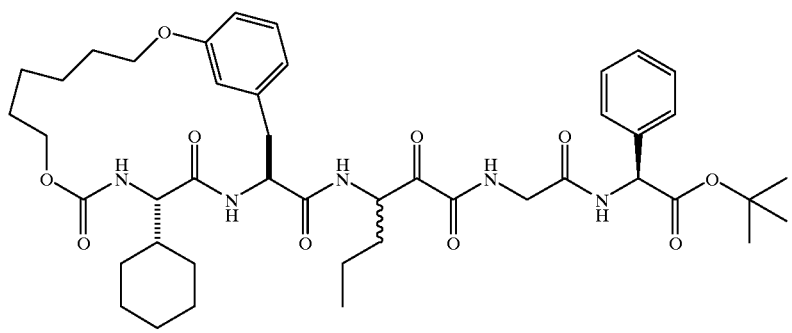
21
Step A:
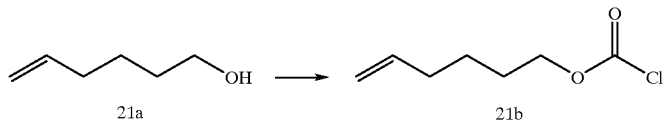

A solution of 5-hexene-1-ol 21a (10 g, 50 mmol) in diethylether (100 mL) was treated with triethylamine (10.1 g, 100 mmol, 2.0 equiv) and cooled to 0° C. A solution of phosgene in benzene (20%, 100 mL, 20 g, 200 mmol, 4.0 equiv.) was added dropwise and the reaction mixture was stirred at rt for 12 h. The triethylamine hydrochloride separating out was filtered and the filtrate was concentrated in vacuo. The residue 21b was used directly for further studies without purification.

Step B:

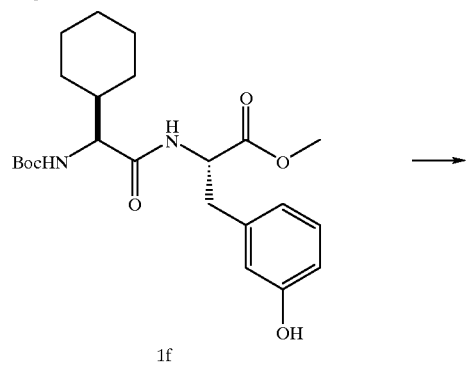

1f

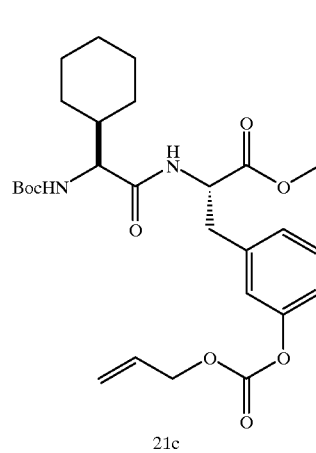

21c

A solution of 1f (8.0 g, 18.43 mmol) in CH$_2$Cl$_2$ (100 mL) was treated with triethylamine (2.43 g, 24.0 mmol, 1.3 equiv). The reaction mixture was cooled to −78° C. and allychloroformate (2.9 g, 24 mmol, 1.3 equiv.) was added dropwise. The reaction mixture was stirred at rt for 12 h and the reaction mixture was diluted with H$_2$O (100 mL) and aq. HCl (2M, 200 mL). The aq. layer was extracted with EtOAc (3×200 mL). The combined EtOAc layer were extracted with brine, dried (Na$_2$SO$_4$), filtered concentrate in vacuo and the residue 21c was directly used for Boc deprotection. $^1$H NMR (CHCl$_3$, 300 MHz, δ, ppm) 7.29 (t, 1H, J=6.0 Hz), 7.06–6.98 (m, 3H), 6.41 (d, 1H, J=5.4 Hz), 6.05–5.95 (m, 1H), 5.42 (dd, 1H, J=1.2, 13.2), 5.31 (dd, 1H, J=1.2, 13.2), 5.10 (d, 1H, J=6.6 Hz), 4.91–4.87 (q, 1H), 4.74 (d, 1H, J=4.5 Hz), 3.95–3.92 (m, 1H), 3.70 (s, 3H), 3.12 (d, 1H J=4.2 Hz),1.81–1.51 (m, 6H), 1.43 (s, 9H), 1.21–0.91 (m, 6H).

Step C:

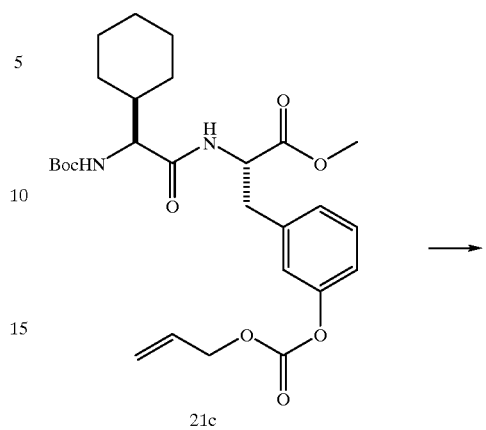

21c

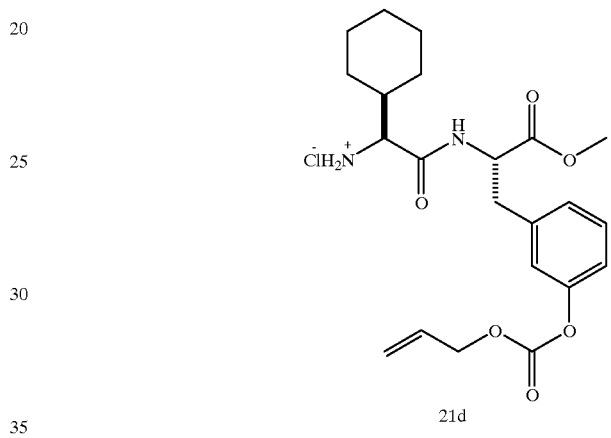

21d

A solution of 21c (1.5 g) in HCl (4M in dioxane, 100 mL) was stirred at rt for 3 h. The disappearance of the starting material was followed by TLC and once the starting material disappeared the reaction mixture was concentrated in vacuo and the residue 21d was dried in pump. It was used for coupling without further purification.

Step D:

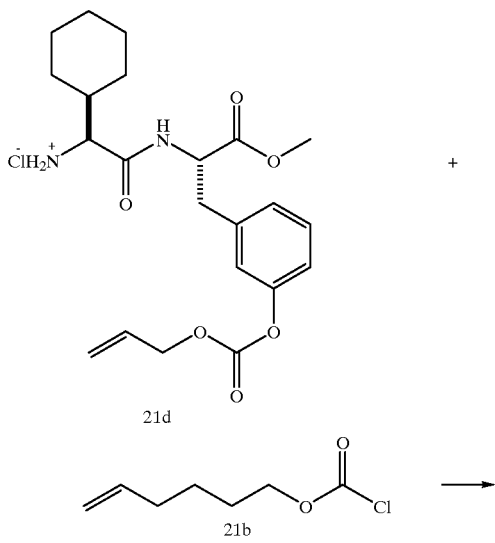

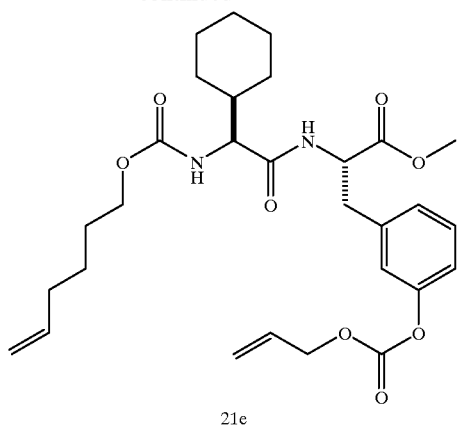

21e

A solution of the aminehydrochloride 21d (4.0 g, 8.9 mmol) in CH$_2$Cl$_2$ (50 mL) was treated with triethylamine (2.73 g, 27 mmol, 3.0 equiv, 3.8 mL) and cooled to −78° C. A solution of chloroformate 21b (2.3 g, 13.3 mmol, 1.5 equiv) in CH$_2$Cl$_2$ (30 mL) was added dropwise. The reaction mixture was stirred overnight at rt and diluted with aq. HCl (1M, 150 mL). The aqueous layer was extracted with EtOAc (3×100 mL). The combined ethyl acetate layers were extracted with H$_2$O (100 mL), brine (100 mL), dried (Na$_2$SO$_4$) filtered concentrated in vacuo and the residue was purified by chromatography (SiO$_2$, EtOAc/Hexanes 3:7) to yield 21e as colorless solid (5 g, 80%).

Step E:

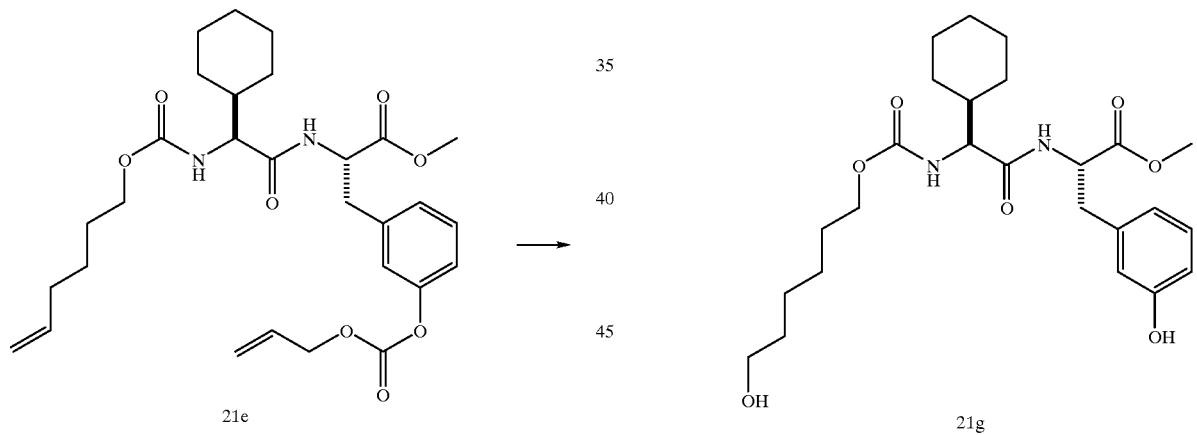

21e

21f

A solution of alloc-protected compound 21e (4.0 g, 7.2 mmol) in dry THF (60.0 mL) was treated with dimedione (2.01 g, 14.4 mmol, 2.0 equiv.), Pd(PPh$_3$)$_4$ (830 mg, 0.71 mmol, 10 mol %) at 0° C. and stirred at rt for 1 h. The reaction mixture was concentrated in vacuo and the residue was purified by chromatography (SiO$_2$, EtOAc/Hexanes, 3:7) to yield a deprotected alcohol 21f as a colorless solid (2.7 g, 79%) H NMR (CDCl$_3$, 300 MHz, δ ppm) 7.44 (bs, 1H), 7.09 (s, 1H, J=6.0 Hz), 6.75–6.72 (m, 2H), 6.58–6.48 (m, 2H), 5.81–5.71 (m, 1H), 5.55 (d, 1H, J=7.2 Hz, 4.98 (ddd, 1H, J=1.5, 1.2, 9 Hz), 4.92 (dd, 1H, J=4.5, 0.9 Hz), 4.88–4.83 (m, 1H), 4.12–3.97 (m, 1H), 3.71 (s, 3H), 3.09–2.98 (m, 2H), 2.08–2.03 (m, 2H), 1.722–1.40 (m, 10H), 1.24–0.94(m, 5H); $^{13}$C NMR (100 MHz, δ) 171.6, 157.3, 156.6, 138.3, 136.6, 129.8, 123.5, 120.6, 117.0, 114.9, 114.6, 65.7, 60.1, 53.2, 52.5, 40.4, 37.1, 33.3, 29.6, 28.6, 28.3, 26.0, 25.9, 25.1;.CHN: calcd for C$_{25}$H$_{36}$N$_2$O$_6$: C=65.20% H=7.88% N=6.08%; Found: C=64.90% H=7.98% N=6.01%.

Step F:

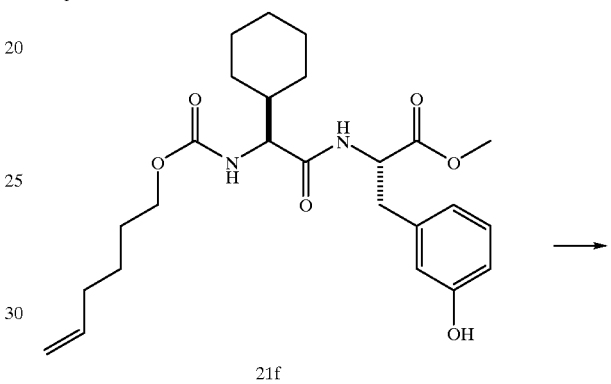

21f

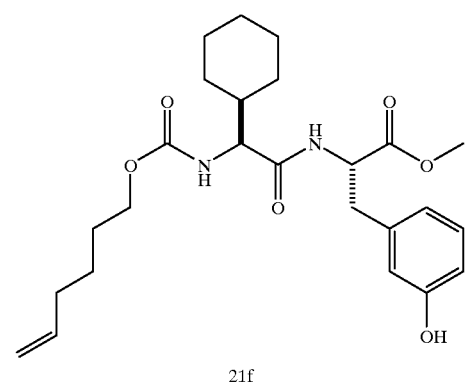

21g

A solution of alkene 21f (650 mg, 1.4 mmol) in anhydrous THF (5.2 mL) was cooled to 0° C. and treated with BH$_3$.THF (1M soln in THF, 4.2 mL, 4.2 mmol, 3.0 equiv.) The reaction mixture was stirred at rt for 2 h and EtOH (2.0 mL) was added carefully with the evolution of hydrogen gas. After the H$_2$ evolution was complete the reaction mixture was treated with pH 7 buffer and treated with aq. H$_2$O$_2$ (30%, 5.0 mL) at 0° C. The ice bath was removed and the mixture was stirred at rt for 3–4 h. The reaction mixture was extracted with EtOAc (3×100 mL). The combined organic layers were extracted with H$_2$O, brine, dried (MgSO$_4$), filtered, concentrated in vacuo and the residue was purified by chromatography (SiO$_2$, EtOAc/Hexanes 3:7) to yield hydroborated product as a colorless solid 21 g (400 mg, 60%) [a]$_D$ 86.4 (c 0.3 CHCl$_3$, 25° C.); $^1$H NMR (CDCl$_3$, 400 MHz, δ) 7.26 (s, 1H), 7.08 (t, 1H, J=5.7 Hz), 6.83 (d, 1H, J=6.0 Hz), 6.71 (dd, 1H, J=1.2, 4.5 Hz), 6.57 (bs, 1H), 6.54

(d, 1H, J=5.7 Hz), 5.68 (d, 1H, J=6.9 Hz), 4.85 (dq, 1H, J=4.2, 1.8 Hz), 4.05–3.97 (m, 3H), 3.69 (s, 3H), 3.60 (t, 2H, J=4.8 Hz), 3.08–2.97 (m, 2H), 1.77–1.53 (m, 10H), 1.42 1.25 (m, 4H), 1.24–0.92 (m, 5H); $^{13}$C NMR (CDCl$_3$, 100 MHz, δ) 171.8, 171.8, 157.6, 156.9, 136.9, 130.0, 120.8, 117.0, 114.8, 65.7, 62.7, 60.3, 53.3, 52.7, 40.5, 37.4, 32.5, 29.7, 29.0, 28.8, 26.2, 26.0, 25.6, 25.4 MS (FAB, NBA/DMSO, m/z, relative intensity) 479 ([M+1]$^+$, 100), 296 (40), 196 (25), 156 (25), 136 (25), 112 (20). HRMS calcd. for C$_{25}$H$_{39}$N$_2$O$_7$ (M+1)$^+$: 479.2760; found 479.2757.

Step G:

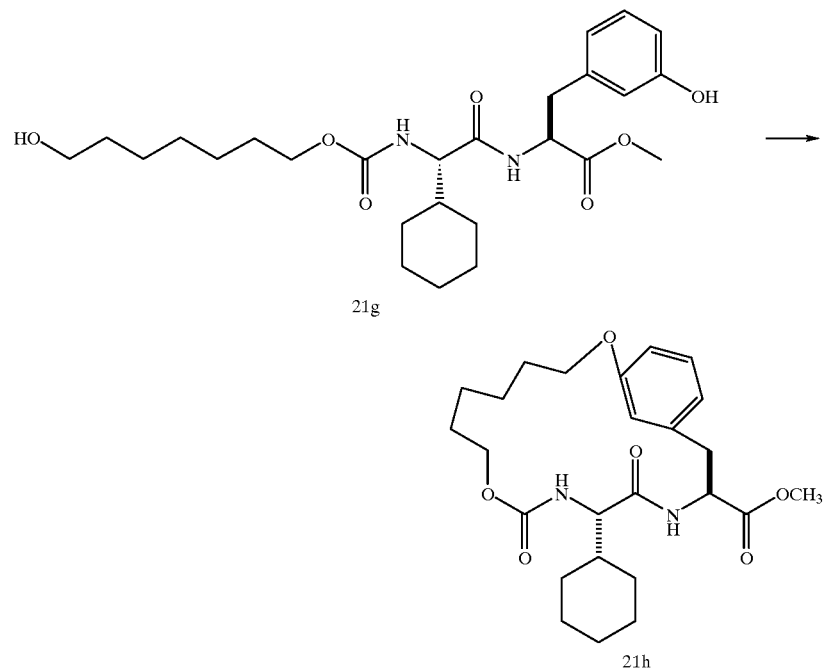

A solution of PPh$_3$ (385 mg, 1,47 mmol, 1.75 equiv)) in CH$_2$Cl$_2$ (10 mL) was treated with the compound 21 g (400 mg, 0.84 mmol) and cooled to 0° C. A solution of DEAD (220 mg, 1.26 mmol, 1.5 equiv.) in CH$_2$Cl$_2$ (10 mL) was added dropwise and stirred at rt for 3 h. The reaction mixture was concentrated in vacuo and the residue was purified by chromatography (SiO$_2$, EtOAc/Hexanes 1:9) to yield cyclic product 21 h as a colorless solid. (110 mg, 25%)

Step H:

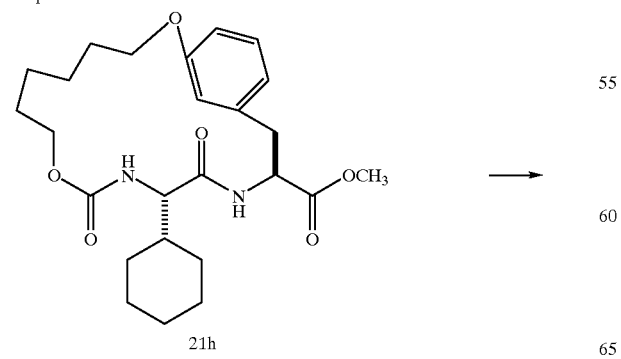

-continued

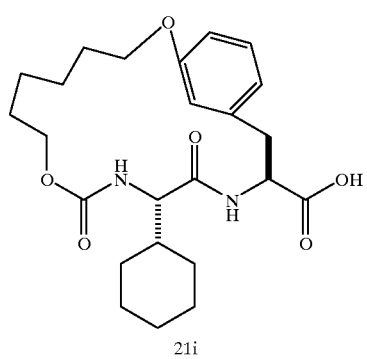

A solution of cyclic carbamate 21 h (200 mg, 0.44 mmol) in dioxane (30 mL), CH$_3$OH (20 mL) and CH$_2$Cl$_2$ (20 mL) was treated with LiOH.H$_2$O (80 mg, 2.0 mmol, 4.5 equiv) and stirred at rt for 4 h. The reaction was concentrated in vacuo and diluted with HCl (4M soln in dioxane, 10 mL) The water was removed by lyophilizer to yield the crystalline acid 21i directly used for coupling.

Step I:

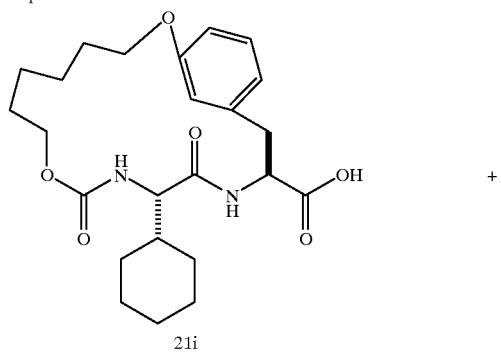

21i

+

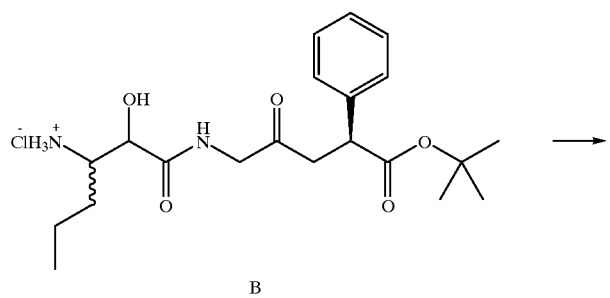

B

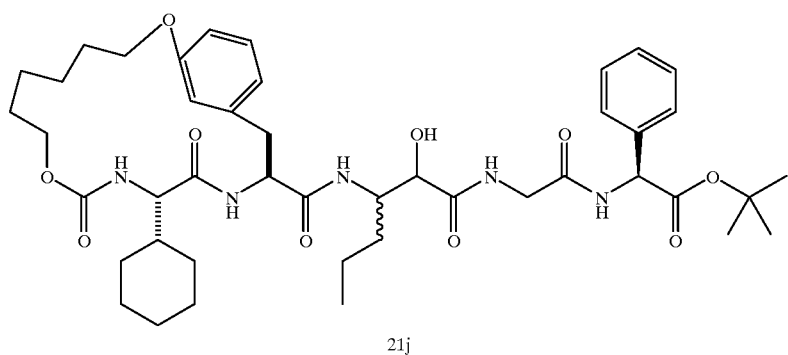

21j

A solution of the hydrolyzed acid 21i (210 mg, 0.47 mmol) in dry DMF (5.0 mL) and $CH_2Cl_2$ (5.0 mL) was treated with HOOBt (125 mg, 0.70 mmol, 1.5 equiv) and cooled to 0° C. and Hünigs base (258 mg, 2.0 mmol, 4.0 equiv, 369 μL) was added. To this mixture was added EDCl (134 mg, 0.70 mmol, 1.5 equiv) and the reaction mixture was stirred at 0° C. for 0.5 h and treated with the amine hydrochloride B (253 mg, 0.58 mmol, 1.25 equiv.). The reaction mixture was stored in freezer for 24 h and concentrated in vacuo to remove DMF and $CH_2Cl_2$. The residue was diluted with aq. HCl (2M, 30 mL) and extracted with $CH_2Cl_2$ (3×50 mL) The combined organic layer was extracted with aq. HCl (2M, 30 mL), aq. NaOH (1M) brine (2×50 mL), dried ($MgSO_4$) and concentrated in vacuo. The residue 21j (220 mg) was oxidized without further purification.

Step J:

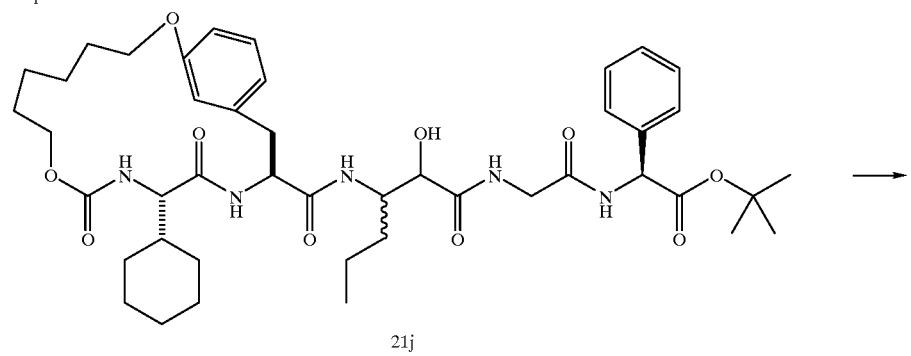

21j

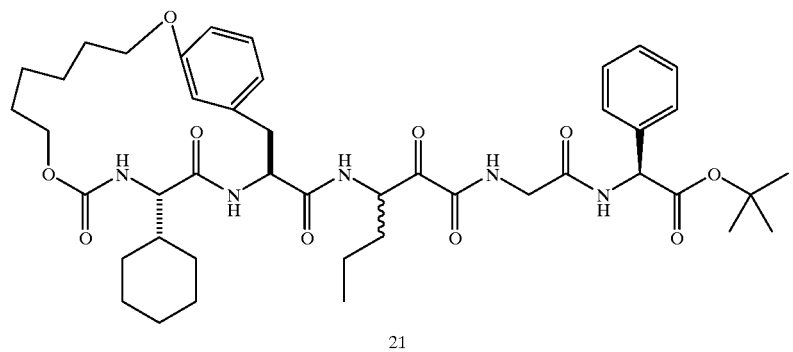

21

A solution of alcohol 21j (220 mg, 0.26 mmol) in CH$_2$Cl$_2$ (5.0 mL) was treated with Dess-Martin reagent (200 mg, 0.47 mmol, 1.8 equiv.). The reaction mixture was stirred at rt for 1 h and diluted with aq. NaHCO$_3$ (15 mL) and aq. Na$_2$S$_2$O$_3$ (15 mL). The reaction mixture was stirred at rt for 20 min and the reaction mixture was extracted with CH$_2$Cl$_2$ (3×30 mL). The combined organic layers were extracted with aq. Na$_2$CO$_3$, dried (Na$_2$SO$_4$), filtered, concentrated in vacuo and the residue was purified by chromatography (SiO$_2$, CH$_3$OH (2M NH$_3$)/CH$_2$C$_2$ 1:20) to yield ketoamide 21 (60 mg, 27%) of a colorless solid.

Example 22

Preparation of Compound of Formula 22:

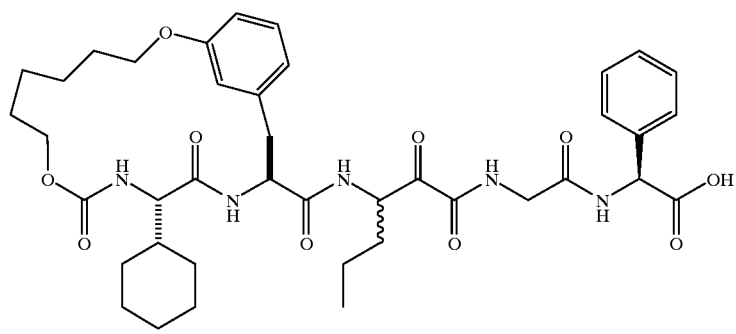

22

Step A:
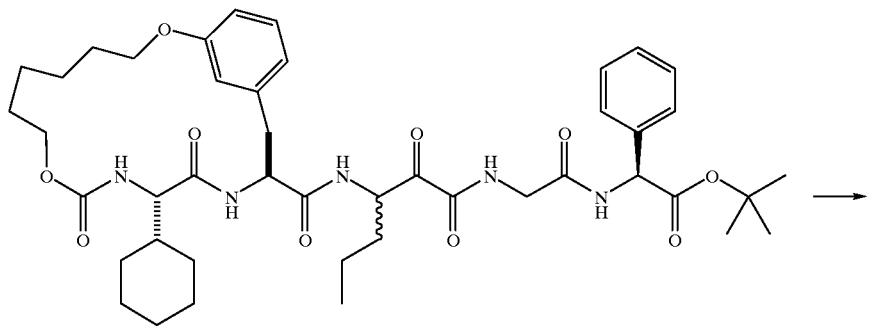
21
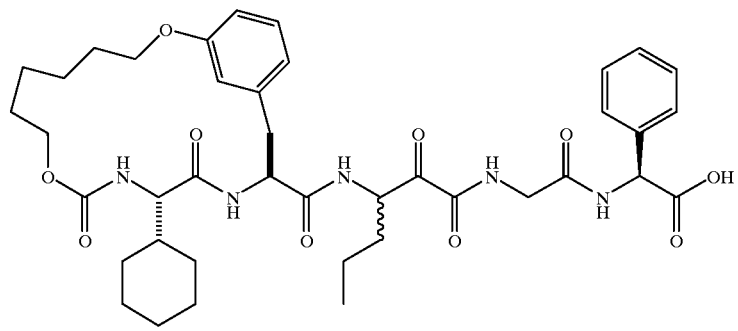
22
A solution of tert-butyl ester 21 (50 mg, 0.059 mmol) in dry CH₂Cl₂ (2.0 mL) was treated with TFA (2.0 mL) and stirred at rt. for 4 h. The reaction mixture was concentrated in vacuo and the residue was repeatedly dissolved in heptanes/CH₂Cl₂ and concentrated in vacuo several times to yield a fine tan solid 22 (47 mg), which was dried in vacuo.
Example 23
Preparation of Compound of Formula 23:
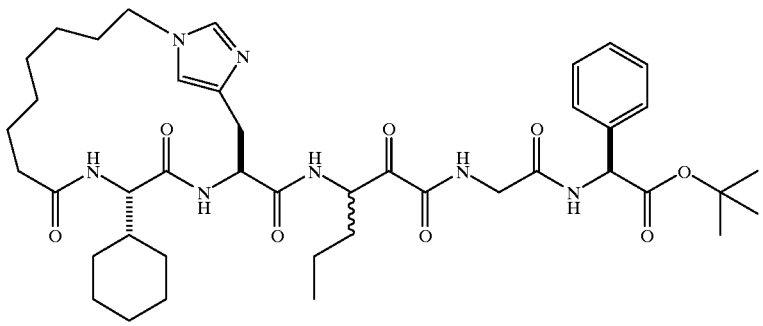
23

Step A:

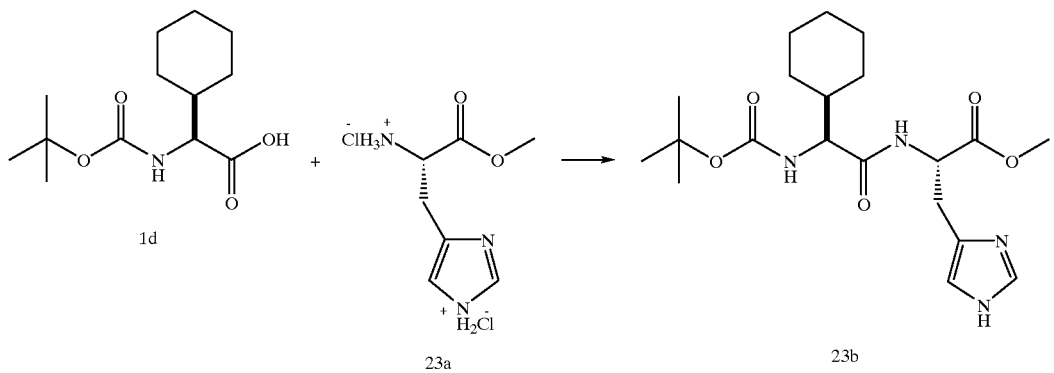

A solution of acid 1d (255 mg, 1.0 mmol) in DMF (2.0 mL) was treated with HOBt (202 mg, 1.5 equiv) and Hünigs base (517 mg, 4.0 mmol, 4.0 equiv, 738 µL). The reaction mixture was cooled to 0° C. and treated with DCC (258 mg, 1.25 mmol, 1.25 equiv.) After stirring the mixture for 1 h Histidine-OCH$_3$.HCl 23a (242.0 mg, 1.0 mmol) was added and stirred at rt overnight. The reaction mixture was concentrated in vacuo and extracted in EtOAc (3×50 mL) and aq. NaHCO$_3$ (50 mL). The combined organic layer was concentrated in vacuo and the residue was purified by chromatography (SiO$_2$, CH$_3$OH/CH$_2$Cl$_2$ 1:19) to yield dipeptide 23b as a colorless solid (380 mg, 93%) $^1$H NMR (d$_6$-DMSO, 400 MHz, δ, ppm) 8.17 (d, 1H, J=7.2 Hz), 7.48 (s, 1H), 6.77 (s, 1H) 6.57 (bs, 1H), 5.54 (d, 1H, J=7.6 Hz), 4.47 (q, 1H, J=7.2 Hz), 3.79 (t, 1H, J=8.4 Hz), 3.55 (s, 3H), 3.36–3.20 (m, 2H), 2.94–2.82 (m, 2H), 1.70–1.47 (bm, 6H), 1.35 (s, 9H), 1.46–0.85 (m, 5H): $^{13}$C NMR (d$_6$-DMSO, 100 MHz, δ ppm) 172.5, 171.9, 157.3, 155.9, 135.4, 78.6, 59.5, 52.9, 52.3, 34.1, 29.6, 28.9, 28.6, 26.5, 26.3, 26.0, 25.2 FAB MS: (NBA-G/TG-DMSO, m/z relative intensity) 409. [(M+1)$^+$, 100], 353. (10), 170 (20); HRMS calcd for C$_{20}$H$_{33}$N$_4$O$_6$: 409.2451: found 409.2466; CHN Calcd for C$_{20}$H$_{32}$N$_4$O$_5$: C=58.81% H=7.90%, N=13.72%; Found: C=58.70% H=7.78% N=13.43%.

Step B:

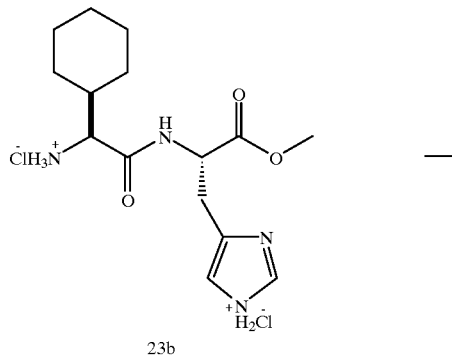

-continued

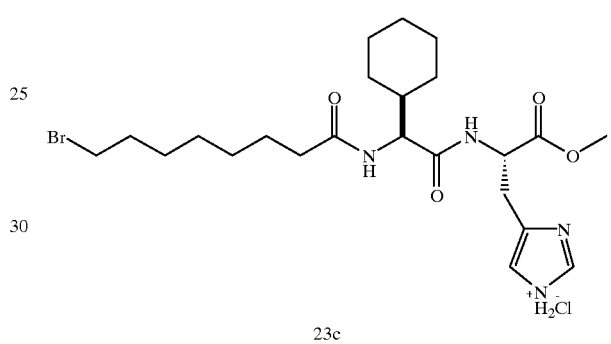

A solution of ω-bromoheptenoic acid (223 mg, 1.0 mmol) in DMF (3.0 mL) was treated with deprotected amine hydrochloride 23b (380 mg, 1.0 mmol, 1.0 equiv) and Hünigs base (387 mg, 3.0 mmol, 3.0 equiv) was added. The reaction mixture was treated with PyBroP (465 mg, 1.0 mmol) and stirred at rt for 3 h. The reaction mixture was concentrated in vacuo and the residue was purified by chromatography (SiO$_2$, CH$_3$OH/CH$_2$Cl$_2$, 1:19) to yield a colorless solid (220 mg, 50%) MS (FAB) 515.2 [(M+1)$^+$, 100], 513.2 [(M+1)$^+$, 95)], 469 (60), 433 (20), 170 (40). HRMS calcd. for C$_{23}$H$_{38}$BrN$_4$O$_4$: 513.2076 found: 513.2073.

Step C:

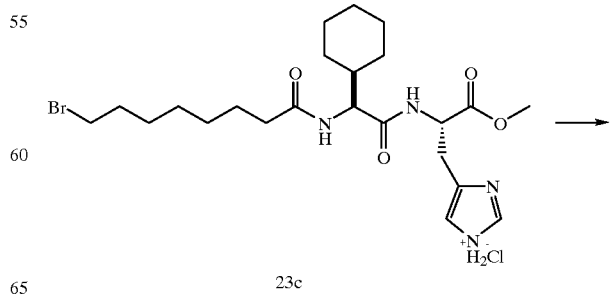

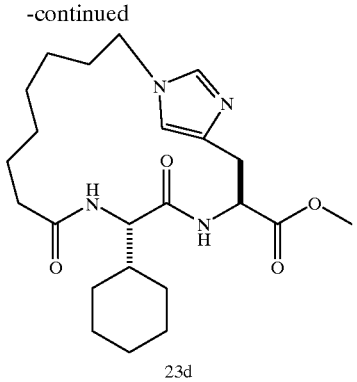

23d

A solution of bromo-compound 23c (100 mg, 0.23 mmol), in 2-butanone (4.0 mL) was treated with Na$_2$CO$_3$ (31.0 mg, 0.29 mmol, 1.25 equiv) and with LiI (50 mg, 0.37 mmol 1.3 equiv.) and heated at reflux for 24 h. The reaction mixture was concentrated in vacuo and the residue was diluted with water. The residue was extracted with CH$_2$Cl$_2$ (3×30 mL). The combined organic layer was dried(Na$_2$SO$_4$) and purified by chromatography (SiO$_2$, CH$_3$OH:CH$_2$Cl$_2$ 1:19) to yield the cyclized compound 23d (25 mg, 31%); R$_f$: 0.68 (2M NH$_3$ in CH$_3$OH:CH$_2$Cl$_2$: 1:19) $^1$H NMR (CDCl$_3$, 400 MHz, δ, ppm) 8.17 (d, 1H, J=8.8 Hz) 7.33 (s, 1H), 6.48 (d, 1H, J=8.4 Hz), 4.90–4.85 (m, 1H), 4.26 (t, 1H, J=8.0 Hz), 3.82–3.74 (m, 2H), 3.69 (s, 3H), 3.16–3.11 (m, 2H) 2.91–2.84 (m, 1H), 2.30–2.01 (m, 2H), 1.65–1.59 (m, 11H), 1.18–0.96 (m, 11H): $^{13}$C NMR (CDCl$_3$, 100 MHz, δ ppm): 172.8, 172.4, 171.9, 138.2, 136.8, 57.6, 52.5, 51.7, 46.6, 41.6, 36.0, 30.9, 29.5, 28.8, 27.3, 26.7, 26.4, 26.3, 26.2, 25.2, 24.8 MS: (Electron spray, m/z relative intensity): 433.1 [(M+1)$^+$, 100]; HRMS: Calcd. for C$_{23}$H$_{37}$N$_4$O$_4$ 433.2815 found 433.2822.

Step D:

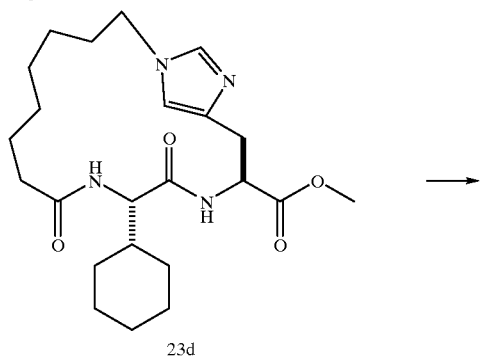

23d

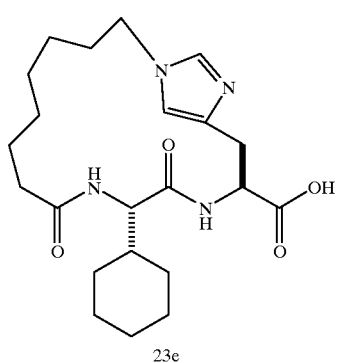

23e

A solution of methyl ester 23d (200 mg, 0.46 mmol) in CH$_3$OH (5.0 mL) H$_2$O (0.5 mL) was treated with LiOH.H$_2$O (30 mg, 0.75 mmol, 1.6 equiv.) The reaction mixture was stirred at rt for 15 h and concentrated in vacuo and dried in pump to yield hydrolyzed compound 23e which was used for coupling directly.

Step E:

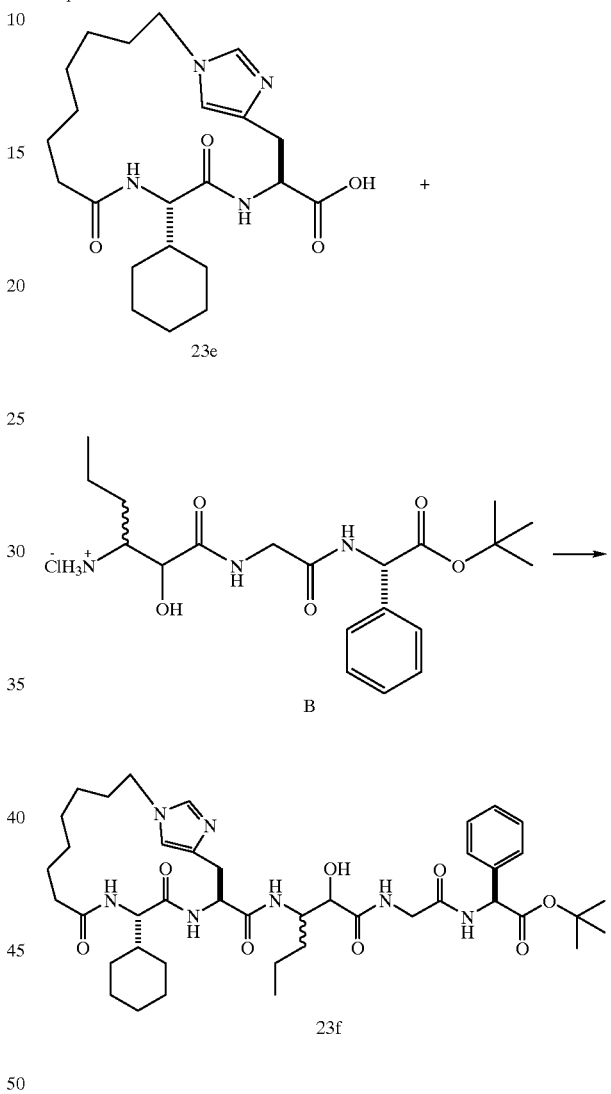

23e

B

23f

A solution of the acid 23e in CH$_2$Cl$_2$ (3.0 mL), DMF (5.0 mL) was treated with HOOBt (115 mg, 0.70 mmol, 1.50 equiv) and EDCl (113 mg, 0.60 mmol, 1.25 equiv). The reaction mixture was then treated with Et$_3$N (190 mg, 1.88 mmol, 271 μL, 4.0 equiv) and amine hydrochloride B (201 mg, 0.5 mmol, 1.1 equiv.) The reaction mixture was stirred at rt for 13 h and diluted with H$_2$O. The aqueous layer was extracted with CH$_2$Cl$_2$ (3×50 mL) and the combined organic layers were extracted with aq. NaOH (1M, 50 mL) and dried (Na$_2$SO$_4$). The dried organic layer was filtered and concentrated in vacuo to yield a colorless residue 23f (442 mg) which was dried in vacuo and directly used for further oxidation. MS: (Electron spray, m/z relative intensity): 794 [(M+1)$^+$, 100].

Step F:

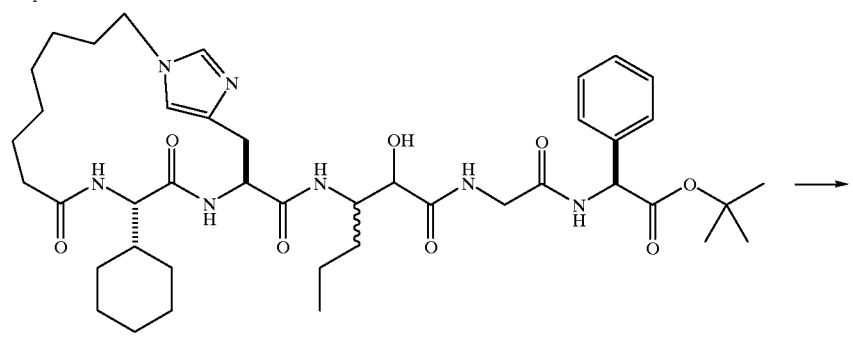

23f

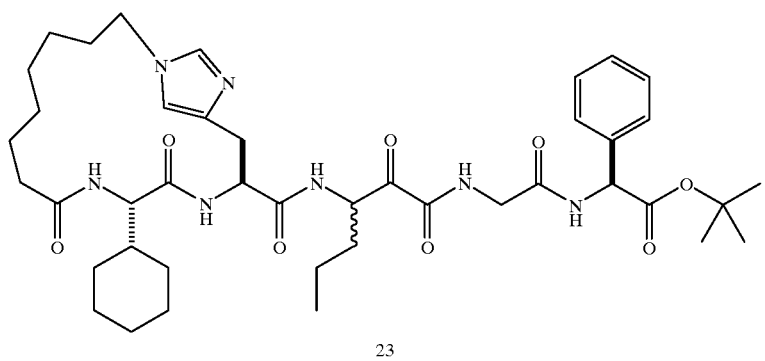

23

A solution of hydroxy-amide 23f (50 mg, 0.064 mmol) in CH$_2$Cl$_2$ (3.0 mL) was treated with Dess Martin reagent (53 mg, 0.13 mmol, 2.0 equiv) and stirred at rt for 3 h. The reaction mixture was diluted with aq. satd. Na$_2$S$_2$O$_3$ (20 mL) and stirred at rt for 15 min. The aqueous layer was extracted with CH$_2$Cl$_2$ (3×30 mL). The organic layer was dried (Na$_2$SO$_4$) filtered concentrated in vacuo and purified by chromatography (SiO$_2$, CH$_3$OH/CH$_2$Cl$_2$, 1:15) to yield ketoamide 23 (20 mg, 40%); MS (FAB, NBA-G/TG-DMSO, m/z relative intensity) 824 [(M+CH$_3$OH)$^+$, 100], 792 [(M+1)$^+$, 60], 447 (20); HRMS calcd for C$_{42}$H$_{62}$N$_7$O$_8$ (M+1)$^+$: 792.4660: found 792.4659.

Example 24

Preparation of Compound of Formula 24:

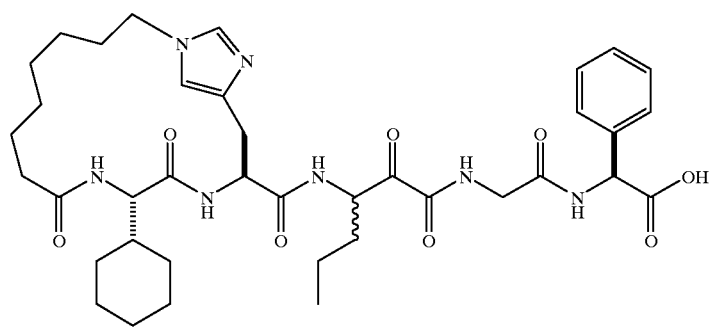

24

Step A:

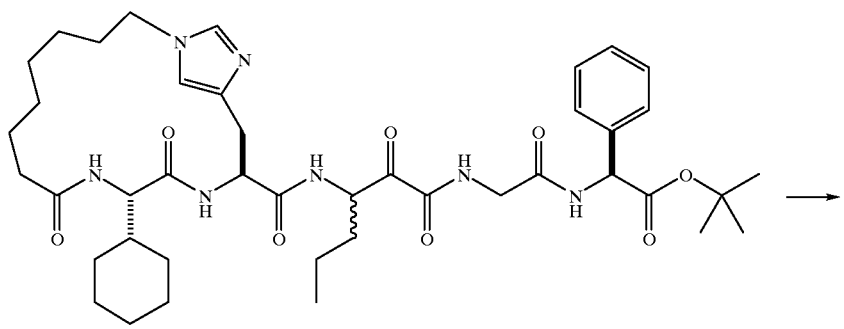

23

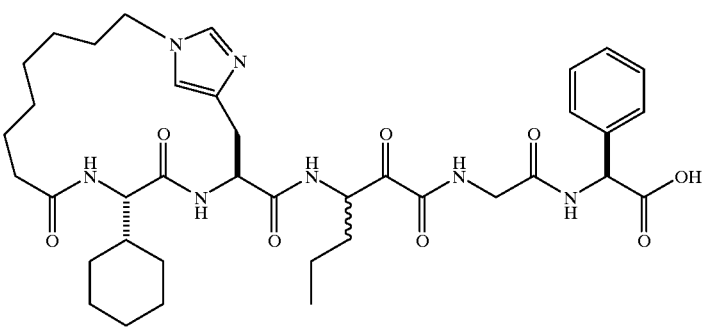

24

A solution of tert-butyl ester 23 (17 mg, 21.5 μmol) in dry CH$_2$Cl$_2$ (2.0 mL) was treated with TFA (2.0 mL) and stirred at rt. for 8 h. The disappearance of the ester to the base line was followed by TLC (CH$_3$OH/CH$_2$Cl$_2$, 1:19). The reaction mixture was concentrated in vacuo and the residue was repeatedly dissolved in CH$_3$OH/heptanes/CH$_2$Cl$_2$ and concentrated in vacuo several times to yield 24 as fine colorless solid (7 mg). MS: (Electron spray, m/z relative intensity: 768 [(M+CH$_3$OH)$^+$, 100], 736 [(M+1)$^+$, 60], 46 (10).

Example 25

Preparation of Compound of Formula 25:

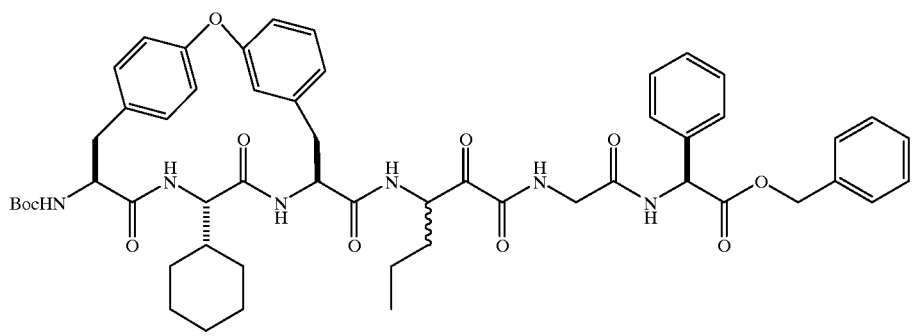

25

Step A:

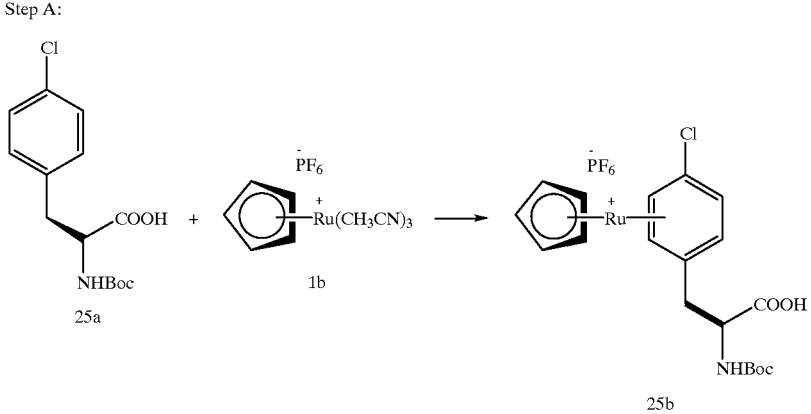

A solution of Boc-4-Chlorophenylalanine 25a (523 mg, 1.75 mmol) in dichloroethane (37 mL) was treated with CpRu(CH$_3$CN)$_3$ PF$_6$ 1b (760 mg, 1.75 mmol, 1.0 equiv) and heated at reflux for 2 h. The reaction mixture was cooled to 0° C. and filtered. The filtrate was concentrated in vacuo and dissolved in minimum CH$_3$CN and treated with a large excess of Et$_2$O. The solid separating out was separated and dissolved in CH$_2$Cl$_2$/CH$_3$OH (1:1, 50 mL) and concentrated in vacuo to obtain 25b as a brown foam (640 mg, 69%).

Step B:

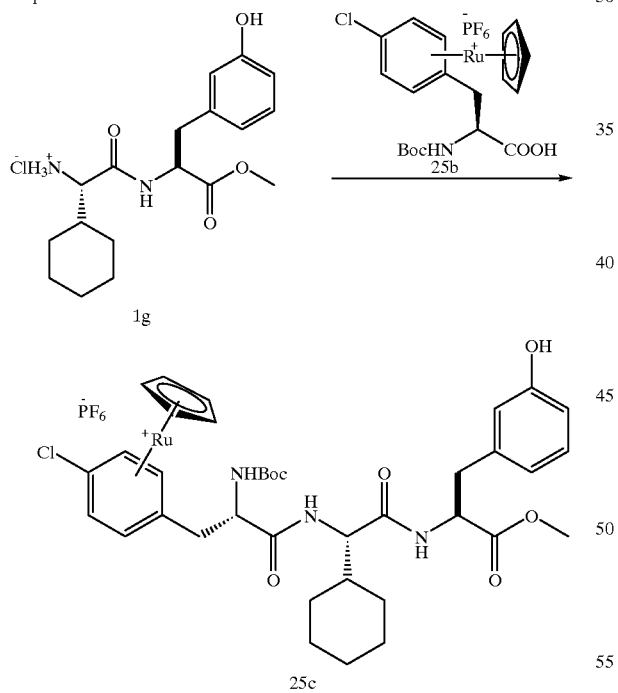

A solution of carboxylic acid 25b (2.4 g, 3.80 mmol) in dry DMF (15 mL) was treated with Hünigs base (1.64 g, 12.64 mmol, 4.0 equiv, 2.9 mL) and HOBt (661 mg, 4.38 mmol, 1.5 equiv). The reaction mixture was cooled to 0° C. and the treated with EDCl (699 mg, 3.95 mmol, 1.25 equiv) and stirred for 15 min. To this reaction mixture was added amine hydrochloride 1g (1.50 g, 4.00 mmol, 1.2 equiv) and the reaction mixture was stirred at rt for 12 h. The DMF was distilled out and the residue was diluted with water (30 mL) and the aqueous layer was extracted with CH$_2$Cl$_2$ (3×50 mL). The combined organic layers were extracted with aq NaHCO$_3$ (30 mL), aq. HCl (30 mL), brine, dried (Na$_2$SO$_4$) filtered concentrated in vacuo and the crude product 25c (2.5 g, 69%) was used for further cyclization without purification.

Step C:

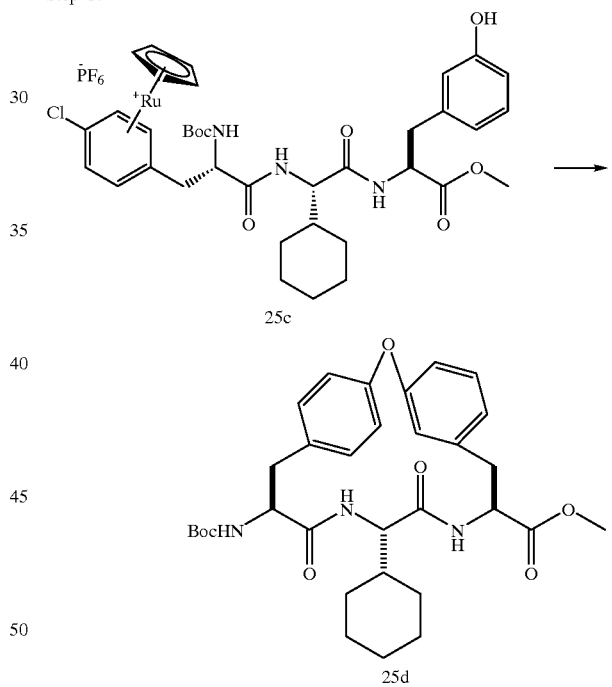

A solution of compound 25c (100 mg 0.11 mmol) in dry DMF (10 mL) was degassed with dry N$_2$ and treated with Cs$_2$CO$_3$ (170 mg, 0.5 mmol, 5.0 equiv) and stirred at rt. for 12 h. The solvent DMF was distilled off and the residue was diluted with water (35 mL) and extracted with CH$_2$Cl$_2$ (3×100 mL). The combined organic layers were dried (Na$_2$SO$_4$) filtered, concentrated in vacuo and dried in vacuum overnight. It was used for photolytic removal of Ru without further purification.

The cyclized compound from the previous step was dissolved in CH$_3$CN and photolysed in a Raynot ($\lambda$=350 nm) for 48 h. The reaction mixture was concentrated in vacuo and the residue was purified by chromatography (SiO$_2$, EtOAc/Hexanes 2:1) to yield 25d as a tan colored solid (29 mg, 46%). MS (FAB, NBA-G/TG-DMSO, m/z relative intensity), 580 [(M+1)+, 80], 524 (100), 418 (40), 462 (30), 452 (20), 313 (60), 253 (20).

Step D:

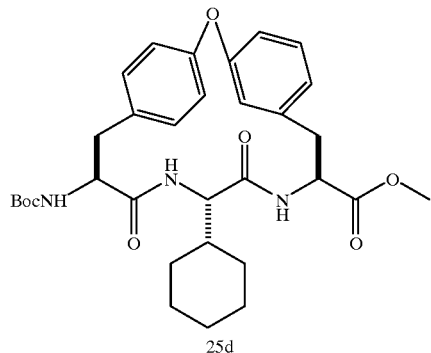

25d

→

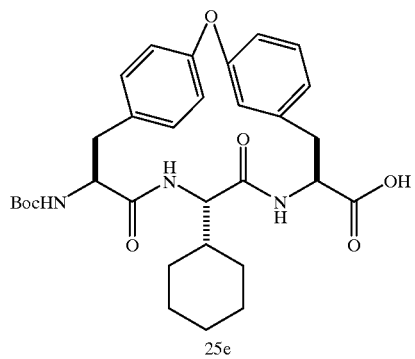

25e

A solution of ester 25d (150 mg, 0.26 mmol) in THF (3 mL), CH$_3$OH (3.0 mL) and H$_2$O (3.0 mL) was treated with LiOH.H$_2$O (18 mg, 0.43 mmol, 1.65 equiv.) and stirred at rt for 35 min. The reaction mixture was acidified with conc HCl (13 M, 1 mL) and extracted in CH$_2$Cl$_2$ (3×50 mL). The combined organic layers were dried (Na$_2$SO$_4$) filtered and concentrated in vacuo to yield acid 25e which was used directly for the coupling without further purification.

Step E:

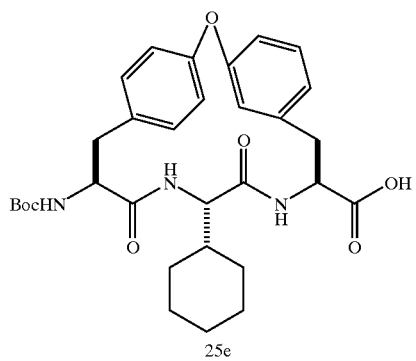

25e

+

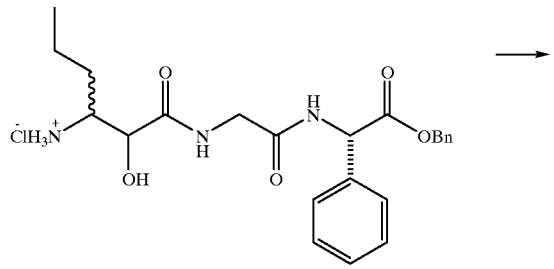

F

→

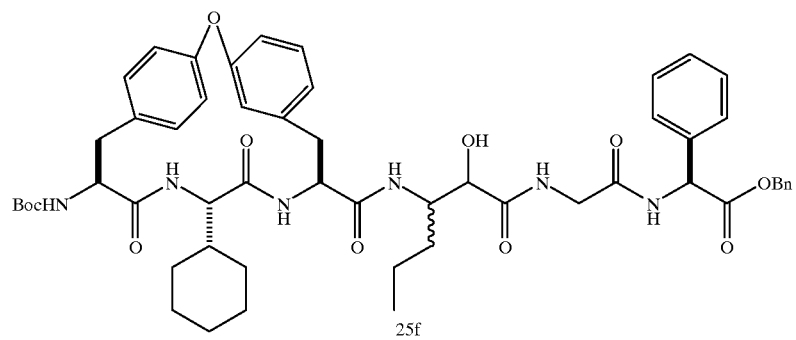

25f

A solution of acid 25e (150 mg, 0.27 mmol) in dry CH₂Cl₂ (2.0 mL), was treated with HOBt (62 mg, 0.40 mmol) and Hünigs base (139 mg, 1.1 mmol, 4.0 equiv.) The reaction mixture was cooled to 0° C. and treated with EDCl (53 mg, 0.34 mmol, 1.25 equiv) and stirred for 30 min. The reaction mixture was treated with amine F (88 mg, 0.29 mmol, 1.22 equiv.) and stored in the freezer for 12 h. The reaction mixture was concentrated in vacuo and diluted with H₂O (50 mL). The aqueous layer were extracted with CH₂Cl₂ (3×50 mL). The combined organic layers were extracted with aq. HCl (1M, 3×20 mL) aq. NaOH (1 M, 3×20 mL), dried (Na₂SO₄) filtered concentrated in vacuo to obtain a colorless solid 25f (138 mg) which was used for oxidation.

Step F:

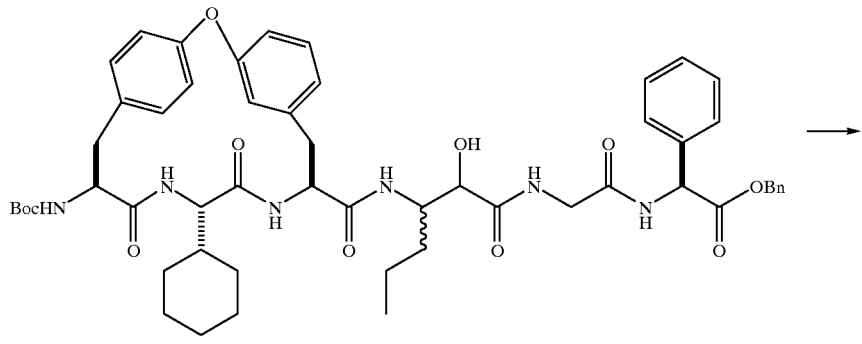

25f

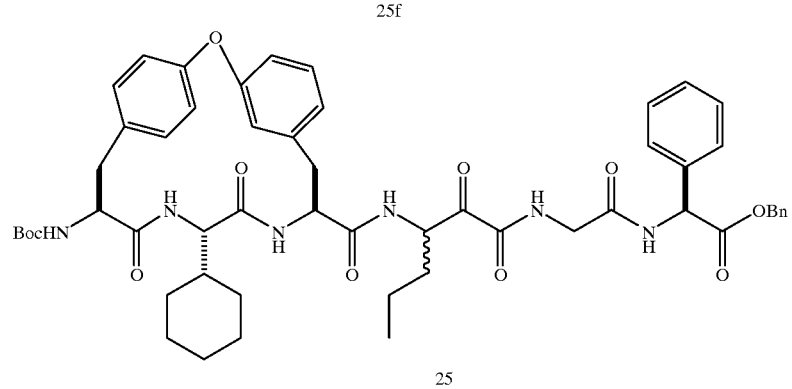

25

A solution of alcohol 25f (140 mg, 0.143 mmol) in CH₂Cl₂:THF (1:1, 5.0 mL) was treated with Dess-Martin reagent (121 mg, 0.42 mmol, 3.0 equiv.) The reaction mixture was stirred at rt for 2 h and the mixture was concentrated in vacuo. The residue was purified by chromatography (SiO₂, CH₃OH/CH₂Cl₂ 1:32) to yield oxidized product 25 (57 mg, 41%) as a colorless solid.

Example 26
Preparation of Compound of Formula 26:

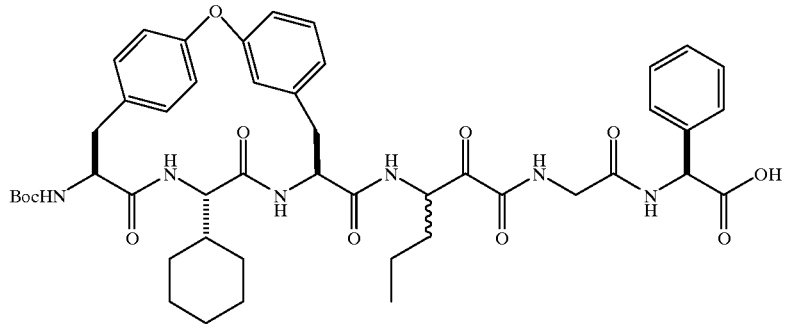

26

Step A:

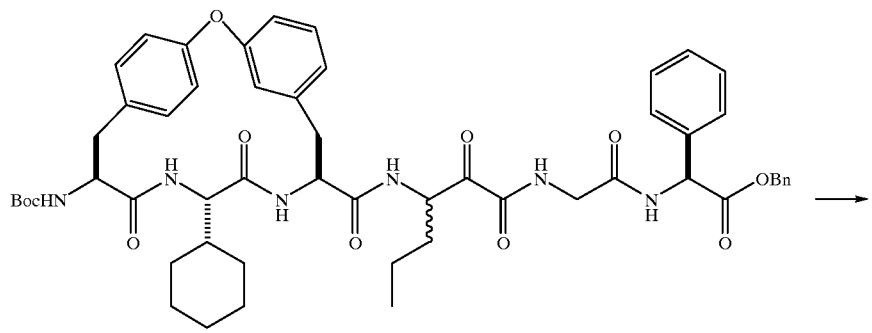

25

A solution of the benzyl ester 25 (30 mg, 38.0 μmol) in CH₃OH/THF (1:1, 4.0 mL) was treated with Pd/C (20 mg, 10%) and H₂ was bubbled through it. A drop of acetic acid was added to accelerate the reduction. The reaction mixture was filtered through a plug of celite and the filtrate was concentrated in vacuo. The residue 26 was analyzed without further purification.

Example 27
Preparation of Compound of Formula 27:

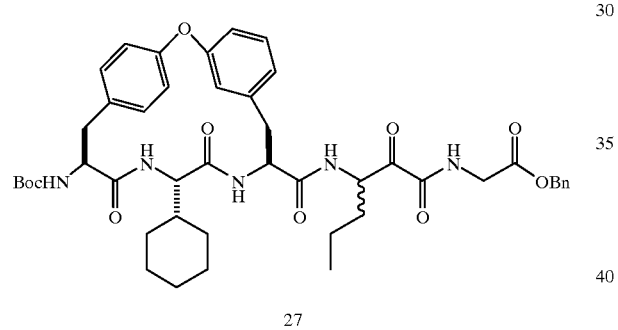

27

Step A:

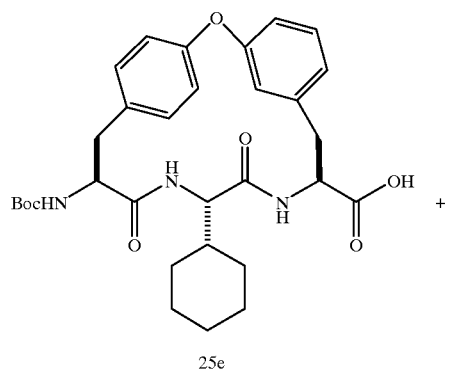

25e

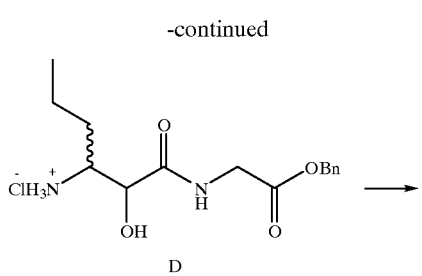

D

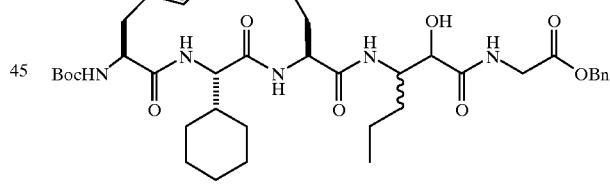

27a

A solution of acid 25e(100 mg, 0.17 mmol) in dry CH₂Cl₂ was treated with HOOBt (41 mg, 0.26 mmol) and Hünigs base (91 mg, 0.70 mmol, 4.0 equiv.) The reaction mixture was cooled to 0° C. and treated with EDCl (35 mg, 0.22 mmol, 1.25 equiv) and stirred for 30 min. The reaction mixture was treated with amine D (71 mg, 0.22 mmol, 1.22 equiv.) and stored in the freezer for 12 h. The reaction mixture was concentrated in vacuo and diluted with H₂O (30 mL). The aqueous layers was extracted with CH₂Cl₂ (3×30 mL). The organic layers were extracted with aq. HCl (1M, 30 mL) aq. Na₂CO₃ (1M, 30 mL), dried (Na₂SO₄) filtered concentrated in vacuo to obtain 27a colorless solid (119 mg) which was used for oxidation. MS (FAB), 842 [(M+1), 100], 765 (20), 735 (10), 657 (20), 575 (10), 492 (10), 464 (20), 446 (30). HRMS calcd. for $C_{46}H_{60}N_5O_{10}$ (M+1)⁺: 842.4339; found 842.4336.

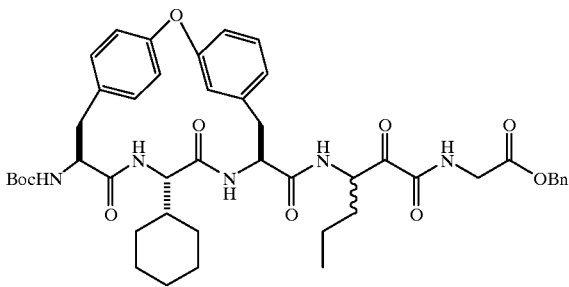

27

A solution of alcohol 27a (120 mg, 0.143 mmol) in CH₂Cl₂:THF (1:1, 3.0 mL) was treated with Dess-Martin reagent (180 mg, 0.42 mmol, 3.0 equiv.) The reaction mixture was stirred at rt. for 2 h and the mixture was concentrated in vacuo. The residue was purified by chromatography (SiO₂, CH₃OH/CH₂Cl₂ 1:32) to yield oxidized product 27 as a colorless solid. MS (FAB, NBA-G/TG-DMSO, m/z rel int), 840 [(M+1)⁺, 50]. HRMS calcd. for $C_{46}H_{58}N_5O_{10}$ (M+1)⁺: 840.4184; found 840.4199.

Step B:

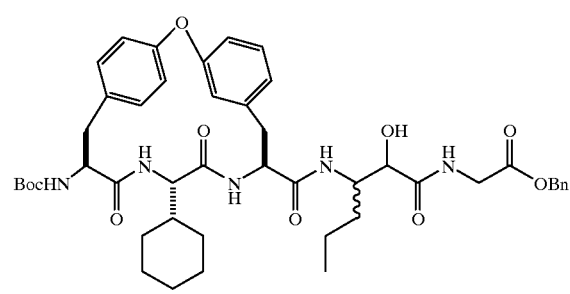

27a

Example 28

Preparation of Compound of Formula 28:

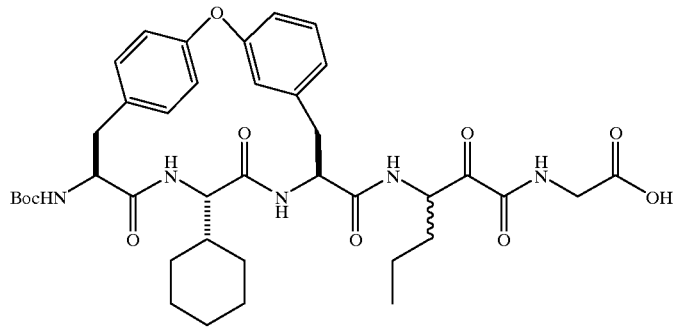

28

Step A:

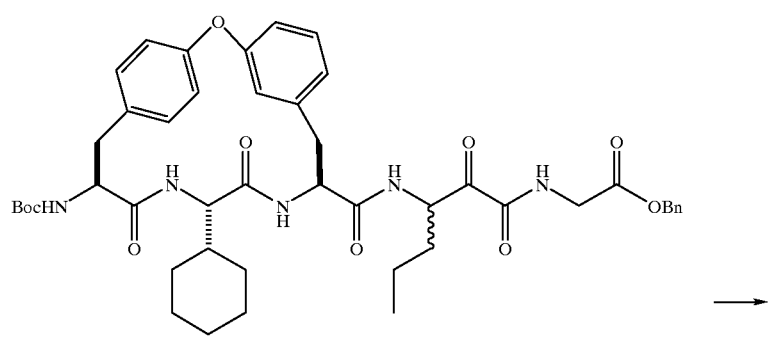

27

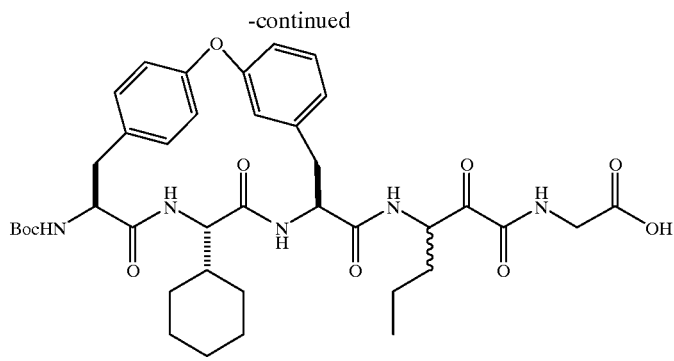

28

A solution of benzyl ester 27 (40 mg, 47.0 μmol) in CH₃OH/THF (1:1, 6.0 mL) was treated with Pd/C (30 mg, 10%) and H₂ was bubbled through it. A drop of acetic acid was added to accelerate the reduction. The reaction mixture was filtered through a plug of celite and the filtrate was concentrated in vacuo to yield 28.

Example 29

Preparation of Compound of Formula 29:

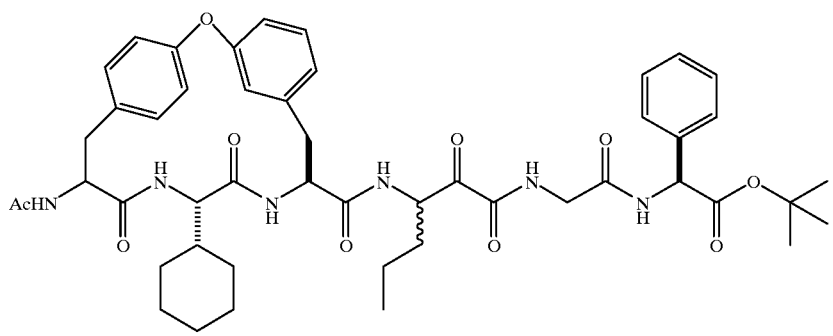

29

Step A:

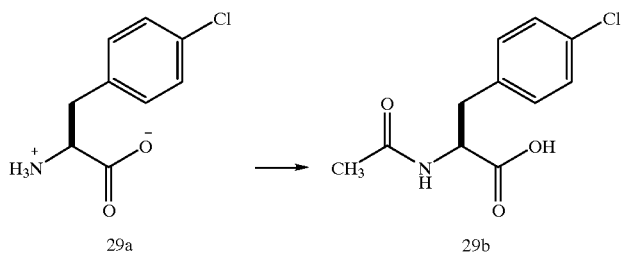

A solution of 4-chlorophenylalanine 29a (1.5 g, 7.5 mmol) in THF (20 mL) and H₂O (20 mL) was treated with NaOH (900 mg, 22.5 mmol, 3.0 equiv.) and cooled to 0° C., A solution of acetyl chloride (707 mg, 9.00 mmol, 1.25 mmol) in THF (10 mL) was added dropwise and the reaction mixture was stirred overnight at rt. The reaction mixture was acidified with aq. HCl (1M, 10 mL) and extracted with CH₂Cl₂ (3×30 mL). The combined organic layers were dried (Na₂SO₄) filtered concentrated in vacuo to yield 29b which was used in the next step without purification.

Step B:

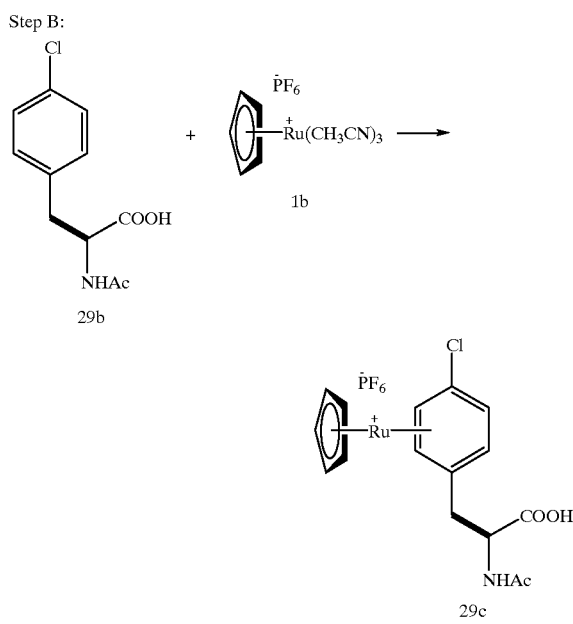

A solution of N-acetyl-4-chlorophenylalanine 29b (1.39 g, 5.75 mmol) in dichloroethane (118 mL) was treated with CpRu(CH$_3$CN)$_3$ PF$_6$ 1b (2.5 g, 5.8 mmol, 1.0 equiv.) and heated at reflux for 2 h. The reaction mixture was cooled to 0° C. and filtered. The filtrate was concentrated in vacuo and dissolved in CH$_3$CN (15 mL) and treated with Et$_2$O (150 mL). The gum separating out was separated by decanting the ether and the residue was dissolved in CH$_2$Cl$_2$/CH$_3$OH (1:1, 50 mL) and concentrated in vacuo to obtain 29c as a brown foam (2.2 g, 69%). MS: (Electron spray, m/z rel int): 408 [(M-PF$_6$)$^+$, 100].

Step C:

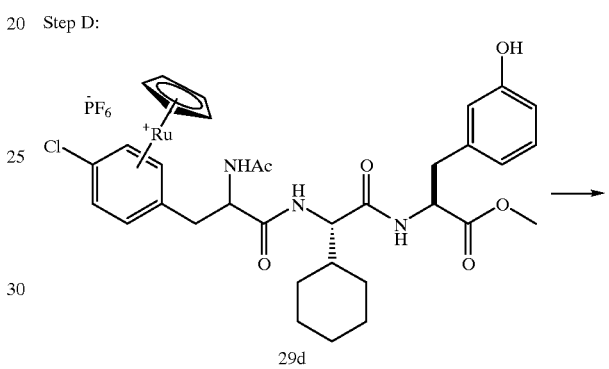

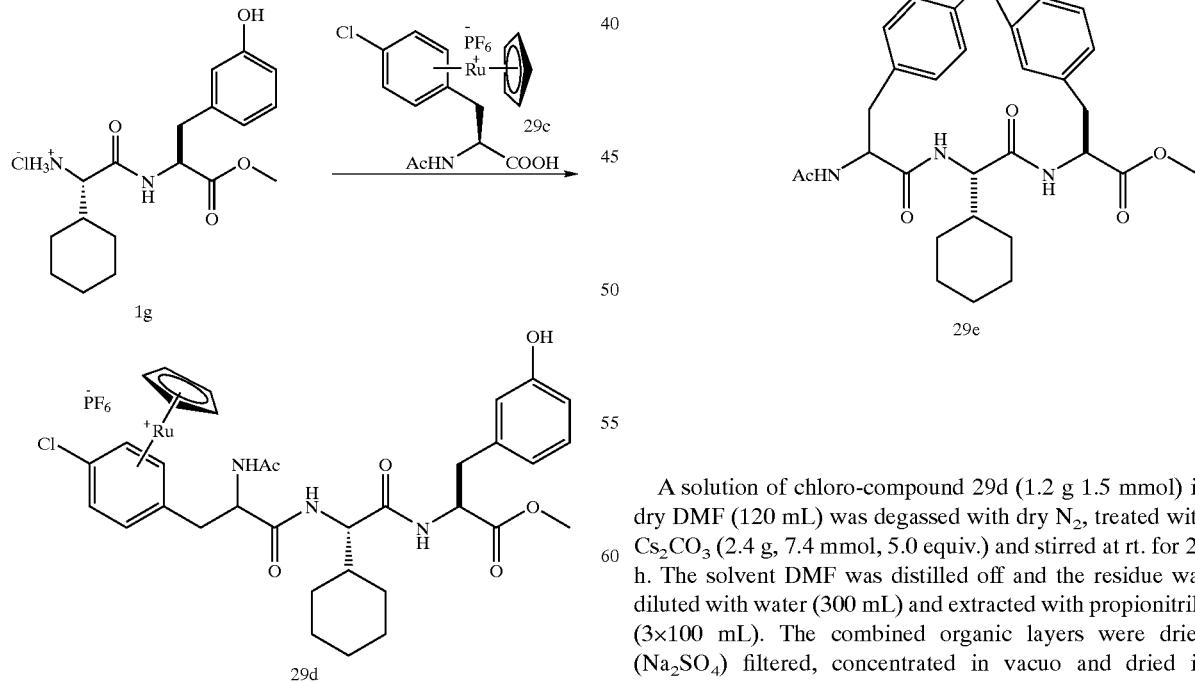

A solution of carboxylic acid 29c (2.0 g, 4.00 mmol) in dry DMF (20 mL) was treated with Hünigs base (2.06 g, 16.0 mmol, 4.0 equiv., 2.9 mL) and HOBt (810 mg, 6.0 mmol, 1.5 equiv.). The reaction mixture was cooled to 0° C. and then treated with EDCl (888 mg, 5.0 mmol, 1.25 equiv.) and stirred for 0.5 h. To this reaction mixture was added amine hydrochloride 1g (1.48 g, 7.14 mmol, 1.2 equiv.) and the reaction mixture was stirred at rt. for 12 h. The DMF was distilled out and the residue was diluted with water and the aqueous layer was extracted with CH$_2$Cl$_2$ (3×100 mL). The combined organic layers were extracted with aq. NaHCO$_3$ (200 mL), aq. HCl (100 mL), brine, dried (Na$_2$SO$_4$) filtered concentrated in vacuo and the crude product 29d (1.2 g, 38%) was used for cyclization without further purification.

Step D:

A solution of chloro-compound 29d (1.2 g 1.5 mmol) in dry DMF (120 mL) was degassed with dry N$_2$, treated with Cs$_2$CO$_3$ (2.4 g, 7.4 mmol, 5.0 equiv.) and stirred at rt. for 23 h. The solvent DMF was distilled off and the residue was diluted with water (300 mL) and extracted with propionitrile (3×100 mL). The combined organic layers were dried (Na$_2$SO$_4$) filtered, concentrated in vacuo and dried in vacuum overnight. It was used for photolytic removal of Ru without further purification.

The cyclized compound from the previous step was dissolved in CH₃CN (40 mL) and photolyzed in a Raynot (λ=350 nm) for 48 h. The reaction mixture was concentrated in vacuo and the residue was purified by chromatography (SiO₂, EtOAc/Hexanes 4:1) to yield a tan colored solid 29e (240 mg, 38%). MS (FAB, NBA-G/TG-DMSO, m/z relative intensity), 522[(M+1)⁺, 100].

Step E:

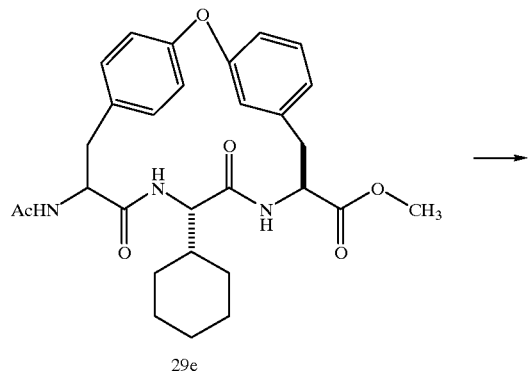

29e

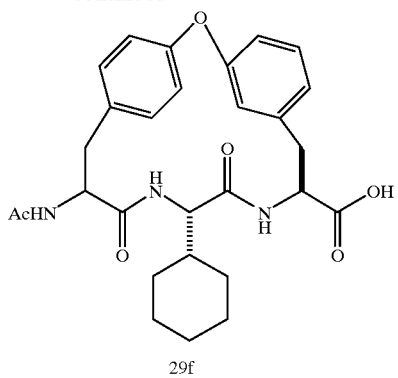

29f

A solution of ester 29e (200 mg, 0.42 mmol) in CH₃OH (5 mL), CH₂Cl₂ (13 mL) and H₂O (2.0 mL) was treated with LiOH.H₂O (41 mg, 1.0 mmol, 2.4 equiv.) and stirred at rt. for 3 h. The reaction mixture was acidified with aq. HCl (13 M, 1 mL) and extracted in CH₂Cl₂ (3×50 mL) and EtOAc (3×50 mL) The combined organic layers were dried (Na₂SO₄) filtered and concentrated in vacuo to yield acid 29f (178 mg) which was used directly for the coupling without further purification.

Step F:

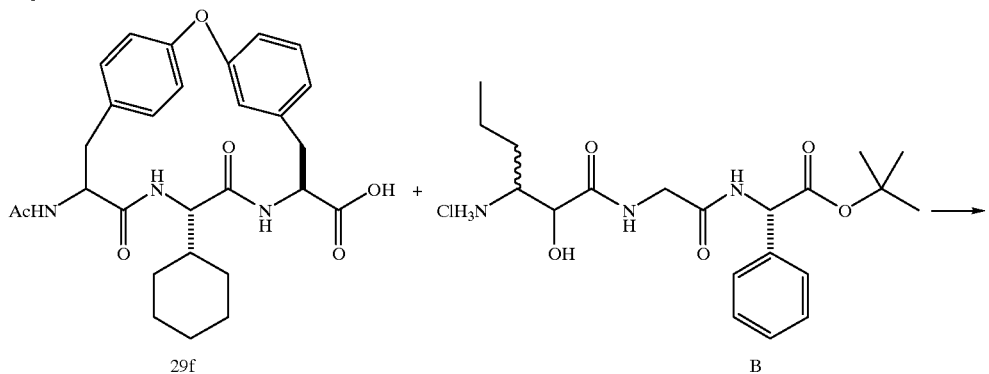

29f + B

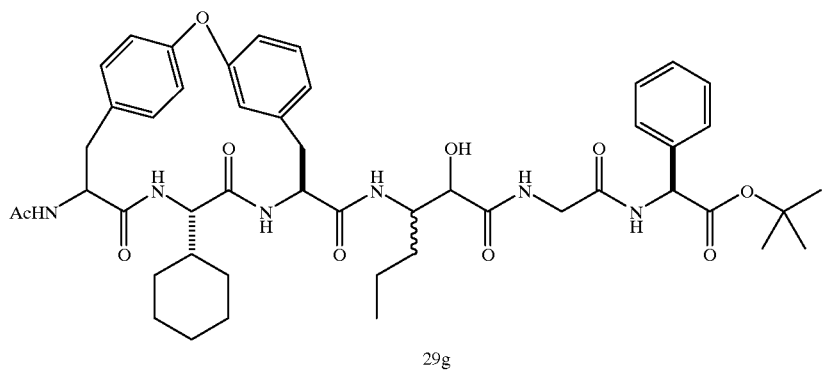

29g

A solution of acid 29f (90 mg, 0.18 mmol) in dry DMF (1.0 mL) was treated with HOBt (45 mg, 0.33 mmol, 1.6 equiv.), Hünigs base (142 mg, 1.1 mmol, 5.0 equiv.) and amine B (118 mg, 0.28 mmol, 1.47 equiv.) The reaction mixture was cooled to 0° C. and treated with EDCl (63 mg, 0.33 mmol, 1.6 equiv.) and stirred at 0° C. for 20 min. for 12 h. The reaction mixture was concentrated in vacuo and diluted with H₂O (30 mL). The combined aqueous layers were extracted with CH₂Cl₂ (3×30 mL) and EtOAc (3×30 mL). The organic layers were extracted with aq. NaOH (2M, 30 mL), dried (Na₂SO₄) filtered concentrated in vacuo to obtain a colorless solid 29g (50 mg, 32%) which was used for oxidation. MS: (Electron spray, m/z rel int): 883 [(M+ 1)⁺, 100], 522 (30), 394 (60).

Step G:

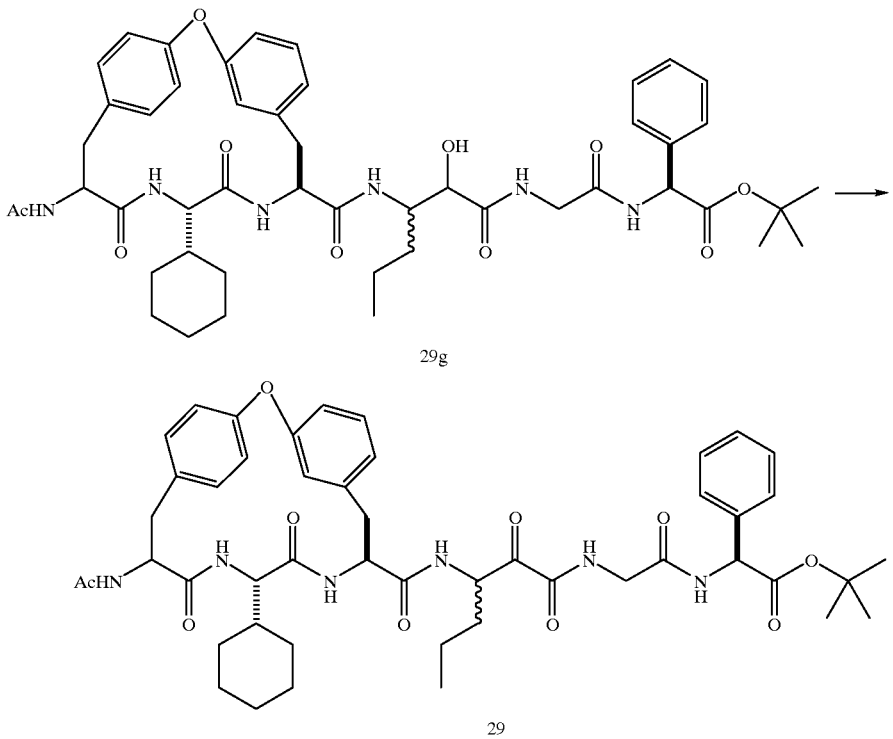

A suspension of alcohol 29g (50 mg, 60.0 μmol) in CH₂Cl₂ (2.0 mL) was treated with Dess-Martin reagent (40 mg, 0.94 mmol, 2.0 equiv.) The reaction mixture was stirred at rt. for 3 h and the mixture was concentrated in vacuo. The residue was purified by chromatography (SiO₂, CH₃OH/ CH₂Cl₂: 1:32) to yield oxidized product 29 (41 mg, 80%) as a colorless solid. MS: (FAB, m/z, rel. int.) 881 [(M+1)⁺, 100), 825 (170), 248 (100).

Example 30
Preparation of Compound of Formula 30:

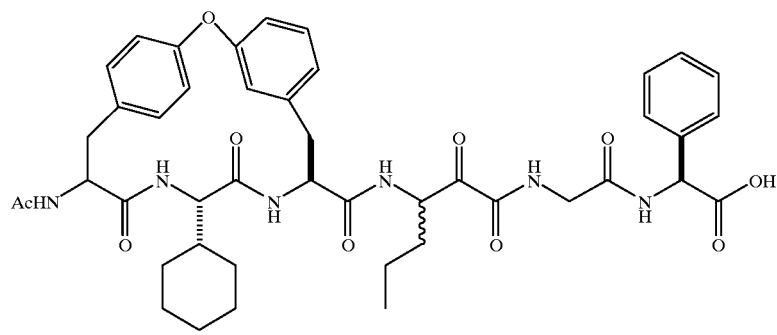

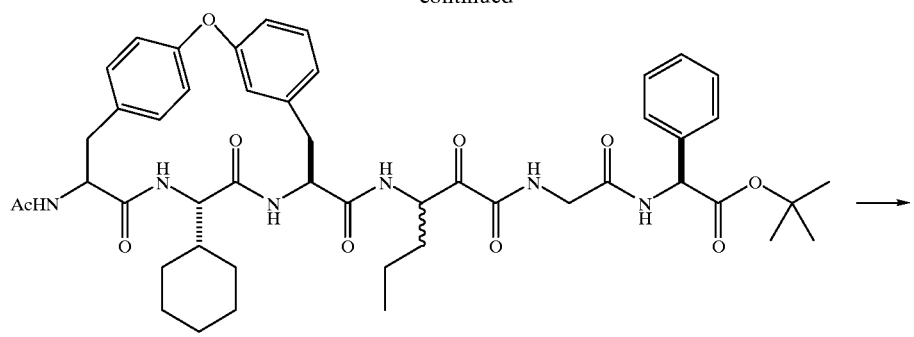

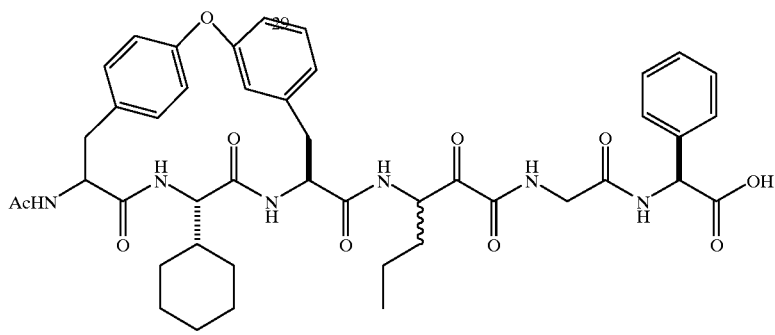

30

A solution of tert-butyl ester 29 (23.0 mg, 26.0 μmol) was treated with TFA/CH$_2$Cl$_2$ (1:1, 2.0 mL) and stirred at rt. for 4 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes/CH$_2$Cl$_2$ (4.0 mL) and concentrated to yield a tan solid 30 (13.0 mg, 100%). MS: (Electron spray, m/z rel int): 825 [(M+1)$^+$, 100].

Example 31
Preparation of Compound of Formula 31:

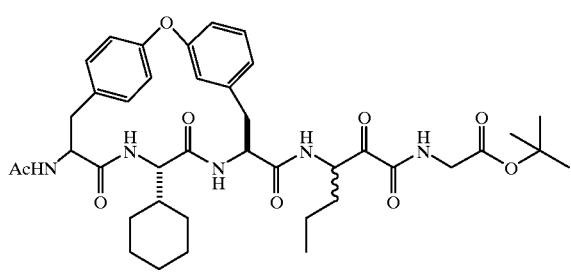

Step A:

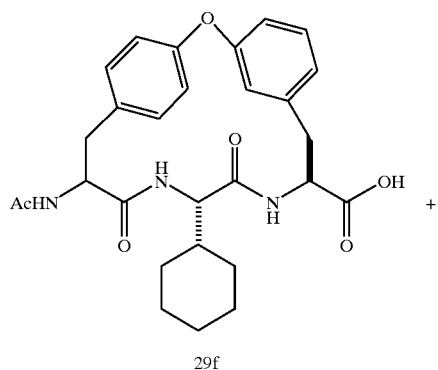

29f

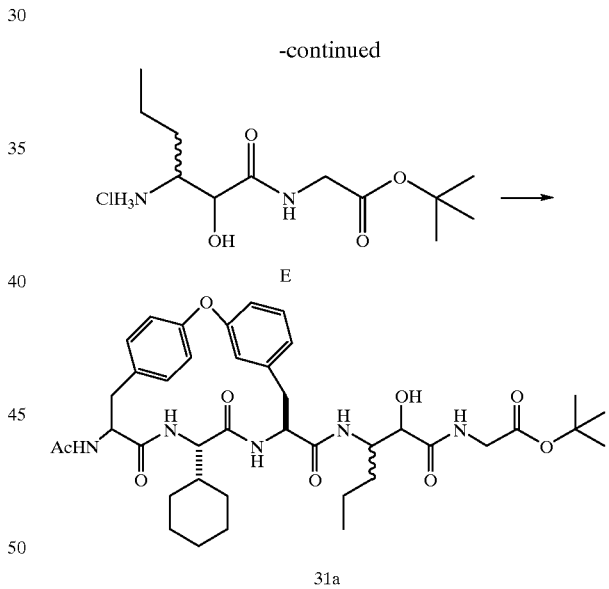

A solution of acid 29f (150 mg, 0.29 mmol) in dry DMF (4.0 mL), CH$_2$Cl$_2$ (3.0 mL) was treated with HOBt (58 mg, 0.44 mmol) and Hünigs base (149 mg, 1.1 mmol, 4.0 equiv.) The reaction mixture was cooled to 0° C. and treated with EDCl (82 mg, 0.44 mmol, 1.5 equiv.) and stirred for 30 min. The reaction mixture was treated with amine E (88 mg, 0.29 mmol, 1.22 equiv.) and stirred at rt. for 12 h. The reaction mixture was concentrated in vacuo and diluted with H$_2$O (30 mL). The aqueous layer was extracted with CH$_2$Cl$_2$ (3×30 mL). The combined organic layers were extracted with aq. HCl (1M, 3×20 mL), aq. NaOH (1M, 3×20 mL), dried (Na$_2$SO$_4$) filtered concentrated in vacuo to obtain a colorless solid 31a (56 mg) which was used for oxidation. MS: (Electron spray, m/z rel int): 750 [(M+1)$^+$, 20], 663 (10), 522 (10), 416 (20), 247 (30).

Step B:

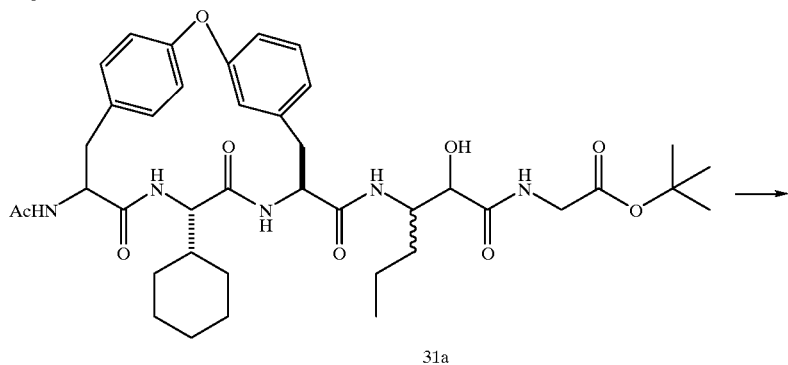

31a

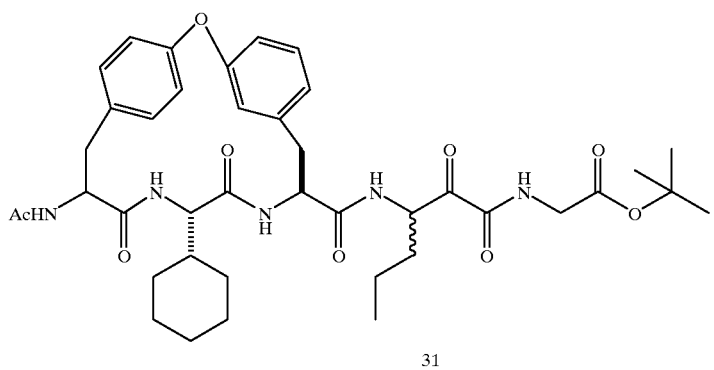

31

A solution of alcohol 31a (56 mg, 75 μmol) in CH$_2$Cl$_2$ (5.0 mL) was treated with Dess-Martin reagent (93 mg, 0.22 mmol, 3.0 equiv.) The reaction mixture was stirred at rt. for 4 h and the mixture was concentrated in vacuo. The residue was purified by chromatography (SiO$_2$, CH$_3$OH/CH$_2$Cl$_2$: 1:19) to yield oxidized product 31 (34 mg, 60%) as a colorless solid. MS: (Electron spray, m/z rel int): 748 [(M+1)$^+$, 35], 692 (5), 279 (100).

Example 32

Preparation of Compound of Formula 32:

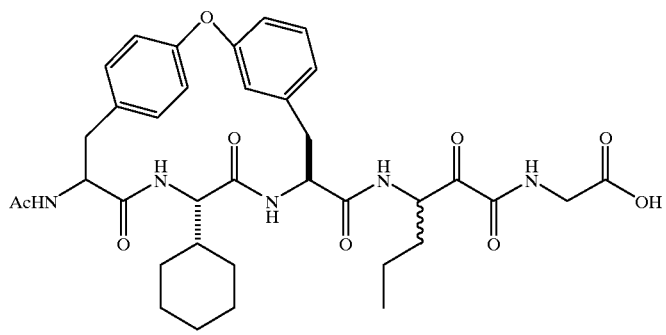

32

Step A:

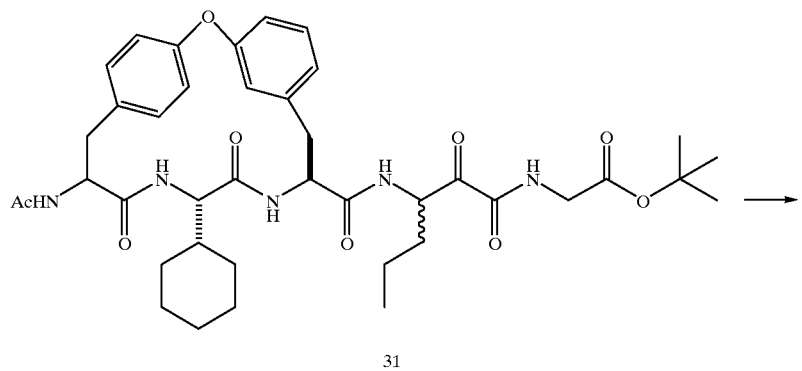

31

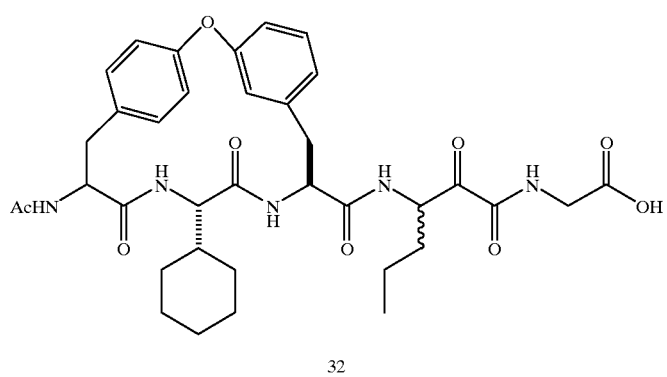

32

A solution of tert-butyl ester 31 was treated with TFA/CH$_2$Cl$_2$ (1:1, 4.0 mL) and stirred at rt. for 4 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with heptanes/CH$_2$Cl$_2$ (4.0 mL) and concentrated to yield 32 as a tan solid.

Example 33

Preparation of Compound of Formula 33:

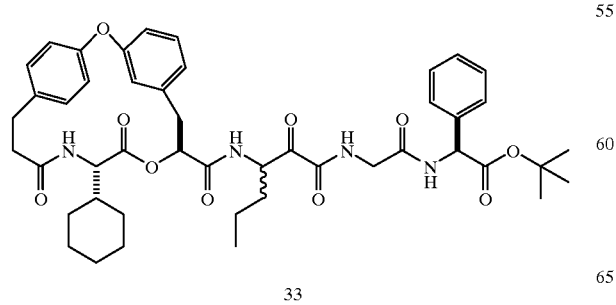

33

Step A:

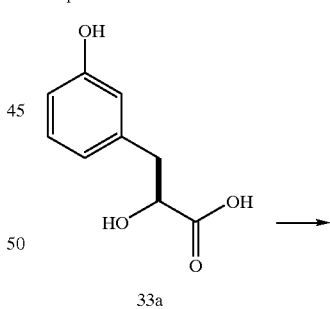

33a

-continued

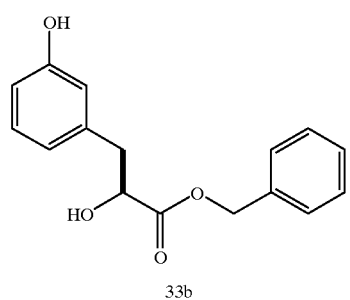

33b

A solution of acid 33a (4.5 g, 25.0 mmol) in dioxane (30 mL) and benzene (80 mL) was treated with BnOH (8.0 g, 74 mmol, 3.0 equiv.) and TsOH.H₂O (713 mg, 3.75 mmol, 10 mol %) The reaction mixture was heated at reflux for 5 h, when the water was separated using a Dean-Stark apparatus. The reaction mixture was concentrated in vacuo and the residue was purified by chromatography (SiO₂, EtOAc/Hexanes 3:7) to yield benzyl ester 33b as a colorless oil (4.2 g, 62%); R$_f$: 0.22 (EtOAc/Hexanes 3:7); ¹³C NMR (CH₃OD, 75 MHz, δ): 175.1, 158.2, 139.7, 130.3, 129.5, 129.3, 121.7, 117.4, 114.6, 73.1, 67.6, 41.6; MS (FAB, G/TG-DMSO, m/z, relative intensity): 351 ([M+DMSO]⁺, 70), 273 ([M+1]⁺, 100), 255 (20), 227 (30), 181 (40); HRMS: Calcd. for C₁₆H₁₇O₄ (M+1)⁺272.1049; found 272.1054.

Step B:

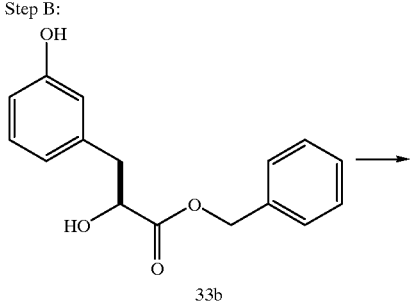

33b

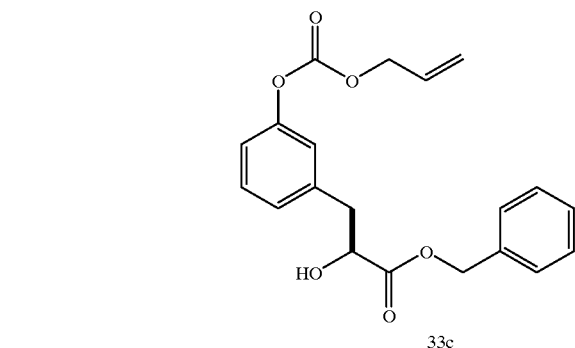

33c

A solution of benzyl ester 33b (3.8 g, 12.9 mmol) in CH₂Cl₂ (100 mL) was treated with Et₃N (1.55 g, 15.4 mmol, 2.2 mL, 1.1 equiv.), cooled to −78° C. (2-PrOH, dry ice) and a solution of allyl chloroformate (1.84 g, 15.36 mmol, 1.1 equiv.) in CH₂Cl₂ (10 mL) was added dropwise. The reaction mixture was allowed to warm up to the rt. and diluted with aq. HCl (1M, 100 mL). The reaction mixture was extracted with EtOAc (3×100 mL). The combined organic layer was washed with aq. HCl (100 ml, 1M), brine (100 mL), dried (MgSO₄) concentrated in vacuo to yield 33c which was used in the next step without further purification. R$_f$:0.43 (EtOAc/Hex 7:13); ¹³C NMR (CH₃OD, 75 MHz, δ) 174.8, 162.5, 155.0, 152.5, 140.3, 137.1, 132.8, 130.3, 129.6, 129.5, 129.4, 123.2, 120.3, 119.4, 72.7, 70.1, 67.7, 41.2, 29.9.

Step C:

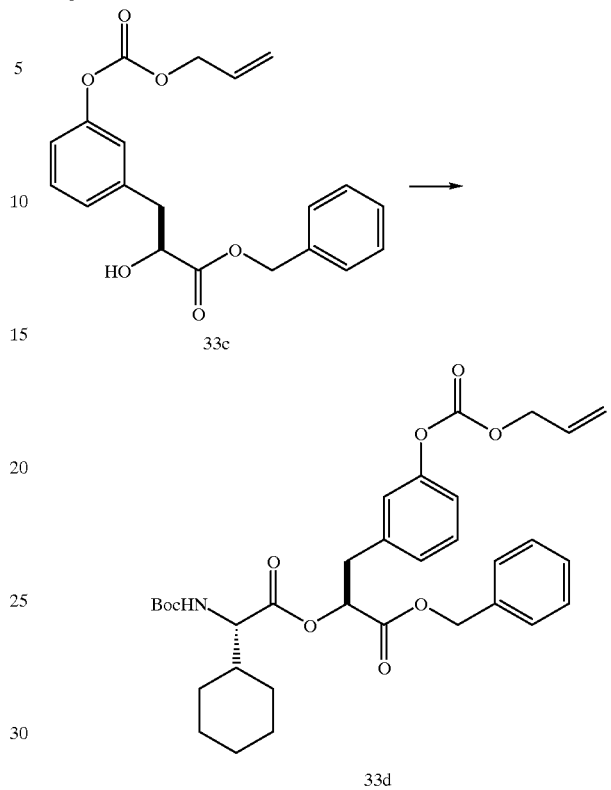

33c

33d

A solution of Boc-cyclohexylglycine monohydrate 1d (6.02 g, 23.4 mmol, 2.0 equiv.) was dissolved in CH₂Cl₂ and dried (MgSO₄). The mixture was filtered and the residue was further azeotropically dried with toluene. The residue was dissolved in CH₂Cl₂, and treated with HOBt (4.73 g, 35.1 mmol, 2.9 equiv.) EDCl (6.7 g, 35.1 mmol, 2.9 equiv.) and Hünigs base (8.31 g, 64.3 mmol, 11 mL) It was stirred at rt. for 30 min. and the alloc protected alcohol 33c (4.3 g, 12.04 mmol) was added. The reaction mixture was stirred at rt. for 36 h and diluted with aq. HCl (1M, 100 mL) and extracted with EtOAc (3×100 mL). The combined organic layers were extracted with aq. NaOH (1M, 100 mL), brine (100 mL), dried, concentrated in vacuo and purified by chromatography (SiO₂, EtOAc/Hex 1:4) to yield depsipeptide 33d (7.1 g 100%). R$_f$: 0.18 (EtOAc/Hex 1:4); HRMS: Calcd. for C₂₈H₃₄O₇ (M-Boc)⁺496.2335: found 496.2333.

Step D:

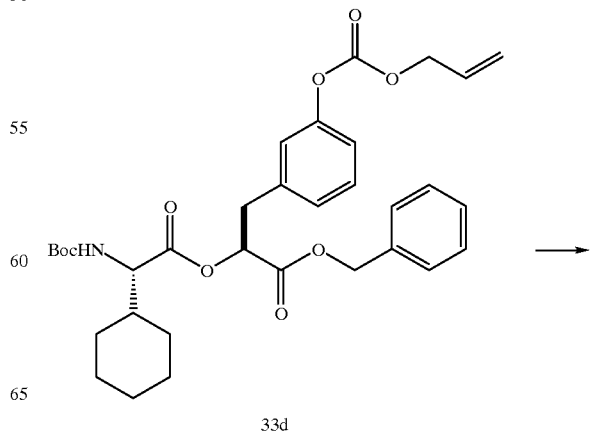

33d

-continued

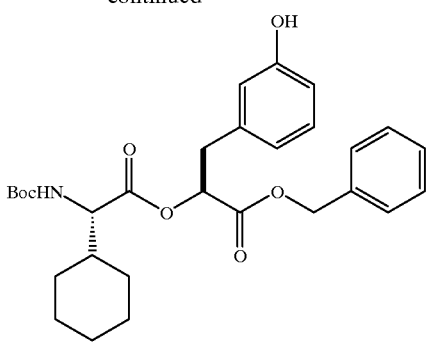

33e

A solution of alloc-protected depsipeptide 33d (7.8 g, 13.0 mmol) in dry THF (200 mL) was treated under N$_2$ with dimedione (3.27 g, 23.4 mmol, 2.0 equiv.) and Pd(Ph$_3$P)$_4$ (780 mg, 0.67 mmol, 5 mol %). The reaction mixture was stirred at rt. for 1 h and the disappearance of reactant was followed by TLC (EtOAc/Hex 1:4). The reaction mixture was concentrated in vacuo and the residue was purified by chromatography (SiO$_2$, EtOAc/Hexanes 1:4) to yield phenol 33e (5.2 g, 78%) as a colorless foam. R$_f$: 0.52 (EtOAc/Hexanes 3:7); $^1$H NMR (d$_4$–CD$_3$OD, 300 MHz, δ) 7.4–7.19 (m, 5H), 7.15–6.99 (m, 1H), 6.68–6.55 (m, 4H) 5.43–5.01 (m, 3H), 4.6 (bs, 2H), 4.11–4.00 (m, 1H), 3.18–2.91 (m, 2H), 1.80–1.55 (bs, 6H) 1.39 (s, 9H) 1.21–0.89 (m, 6H); $^{13}$C NMR (CH$_3$OD, 75 MHz, δ, mixture of diastereomers) 171.6, 169.4, 169.3, 161.1, 157.1, 157.0, 137.2, 136.9, 135.4, 135.3, 129.2, 129.1, 128.2, 128.2, 128.0, 120.3, 120.1, 116.0, 115.9, 113.6, 94.8, 79.3, 73.6, 73.5, 66.7, 66.6, 58.6, 58.5, 40.0, 39.9, 36.8, 29.1, 27.7, 27.3, 25.5. MS (Electron spray, m/z, relative intensity) 1023 ([2M+1]$^+$, 20), 512 ([M+1]$^+$, 20), 412 ([M-Boc]$^+$, 100), 202 (40) HRMS Calcd. for C$_{24}$H$_{30}$NO$_5$ (M-Boc)$^+$412.2123: found 412.2119.

Step E:

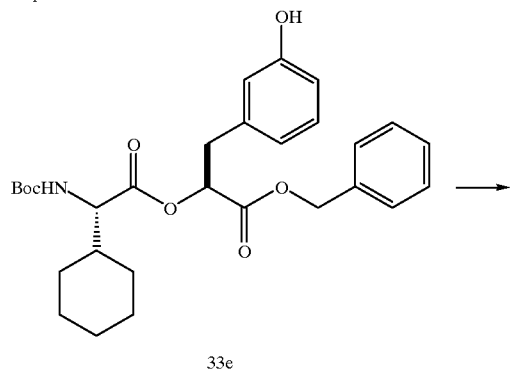

33e

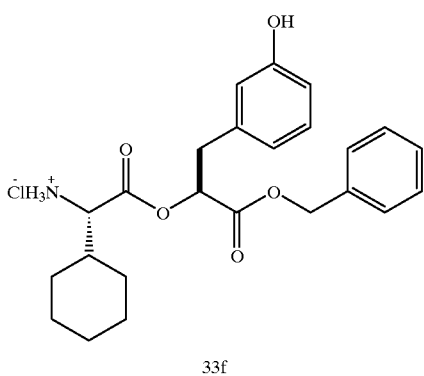

33f

A solution of Boc protected amine 33e (5.2 g, 10.7 mmol) was stirred with HCl (4M, dioxane, 200 mL, 800 mmol, 80 equiv.) until the starting material disappeared to the base line as indicated by TLC (EtOAc/Hex 3:7). The reaction mixture was concentrated in vacuo and dried in high vacuum and the residue 33f was directly used in the next step. $^1$H NMR (d$_4$–CD$_3$OD, 300 MHz, δ) 7.40–3.23 (m, 5H), 7.07 (q, 1H, J=13 Hz) 6.77–6.6 (m, 3H), 5.33–5.41 (m, 1H), 5.3–5.05 (2 AB, 2H) 3.99–3.85 (m, 1H) 3.35–22 (m, 2H) 2.00–1.5 (m, 5H), 1.50–0.80 (m, 6H); MS (FAB, G/TG-DMSO, m/z, relative intensity): 412 ([M+1]$^+$, 100); HRMS: Calcd. for C$_{24}$H$_{30}$NO$_5$; M$^+$412.2123: found 412.2139.

Step F:

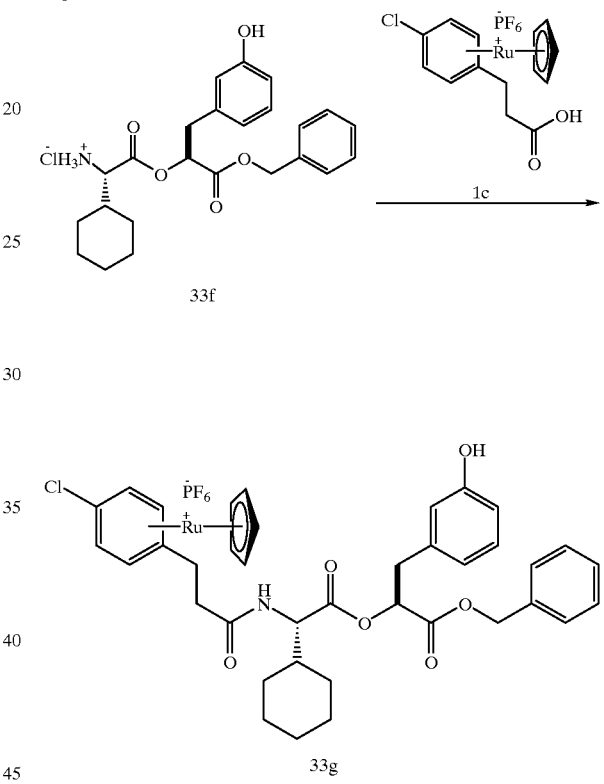

A solution of [CpRu(η$^6$–4-chlorophenylpropionic acid)] PF$_6$ 1c (2.0 g, 4.03 mmol) in dry DMF (20 mL) was treated with HOBt (835 mg 6.0 mmol, 1.5 equiv.) and Hünigs base (2.06 g, 2.95 mL, 16 mmol, 4.0 equiv.) The reaction mixture was cooled to 0° C. and treated with EDCl (1.15 g, 6.0 mmol, 1.5 equiv.) The reaction mixture was stirred at 0° C. for 30 min. and the amine hydrochloride was added 33f (1.8 g, 4.03 mmol, 1.0 equiv.) in dry DMF (10 mL). The reaction mixture was stirred at rt. for 12 h and the DMF was distilled out vacuo. The residue was diluted with aq. HCl (1M, 100 mL) and extracted into CH$_2$Cl$_2$ (3×100 mL). The combined organic layers were extracted with aq. NaHCO$_3$ (3×50 mL), brine (100 mL), dried (Na$_2$SO$_4$), filtered, concentrated in vacuo to yield a brown solid 33g (3.5 g) which was used for cyclization; MS: Electron spray, m/z, relative intensity) 743 [(M-PF$_6$)$^+$, 100], 304 (60); HRMS: Calcd. for C$_{38}$H$_{41}$NO$_6$Cl$^{102}$Ru (M-PF$_6$)$^+$744.1666: found 744.1694.

Step G:

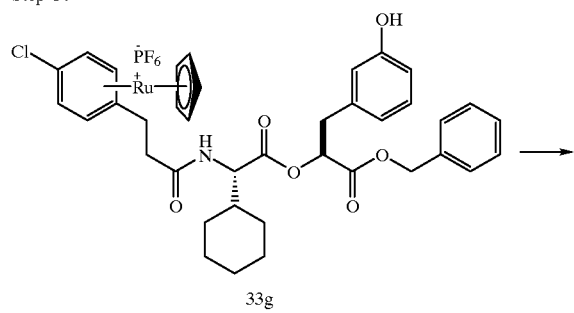

33g

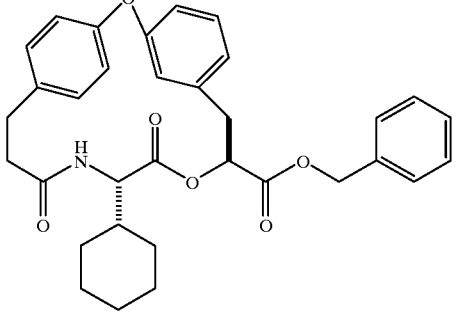

33i

+

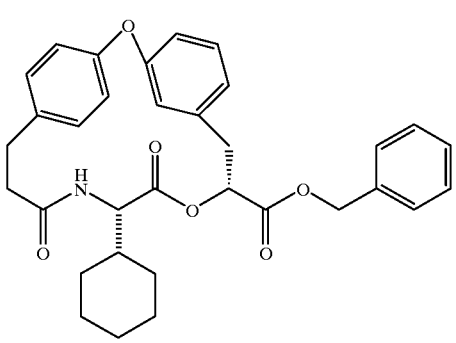

33j

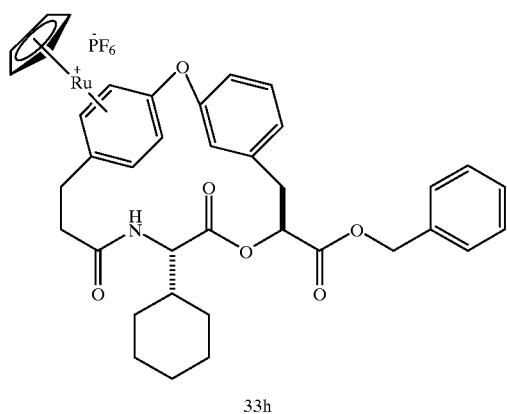

33h

Step H:

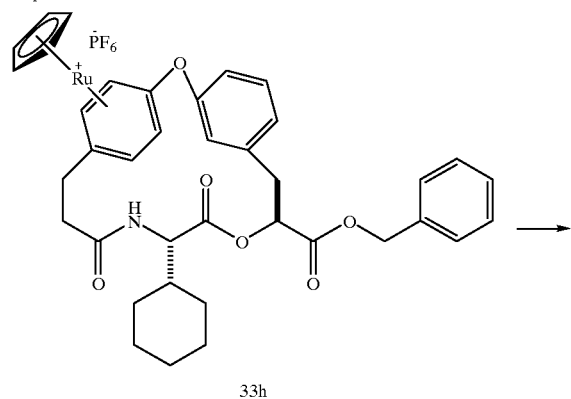

33h

A solution of η⁶-ruthenium complex 33g (3.5 g, 3.93 mmol) in dry DMF (300 mL) was degassed with dry $N_2$ and treated with $Cs_2CO_3$ (6.5 g, 19.95 mmol, 5.0 equiv.) and stirred at rt. for 16 h. The reaction mixture was concentrated in vacuo to remove the DMF and the residue was diluted with $H_2O$ (100 mL). The reaction mixture was extracted with $CH_2Cl_2$ (3×100 mL). The combined $CH_2Cl_2$ layers were extracted with brine, dried ($Na_2SO_4$), filtered, concentrated in vacuo to yield 33 h which was directly used for photolysis; MS: (Electron spray, m/z, relative intensity) 708 [(M-$PF_6$)⁺, 100]; HRMS: Calcd. for $C_{38}H_{40}NO_{61}O_2Ru$ (M-$PF_6$)⁺: 708.1892; found: 708.1918.

A solution of cyclized ruthenium complex 33h (3.5 g, 3.9 mmol) in $CH_3CN$ (60 mL) was degassed and photolyzed in a quartz tube at λ=350 nm in two batches for 48 h each. The reaction mixture were pooled together and purified by chromatography ($SiO_2$, $CH_2Cl_2/Et_2O$ 9/1) to yield cyclic depsipeptide as a mixture of diastereomers. (700 mg, 34%). The diastereomers were separated by additional chromatography (Hexanes/$CH_2Cl_2/Et_2O$ 6:3:1) to yield the two diastereomers 33i (370 mg, 18%) and 33j (216 mg 11%) as colorless solid. $R_f$ 0.28 (Hexanes: EtOAc: 3:2); $[α]_D$=25 (c 0.15, CHCl₃, 20° C.): IR (neat, cm⁻¹) 3329 (w), 2960 (m) 2926 (s), 2854 (s), 1745 (s), 1680 (m), 1589 (m), 1506 (m), 1446 (m), 1365 (w), 1259 (s) 1099 (m), 1030 (s), 800 (s), 752 (m), 698 (w) 619 (w): ¹H NMR (CDCl₃, 300 MHz, δ) 7.36–7.23 (m, 5H), 7.18–6.99 (m, 4H), 6.81 (d, 1H, J=7.5 Hz), 6.74 (dd, 1H, J=2.7, 5.7 Hz), 6.30 (s, 1H), 5.75 (d, 1H, J=7.2 Hz), 5.61 (dd, 1H, J=2.4 Hz, 5.4 Hz), 5.18, 5.14 (AB, 2H, J=12.3 Hz), 4.23 (dd, 1H, J=4.2 Hz, 3.3 Hz), 3.26–3.01 (m, 2H), 2.98–2.85 (m, 2H), 2.68–2.64 (m, 1H) 2.38–2.34 (m, 1H),1.96–1.51 (m, 6H), 1.51–0.96 (M, 5H) ¹³C NMR: (CDCl₃, 75 MHz, δ, ppm) 177.3, 171.1, 168.7, 159.8, 155.3, 138.6, 135.4, 134.9, 131.2, 129.7, 129.2, 128.7, 126.6, 126.1, 123.3, 120.8, 120.8, 117.5, 114.2, 71.8, 57.5, 56.9, 41.5, 39.0, 35.7, 32.6, 31.3, 29.0, 27.6, 26.0, 25.9. FAB (NBA/DMSO, m/e, relative intensity) 542 [(M+1)⁺100], 514 (15), 450 (5), 307 (8), 232 (5), 154.1 (17), 136 (14) HRMS: Calcd for $C_{33}H_{36}NO_6$ (M+1)⁺542.2543: found: 542.2541 CHN Calcd for $C_{33}H_{35}NO_6 \cdot 0.5H_2O$; C 71.98% H 6.59% N 2.54%; :Found C 72.56% H 7.05% N 2.63%.

Step I:

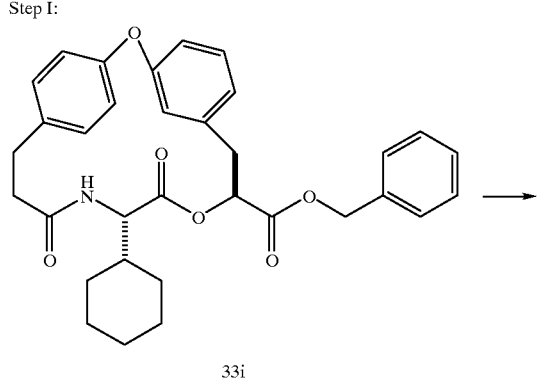

33i

33k

A solution of benzyl ester 33i (360 mg, 0.66 mmol) in CH$_3$OH/EtOAc (1:1, 50 mL), was treated with Pd(OH)2 and hydrogenated (50 psi) for 12 h. The reaction mixture was filtered through a plug of celite and the cake was rinsed with CH$_3$OH/CH$_2$Cl$_2$ (1:1, 50 mL). The filtrate was concentrated in vacuo and the residue 33k (330 mg) was used for coupling without purification. R$_f$: 0.58 (CH$_3$OH/CH$_2$Cl$_2$ 1:19): MS: (Electron spray, m/z, relative intensity) 827.2 [(M+1)$^+$, 100], 694 (20), 539 (40), 466 (10), 174 (70). HRMS: Calcd for C$_{46}$H$_{58}$N$_4$O$_{10}$ (M+1)$^+$827.4231: found: 827.4215.

Step J:

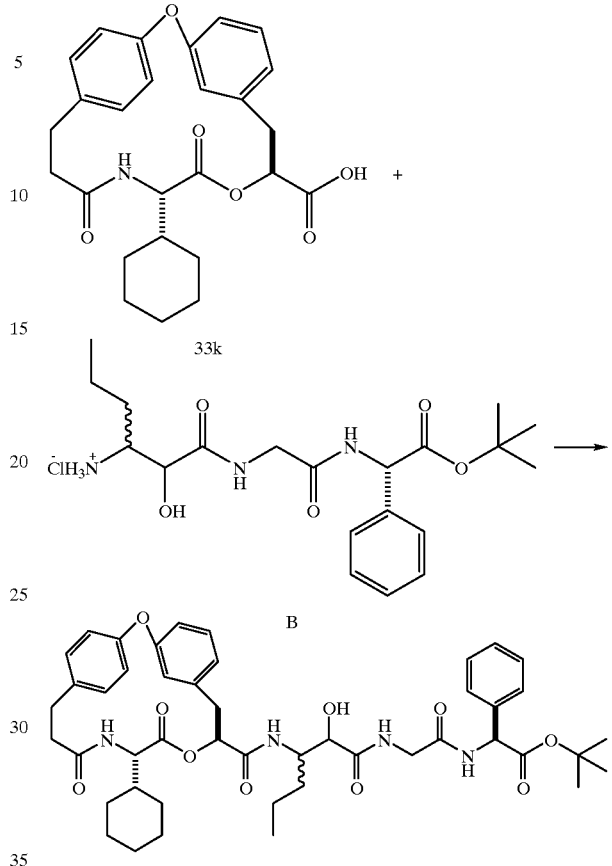

33k

B

A solution of acid 33k (165 mg, 0.31 mmol) in dry DMF (5.0 mL) and CH$_2$Cl$_2$ (5.0 mL) was treated with HOBt (83 mg, 0.46 mmol, 1.5 equiv.) and cooled to 0° C. and Hünigs base (159 mg, 1.23 mmol, 4.0 equiv., 229 µL) was added. To this mixture was added EDCl (89 mg, 0.47 mmol, 1.5 equiv.) and the reaction mixture was stirred at 0° C. for 1 h and treated with the amine hydrochloride B (159 mg, 0.372 mmol, 1.2 equiv.). The reaction mixture was stirred at rt. for 48 h and concentrated in vacuo to remove DMF and CH$_2$Cl$_2$. The residue was diluted with water and extracted with CH$_2$Cl$_2$ (3×50 mL). The combined organic layer were extracted with aq. HCl (1M, 3×50 mL), aq. NaOH (1M, 3×50 mL) brine (100 mL) and concentrated in vacuo. The residue 33l was oxidized without further purification.

Step K:

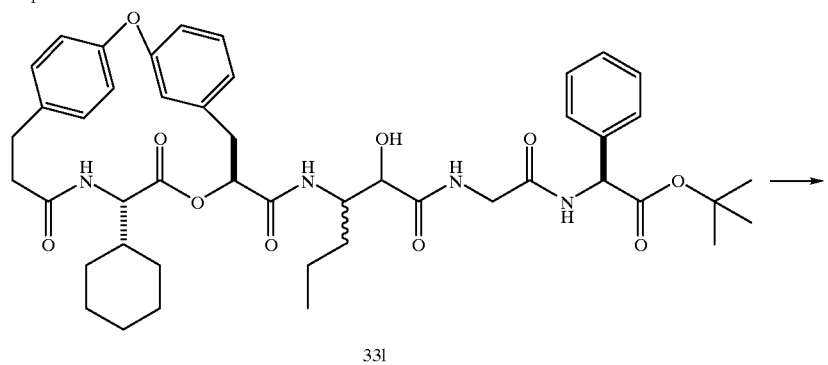

33l

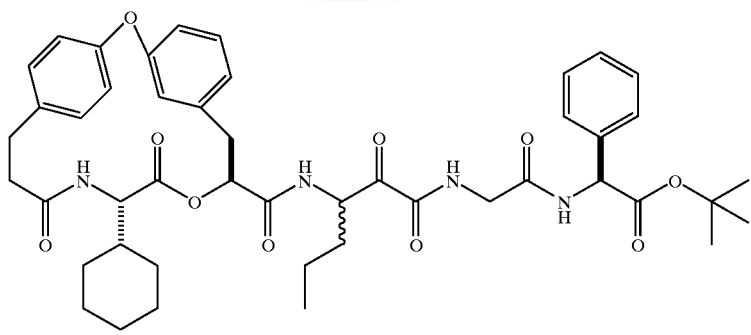

33

A solution of alcohol 331 (330 mg, 0.4 mmol) in CH$_2$Cl$_2$ (5.0 mL) was treated with Dess-Martin reagent (424 mg, 1.00 mmol, 2.5 equiv.). The reaction mixture was stirred at rt. for 1 h and diluted with aq. NaHCO$_3$ (50 mL) and aq. Na$_2$S$_2$O$_3$ (50 mL). The reaction mixture was stirred at rt for 20 min and the reaction mixture was extracted with CH$_2$Cl$_2$ (3×50 mL). The combined organic layers were extracted with brine (50 mL), dried (Na$_2$SO$_4$), filtered, concentrated in vacuo and the residue was purified by chromatography (SiO$_2$, EtOAc/Hexanes 1:1) to yield ketoamide 33 (180 mg, 55%) of a colorless solid. R$_f$: 0.63 (CH$_3$OH/CH$_2$Cl$_2$ 1:19); MS (Electron spray, m/z relative intensity): 857.2 ([M+CH$_3$OH]$^+$, 40), 825.2 ([M+1]$^+$100).

Example 34

Preparation of Compound of Formula 34:

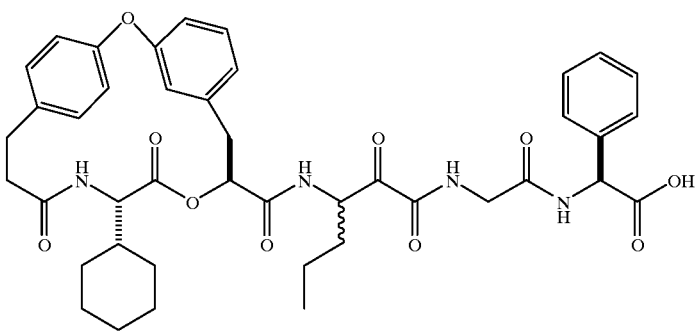

34

Step A:

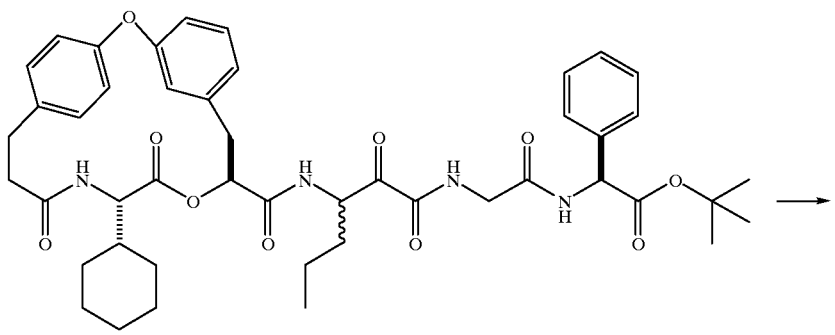

33

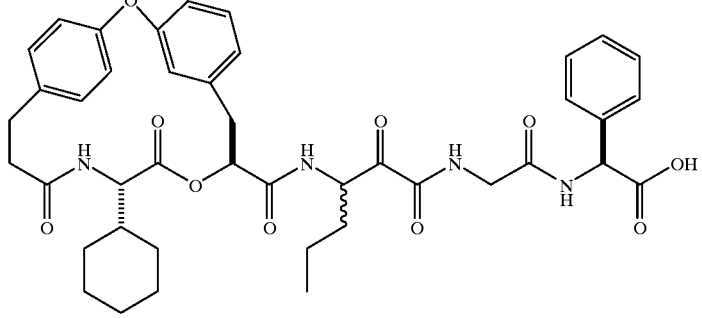

34

A solution of oxidized depsipeptide 33 (160 mg, 0.2 mmol) in dry CH$_2$Cl$_2$ (5.0 mL) was treated with TFA (5.0 mL) and stirred at rt. for 7 h. The reaction mixture was concentrated in vacuo and the residue was repeatedly dissolved in CH$_3$OH/CH$_2$Cl$_2$/Hexanes (1:1:1) and concentrated in vacuo several times to yield a tan colored solid 34 (133 mg, 86%) which was dried in vacuo MS: (Electron spray, m/z relative intensity): 769.2 [(M+1)$^+$, 100], 481 (5), 269 (25) 191 (90).

Example 35

Preparation of Compound of Formula 35:

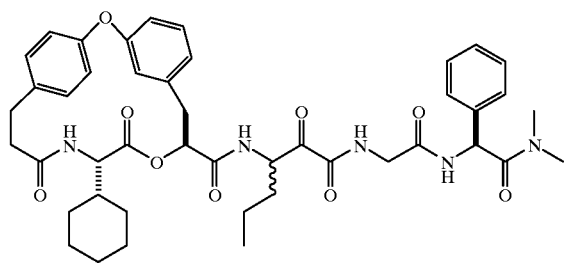

35

Step A:

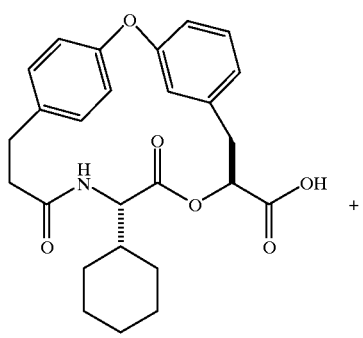

33k

+

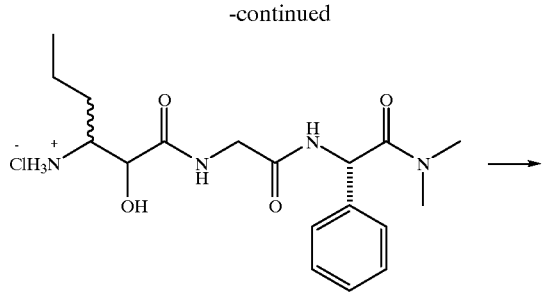

A

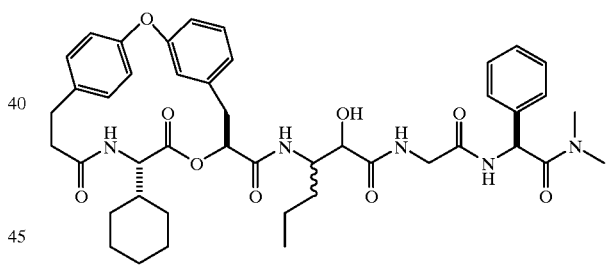

35a

A solution of acid 33k (165 mg, 0.31 mmol) in dry DMF (5.0 mL) and CH$_2$Cl$_2$ (5.0 mL) was treated with HOBt (83 mg, 0.46 mmol, 1.5 equiv) and cooled to 0° C. and Hünigs base (159 mg, 1.23 mmol, 4.0 equiv., 229 µL) was added. To this mixture was added EDCl (89 mg, 0.47 mmol, 1.5 equiv.) and the reaction mixture was stirred at 0° C. for 1 h and treated with the amine hydrochloride A (159 mg, 0.372 mmol, 1.2 equiv.). The reaction mixture was stirred at rt. for 48 h and concentrated in vacuo to remove DMF and CH$_2$Cl$_2$. The residue was diluted with water and extracted with CH$_2$Cl$_2$ (3×50 mL) The combined organic layer was extracted with aq. HCl (1M, 3×50 mL), aq. NaOH (1M, 3×50 mL), brine (100 mL) and concentrated in vacuo. The residue 35a was oxidized without further purification. MS: (Electron spray, m/z relative intensity): 798.2 [(M+1)$^+$, 30], 479 (10), 391 (20) 180 (100).

Step B:

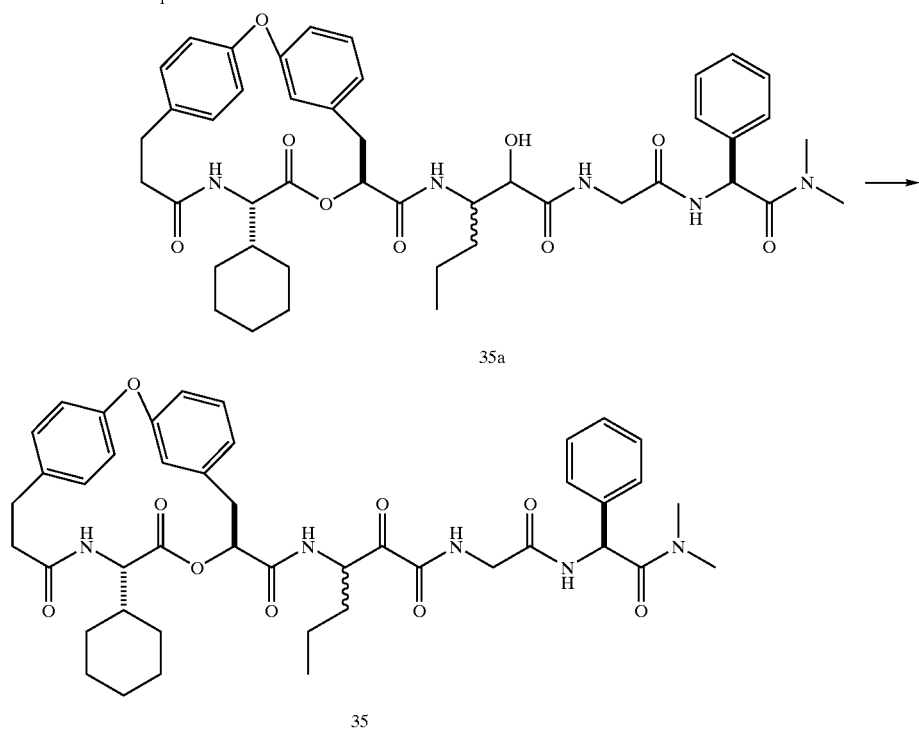

A solution of alcohol 35a (190 mg, 0.24 mmol) in CH$_2$Cl$_2$ (10 mL) was treated with Dess-Martin reagent (423 mg 1.0 mmol, 4.0 equiv.) and stirred at rt. for 1 h. The reaction mixture was diluted with aq. NaHCO$_3$ (50 mL) and extracted in CH$_2$Cl$_2$ (3×50 mL). The combined organic layers were extracted with aq. satd. Na$_2$S$_2$O$_3$, brine (3×50 mL), dried (Na$_2$SO$_4$), filtered concentrated in vacuo and purified by chromatography (SiO$_2$, acetone/Hexanes 3:7->1:1 to yield oxidized product 35 (163 mg, 86%) as a colorless solid. MS (Electron spray, m/z relative intensity): 796 [(M+1)$^+$, 100], 508 (20), 269 (20).

Example 36

Preparation of Compound of Formula 36:

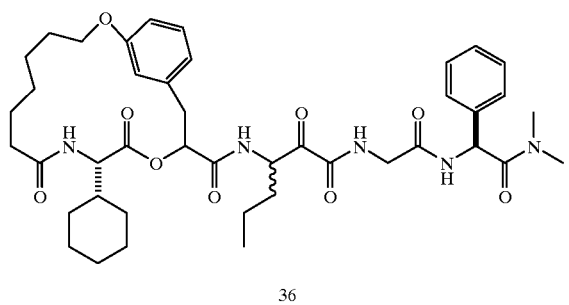

Step A:

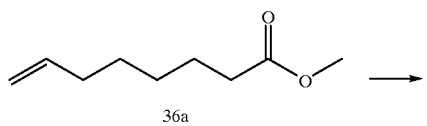

-continued

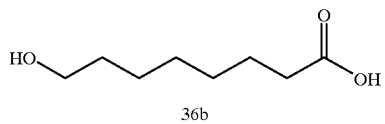

A solution of BH$_3$.THF (1M in THF, 100 mmol, 100 mL, 3.0 equiv.) was added dropwise to a solution of alkene (5.0 g, 35 mmol) in THF (100 mL) at 0° C. and stirred for 1 h. The reaction mixture was treated with ethanol (20 mL) dropwise. After the evolution of hydrogen gas was complete the reaction mixture was treated with pH 7 buffer (100 mL) and H$_2$O$_2$ (30 volumes, 100 mL). The reaction mixture was stirred at rt. for 4 h and quenched with aq. HCl (100 mL). The aqueous layer was extracted with Et$_2$O (3×100 mL). The combined ether layers were extracted with aq. NaOH (1M, 100 m L), brine (100 mL), dried (MgSO$_4$), filtered, concentrated in vacuo and purified by chromatography (SiO$_2$, EtOAc/Hexanes 2/3) to yield alcohol as a colorless liquid (2.9 g, 52%).

A solution of the hydroxylated ester in THF/H$_2$O/CH$_3$OH (100 mL, 1:1:1) was treated with LiOH.H$_2$O (2.1 g, 51.2 mmol, 3.0 equiv.) and stirred at rt. for 3 d. The reaction mixture was concentrated in vacuo and the aqueous layer was extracted with ether (2×40 mL). The aqueous layer was acidified to pH~1 and extracted into EtOAc (3×50 mL). The combined organic layers were extracted with brine (100 mL), dried (MgSO$_4$) filtered concentrated in vacuo and the residue 36b was used as is for coupling in Step B. $^1$H NMR (300 MHz, CD$_3$OD, δ) 3.53 (t, 2H, J=6.6 Hz), 2.72 (t, 2H, J=7.2 Hz), 1.59 (t, 2H, J=7.5 Hz), 1.5 (t, 2H, J=7.5 Hz), 1.38–1.33 (m, 6H).

Step B:

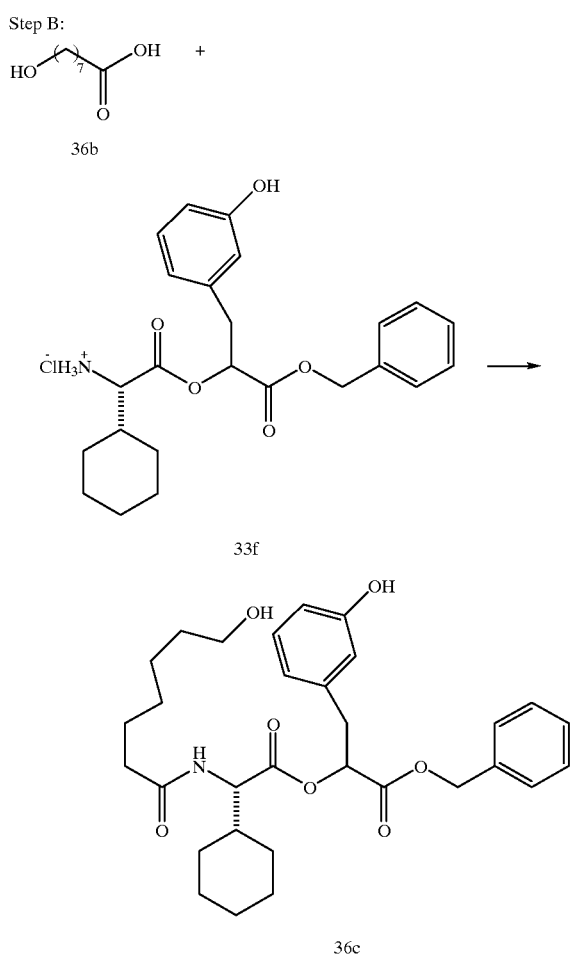

A solution of ω-hydroxyl heptanoic acid 36b (1.01 g, 6.93 mmol) in CH$_2$Cl$_2$ (40 mL) was treated with Hünigs base (1.97 g, 15.24 mmol, 2.2 equiv. 2.81 mL) and amine hydrochloride 33f (3.1 g, 6.93 mmol, 1.0 equiv.). The reaction mixture was cooled to 0° C. and treated with PyBrOP (3.22 g, 6.93 mmol, 1.0 equiv.) The reaction mixture was stirred overnight at rt. and the reaction mixture was concentrated in vacuo. The residue was purified by chromatography (EtOAc/Hexanes 1:1) to yield depsipeptide 36c (2.5 g, 66%) as a colorless viscous oil. $^1$H NMR (CD$_3$OD, 400 MHz, δ, ppm) 8.07 (t, 1H), 7.33–7.21 (m, 4H), 7.09–7.02 (m, 1H), 6.67–6.63 (m, 3H), 5.25–5.06 (m, 1H), 5.08 (q, 2H, J=7.5 Hz), 4.36–4.33 (m, 1H), 3.51 (dd, 2H, J=5.4 Hz, 0.9 Hz), 3.11–2.96 (m, 2H), 2.22–2.17 (m, 1H), 1.99–0.90 (m, 14H). $^{13}$C NMR: (CD$_3$OD, 75 MHz, δ, ppm, mixture of diastereomers): 172.1, 172.0, 171.8, 171.1, 170.9, 169.5, 169.3, 157.1, 157.0, 137.3, 137.0, 135.3, 135.2, 129.2, 129.1, 128.2, 128.0, 127.9, 120.3, 120.0, 116.0, 115.9, 113.6, 94.8, 73.6, 73.4, 66.8, 66.7, 60.2, 57.3, 39.6, 36.7, 28.9, 28.0, 25.6, 20.9, 19.5, 13;. MS (FAB, NBA DMSO, m/z rel. int): 562. [(M+Na)$^+$, 20], 540. [(M+1)$^+$, 100), 412 (15), 240 (50), 112 (80).

Step C:

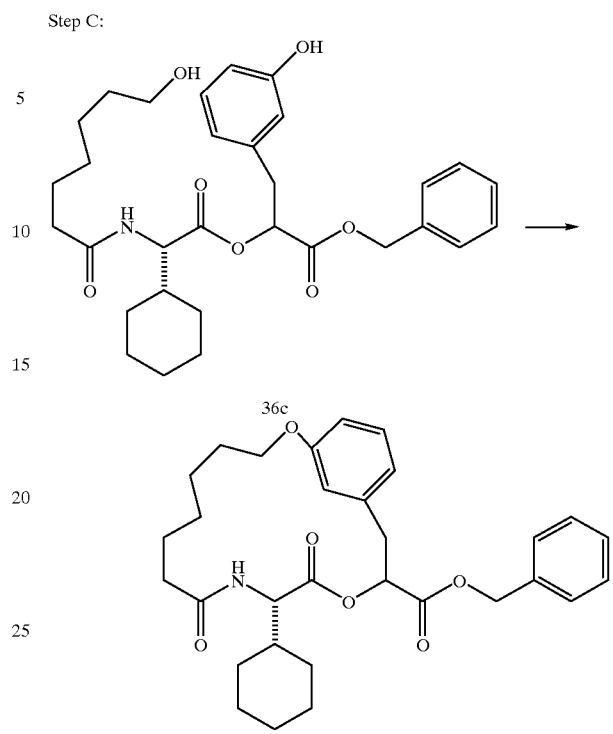

A solution of alcohol 36c (2.56g, 4.63 mmol) in dry CH$_2$Cl$_2$ (50 mL) was treated with triphenylphosphine (2.67 g, 10.2 mmol, 2.2 equiv.) under N$_2$ and cooled to 0° C. The reaction mixture was treated with DEAD (1.61 g, 9.26 mmol, 2.0 equiv.) in CH$_2$Cl$_2$ (30 mL). The reaction mixture was warmed to rt. and stirred for 2 h. It was concentrated in vacuo and purified by chromatography (Et$_2$O/Hex 1:3) to yield cyclic product 36d (530 mg, 21%) as a colorless solid. MS (FAB, NBA, DMSO, m/z rel. in), 522 [(M+1)$^+$, 100], 494. (60), 268 (20), 222(20); HRMS calcd. for C$_{31}$H$_{40}$NO$_6$: (M+1)$^+$: 522.2856; Found: 522. 2864.

Step D:

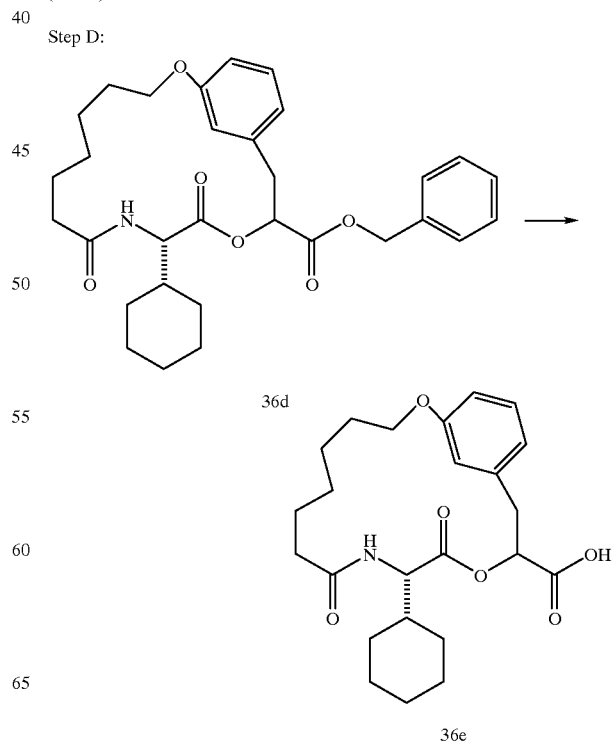

A solution of the benzyl ester (242 mg, 0.47 mmol) in methanol (30 mL) was treated with Pd/C (10 wt %) and hydrogenated on a Parr at 40 psi for 14 h. The reaction mixture was filtered through a plug of celite and the filtrate was concentrated in vacuo to yield a colorless solid 36e (181 mg, 93%) which was used for coupling.

Step E:

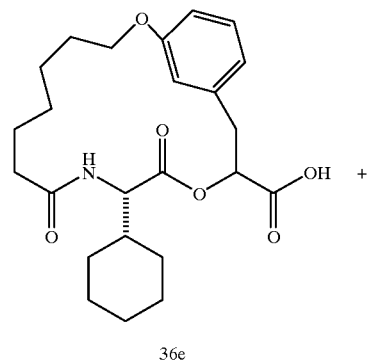

36e

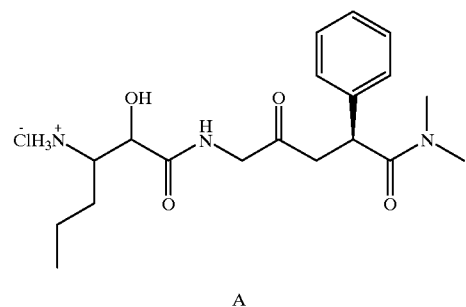

A

Step F:

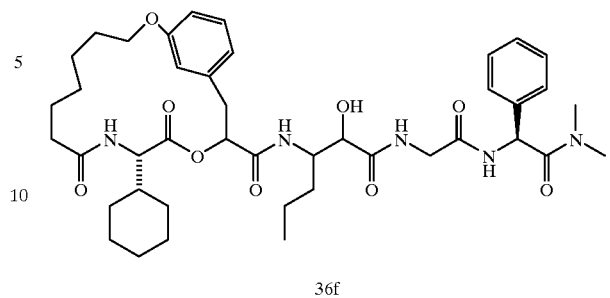

36f

A solution of the hydrolyzed acid 36e (167 mg, 0.39 mmol) in $CH_2Cl_2$ (4.0 mL) was treated with HOOBt (95 mg, 0.58 mmol, 1.5 equiv.) and cooled to 0° C. and Hünigs base (202 mg, 1.56 mmol, 4.0 equiv. 288 µL) was added. To this mixture was added EDCl (111 mg, 0.58 mmol, 1.5 equiv.) and the reaction mixture was stirred at 0° C. for 0.5 h and treated with the amine hydrochloride (186 mg, 0.47 mmol, 1.20 equiv.). The reaction mixture was stored in freezer for 24 h and concentrated in vacuo to remove DMF and $CH_2Cl_2$. The residue was diluted with aq. HCl (2M, 30 mL) and extracted with $CH_2Cl_2$ (3×50 mL) The combined organic layer was extracted with aq. HCl (2M, 30 mL), aq. NaOH (1 M) brine (2×50 mL), dried ($MgSO_4$) and concentrated in vacuo. The residue 36f (100 mg) was oxidized without further purification. HRMS calcd. for $C_{42}H_{60}N_5O_9$ $(M+1)^+$: 778.4391; Found: 778.4399.

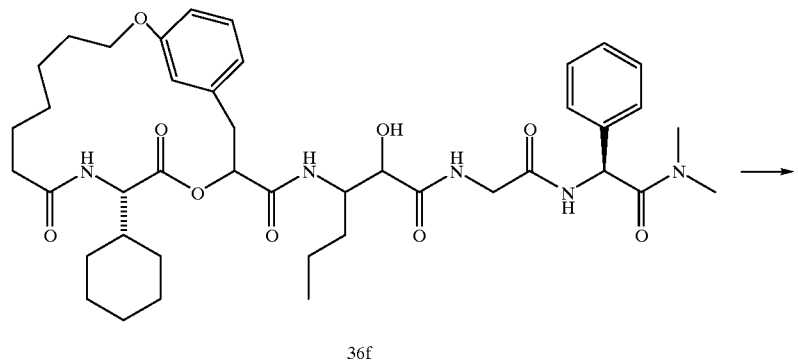

36f

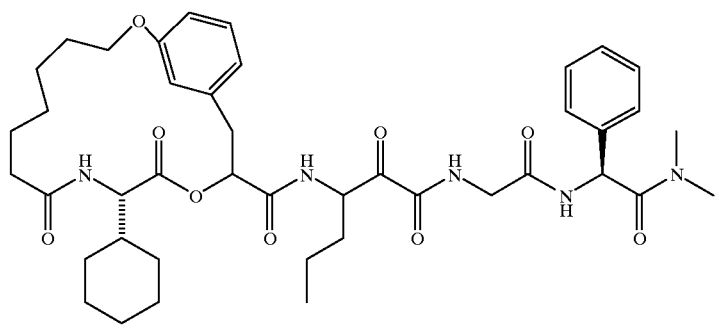

36

A solution of alcohol 36f (100 mg, 0.13 mmol) in CH$_2$Cl$_2$ (5.0 mL) was treated with Dess-Martin reagent (100 mg, 0.0.23 mmol, 1.8 equiv.). The reaction mixture was stirred at rt. for 2 h and diluted with aq. NaHCO$_3$ (15 mL) and aq. Na$_2$S$_2$O$_3$ (15 mL). The reaction mixture was concentrated in vacuo and the residue was purified by chromatography (SiO$_2$, acetone/Hexanes: 3:7) to yield ketoamide 36 (61 mg, 61%) as a colorless solid; MS (FAB, NBA/DMSO, m/z rel. int): 776 [(M+1)$^+$, 100], 731 (10), 598 (25), 570 (15), 485 (20), 358 (20), 247 (50).

Example 37

Preparation of Compound of Formula 37:

Step A:

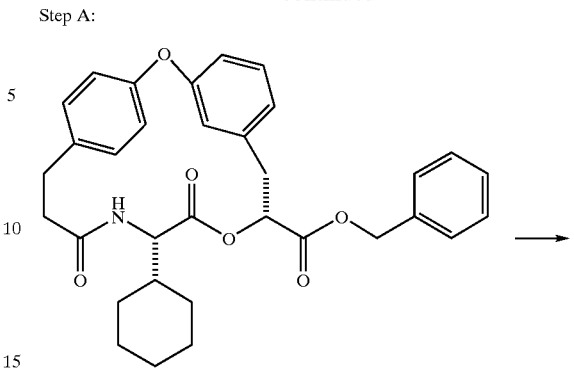

33j

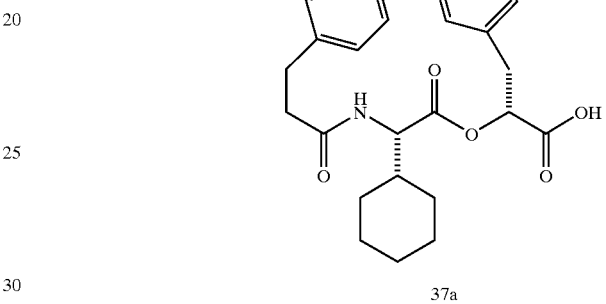

37a

A solution of benzyl ester 33j (230 mg, 0.42 mmol) in CH$_3$OH/EtOAc (1:1, 50 mL), was treated with Pd(OH)2 and hydrogenated (50 psi). for 12 h. The reaction mixture was filtered through a plug of celite and the cake was rinsed with CH$_3$OH/CH$_2$Cl$_2$ (1:1, 50 mL). The reaction mixture was concentrated in vacuo and the residue 37a (177 mg, 93%) was used for coupling without purification.

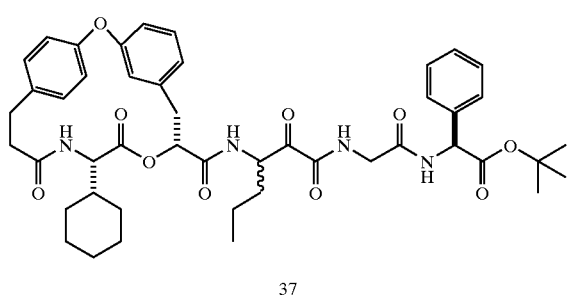

37

Step B:

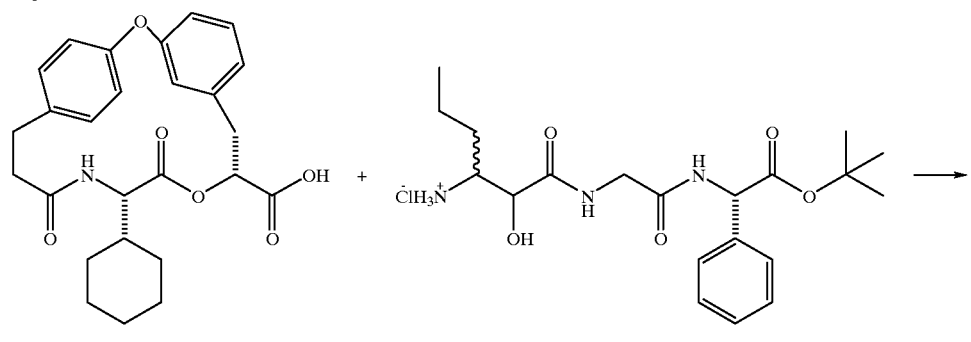

37a                    B

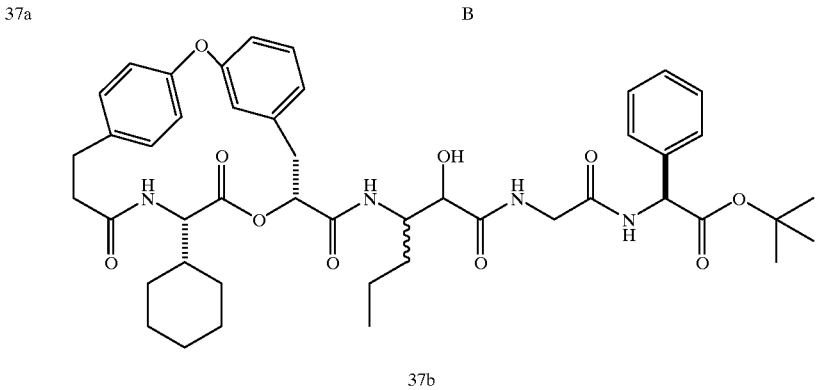

37b

A solution of acid 37a (177 mg, 0.33 mmol) in dry DMF (5.0 mL) and CH$_2$Cl$_2$ (5.0 mL) was treated with HOBt (88 mg, 0.49 mmol, 1.5 equiv) and cooled to 0° C. and Hünigs base (175 mg, 1.35 mmol, 4.0 equiv, 251 μL) was added. To this mixture was added EDCl (95 mg, 0.49 mmol, 1.5 equiv) and the reaction mixture was stirred at 0° C. for 1 h and treated with the amine hydrochloride B (170 mg, 0.39 mmol, 1.2 equiv.). The reaction mixture was stirred at rt for 48 h and concentrated in vacuo to remove DMF and CH$_2$Cl$_2$. The residue was diluted with water and extracted with CH$_2$Cl$_2$ (3×50 mL) The combined organic layer was extracted with aq. NaOH (1M, 2×50 mL), brine (100 mL) and concentrated in vacuo. The residue 37b (315 mg) was oxidized without further purification.

Step C:

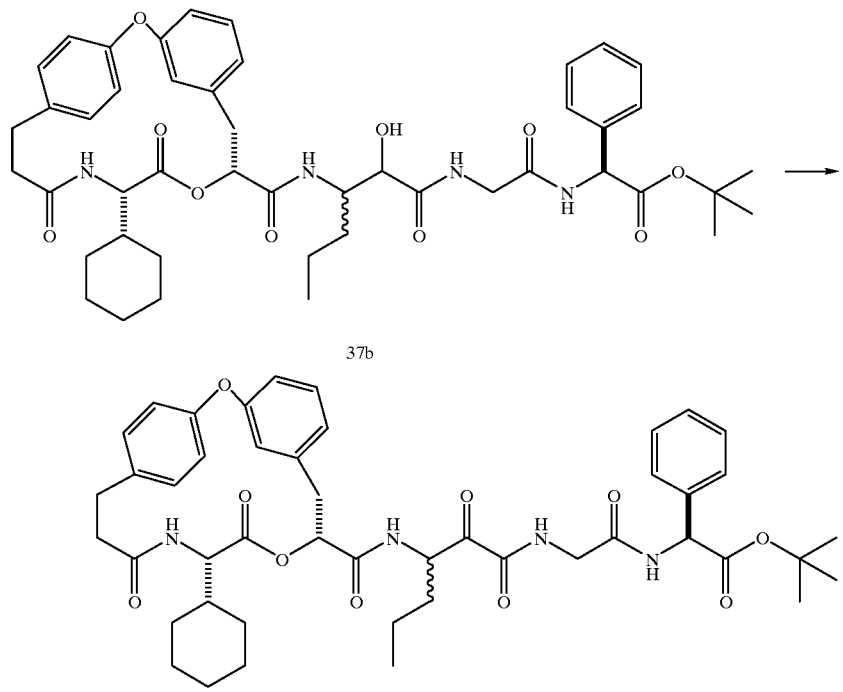

A solution of alcohol 37b (315 mg, 0.4 mmol) in CH$_2$Cl$_2$ (5.0 mL) was treated with Dess-Martin reagent (424 mg, 1.00 mmol, 2.5 equiv.). The reaction mixture was stirred at rt. for 1 h and diluted with aq. NaHCO$_3$ (50 mL) and aq. Na$_2$S$_2$O$_3$ (50 mL). The reaction mixture was stirred at rt. for 20 min and the reaction mixture was extracted with CH$_2$Cl$_2$ (3×50 mL). The combined organic layers were extracted with brine, dried (Na$_2$SO$_4$), filtered concentrated in vacuo and the residue was purified by chromatography (SiO$_2$, EtOAc/Hexanes 1:1) to yield ketoamide 37 (210 mg, 66%) of a colorless solid. R$_f$: 0.63 (CH$_3$OH/CH$_2$Cl$_2$ 1:19); MS: (Electron spray, m/z relative intensity): 857 ([M+CH$_3$OH]$^+$, 33), 825 [M+1]$^+$40), 191 (100).

Example 38
Preparation of Compound of Formula 38:

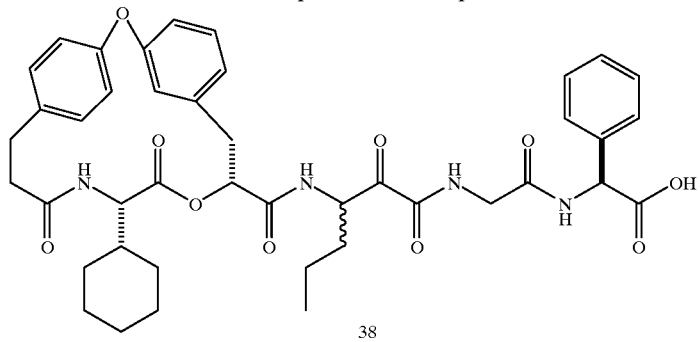

Step A:

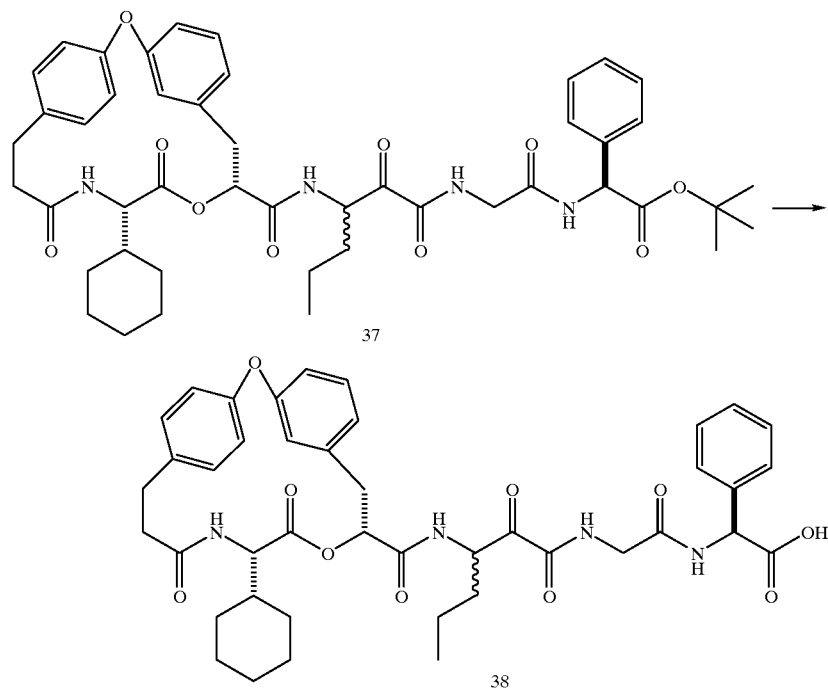

A solution of oxidized depsipeptide 37 (200 mg, 0.24 mmol) in dry CH$_2$Cl$_2$ (5.0 mL) was treated with TFA (5.0 mL) and stirred at rt. for 7 h. The reaction mixture was concentrated in vacuo and the residue was repeatedly dissolved in CH$_3$OH/CH$_2$Cl$_2$/Hexanes (1:1:1) and concentrated in vacuo several times to yield a tan colored solid 38 (130 mg, 87%) which was dried in vacuo; MS: (Electron spray, m/z relative intensity): 769 ([M+1]$^+$, 45), 294 (45), 191 (100).

Example 39

Preparation of Compound of Formula 39:

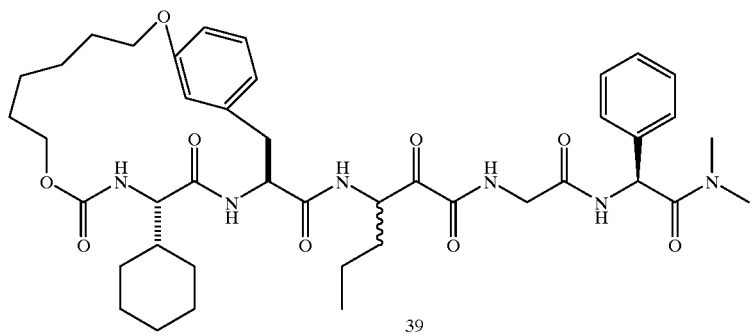

Step A:

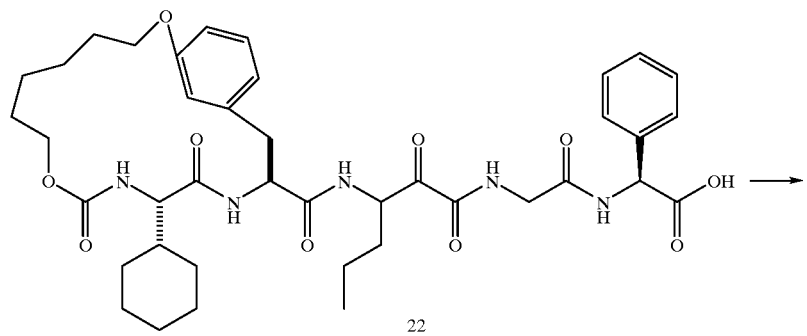

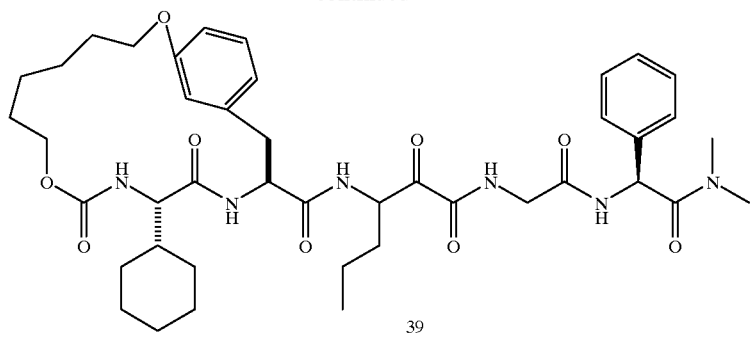

39

A solution of acid 22 (40 mg, 0.06 mmol) in $CH_2Cl_2$ (0.5 mL) and DMF (0.5 mL) was cooled to 0° C. and treated with $Me_2NH.HCl$ (15 mg, 0.18 mmol, 3.0 equiv) and Hünigs base (31 mg, 0.24 mmol, 44 μL, 4.0 equiv). The reaction mixture was then treated with PyBrOP (55 mg, 0.12 mmol, 2.0 equiv) and stored for 12 h in the freezer. The yellow reaction mixture was concentrated in vacuo and the residue was purified by chromatography ($SiO_2$, EtOAc/Hexanes gradient 3:2--->1:0) to obtain impure product which was purified once again using (acetone/Hexanes 1:6) to yield dimethyl amide 39 as a colorless solid (14 mg, 35%). MS: (Electron spray, m/z relative intensity): 791 [$(M+1)^+$, 50], 391 (40), 276 (50), 176 (100).

Example 40
Preparation of Compound of Formula 40:

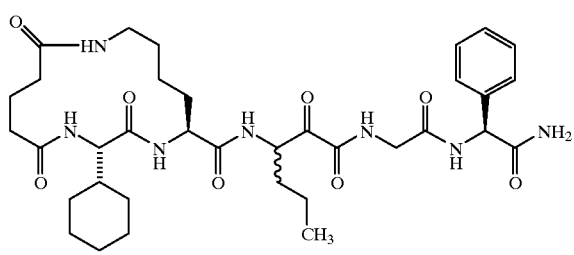

40

General Procedure for Solid-phase Coupling Reactions:

The synthesis was done in a reaction vessel which was constructed from a polypropylene syringe cartridge fitted with a polypropylene frit at the bottom. The Fmoc-protected amino acids were coupled under standard solid-phase techniques. Each reaction vessel was loaded with 100 mg of the starting Fmoc-Sieber resin (approximately 0.035 mmol). The resin was washed with 2 mL portions of DMF (2 times). The Fmoc protecting group was removed by treatment with 2 mL of a 20% v/v solution of piperidine in DMF for 20 min. The resin was washed with 2 mL portions of DMF (4 times). The coupling was done in DMF (2 mL), using 0.12 mmol of Fmoc-amino acid, 0.12 mmol of HATU and 0.24 mmol of DIPEA. After shaking for 2 h, the reaction vessel was drained and the resin was washed with 2 mL portions of DMF (4 times). The coupling cycle was repeated with the next Fmoc-amino acid or capping group.

Scheme 10

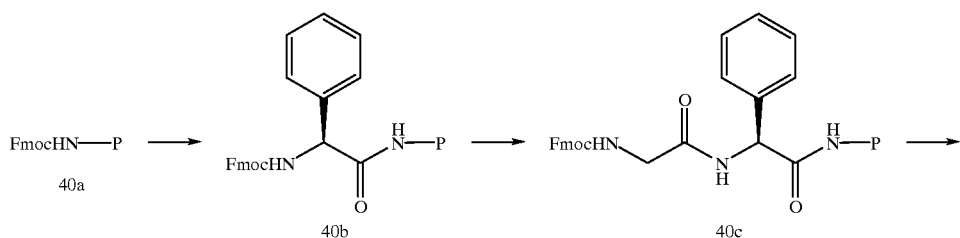

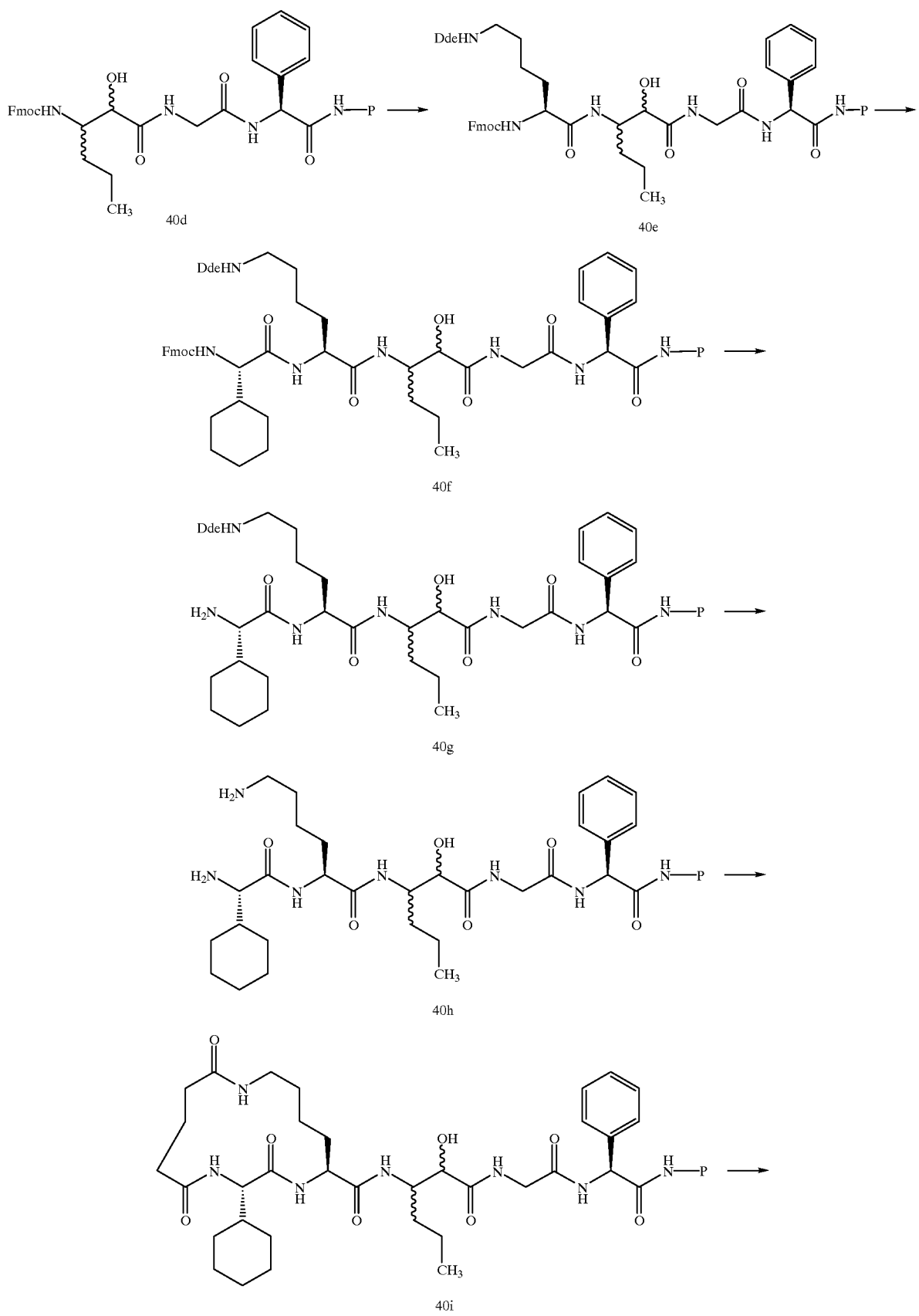

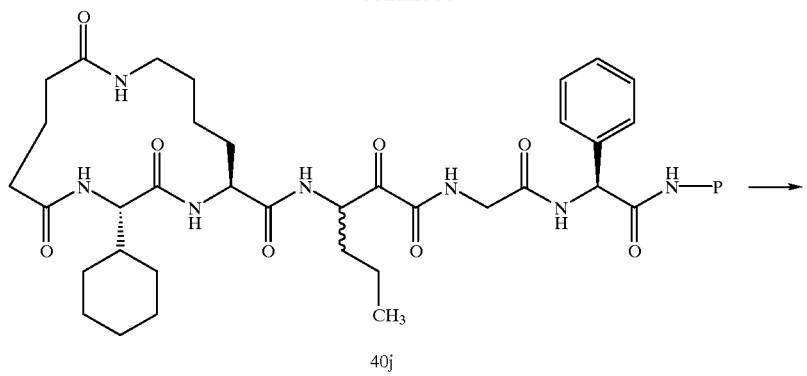

40j

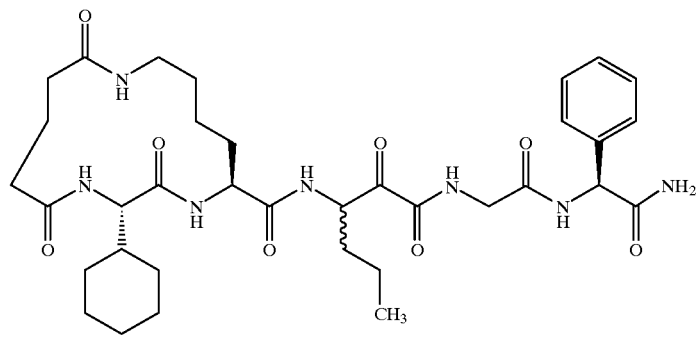

40

Fmoc-Sieber resin 40a (0.035 mmol) was treated with 2 mL of a 20% v/v solution of piperidine in DMF for 20 min. followed by washing with 2 mL portions of DMF (4 times). DMF (2 mL) was added to the resin followed by Fmoc-phenylglycine (0.12 mmol), HATU (0.12 mmol) and DIPEA (0.24 mmol). After shaking at room temperature for 2 h, the resin was washed with 2 mL portions of DMF (4 times) to afford resin-bound compound 40b. Resin-bound compound 40b was treated with 2 mL of a 20% v/v solution of piperidine in DMF for 20 min. followed by washing with 2 mL portions of DMF (4 times). DMF (2 mL) was added to the resin followed by Fmoc-glycine (0.12 mmol), HATU (0.12 mmol) and DIPEA (0.24 mmol). After shaking at room temperature for 2 h, the resin was washed with 2 mL portions of DMF (4 times) to afford resin-bound compound 40c. Resin-bound compound 40c was treated with 2 mL of a 20% v/v solution of piperidine in DMF for 20 min. followed by washing with 2 mL portions of DMF (4 times). DMF (2 mL) was added to the resin followed by N-Fmoc-propylisoserine (0.12 mmol), HATU (0.12 mmol) and DIPEA (0.24 mmol). After shaking at room temperature for 2 h, the resin was washed with 2 mL portions of DMF (4 times) to afford resin-bound compound 40d. Resin-bound compound 40d was treated with 2 mL of a 20% v/v solution of piperidine in DMF for 20 min. followed by washing with 2 mL portions of DMF (4 times). DMF (2 mL) was added to the resin followed by Fmoc-lysine(Dde) (0.12 mmol), HATU (0.12 mmol) and DIPEA (0.24 mmol). After shaking at room temperature for 2 h, the resin was washed with 2 mL portions of DMF (4 times) to afford resin-bound compound 40e. Resin-bound compound 40e was treated with 2 mL of a 20% v/v solution of piperidine in DMF for 20 min. followed by washing with 2 mL portions of DMF (4 times). DMF (2 mL) was added to the resin followed by Fmoc-cyclohexylglycine (0.12 mmol), HATU (0.12 mmol) and DIPEA (0.24 mmol). After shaking at room temperature for 2 h, the resin was washed with 2 mL portions of DMF (4 times) to afford resin-bound compound 40f. Resin-bound compound 40f was treated with 2 mL of a 20% v/v solution of piperidine in DMF for 20 min. The resin was washed with 2 mL portions of DMF (4 times) to provide resin-bound compound 40g. Resin-bound compound 40g was treated with 2 mL portions of a 2% v/v solution of hydrazine in DMF for 5 min. (3 times). The resin was washed with 2 mL portions of DMF (4 times) to provide resin-bound compound 40h. Resin-bound compound 40h was treated with 0.035 mmol of glutaric acid, 0.07 mmol of HATU and 0.14 mmol of DIPEA in 2 mL of DMF at room temperature for 16 h. The resin was washed with 2 mL portions of DMF (4 times), THF (4 times) and DCM (4 times) to provide resin-bound compound 40i. Resin-bound compound 40i was treated with a solution of 0.14 mmol of Dess-Martin periodinane and 0.14 mmol of t-BuOH in 2 mL of DCM at room temperature for 4 h. The resin was washed with 2 mL portions of a 20% v/v solution of iPrOH in DCM, THF, a 50% v/v solution of THF in water (4 times), THF (4 times) and DCM (4 times) to provide resin-bound compound 40j. The resin-bound compound 40j was treated with 4 mL of a 2% v/v solution of TFA in DCM for 5 min. The filtrate was added to 1 mL of AcOH and the solution was concentrated by vacuum centrifugation to provide compound 40 (0.0117 g, 48% yield). MS (LCMS-Electrospray) 698.2 MH[+].

Example 41–53
Preparation of Compounds of Formula 41 to 53:
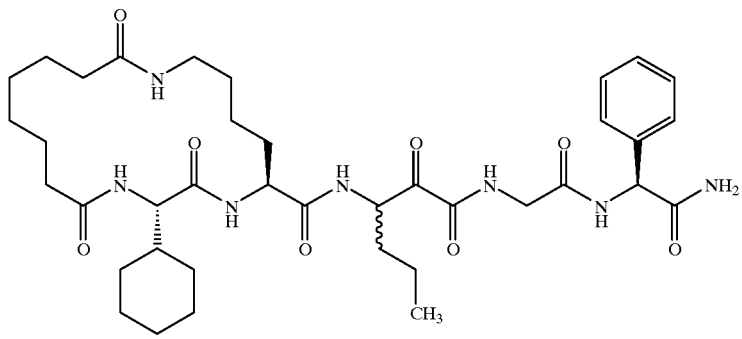
41
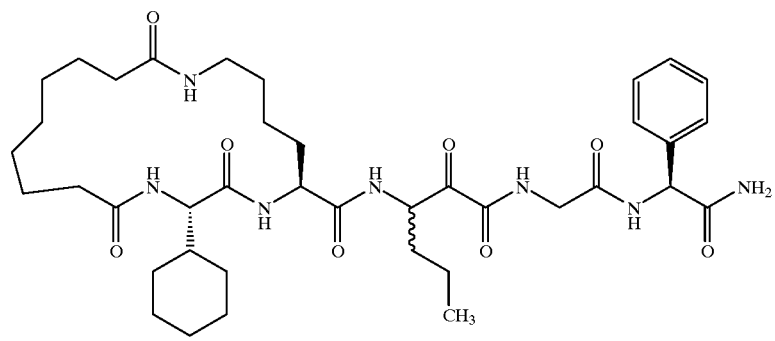
42
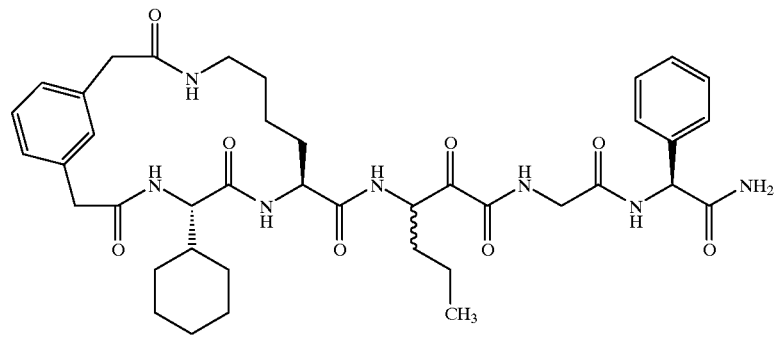
43
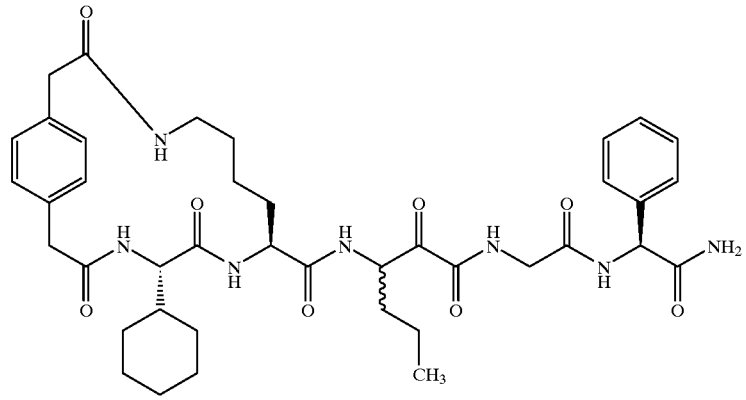
44

45
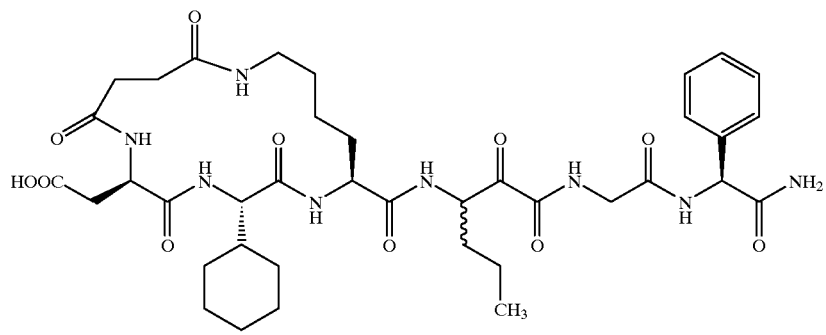
46
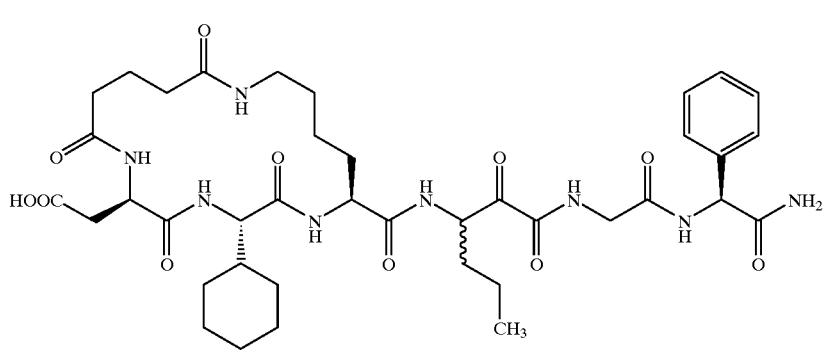
47
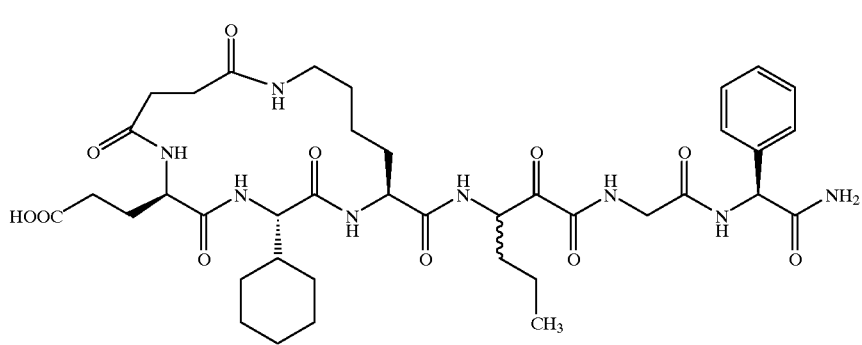
48
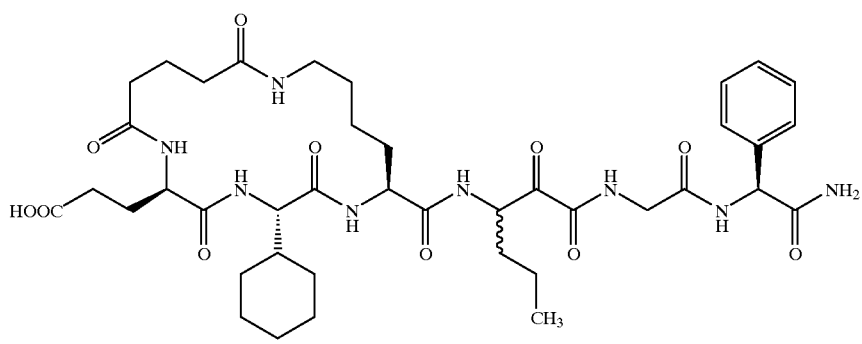

49
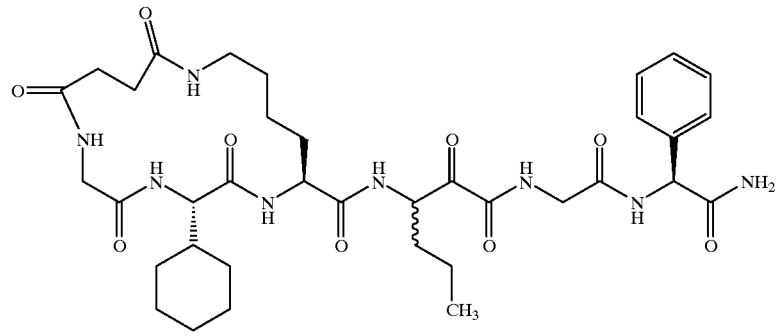
50
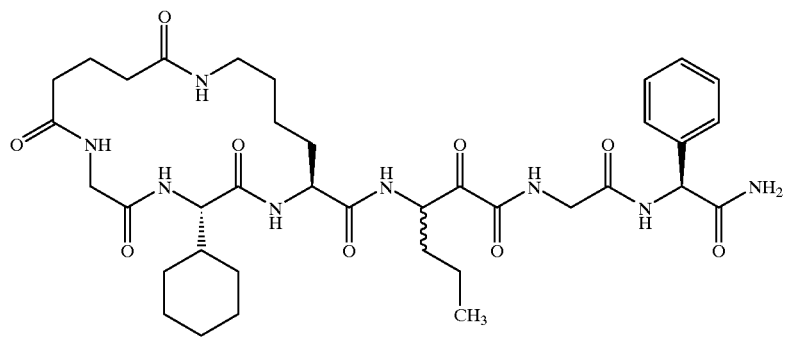
51
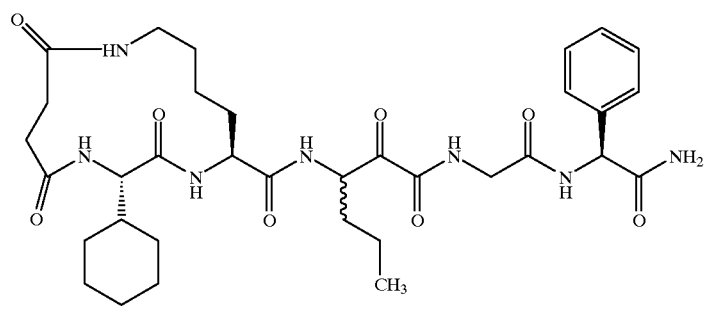
52
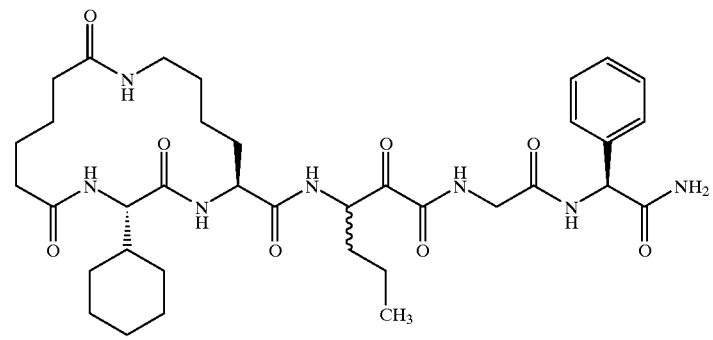

-continued

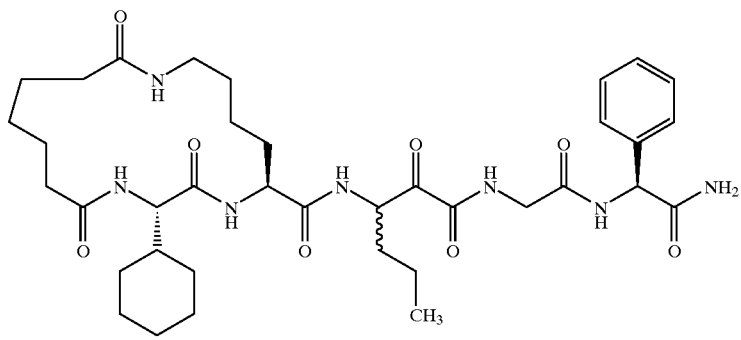

53

Compounds 41–53 were synthesized using solid phase methodology similar to the procedure outlined for the synthesis of Example 40.

Example 54

Preparation of Compound of Formula 54:

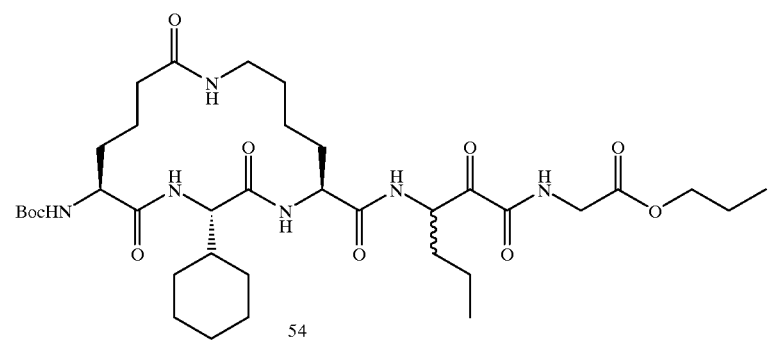

54

Step A:

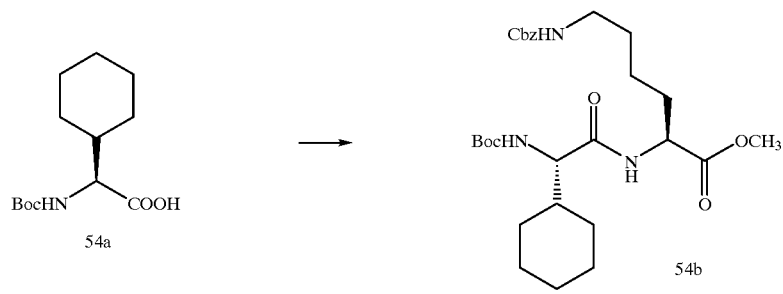

To a stirred solution of Boc-Cyclohexylglycine-OH (2.33 g, 9.07 mmol) in DMF (20 mL) and $CH_2Cl_2$ (20 mL) was added HOBT (1.48 g, 9.07 mmol), EDCl (1.91 g, 9.97 mmol) and NMM (2.99 mL, 27.2 mmol). The solution was stirred at −20° C. for 10 minutes, followed by addition of H-Lys(Z)-OMe.HCl and stirred for half an hour at −20° C. and kept in freezer overnight. The solution was then concentrated to dryness, followed by extraction with EtOAc, saturated $NaHCO_3$. The combined organic layer was washed with $H_2O$, brine, dried over $Na_2SO_4$ and concentrated to dryness to give a white solid (4.83 g, $MH^+$=534.1).

Step B:

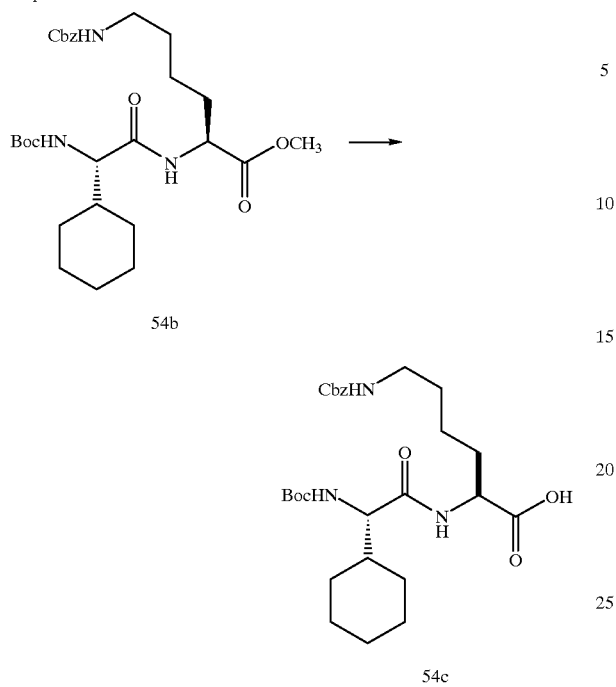

54b

54c

To a stirred solution of 54b (4.86 g, 8.76 mmol) in MeOH (10 mL) and $H_2O$ (7 mL) was added LiOH (70 mg, 11.4 mmol). The white precipitate was formed and the solution was allowed to stir at room temperature overnight and then concentrated to dryness. This crude material was then partitioned between $CH_2Cl_2$ and water. The organic layer was separated and washed with brine, dried over $Na_2SO_4$, filtered and concentrated to dryness to give 54c (4.55 g, $MH^+=520.1$).

Step C:

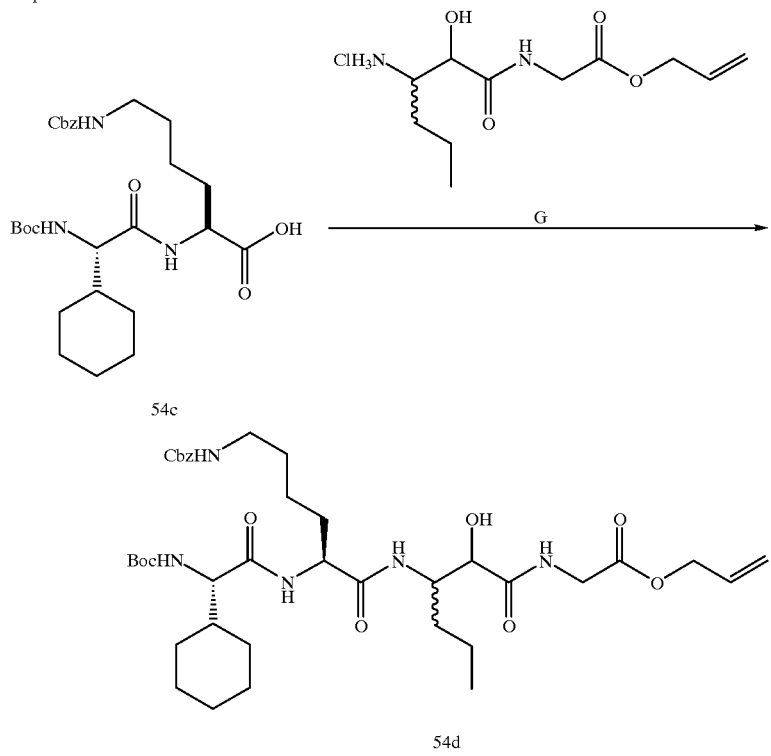

54c

54d

To a stirred cooling solution of 54c (4.3 g, 8.27 mmol) in DMF (40 mL) and CH$_2$Cl$_2$ (40 mL) at −20° C. was added HOBT (1.35 g, 8.27 mmol), EDCl (1.74 g, 9.1 mmol) and NMM (2.73 mL, 8.27 mmol). The resulting solution was stirred at −20° C. for 10 minutes, followed by addition of amine G (2.32 g, 8.27 mmol) and stirred at −20° C. for half an hour and kept in freezer overnight. The work up procedure from step A was followed to give a 54d (6.21 g, MH$^+$=746.2).

Step D:

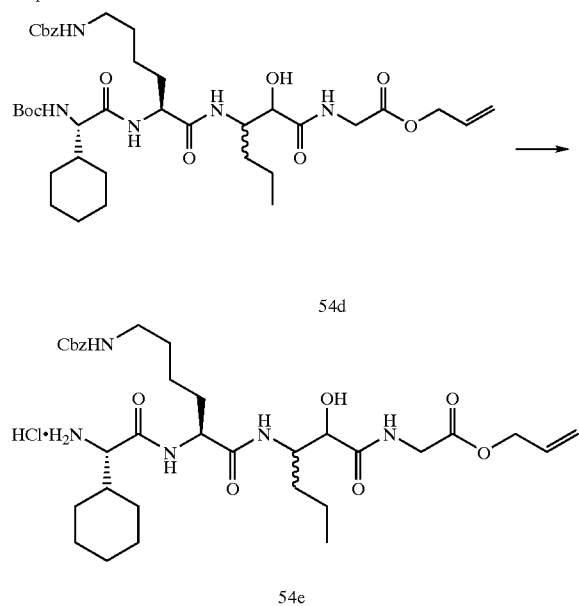

The solution of 54d (6.16 g, 8.26 mmol) in 4N HCl/Dioxane (40 mL) was stirred at room temperature for 1 hr and concentrated to dryness to give a crude product 54e (5.70 g, 100% yield, MH$^+$=646.3).

Step E:

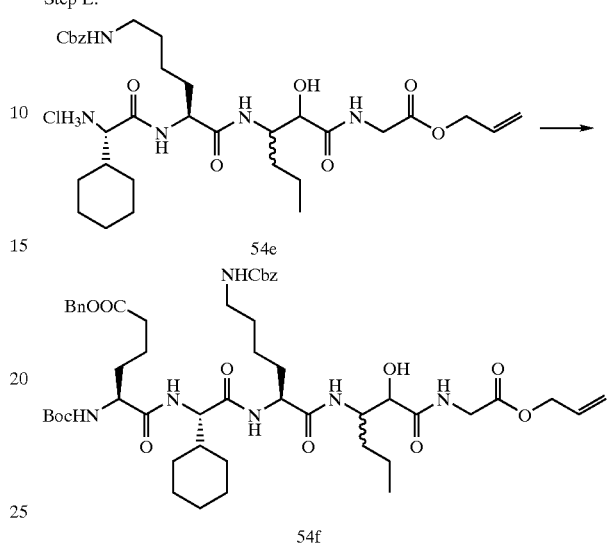

To a stirred cooling solution of Boc-Glu(OBn)-OH in DMF (25 mL) and CH$_2$Cl$_2$ (25 mL) at −20° C., was added HOBT (1.29 g, 7.92 mmol), EDCl (1.66 g, 8.71 mmol) and NMM(2.61 mL, 23.7 mmol). The resulting solution was stirred for 10 minutes at −20° C., followed by addition 54e (5.4 g, 7.916 mmol) and stirred for half an hour at −20° C. and kept in freezer overnight. Followed the work up procedure from step A to give a crude product (7.14 g, 93.5% yield).

Step F:

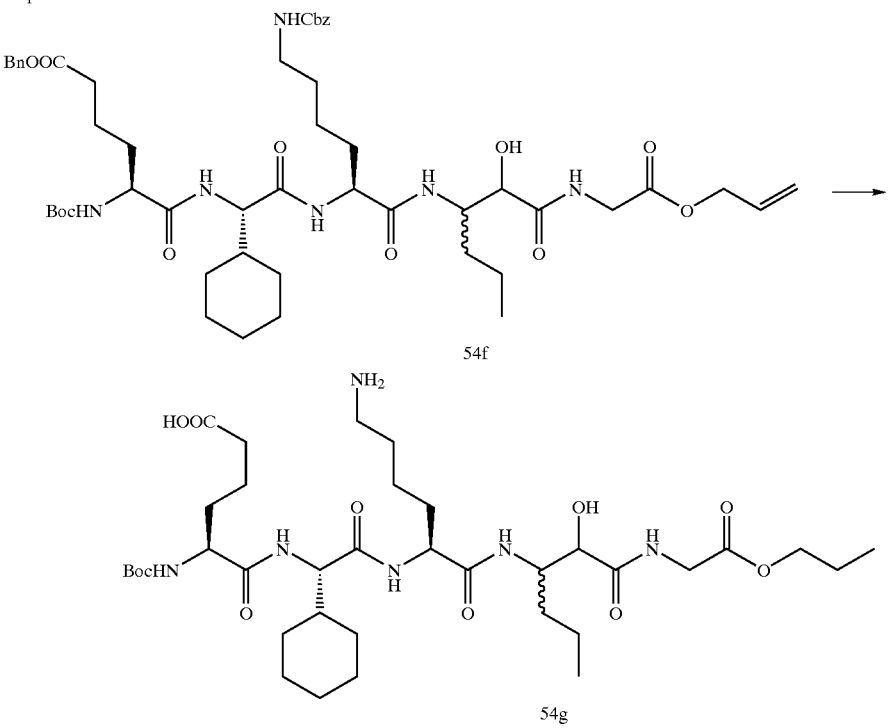

To a stirred solution of 54f (6.9 g, 7.15 mmol) in absolute EtOH (350 mL), was added 10% Pd/C (2.8 g) in 50% $H_2O$ (w/w). The resulting solution was purged with $H_2$ and stirred under $H_2$ balloon overnight. The solution was then filtered through celite and the filtrate was washed with EtOH/ $CH_2Cl_2$ and then concentrated to dryness to give a white solid (1.44 g). The solid was washed with 25% $H_2O$/MeOH and filtered through sintered funnel, then freezed and lyophilized to give 54g (4.12 g, 77.5% yield, $MH^+$=743.2).

Step G:

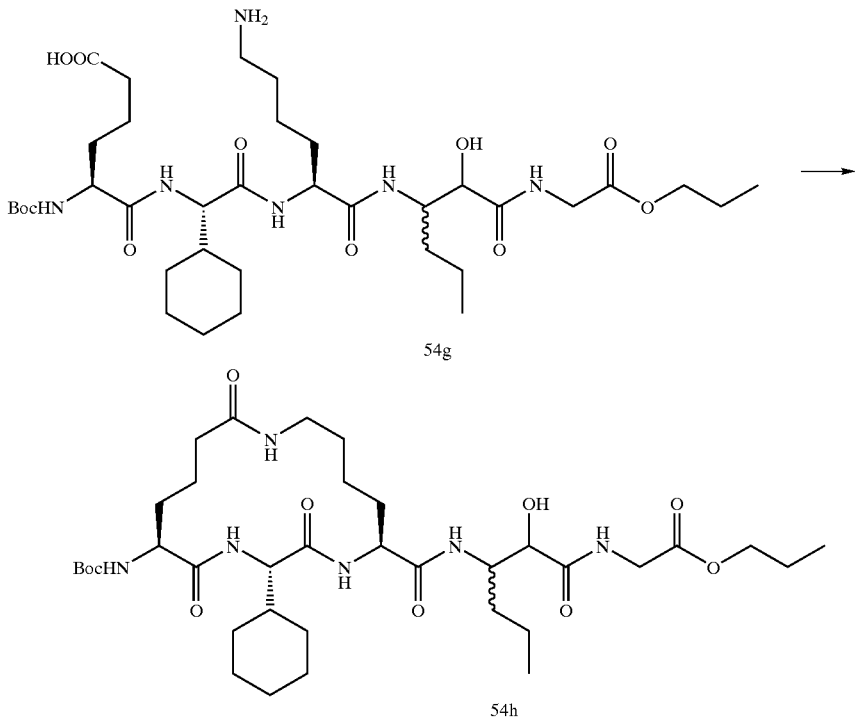

54g

54h

To a stirred cooling solution of 54g (0.5 g, 6.7 mmol) in DMF (50 mL) and $CH_2Cl_2$ (50 mL) at −20° C., was added HOBT (0.219 g, 1.34 mmol), EDCl (0.271 g, 1.41 mmol) and NMM (0.296 mL, 2.69 mmol). The resulting solution was stirred at −20° C. for 25 minutes and then kept in freezer overnight. The solution was concentrated to dryness, followed by extraction with EtOAc saturated $NaHCO_3$. The combined organic layer was then concentrated to dryness to give 54h (254 mg, $MH^+$=725.2).

Step H:

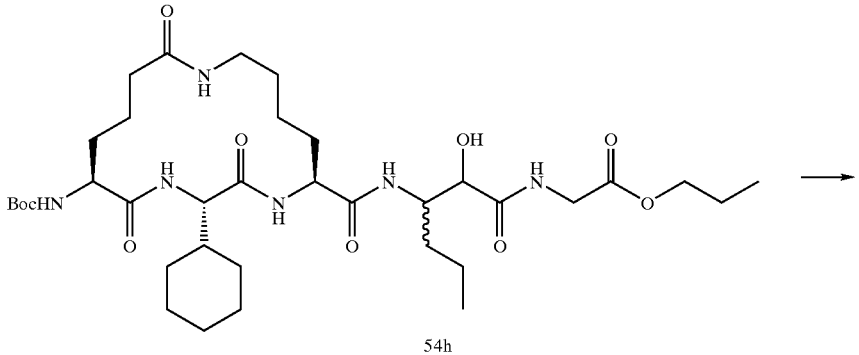

54h

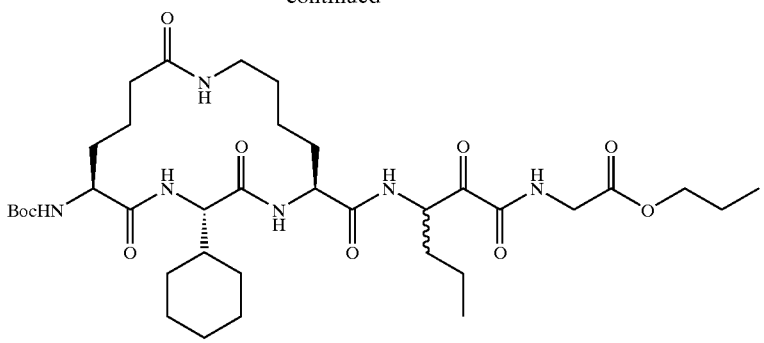

54

To a stirred solution of 54h (0.2 g, 0.27 mmol) in anhydrous CH$_2$Cl$_2$ (20 mL), was added Dess-Martin periodinane (0.234 g, 0.55 mmol). The resulting solution was stirred at room temperature for 1 hr. To this solution was added dropwise over half an hour the solution of H$_2$O (0.010 mL) in CH$_2$Cl$_2$ (20 mL) and stirred vigorously for additional 2 hrs. The solution was then stirred for half an hour with 50% Na$_2$S2O3/50% sat. NaHCO$_3$. The organic layer was separated and washed with H$_2$O, brine, dried over Na$_2$SO$_4$, filtered, concentrated to dryness and purified by column chromatography on silica gel, eluting with 10% MeOH/CH$_2$Cl$_2$ to yield 54 (17 mg, 62% MH$^+$=723.2).

Assay for HCV Protease Inhibitory Activity:

Spectrophotometric Assay: Spectrophotometric assays for the HCV serine protease was performed on the inventive compounds by following the procedure described by R. Zhang et al. *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A–NS5B junction sequence (Ac-DTEDVVX(Nva); SEQ ID NO: 1), where X=A or P) whose C-terminal carboxyl groups were esterified with one of four different.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 μM EDTA and 5 μM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, *Int. J. Pept. Protein Res.*, 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous Na$_2$CO$_3$ solution) to remove the acid used in cleavage. The DCM phase was dried over Na$_2$SO$_4$ and evaporated.

The ester substrates were assembled using standard acid-alcohol coupling procedures (K. Holmber et al, *Acta Chem. Scand.*, B33 (1979) 410–412). Peptide fragments were dissolved in anhydrous pyridine (30–60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD–substrate OD)/substrate OD).

Protease Assay: HCV protease assays were performed at 30° C. using a 200 μl reaction mix in a 96-well microtiter plate.

Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO·4% v/v) and allowed to preincubate at 30° C. for approximately 3 minutes. Fifty µls of pre-warmed protease (12 nM, 30° C.) in assay buffer, was then used to initiate the reaction (final volume 200 µl).The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants ($K_i$) for the competitive inhibitors Ac-D-(D-Gla)-L-I-(Cha)-C-OH (27: SEQ ID NO: 2), Ac-DTEDVVA(Nva)-OH (SEQ ID NO: 3) and Ac-DTEDVVP(Nva)-OH (SEQ ID NO: 4) were determined experimentally at fixed concentrations of enzyme and substrate by plotting $v_o/V_i$ vs. inhibitor concentration ($[I]_o$) according to the rearranged Michaelis-Menten equation for competitive inhibition kinetics: $v_o/v_1 = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i$ value.

The obtained $K_i$ values for the various macrocycles of the present invention are given in the afore-mentioned Table 1 wherein the compounds have been arranged in the order of ranges of $K_i$ values. From these test results, it would be apparent to the skilled artisan that the compounds of the invention have excellent utility as NS3-serine protease inhibitors.

Cell Bioassay Method: The cell bioassays for the HCV serine protease was performed on the inventive compounds by following the procedure described by S. Agrawal et al, "Development and Characterization of Hepatitis C Virus Serine Protease Cell-based Trans-Cleavage Assay", Hepatology Supplement to Volume 30 (No. 4, Part 2, October 1999), Abstract No. 615 (Proceedings of AASLD 50$^{th}$ Annual Meeting, Dallas, Tex., Nov. 5–9, 1999), the disclosure of which is incorporated herein by reference. The assay was performed in HeLa/Huh7 cells that were co-transfected with a plasmid that expresses a reporter protein substrate containing the NS5A/5B cleavage recognition sequence and an 1 BNS4A$_{21-32}$ GS-GSNS$_{3-81}$ I17K expression vector and YFPn1 as a internal standard protein to control cytotoxicity. Protease activity was measured by SDS-PAGE of total cell lysates followed by Western blot detection using a monoclonal antibody directed against the reporter substrate. Quantitation of substrate cleavage was performed by scanning the immunoblot on the phosphoimager.

Materials:
Plasmid DNAs
pBFP-5A/5B-GFP: The reporter gene that expresses the substrate encodes a fusion protein comprised of an N' terminal blue fluorescent protein (BFP) domain and a C' terminal green fluorescent protein (GFP) domain, separated by a 25 amino acids derived from the NS5A/5B cleavage recognition sequence. Both GFP and BFP are essentially homologous autofluorescent proteins that emit green or blue light, respectively, when excited by UV light of the appropriate wavelength. Four amino acid substitutions in the chromophore of GFP alter the emission wavelength and convert the protein to BFP.

The substrate and the resulting GFP and BFP products can be detected in cell lysates by immunologic methods using a monoclonal antibody that recognizes both proteins.

The BFP-5A/5B-GFP reporter gene contains the BFP and GFP autofluorescent protein coding sequences (Quantum Biotechnologies, Inc., Montreal, Canada) separated by the NS5A/5B cleavage recognition sequence, cloned between the Nhe I and Barn HI restriction endonuclease sites of the pQBI25 cloning vector (Quantum Biotechnologies, Inc.). Expression of the fusion protein is under the control of the CMV IE promoter-enhancer. The bovine growth hormone p (A) sequence of the vector provides the potyadenylation signal for the mRNA. The NS5A/5B cleavage sequence is: SSGADTEDVVCCSMSYTWTGALVTP (SEQ ID NO: 5). DNA sequencing was used to validate the clone.

P1BOO2: 1bNS4A21-32GS-GS NS 3–81 I17K: The subtype 1b protease was cloned as an Xba1/Not1 fragment behind the CMV promoter in vector pC1 neo.

YFPn1: YFPn1 was purchased from CLONTECH (Palo Alto, Calif.). Addition of third plasmid to the transfection supplies an internal standard protein to control for cytotoxicity and does not affect percentage of protease cleavage.

Plasmid DNAs were maintained and propagated in DH5α cells (obtained from LifeTechnologies) in LB medium under the appropriate antibiotic selection, and purified using QIAfilter Plasmid Kits (Qiagen, Valencia, Calif.).

Cell Culture:
HeLa cells were maintained and propagated in Eagle's Minimum Essential Media (EMEM; BioWhittaker, Walkersville, Md.) supplemented with 10% fetal calf serum (FCS), 2 mM glutamine, and 100 u/ml penicillin-streptomycin (BioWhitaker), 2% NaHCO$_3$.

Huh7 cells were maintained and propagated in Dulbecco's Modified Eagle's medium (DMEM; BioWhittaker) supplemented with 10% fetal calf serum (FCS), 100 u/ml penicillin-streptomycin (BioWhitaker) and 5 ml NEAA (100×; BioWhittaker)/L.

SOP Procedure
Day Preceding Transfection:
HeLa cells were seeded in 24 well plates (Falcon 3047 plates) at a density of 6×10$^4$ cells/well and grown overnight at 37° C. in a 5% CO$_2$ incubator.

Day of Transfection:
Plasmid DNAs were diluted to a final concentration of 0.05 µg/µl in nuclease free water (Promega, Madison, Wis., cat # P119C). 0.75 µg BFP-5A/5B-GFP was combined and mixed with 0.175 µg P1 B002 (0.23X) and 0.02 µg of YFPn1. The DNAs were brought to a final volume of 60 µl with EMEM lacking FBS, glutamine, and antibiotics. A ratio of 5 µl volumes of SuperFect Reagent (Qiagen, cat # 301305) per total µgs of DNA was added and the mixture vortexed about 10 seconds and incubated 10 min. at room temperature to allow complex formation. While complex formation was taking place, growth medium from cell culture plates was aspirated and cells washed 1× with 1 ml PBS without $Ca^{2+}$, $Mg^{2+}$ (BioWhitaker). 350 µl EMEM (supplemented with appropriate suplements-compleat medium) was added to the tube containing the transfection complexes and the mixture pipetted up and down 2–3 times. Total volume was transferred to one well of the 24 well culture plate. The HeLa cells were incubated with the transfection complexes for about 3 hr. at 37° C. and 5% $CO_2$. The media containing the transfection complexes was removed from the cells by aspiration. The cells were washed once in about 1 ml PBS, the PBS was aspirated and 495 µl of complete EMEM was added followed by 5 µl compound/well. The cells were incubated 22–24 hr. at 37° C. and 5% $CO_2$.

Preparation of Cell Lysates

The medium from each well was aspirated and washed once 1× with DPBS. Cells were harvested in 100 µl of 1× Tris-SDS-BME sample buffer (OWL separation system, Portsmouth, N.H., cat # ER33) and transferred to microcentrifuge tubes. It was then boiled 3–5 min. to lyse cells. Loading was done at 10 µl/well on SDS-PAGE gel. The lysates were resolved by electrophoresis on 10 cm×10 cm 12.5% SDS-PAGE (Owl Scientific, cat # OG-0125B) run at 30 mamp in Tris-Glycine-SDS buffer (Owl Scientific). Prior to use, PVDF membrane (Immobilon-P; 0.45 µm pore size; Millipore, Bedford, Mass.) was soaked in 100% methanol for 10 seconds and then the blot was placed in distilled water. The proteins were transferred to PVDF filter membranes (0.45 µm, Millipore) at 108 mamp per gel for 90 minutes using a semi-dry electroblotter.

Detection of Proteins by ECF Western Blot (Amersham Pharmacia Biotech, Little Chalfont, England), catalog #RPN 5780). The PVDF filter membranes were blocked by 5% blocking reagent (from kit) in ~10 ml PBS containing 0.05% Tween 20, pH 7.4 (Sigma Chemicals, St. Louis, Mo., cat # 3563) for overnight at 2–4 C in refrigerator. The next day, the membranes were rinsed briefly twice with TPBS containing 0.05% Tween 20 washing buffer, then washed three times each time 5 min. in PBS containing 0.05% Tween 20, pH 7.4. The membranes were incubated in 12 mls of a 1:3000 dilution of anti-GFP monoclonal antibody for 30 minutes (Clontech, Palo Alto, Calif.) in PBS containing 0.05% Tween 20, pH7.4 while at the same time 1% BSA (Albumin, bovine cat # A-2153 from Sigma) was added to reduce background. The membranes were washed briefly twice with TPBS, then thrice, for 5 min. each time, in TPBS washing buffer. The membranes were incubated in 12 mls of a 1:600 dilution anti fluorescein-linked anti mouse Ig in TPBS for 30 minutes. The membranes were washed briefly with TPBS twice, then for 5 min. in TPBS washing buffer thrice. For signal amplification with ECF substrate membranes were incubated in 10 ml of 1:2500 anti fluorescein alkaline phosphatase conjugate for 30 minutes. The membranes were rinsed briefly with TPBS twice, then 5 min. in TPBS washing buffer thrice. The ECF substrate solution was prepared as per manufacturer's instructions (aliquot and freeze), membranes were incubated for 2–3 minutes, excess reagent was drained off, then were blotted with filter papers, air-dried for 9–10 minutes and then scanned.

Scanning the membrane: The blot was placed on the glass of phosphoimager Storm 860. The blue chemiluminiescent was set up, 200 pixcels size, 700 PMT voltage. The file was opened in ImageQuant and quantitated by creating squares around the bands representing the substrate (S), the product (P) and the internal control (IC). The % cleavage of the substrate was measured as P/(S+P)×100. The inhibition in cleavage due to drug was measured compared duplicate to drug controls included on each blot. A report was created in Excel. The results for some of the compounds are given below:

Compound of Example 36: $EC_{50}$=9 µm

Compound of Example 35: $EC_{50}$=20 µm

From these test results, it would be apparent to the skilled artisan that the compounds of the invention have excellent utility as NS3-serine protease inhibitors.

What is claimed is:

1. A macrocyclic compound, or enantiomers, stereoisomers, rotomers or tautomers of said compound, or pharmaceutically acceptable salts or solvates of said compound, said compound having the general structure shown in Formula I:

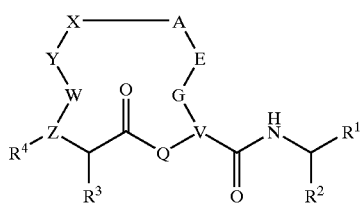

Formula I wherein:

E, X and Y may be independently present or absent, and if present are independently selected from the moieties: alkyl, aryl, alkyl-aryl, heteroalkyl, heteroaryl, aryl-heteroaryl, alkyl-heteroaryl, cycloalkyl, alkyl ether, alkyl-aryl ether, aryl ether, alkyl amino, aryl amino, alkyl-aryl amino, alkyl sulfide, alkyl-aryl sulfide, aryl sulfide, alkyl sulfone, alkyl-aryl sulfone, aryl sulfone, alkyl-alkyl sulfoxide, alkyl-aryl sulfoxide, alkyl amide, alkyl-aryl amide, aryl amide, alkyl sulfonamide, alkyl-aryl sulfonamide, aryl sulfonamide, alkyl urea, alkyl-aryl urea, aryl urea, alkyl carbamate, alkyl-aryl carbamate, aryl carbamate, alkyl-hydrazide, alkyl-aryl hydrazide, alkyl hydroxamide, alkyl-aryl hydroxamide, alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof, with the proviso that E, X and Y may optionally be additionally substituted with moieties selected from the group consisting of aromatic, alkyl, alkyl-aryl, heteroalkyl, aryl-heteroaryl, alkyl-heteroaryl, cycloalkyl, alkyl ether, alkyl-aryl ether, alkyl sulfide, alkyl-aryl sulfide, alkyl sulfone, alkyl-aryl sulfone, alkyl amide, alkyl-aryl amide, alkyl sulfonamide, alkyl amines, alkyl-aryl amines, alkyl-aryl sulfonamide, alkyl urea, alkyl-aryl urea, alkyl carbamate, alkyl-aryl carbamate, halogen, hydroxylamino, alkyl carbazate, aryl carbazate;

$R^1$=$COR^5$ or $B(OR)_2$, wherein $R^5$=H, $CF_3$, $C_2F_5$, $C_3F_7$, $CF_2R^6$, $R^6$, $COR^7$ wherein $R^7$=H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COO\ R^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO\ R^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COO\ R^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COO\ R^{11}$, $CH(R^{1'})CONHCH(R^{2'})CONHCH(R^{3'})CONHCH(R^{4'})CONHCH(R^{5'})CONR^{12}R^{13}$, wherein $R^{1'}$, $R^{2'}$, $R^{3'}$, $R^{4'}$, $R^{5'}$, $R^{11}$, $R^{12}$, $R^{13}$, and R' are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W may be present or absent, and if W is present, W is selected from C=O, C=S, $SO_2$ or C=NR;

Q is $(NR)_p$, O, S, $CH_2$, CHR, CRR' or a double bond towards V;

A is O, $CH_2$, $(CHR)_p$, $(CHR—CHR')_p$, $(CRR')_p$, NR, S, $SO_2$, C=O or a bond;

G is $(CH_2)_p$, $(CHR)_p$, $(CRR')_p$, NR, O, S, $SO_2$, $S(O)_2NH$, C=O, or a double bond towards E or V;

V is CH, CR or N;

R is selected from the group consisting of H; C1–C10 alkyl; C2–C10 alkenyl; C3–C8 cycloalkyl; C3–C8 heterocycloalkyl, aryl, alkoxy, aryloxy, alkylthio, arylthio, amino, carbamate, urea, ketone, aldehyde, cyano, nitro; heteroaryl; alkyl-aryl; alkyl-heteroaryl; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

p is a number from 0 to 6; and

R, R', $R^3$ and $R^4$ are independently selected from the group consisting of H; C1–C10 alkyl; C2–C10 alkenyl; C3–C8 cycloalkyl; C3–C8 heterocycloalkyl, aryl, alkoxy, aryloxy, alkylthio, arylthio, amino, amido, ester, carboxylic acid, carbamate, urea, ketone, aldehyde, cyano, nitro; heteroaryl; alkyl-aryl; alkyl-heteroaryl; (cycloalkyl)alkyl and (heterocycloalkyl) alkyl, wherein said cycloalkyl is made of three to eight carbon atoms, and zero to six oxygen, nitrogen, sulfur, or phosphorus atoms, and said alkyl is of one to six carbon atoms;

with said alkyl, heteroalkyl, alkenyl, heteroalkenyl, aryl, heteroaryl, cycloalkyl and heterocycloalkyl moieties may be optionally substituted, with said term "substituted"referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, hydroxamate and thiourea, with the proviso that the macrocycle ring represented by:

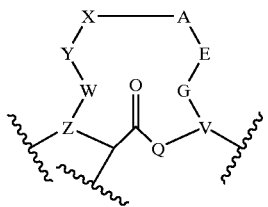

in Formula I represents at least a 11-membered macrocycle.

2. The compound of claim 1, wherein $R^1=COR^5$, and $R^5$ is H, $COOR^8$, or $CONR^9R^{10}$.

3. The compound of claim 2, wherein $R^1=COCONR^9R^{10}$, and is $R^9$ is H, $R^{10}$ is H, $CH(R^{1'})COOR^{11}$, $CH(R^{1'})CONR^{12}R^{13}$, $CH(R^{1'})CONHCH(R^{2'})COOR^{11}$, $CH(R^{1'})CONHCH(R^{2'})CONR^{12}R^{13}$, or $CH(R^{1'})CONHCH(R^{2'})(R')$.

4. The compound of claim 3, wherein $R^{10}=CH(R^{1'})CONHCH(R^{2'})COOR^{11}$, $CH(R^{1'})CONHCH(R^{2'})CONR^{12}R^{13}$, or $CH(R^{1'})CONHCH(R^{2'})(R')$, wherein $R^{1'}$ is H or alkyl, and $R^{2'}$ is selected from the group consisting of phenyl, substituted phenyl, hetero atom-substituted phenyl, thiophenyl, cyclohexyl, cyclopentyl, cyclopropyl, piperidyl pyridyl and 2-indanyl.

5. The compound of claim 4, wherein $R^{1'}$ is H.

6. The compound of claim 5, wherein $R^{2'}$=phenyl, thiophenyl, cyclohexyl, 2-indanyl, cyclopentyl, pyridyl, phenyl(4-$HNSO_2NH_2$), $R^{11}$ is H or tert-butyl, $R^{12}$ and $R^{13}$ are methyl, and R' is hydroxymethyl or tert-butoxymethyl.

7. The compound of claim 1, wherein $R^2$ is selected from the group consisting of the following moieties:

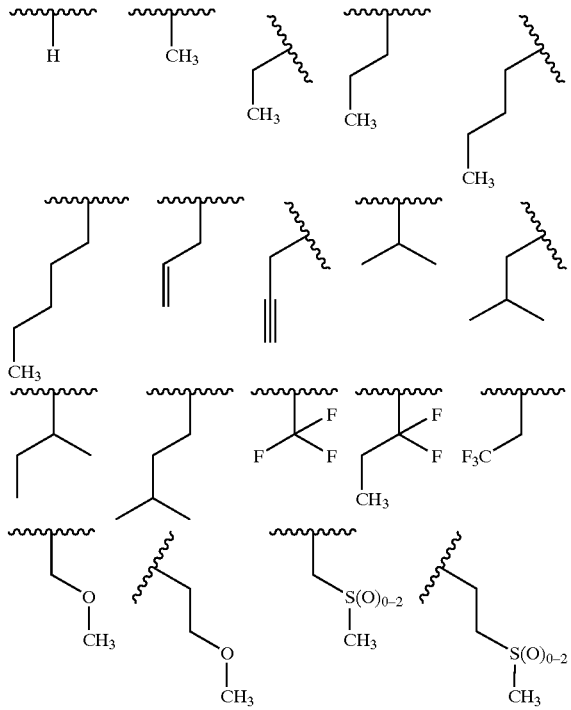

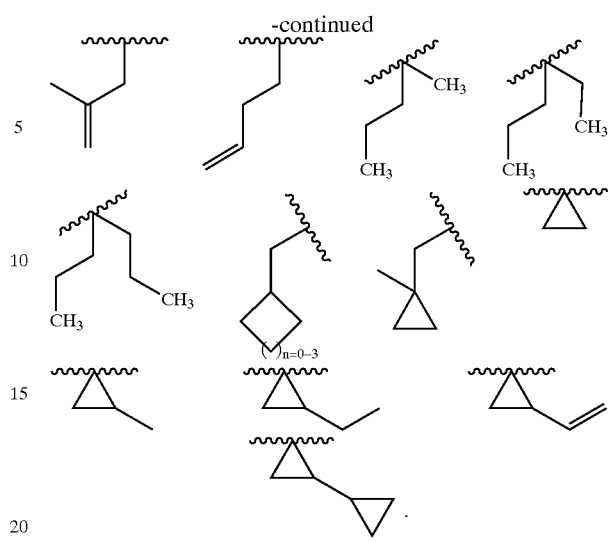

8. The compound of claim 7 wherein $R^1=COR^5$, and $R^5$ is H, $COOR^8$, or $CONR^9R^{10}$.

9. The compound of claim 8 wherein V is CH.

10. The compound of claim 9 wherein Q is NR or O.

11. The compound of claim 10 wherein G is $CH_2$.

12. The compound of claim 11 wherein A is O, NR, CH=CH or $CH_2$.

13. The compound of claim 12 wherein E is alkyl, aryl, hereroalkyl, heteroaryl, alkyl, aryl, or cycloalkyl.

14. The compound of claim 13 wherein E is selected from the group consisting of the moieties:

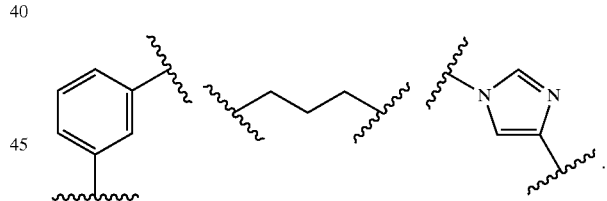

15. The compound of claim 14 wherein $R^3$ is selected from the group consisting of the moieties:

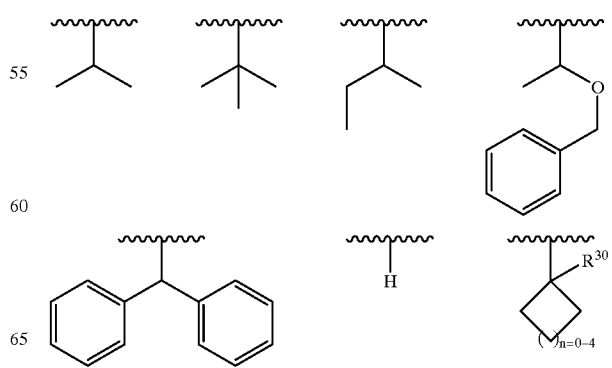

-continued

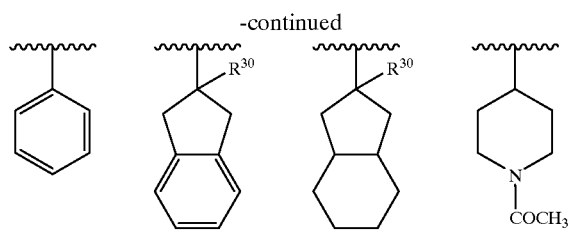

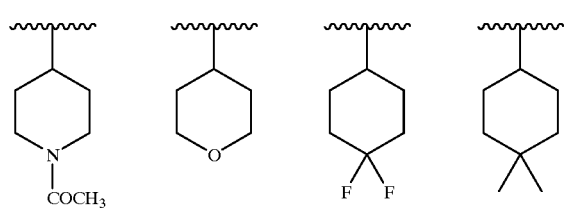

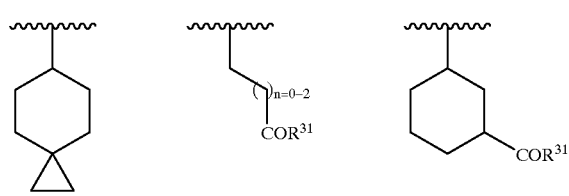

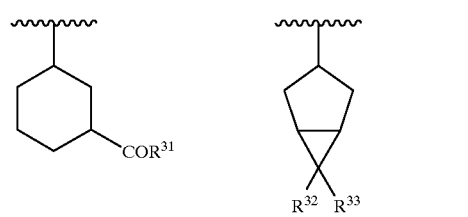

wherein R³⁰=H, CH, or other alkyl groups;
R³¹=OH, O-alkyl, NH₂, N-alkyl; and
R³² and R³³ may be the same or different and are selected independently from H, F, Cl, Br and CH₃.

16. The compound of claim 15 wherein Z=N and R⁴=H.
17. The compound of claim 16 wherein W is C=O.
18. The compound of claim 17 wherein the moiety X-Y is selected from the group consisting of: C1–C10 alkyl, alkyl, cycloalkyl, heteroalkyl, arylalkyl, aryl, hereroaryl and alkylaryl.
19. The compound of claim 18, wherein:

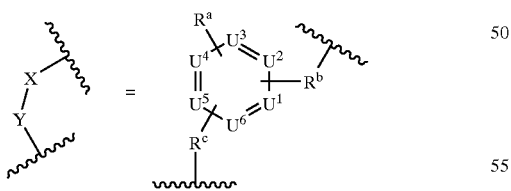

wherein R$^b$ is connected directly to A and R$^c$ is connected directly to W; and the moiety U¹, U², U³, U⁴, U⁵ and U⁶ form either a six membered carbon ring, or a five or six membered ring with one or more heteroatoms;
R$^a$=H, alkyl, alkoxy, hydroxy, alkylthio, halogen, nitro, cyano, carboxylic acid, ester, amide, amino, nitrile, or CF₃;
R$^b$ is a bond, C₁–C₆ alkyl, C₂–C₆ alkenyl, C₂–C₆ alkynyl, O, S, SO₂, NH, O(alkyl), S(alkyl), SO₂(alkyl) or N(alkyl); and R$^c$ is a bond, C₁–C₆ alkyl, C₂–C₆ alkenyl, C₂–C₆ alkynyl, O, S, SO₂, NH, O(alkyl), S(alkyl), SO₂(alkyl), N(alkyl) or CH₂—N(alkyl) with the CH₂ being linked to the aromatic ring.

20. The compound of claim 18 wherein the moiety X-Y is selected from the group consisting of the following structures:

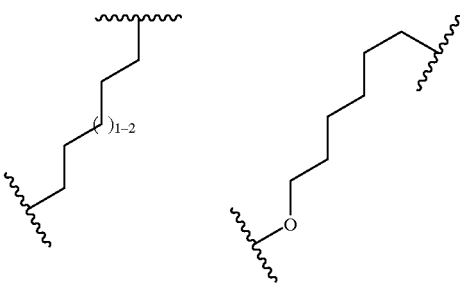

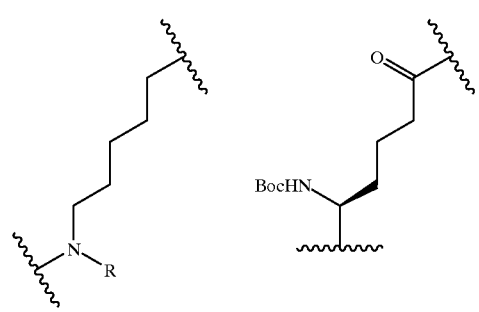

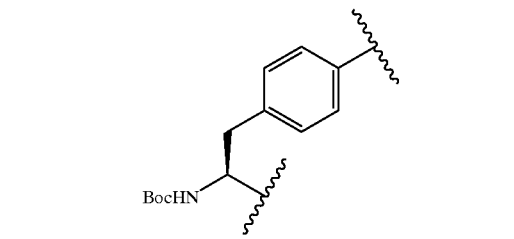

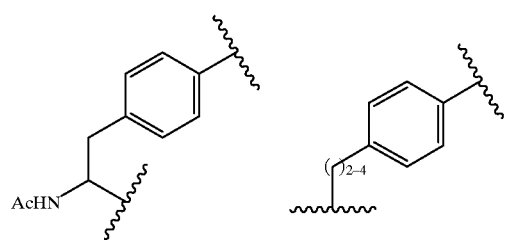

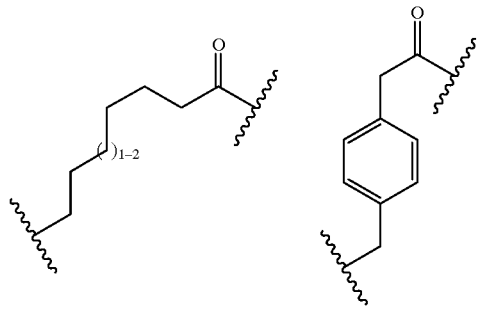

-continued

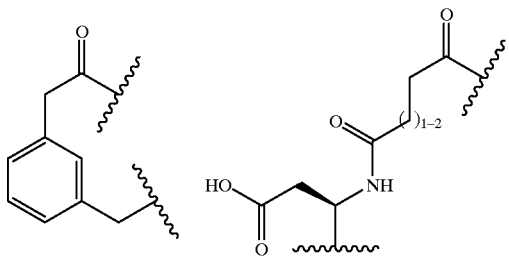

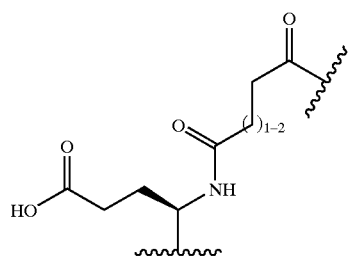

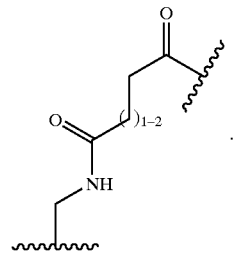

21. A composition comprising as an active ingredient a compound of claim 1 and a pharmaceutical acceptable carrier.

22. The composition of claim 21 wherein said compound of claim 1 is present in amounts effective to inhibit hepatitis C nonstructural protein-3 protease (HCV NS3 protease).

23. A method of preparing a composition for inhibiting hepatitis C nonstructural protein-3 protease (HCV NS3 protease), said method comprising bringing into intimate contact a compound of claim 1 in an amount effective to cause said inhibition and a pharmaceutically acceptable carrier.

24. A compound exhibiting HCV NS3 protease inhibitory activity, or enantiomers, stereoisomers, rotamers or tautomers of said compound, or pharmaceutically acceptable salts or solvates of said compound, said compound being selected from the group of compounds with structures listed below:

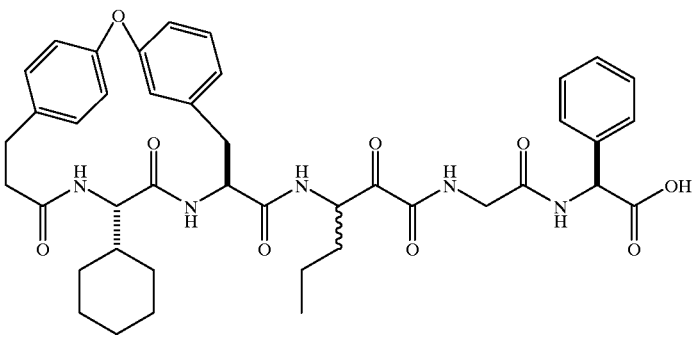

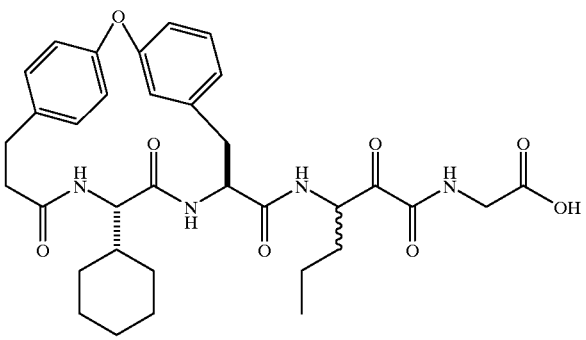

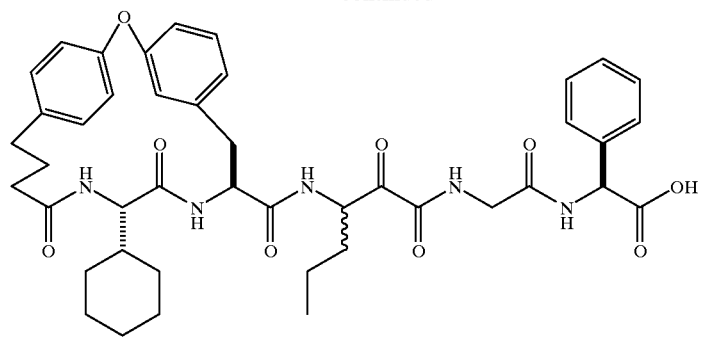
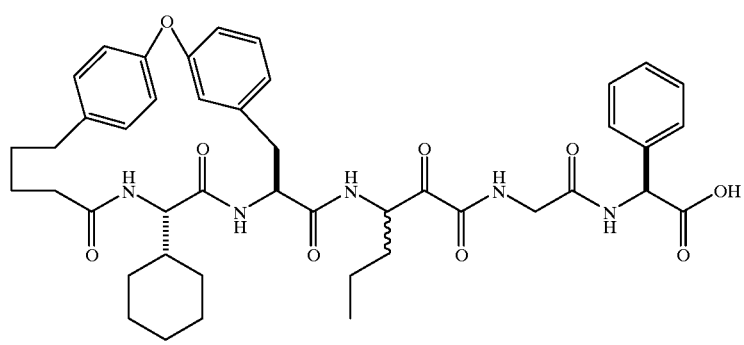
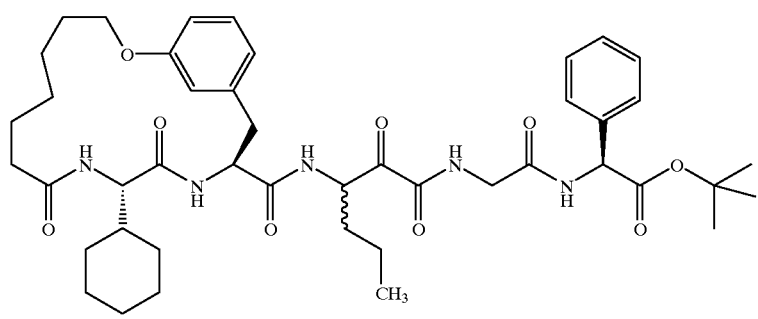
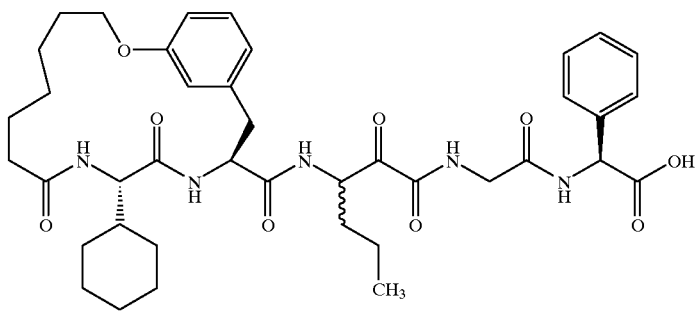

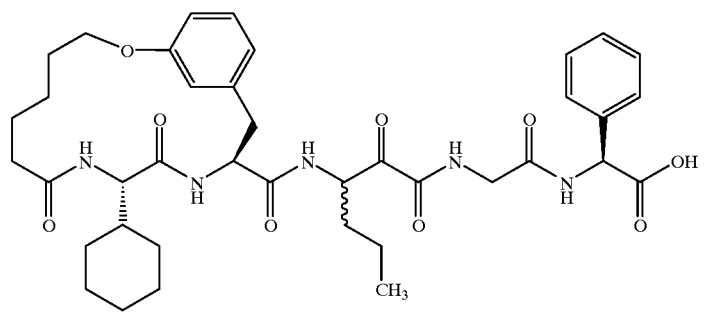
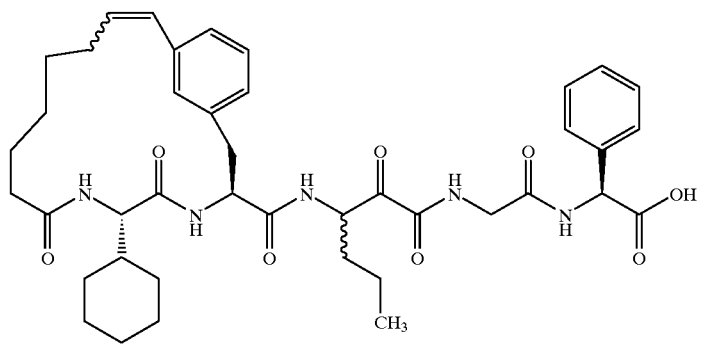
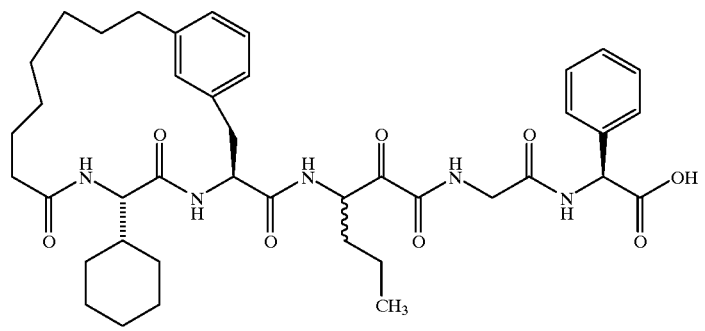
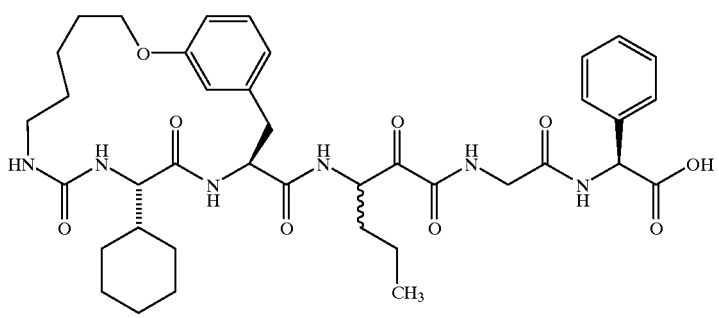
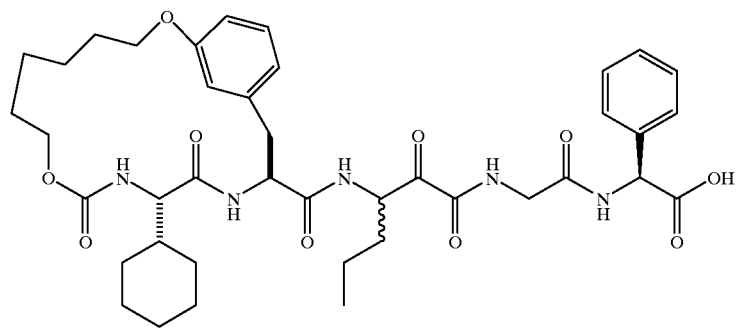

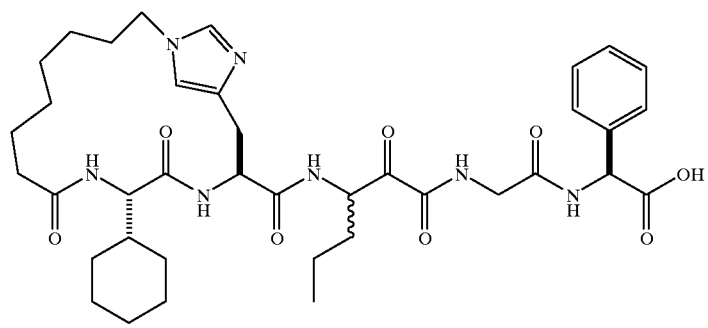
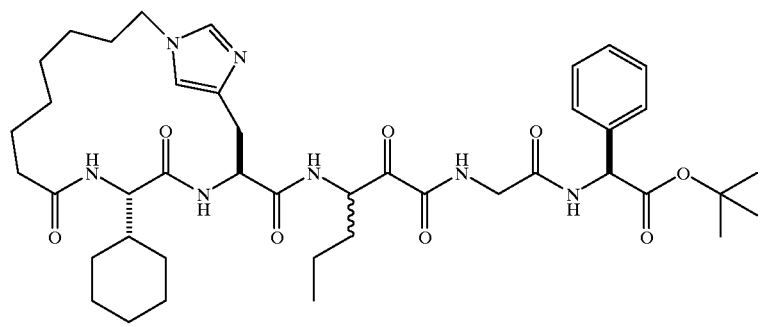
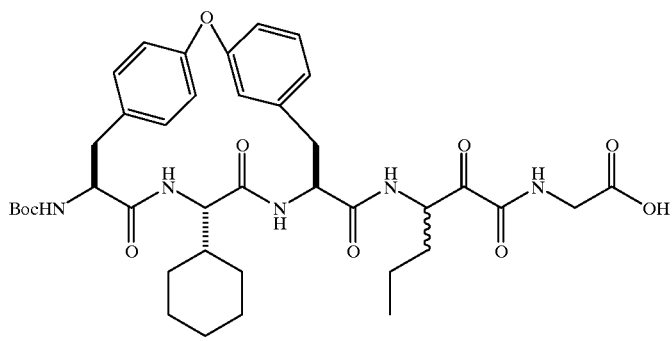
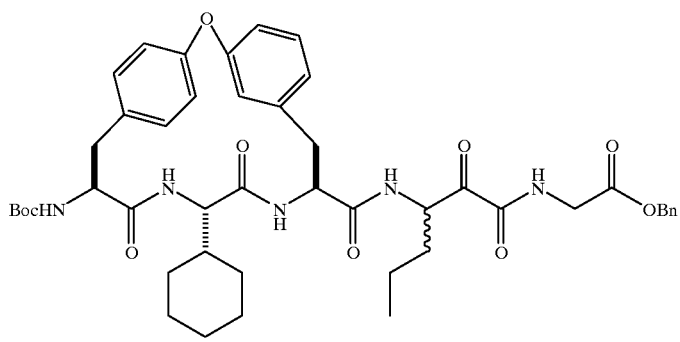

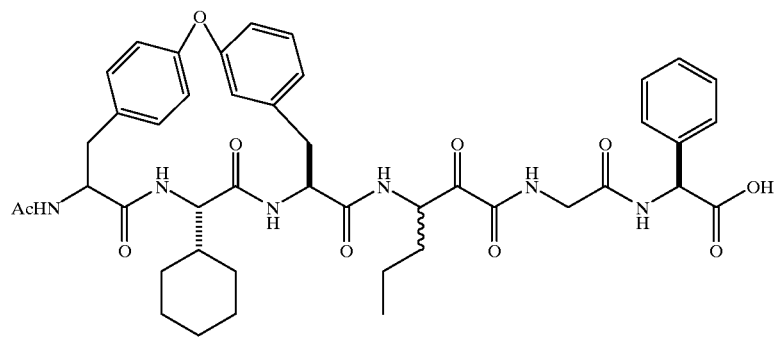
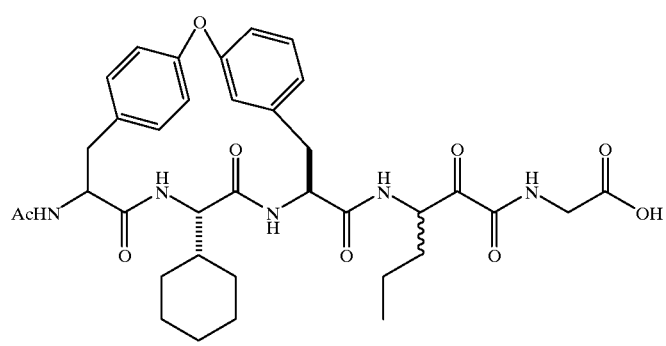
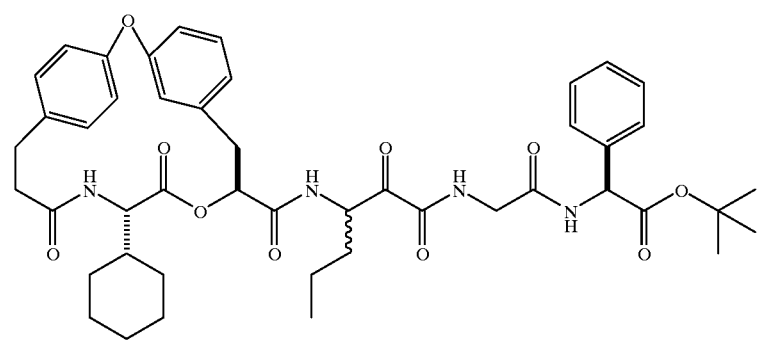
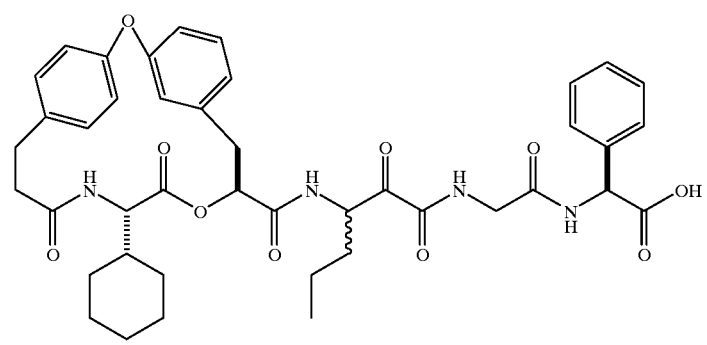

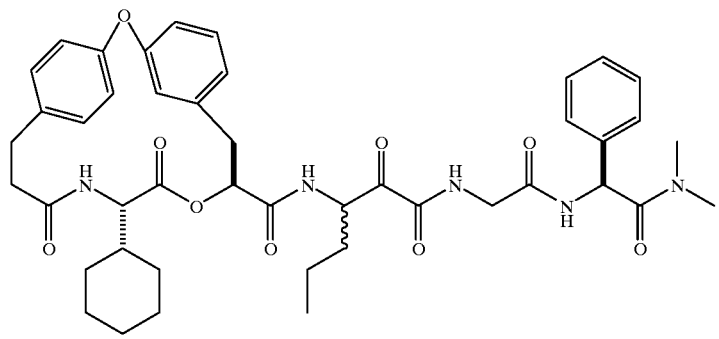
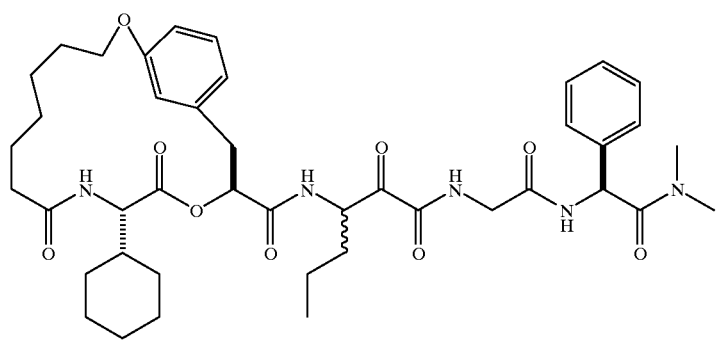
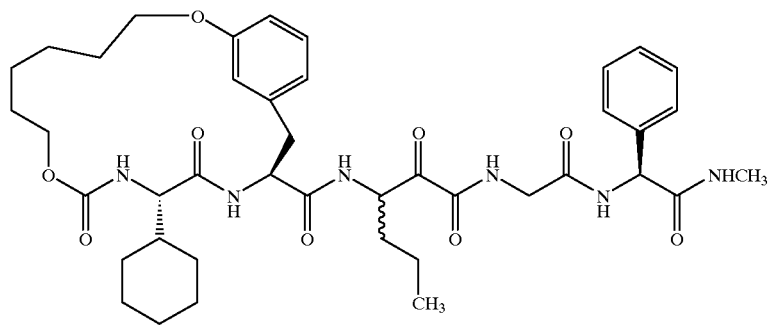
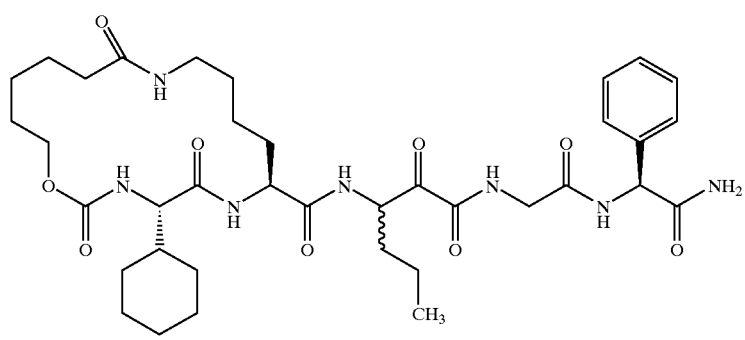

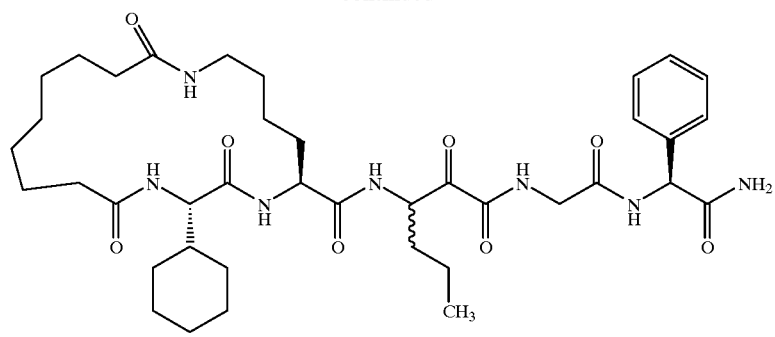
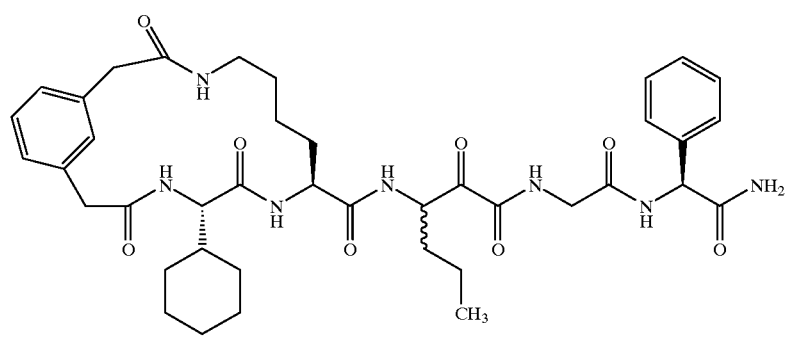
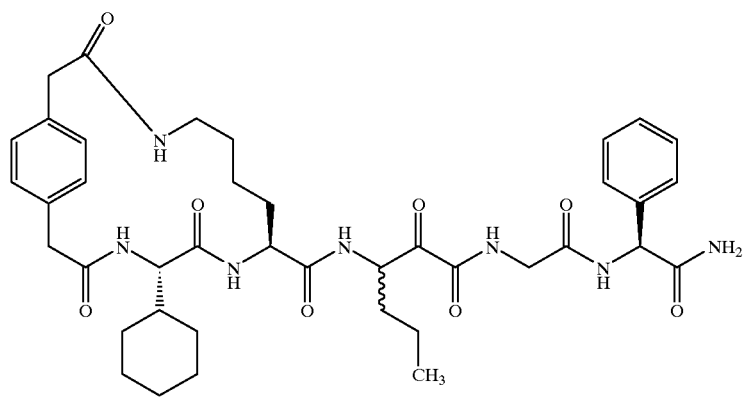
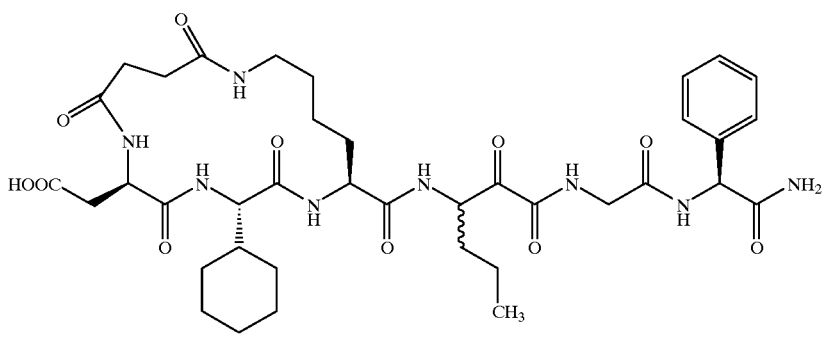

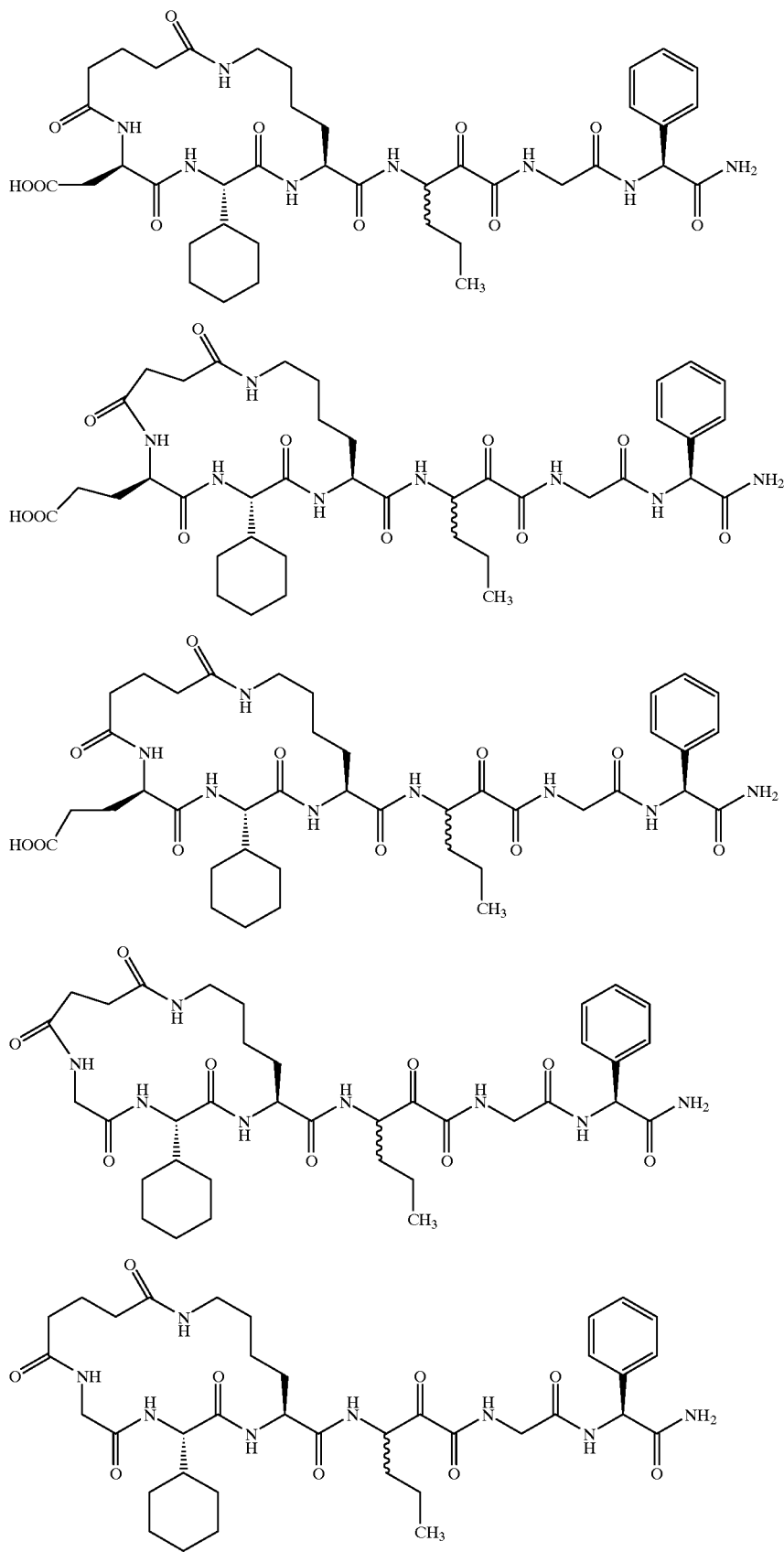

25. A composition for inhibiting hepatitis C nonstructural protein-3 protease (HCV NS3 protease), said composition comprising one or more compounds in claim 24 in amounts to cause said inhibition and a pharmaceutically acceptable carrier.

26. The composition of claim 25, additionally containing an antiviral agent.

27. The composition of claim 25 or claim 26 still additionally containing an interferon.

28. The composition of claim 27, wherein said antiviral agent is ribavirin and said interferon is α-interferon.

29. A method of inhibiting HCV NS3 protease comprising administering a compound of claim 1 to a patient in need thereof for a time and under conditions effective to inhibit HCV NS3 protease.

30. A method of inhibiting HCV NS3 protease comprising administering a composition of claim 21 to a patient in need thereof for a time an under conditions effective to inhibit HCV NS3 protease.

31. A method of inhibiting HCV NS3 protease comprising administering a compound of claim 24 to a patient in need thereof for a time and under conditions effective to inhibit HCV NS3 protease.

32. A method of inhibiting HCV NS3 protease comprising administering a compound of claim 25 to a patient in need thereof for a time and under conditions effective to inhibit HCV NS3 protease.

33. A method of inhibiting HCV NS3 protease comprising administering a compound of claim 1 to a patient in need thereof for a time and under conditions effective to inhibit HCV NS3 protease.

34. A method of inhibiting HCV NS3 protease comprising administering a compound of claim 21 to a patient in need thereof for a time and under conditions effective to inhibit HCV NS3 protease.

35. A method of inhibiting HCV NS3 protease comprising administering a compound of claim 24 to a patient in need thereof for a time and under conditions effective to inhibit HCV NS3 protease.

36. A method of inhibiting HCV NS3 protease comprising administering a compound of claim 25 to a patient in need thereof for a time and under conditions effective to inhibit HCV NS3 protease.

* * * * *

UNITED STATES PATENT AND TRADEMARK OFFICE
CERTIFICATE OF CORRECTION

PATENT NO.     : 6,914,122 B2
DATED          : July 5, 2005
INVENTOR(S)    : Venkatraman, Srikanth It is certified that error appears in the above-identified patent and that said Letters Patent is hereby corrected as shown below:

Column 236,
Line 36, correct "R is selected" to -- $R^2$ is selected --.

Column 237,
Line 29, insert -- , -- after "piperidyl".

Column 238,
Line 36, correct "hereroalkyl" to -- heteroalkyl --.

Column 239,
Lines 10-18, delete the following duplicate structure on the left:

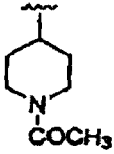

Lines 29-35, correct the following structure on the left:

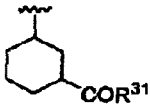

to:

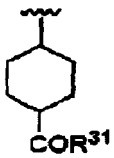

Line 38, correct "CH" to -- $CH_3$ --.

UNITED STATES PATENT AND TRADEMARK OFFICE
CERTIFICATE OF CORRECTION

PATENT NO.   : 6,914,122 B2
DATED        : July 5, 2005
INVENTOR(S)  : Venkatraman, Srikanth It is certified that error appears in the above-identified patent and that said Letters Patent is hereby corrected as shown below:

Column 251,
Bottom structure, correct the following structure:

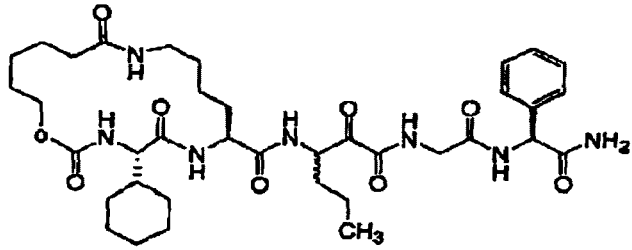

to:

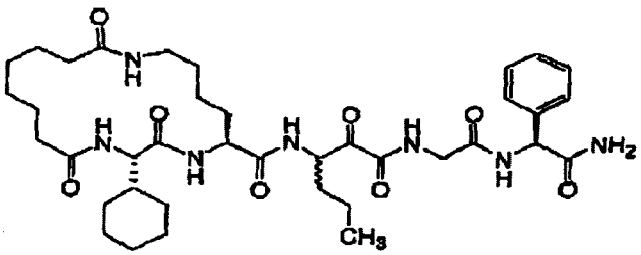

Column 258,
Lines 9, 14 and 18, correct "HCV NS3 protease" to -- HCV replication --.
Lines 10 and 19, correct "compound" to -- composition --.

Signed and Sealed this

Thirtieth Day of May, 2006

JON W. DUDAS
*Director of the United States Patent and Trademark Office*